US009428456B2

(12) United States Patent
Fretz et al.

(10) Patent No.: US 9,428,456 B2
(45) Date of Patent: Aug. 30, 2016

(54) 1-[M-CARBOXAMIDO(HETERO)ARYL-METHYL]-HETEROCYCLYL-CARBOXAMIDE DERIVATIVES

(71) Applicant: Actelion Pharmaceuticals Ltd., Allschwil (CH)

(72) Inventors: Heinz Fretz, Allschwil (CH); Markus Gude, Allschwil (CH); Philippe Guerry, Allschwil (CH); Thierry Kimmerlin, Allschwil (CH); Francois Lehembre, Allschwil (CH); Thomas Pfeifer, Allschwil (CH); Anja Valdenaire, Basel (CH)

(73) Assignee: ACTELION PHARMACEUTICALS LTD, Allschwil (CH)

( * ) Notice: Subject to any disclaimer, the term of this patent is extended or adjusted under 35 U.S.C. 154(b) by 0 days.

(21) Appl. No.: 14/410,426

(22) PCT Filed: Jun. 21, 2013

(86) PCT No.: PCT/IB2013/055095
§ 371 (c)(1),
(2) Date: Dec. 22, 2014

(87) PCT Pub. No.: WO2013/190508
PCT Pub. Date: Dec. 27, 2013

(65) Prior Publication Data
US 2015/0336893 A1    Nov. 26, 2015

(30) Foreign Application Priority Data
Jun. 22, 2012   (EP) .................................... 12173227

(51) Int. Cl.
| C07D 211/62 | (2006.01) |
| C07D 401/12 | (2006.01) |
| C07D 409/12 | (2006.01) |
| C07D 413/12 | (2006.01) |
| C07D 471/08 | (2006.01) |
| C07D 211/66 | (2006.01) |
| C07D 401/14 | (2006.01) |
| C07D 405/12 | (2006.01) |
| C07D 417/12 | (2006.01) |
| C07D 401/06 | (2006.01) |

(52) U.S. Cl.
CPC ........... *C07D 211/66* (2013.01); *C07D 211/62* (2013.01); *C07D 401/06* (2013.01); *C07D 401/12* (2013.01); *C07D 401/14* (2013.01); *C07D 405/12* (2013.01); *C07D 409/12* (2013.01); *C07D 413/12* (2013.01); *C07D 417/12* (2013.01); *C07D 471/08* (2013.01)

(58) Field of Classification Search
None
See application file for complete search history.

(56) References Cited

U.S. PATENT DOCUMENTS

| 4,447,441 A | 5/1984 | Yellin et al. |
| 7,507,735 B2 * | 3/2009 | Morgan ............... C07D 211/56 514/252.13 |
| 2013/0345199 A1 | 12/2013 | Fretz et al. |

FOREIGN PATENT DOCUMENTS

| WO | WO 2004/099200 A1 | 11/2004 |
| WO | 2008045564 A2 | 4/2008 |
| WO | WO 2008/045564 A2 | 4/2008 |
| WO | 2009076404 A1 | 6/2009 |
| WO | WO 2009/076404 A1 | 6/2009 |
| WO | 2013190508 A2 | 12/2013 |
| WO | WO 2013/190508 A2 | 12/2013 |
| WO | WO 2014/191929 A1 | 12/2014 |

OTHER PUBLICATIONS

Ashley Jarvis et al., "Small Molecule Inhibitors of the Neuropilin-1Vascular Endothelial Growth Factor A (VEGF-A) Interaction," J. Med. Chem. 2010, vol. 53, pp. 2215-2226.
George A. Patani et al., "Bioisosterism: A Rational Approach in Drug Design," Chem. Rev. 1996, vol. 96, pp. 3147-3176.
U.S. Appl. No. 13/923,981, filed Jun. 21, 2013.
Burns, Jennifer M. et al., "A Novel Chemokine Receptor for SDF-1 and I-TAC involved in Cell Survival, Cell Adhesion, and Tumor Development," The Journal of Experimental Medicine (2006), vol. 203, pp. 2201-2213.

(Continued)

*Primary Examiner* — Timothy R Rozof
(74) *Attorney, Agent, or Firm* — Arent Fox LLP

(57) ABSTRACT

The present invention relates to 1-[m-carboxamido(hetero)aryl-methyl]-heterocycyl-carboxamide compounds of formula (I)

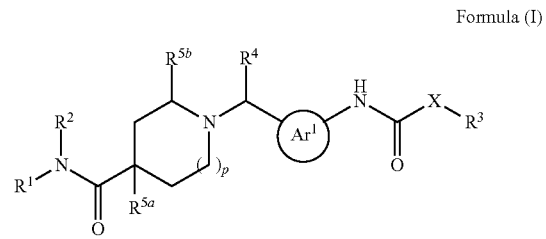

Formula (I)

wherein X, $Ar^1$, $R^1$, $R^2$, $R^3$, $R^4$, $R^{5a}$, $R^{5b}$ and p are as described in the description, to their preparation, to pharmaceutically acceptable salts thereof, and to their use as pharmaceuticals, to pharmaceutical compositions containing one or more compounds of formula (I), and especially to their use as CXCR7 receptor modulators.

23 Claims, No Drawings

(56) References Cited

OTHER PUBLICATIONS

Chemical Abstract, RN 1279884-55-7, XP002716814 (2011).
Chemical Abstract, RN 1287852-41-8, XP002716815 (2011).
Cruz-Orengo Lillian et al., "CXCR7 Influences Leukocyte Entry into the CNS Parenchyma by Controlling Abluminal CXCL12 Abundance during Automimmunity," The Journal of Experimental Medicine (2011) vol. 208, No. 2, pp. 327-339.
Duda, Dan G. et al., "CXCL12 (SDF1a)—CXCR4/CXCR7 Pathway Inhibition: An Emerging Sensitizer for Ati-Cancer Therapies," Clinical Cancer Res. (2011), vol. 17, No. 8, pp. 2074-2080.
Ebsworth, Karen et al., "The Effect of the CXCR7 Inhibitor CCX662 on survival in the ENU Rat Model of Glioblastoma," Journal of Clinical Oncology (2012), vol. 30, No. 15, abstr. e13580.
Gould, Philip L., "Salt selection for basic drugs," International Journal of Pharmaceutics, (1986), vol. 33, pp. 201-217.
Miao, Zhenhua et al., "CXCR7 (RDC1) Promotes Breast and Lung Tumor Growth in vivo and is Expressed on Tumor-Associated Vasculature," PNAS (2007), vol. 14, No. 40, pp. 15735-15740.
Naumann, Ulrike et al., "CXCR7 Functions as a Scavenger for CXCL12 and CXCL11," Plos One (2010), vol. 5, No. 2, e9175.
Remington: The Science and Practice of Pharmacy. Twenty-first Edition. Philadelphia, PA. Lippincott Williams & Wilkins, (2005) (5 pages, TOC).
Sartina, Ecaterina et al., "Antagonism of CXCR7 Attenuates Chronic Hypoxia-Induced Pulmonary Hypertension," Pediatric Research (2012), vol. 71, No. 6, pp. 682-688.
Schadendorf, Torsten et al., "Synthesis of Rigid Photoswitchable Hemithioindigo w-amino Acids," Tetrahedron Letters (2007), vol. 48, No. 51, pp. 9044-9047.
Sun, Xueqing et al., "CXCL12/CXCR4/CXCR7 Chemokine Axis and Cancer Progression," Cancer Metastasis Rev. (2010), vol. 29, No. 4, pp. 709-722.
Wang, Jianhua et al., "The Role of CXCR7/RDC1 as a Chemokine Receptor for CXCL12/SDF-1 in Prostate Cancer," The Journal of Biological Chemistry (2008), vol. 283, No. 7, pp. 4283-4294.
Watanabe, Kaori et al., "Pathogenic Role of CXCR7 in Rheumatoid Arthritis," Arthritis & Rheumatism (2010), vol. 62, No. 11, pp. 3211-3220.
Zheng, Ke et al., "Chemokine Receptor CXCR7 Regulates the Invasion, Angiogenesis and Tumor Growth of Human Hepatocellular Carcinoma Cells," Journal of Experimental & Clinical Cancer Research (2010), vol. 29, No. 31.
Dan G. Duba et al.,"CXCL12 (SDF1• )-CXCR4/CXCR7 Pathway Inhibition: An Emerging Sensitizer for Anti-Cancer Therapies?," Clin. Cancer Res. 2011, vol. 17(8), pp. 2074-2080.
Escaterina Sartina et al., "Antagonism of CXCR7 attenuates chronic hypoxia-induced pulmonary hypertension," Pediatric Res. 2012, vol. 71(6), pp. 682-688.
Jennifer M. Burns et al., "A novel chemokine receptor for SDF-1 and 1-TAC involved in cell survival, cell adhesion, and tumor development," The Journal of Experimental Medicine, 2006, vol. 203(9), pp. 2201-2213.
Jianjua Wang et al., "The Role of CXCR7/RDC1 as a Chemokine Receptor for CXCL 12/SDF-1 in Prostate Cancer," J. Biol. Chem. 2008, vol. 293(7), pp. 4283-4294.
Kaori Watanabe et al., "Pathogenic Role of CXCR7 in Rheumatoid Arthritis," Arthritis Rheum. 2010, vol. 62(11), pp. 3211-3220.
Karen Ebsworth et al., "The effect of the CXCR 7 inhibitor CCX662 on survival in the ENU rat model of glioblastoma," J. Clin. Oncol. 2012, vol. 30 (suppl; abstr e13580), 1 page.
Ke Zheng et al., "Chemokine receptor CXCR7 regulates the invasion, angiogenesis and tumor growth of human hepatocellular carcinoma cells," Journal of Experimental & Clinical Research, 2010, vol. 29, No. 31, pp. 1-14.
Lillian Cruz-Orengo et al., "CXCR7 influences leukocyte entry into the CNS parenchyma by controlling abluminal CXCL12 abundance during autoimmunity," The Journal of Experimental Medicine, 2006, vol. 203(9), pp. 2201-2213.
Philip L. Gould et al., "Salt selection for basic drugs," International Journal of Pharmaceutics, 1986, vol. 33, pp. 201-217.
Remington, The Science of Practice of Pharmacy, 21st Edition, 2005, Part 5, pp. 1-5.
Torsten Schadendorf et al., "Synthesis of rigid photoswitchable hemithioindigo • -amino acids," Tetrahedron Lett. 2007, vol. 48(51), pp. 9044-9047.
Ulrike Naumann et al., "CXCR7 Functions as a Scavenger for CXCL12 and CXCL11," Plos One 2010, vol. 5(2) e9175, pp. 1-11.
Xueging Sun et al., "CXCL12/CXCR4/CXCR7 Chemokine Axis and Cancer Progression," Cancer Metastasis Rev. 2010, vol. 29(4), pp. 709-722.
Zhenhua Miao et al., "CXCR7 (RDC1) promotes breast and lung tumor growth in vivo and is expressed on tumor-associated vasculature," PNAS 2007, vol. 104(40), pp. 15735-15740.

* cited by examiner

1-[M-CARBOXAMIDO(HETERO)ARYL-METHYL]-HETEROCYCLYL-CARBOXAMIDE DERIVATIVES

CROSS-REFERENCE TO RELATED APPLICATIONS

This application is the U.S. National Phase of International Patent Application No. PCT/IB2013/055095, filed Jun. 21, 2013, which claims the benefit of priority to European Patent Application No. EP 12173227.5, filed Jun. 22, 2012, the contents of each are hereby incorporated by reference in their entireties.

The present invention relates to novel 1-[m-carboxamido (hetero)aryl-methyl]-heterocyclyl-carboxamide compounds of formula (I) and their use as pharmaceuticals. The invention also concerns related aspects including processes for the preparation of the compounds, pharmaceutical compositions containing one or more compounds of formula (I), and their use as modulators of the CXCL12 receptor CXCR7.

Chemokine receptors are a group of G-protein coupled receptors (GPCRs) that bind peptidic chemokine ligands with high affinity. The predominant function of chemokine receptors is to guide leukocyte trafficking to lymphoid organs and tissues under resting conditions as well as during inflammation, but a role for certain chemokine receptors on non-hematopoietic cells and their progenitors has also been recognized.

Signaling networks and metabolic profiles of cancer cells differ in a microenvironment dependent manner. This is a major reason for lack of therapeutic response of tumors at certain organ sites and of tumor metastases in comparison to primary tumors. CXCL12 (alias stromal cell-derived factor 1, SDF-1; alias Pre-B cell growth stimulating factor, PBSF), a stroma-derived chemo-attractant, exerts anti-apoptotic effects, displays pro-angiogenic properties and plays a key role in seeding circulating tumor cells to metastatic sites. CXCL12 binds and activates two receptors, CXCR7 (alias RDC1, alias CMKOR1, alias GPR159) and CXCR4 (alias Fusin, alias Leukocyte-derived seven-transmembrane-domain receptor; LESTR, alias D2S201E, alias seven-trans-membrane-segment receptor, alias HM89, alias lipopolysaccharide-associated protein 3; lap3, alias LPS-associated protein 3).

The expression of the CXCL12 receptor CXCR7 correlates with diseases progression in cancer (among others in hormone refractory prostate cancer, in renal cell carcinoma, cervical cancer, papillary thyroid carcinoma, bladder cancer, Ewing's sarcoma, colorectal cancers, lung cancer, meningiomas, MALT lymphoma and in tumors in the brain). CXCR7 is also expressed in hepatocellular carcinoma, breast cancer, osteosarcoma, leukemia, gallbladder cancers, alveolar rhabdomyosarcoma, myeloma, non-small cell lung cancer, oral cancers and pancreas cancer (for review see Sun et al.; CXCL12/CXCR4/CXCR7 Chemokine Axis and Cancer Progression; Cancer Metastasis Rev. 2010, 29(4), 709-722).

CXCR7 silencing and targeting have been shown to reduce tumor growth in experimental disease models [Wang et al.; The role of CXCR7/RDC1 as a chemokine Receptor for CXCL12/SDF-1 in prostate cancer; Journal of Biochemical Chemistry 2008, 293(7), 4283-4294; Ebsworth et al.; The effect of the CXCR7 inhibitor CCX662 on survival in the ENU rat model of gliobastoma; J Clin Oncol 2012, 30, (suppl; abstr e13580); Zheng et al.; Chemokine receptor CXCR7 regulates the invasion, angiogenesis and tumor growth of human hepatocellular carcinoma cells; Journal of Experimental and Clinical Cancer Research. 2010, 29: 31; Miao et al.; CXCR7 (RDC1) promotes breast and lung tumor growth in vivo and is expressed on tumor associated vasculature; PNAS 2007, 104(40), 15735-15740; Burns et al.; A novel chemokine receptor for SDF-1 and I-TAC involved in cell survival, cell adhesion, and tumor development; Journal of Experimental Medicine 2006, 203(9), 2201-2213], including among others hepatocellular carcinoma, Kaposi's sarcoma, T cell leukemia, lymphoma, lung carcinomas, breast cancer, rhabdomyosarcoma, prostate cancer, pancreatic cancer and glioblastoma; to alter tumor-associated blood vessels; to reduce tumor cell seeding; to reduce rheumatoid arthritis clinical scores; to decrease the clinical severity of experimental autoimmune encephalomyelitis; to attenuate chronic hypoxia induced pulmonary hypertension and to improve beneficial effects of mesenchymal stem cells based therapies for renal ischemia/reperfusion injury [Cruz-Orengo et al.; CXCR7 influences leukocyte entry into the CNS parenchyma by controlling abluminal CXCL12 abundance during autoimmunity; Journal of Experimental Medicine 2011, 208(2), 327-339; Sartina et al.; Antagonism of CXCR7 attenuates chronic hypoxia-induced pulmonary hypertension; Pediatric Research 2012, 71(6), 682-688; Watanabe et al.; Pathogenic role of CXCR7 in rheumatoid arthritis; Arthritis and Rheumatism 2010, 62(11), 3211-3220]

Furthermore, CXCL12 depletion sensitizes cancer cells to chemotherapy in vivo and CXCL12 treatment blocks colonic carcinoma metastasis. CXCR7 is also a receptor for CXCL11 (alias small inducible cytokine subfamily b, member 11; scyb11, alias interferon-gamma-inducible protein 9; ip9, alias small inducible cytokine subfamily b, member 9b; scyb9b) and therefore modulators of CXCR7 activity can also be used in indications with CXCL11-associated pathology. CXCR7 has also been shown to function as a scavenger receptor for CXCL12. Thus, CXCR7 targeting has been shown to alter CXCL12 local concentration leading to a deregulation of the CXCL12 concentration gradient. The biological properties of CXCR7 modulators thus include, but are not limited to, any physiological function and/or cellular function linked controlled by CXCL12 (Duda et al.; CXCL12 (SDF1alpha)-CXCR4/CXCR7 pathway inhibition: an emerging sensitizer for anticancer therapies?; Clin. Cancer Res. 2011 17(8) 2074-2080; Naumann et al.; CXCR7 function as a scavenger for CXCL12 and CXCL11; Plos One 2010, 5(2)e9175).

CXCR7 modulation (using small molecules antagonizing CXCL12 binding on CXCR7, or anti-CXCR7 antibodies, or RNA interference techniques to silence CXCR7 expression), CXCL12 modulation of activity/expression, or CXCR7 expression is, thus, associated with diseases and disorders including cancer, notably carcinomas, leukemias, adenocarcinomas, gliomas, glioblastoma, brain metastases, multiple myelomas, renal clear cell carcinoma, prostate cancer, pancreatic adenocarcinoma, melanoma, metastatic melanoma, rhabdomyosarcoma, hepatocellular carcinoma, colon tumors, breast cancer, non-small cell lung cancer, oral tumors, adult T-cell leukemia, gallbladder cancer, brain tumors, Ewing's sarcoma, bladder cancer, meningiomas, lymphoma, viral-induced tumors, Burkitt's lymphoma, Hodgkin's lymphoma, MALT lymphoma, papillary thyroid carcinoma, cervical cancer, osteosarcoma, lymphoproliferative disease, and Kaposi's sarcoma; primary intra-ocular B-cell lymphoma; inflammation; multiple sclerosis; renal allograft rejection; rheumatoid arthritis; auto-immune encephalomyelitis; demyelinating diseases; pulmonary vascular diseases; osteoarthritis; acute renal failure; ischemia; inflammatory bowel disease; injured central nervous system;

HSCs transplantation; cerebral ischemia; pulmonary hypertension; Shiga-toxin-associated heomolytic uremic syndrome; Preeclampsia; choriocarcinoma; chronic rhinosinusitis; HIV; atherosclerosis; acute lung injury; asthma; systemic lupus erythematosus; diseases involving CXCR7 and/or CXCL12 and/or CXCL11 mediated metastasis, chemotaxis, cell adhesion, trans-endothelial migration, cell proliferation and/or survival. Further disorders associated with CXCR7 modulation include proliferative diabetic retinopathy, West Nile virus encephalitis, vascular injury and pulmonary fibrosis.

WO2009/076404 discloses certain carboxamide compounds comprising a bicyclic ring; and WO2008/045564 discloses certain carboxamine compounds, which are antagonists of the chemokine CCR2 receptor.

The present invention provides novel 1-[m-carboxamido(hetero)aryl-methyl]-heterocyclyl-carboxamide compounds which are modulators of the CXCR7 receptor, i.e. they act as CXCR7 receptor agonists and/or as functional antagonists, and are useful for the prevention or treatment of diseases which respond to the activation of the CXCL12 receptors and/or CXCL11 receptors; including autoimmune disorders (e.g. rheumatoid arthritis, multiple sclerosis, inflammatory bowel disease, systemic lupus erythematosus, lupus nephritis, interstitial cystitis, celiac disease), inflammatory diseases (e.g. asthma, chronic obstructive pulmonary disorder, atherosclerosis, myocarditis, sarcoidosis), transplant rejection, hematopoietic stem cell transplantation, fibrosis (e.g. liver cirrhosis), and especially cancer.

1) A first aspect of the invention relates to compounds of the formula (I)

Formula (I)

wherein $Ar^1$ represents a phenylene group or a 5- or 6-membered heteroarylene group, wherein the —$CHR^4$— group and the —NH—CO—X—$R^3$ group are attached in meta arrangement to ring carbon atoms of $Ar^1$; wherein said phenylene or 5- or 6-membered heteroarylene independently is unsubstituted or mono-substituted, wherein the substituent is selected from the group consisting of $(C_{1-4})$alkyl, $(C_{1-4})$alkoxy, halogen, $(C_{1-3})$fluoroalkyl, and $(C_{1-3})$fluoroalkoxy; (notably $(C_{1-4})$alkyl, $(C_{1-4})$alkoxy, and halogen);

X represents a
- direct bond (i.e. $R^3$ is attached directly to the carbonyl group);
- —$(C_{1-4})$alkylene- which is optionally mono-substituted, wherein the substituent is hydroxy;
- —$(C_{3-6})$cycloalkylene-;
- —$CH_2$—O—, wherein the oxygen is linked to the $R^3$ group; or
- —CH=CH—;

$R^3$ represents
   aryl or 5- to 10-membered heteroaryl; wherein said aryl or 5- to 10-membered heteroaryl independently is unsubstituted, mono-, di- or tri-substituted, wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{3-6})$cycloalkyl; —CO—$(C_{1-4})$alkoxy; —$SO_2$—$(C_{1-4})$alkyl; and —$NR^6R^7$, wherein $R^6$ and $R^7$ independently represent hydrogen or $(C_{1-3})$alkyl, or $R^6$ and $R^7$ together with the nitrogen atom to which they are attached to form a 5- or 6-membered ring selected from pyrrolidinyl, morpholinyl, piperidinyl and piperazinyl optionally substituted at the vacant nitrogen atom with $(C_{1-4})$alkyl; wherein in case said 5- to 10-membered heteroaryl is pyridine, such pyridine may additionally be present in form of the respective N-oxide;

or, in case X is a direct bond or a methylene group, $R^3$ may in addition represent
   a partially aromatic bicyclic ring system consisting of a phenyl ring which is fused to a 4- to 6-membered saturated carbocyclic ring optionally containing one or two heteroatoms independently selected from nitrogen and oxygen; wherein said ring system is optionally mono-, or di-substituted with $(C_{1-4})$alkyl or halogen;
   $(C_{3-8})$cycloalkyl, wherein the cycloalkyl may optionally contain a ring oxygen atom, and wherein said cycloalkyl is optionally substituted with up to four methyl groups;

or, in case X is a direct bond, $R^3$ may in addition represent $(C_{2-6})$alkyl;

or, in case X is —CH=CH—, $R^3$ may in addition represent hydrogen, $(C_{1-4})$alkyl, or (dimethylamino)methyl;

$R^1$ represents
   $(C_{1-6})$alkyl which is optionally mono-substituted with $(C_{1-4})$alkoxy or hydroxy;
   $(C_{2-3})$fluoroalkyl;
   $(C_{3-8})$cycloalkyl or $(C_{3-8})$cycloalkyl-$(C_{1-3})$alkyl; wherein the respective $(C_{3-8})$cycloalkyl groups may optionally contain a ring oxygen atom; wherein the $(C_{3-8})$cycloalkyl or $(C_{3-8})$cycloalkyl-$(C_{1-3})$alkyl independently is unsubstituted, or substituted as follows:
      the $(C_{3-8})$cycloalkyl group is mono- or di-substituted wherein the substituents are independently selected from the group consisting of $(C_{1-4})$alkyl, fluoro, hydroxy-methyl, hydroxy, and cyano; or
      the $(C_{1-3})$alkyl group is mono-substituted with hydroxy;
   aryl-$(C_{1-4})$alkyl-, or 5- or 6-membered heteroaryl-$(C_{1-4})$alkyl-, wherein the aryl or 5- or 6-membered heteroaryl independently is unsubstituted, mono-, or di-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy (especially $(C_{1-4})$alkyl, $(C_{1-4})$alkoxy, halogen, and $(C_{1-3})$fluoroalkyl); or
   a 1,2,3,4-tetrahydronaphthalenyl or an indanyl group, which groups are attached to the rest of the molecule through a carbon atom that is part of the non-aromatic ring;

and $R^2$ represents hydrogen, or $(C_{1-3})$alkyl; or $R^1$ and $R^2$ together with the nitrogen atom to which they are attached to represent an azetidine, pyrrolidine, piperidine, morpholine, or azepane ring, wherein said rings independently are unsubstituted, or mono- or di-substituted, wherein the substituents are independently selected from the group consisting of fluorine and methyl;

$R^4$ represents hydrogen, or $(C_{1-3})$alkyl; and $R^{5a}$ represents hydrogen, methyl, or fluorine; $R^{5b}$ represents hydrogen; and p represents the integer 0, 1 or 2; or $R^{5a}$ represents hydrogen; $R^{5b}$ represents methyl; and p represents the integer 1;

with the exception of the following compounds:

1-[1-[3-(benzoylamino)phenyl]ethyl]-N-[(4-fluorophenyl) methyl]-4-piperidinecarboxamide (CAS-Registry No. 1297116-69-8); and N-[3-[1-[4-(1-pyrrolidinylcarbonyl)-1-piperidinyl]ethyl] phenyl]-benzamide (CAS-Registry No. 1279551-37-9).

The compounds of formula (I) may contain one or more stereogenic or asymmetric centers, such as one or more asymmetric carbon atoms. The compounds of formula (I) may thus be present as mixtures of stereoisomers or preferably as pure stereoisomers. Mixtures of stereoisomers may be separated in a manner known to a person skilled in the art.

The present invention also includes isotopically labelled, especially $^2$H (deuterium) labelled compounds of formula (I) according to embodiments 1) to 26), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials. A particular group suitable for deuterium labelling is the group —CHR$^4$— representing, in labelled form, -CD$_2$-.

In this patent application, a bond drawn as a dotted line shows the point of attachment of the radical drawn. For example, the radical drawn below

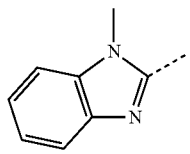

is the 1-methyl-1H-benzoimidazol-2-yl group.

Where the plural form is used for compounds, salts, pharmaceutical compositions, diseases and the like, this is intended to mean also a single compound, salt, or the like.

Any reference to compounds of formula (I) according to embodiments 1) to 26) is to be understood as referring also to the salts (and especially the pharmaceutically acceptable salts) of such compounds, as appropriate and expedient.

The term "pharmaceutically acceptable salts" refers to non-toxic, inorg. or organic acid and/or base addition salts. Reference can be made to "Salt selection for basic drugs", Int. J. Pharm. (1986), 33, 201-217.

The following definitions are applicable to the compounds of formula (I) according to embodiment 1), to compounds of formuly (I$_P$) according to embodiment 25), and to compounds of formula (III) according to embodiment 26), and, mutatis mutandis, throughout the description (especially embodiments 2) to 26) below) and the claims. It is well understood that a definition or preferred definition of a term defines and may replace the respective term independently of (and in combination with) any definition or preferred definition of any or all other terms as defined herein.

The term "halogen" means fluorine, chlorine, or bromine, preferably fluorine or chlorine.

The term "alkyl", used alone or in combination, refers to a saturated straight or branched chain alkyl group containing one to six (especially one to four) carbon atoms. The term "$(C_{x-y})$alkyl" (x and y each being an integer), refers to an alkyl group as defined before, containing x to y carbon atoms. For example a $(C_{1-4})$alkyl group contains from one to four carbon atoms. Examples of alkyl groups are methyl, ethyl, propyl, isopropyl, n-butyl, isobutyl, sec.-butyl and tert.-butyl. Preferred are methyl and ethyl. Most preferred is methyl. Particular examples of $(C_{2-6})$alkyl groups as used for $R^3$ are isopropyl, and 2,2-dimethylpropyl. Particular examples of $(C_{1-6})$alkyl groups as used for $R^1$ are methyl, ethyl, n-propyl, n-butyl, n-pentyl, n-hexyl, isopropyl, tert.-butyl, 1-methylpropyl, 2-methylpropyl, 1-ethylpropyl, 3-methylbutyl, 1,1-dimethylpropyl, 2,2-dimethylpropyl, and 3,3-dimethylbutyl (preferred are tert.-butyl, n-butyl, 1-methylpropyl, and 1,1-dimethylpropyl; especially tert.-butyl, and 1,1-dimethylpropyl).

The term "—$(C_{1-4})$alkylene-", used alone or in combination, refers to bivalently bound alkyl group as defined before containing one to four carbon atoms. Preferably, the points of attachment of any bivalently bound alkyl group are in 1,1-diyl, or in 1,2-diyl arrangement. For the linker X, examples of "—$(C_{1-4})$alkylene- groups are methylene, ethylene, ethane-1,1-diyl, propane-2,2-diyl, 2-methyl-propan-1,1-diyl. An example of such group mono-substituted with hydroxy is —CH(OH)—.

Examples of $(C_{1-6})$alkyl groups mono-substituted with $(C_{1-4})$alkoxy as used for $R^1$ are 2-methoxy-ethyl, 2-methoxy-propyl, and 2-methoxy-1-methyl-ethyl.

Examples of $(C_{1-6})$alkyl groups mono-substituted with hydroxy as used for $R^1$ are 1-hydroxymethyl-propyl, 2-hydroxy-1,1-dimethyl-ethyl, 1-hydroxymethyl-2-methyl-propyl, and 1-hydroxymethyl-2,2-dimethyl-propyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of alkoxy groups are methoxy, ethoxy, n-propoxy, isopropoxy, n-butoxy, isobutoxy, sec.-butoxy and tert.-butoxy. Preferred are ethoxy and especially methoxy.

The term "fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $(C_1)$ fluoroalkyl groups such as trifluoromethyl. An example of a $(C_{2-3})$fluoroalkyl group as used for $R^1$ is 2,2,2-trifluoroethyl.

The term "fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $(C_1)$fluoroalkoxy groups such as trifluoromethoxy and difluoromethoxy.

The term "cyano" refers to a group —CN.

The term "cycloalkyl", used alone or in combination, refers to a saturated mono- or bicyclic carbocyclic ring containing three to eight carbon atoms. The term "$(C_{x-y})$cycloalkyl" (x and y each being an integer), refers to a cycloalkyl group as defined before containing x to y carbon atoms. For example a $(C_{3-8})$cycloalkyl group contains from three to eight carbon atoms. Examples of cycloalkyl groups are cyclopropyl, cyclobutyl, cyclopentyl, cyclohexyl, and cycloheptyl. Preferred are cyclopropyl, cyclopentyl and cyclohexyl.

The term "$(C_{3-8})$cycloalkyl, wherein the cycloalkyl may optionally contain a ring oxygen atom", refers to a mono- or bi-cyclic cycloalkyl group as defined before. In addition, one ring carbon atom of said cycloalkyl may be replaced by an oxygen atom. For the substituent $R^3$, such groups are unsubstituted or may be substituted with up to four methyl groups. Examples are the unsubstituted cycloalkyl groups cyclopropyl, cyclobutyl, cyclopentyl, cyclohexyl, cycloheptanyl, and bicyclo[2,2,1]heptan-2-yl; the substituted cycloalkyl groups 2,2-dimethylcyclopropyl, 2,2,3,3-tetramethylcyclopropyl; as well as tetrahydrofuranyl and tetrahydropyranyl. For the substituent $R^1$, $(C_{3-8})$cycloalkyl groups are unsubstituted or may be mono- or di-substituted wherein the substituents are independently selected from the group consisting of $(C_{1-4})$alkyl, fluoro, hydroxy-methyl, hydroxy, or cyano. Examples are the unsubstituted cycloalkyl groups cyclopropyl, cyclobutyl, cyclopentyl, cyclohexyl, and bicyclo[2,2,1]heptan-2-yl; the substituted cycloalkyl groups 1-cyano-cyclopropyl, 1-hydroxymethyl-cyclopentyl, 4-hydroxy-cyclohexyl, 4-methyl-cyclohexyl, 4-tert.butyl-cyclohexyl, 4,4-difluoro-cyclohexyl; as well as tetrahydrofuranyl and tetrahydropyranyl.

The term "—$(C_{3-6})$cycloalkylene-" refers to a bivalent cycloalkyl group as defined before. Preferably, the points of attachment of such bivalently bound cycloalkyl group are in 1,1-diyl, or in 1,2-diyl arrangement. Examples of —$(C_{3-6})$cycloalkylene- groups as used for X are cyclopropane-1,1-diyl, and cyclopropane-1,2-diyl.

The term "$(C_{3-8})$cycloalkyl-$(C_{1-3})$alkyl" as used for the substituent $R^1$ refers to a $(C_{3-8})$cycloalkyl group as defined before which is linked to the rest of the molecule through a $(C_{1-3})$alkylene group as defined before. For the substituent $R^1$, the $(C_{3-8})$cycloalkyl group part of $(C_{3-8})$cycloalkyl-$(C_{1-3})$alkyl is unsubstituted or substituted as explicitly defined. In case the $(C_{3-8})$cycloalkyl is unsubstituted, the $(C_{1-3})$alkyl group is unsubstituted, or may be mono-substituted with hydroxy. An example of such an unsubstituted $(C_{1-3})$alkyl group is methylene. An example of such $(C_{1-3})$ alkyl group mono-substituted with hydroxy is 2-hydroxy-ethane-1,1-diyl.

The term "aryl", used alone or in combination, means phenyl or naphthyl. The above-mentioned aryl groups are unsubstituted or substituted as explicitly defined.

For the substituent $R^3$ representing aryl, the term means phenyl or naphthyl, especially phenyl. The aryl group as used for the substituent $R^3$ is unsubstituted, or mono-, di-, or tri-substituted, wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; cyano, $(C_{3-6})$cycloalkyl; —CO—$(C_{1-4})$alkoxy; —SO$_2$—$(C_{1-4})$alkyl; —NR$^6$R$^7$, wherein R$^6$ and R$^7$ independently represent hydrogen or $(C_{1-3})$alkyl, or, R$^6$ and R$^7$ together with the nitrogen atom to which they are attached to form a 5- or 6-membered ring selected from pyrrolidinyl, morpholinyl, piperidinyl and piperazinyl, optionally substituted at the vacant nitrogen atom with $(C_{1-4})$alkyl. In a sub-embodiment, it is unsubstituted, or mono-, di-, or tri-substituted, wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; cyano, $(C_{3-6})$cycloalkyl; —NR$^6$R$^7$, wherein R$^6$ and R$^7$ independently represent hydrogen or $(C_{1-3})$alkyl, or, R$^6$ and R$^7$ together with the nitrogen atom to which they are attached to form a 5- or 6-membered ring selected from pyrrolidinyl, morpholinyl, piperidinyl and piperazinyl, optionally substituted at the vacant nitrogen atom with $(C_{1-4})$alkyl. In a further sub-embodiment, it is unsubstituted, or mono-, di-, or tri-substituted, wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; and cyano.

Examples of $R^3$ representing aryl (especially for X being a direct bond) are phenyl, 1-naphthyl, 2-naphthyl, 4-chlorophenyl, 3-chlorophenyl, 2-chlorophenyl, 4-fluorophenyl, 3-fluorophenyl, 2-fluorophenyl, 4-methylphenyl, 3-methylphenyl, 2-methylphenyl, 4-ethylphenyl, 3-chloro-2-methylphenyl, 4-chloro-2-methyl-phenyl, 3-fluoro-5-methyl-phenyl, 3-fluoro-2-methyl-phenyl, 2-fluoro-4-methyl-phenyl, 2-fluoro-5-methyl-phenyl, 4-fluoro-2-methyl-phenyl, 4-fluoro-3-methyl-phenyl, 3,5-dimethylphenyl, 2,6-dimethylphenyl, 2,5-dimethylphenyl, 2,4-dimethylphenyl, 2,3-dimethylphenyl, 3,4-dimethylphenyl, 3,4-dichlorophenyl, 2,4-dichlorophenyl, 3,5-dichlorophenyl, 2,5-dichlorophenyl, 4-chloro-3-fluorophenyl, 4-chloro-2-fluorophenyl, 5-chloro-3-fluorophenyl, 2-chloro-4-fluorophenyl, 2,3-difluorophenyl, 3,4-difluorophenyl, 3,5-difluorophenyl, 2,6-difluorophenyl, 2-methoxyphenyl, 3-methoxyphenyl, 4-methoxyphenyl, 3-cyanophenyl, 4-cyanophenyl, 4-(2-fluoroethyl)-phenyl, 4-isopropylphenyl, 3-fluoro-4-methoxyphenyl, 3-fluoro-5-methoxyphenyl, 3-methyl-4-methoxyphenyl, 4-dimethylamino-phenyl, 3-dimethylamino-phenyl, 3-trifluoromethyl-phenyl, 4-tert.butyl-phenyl, 4-isobutyl-phenyl, 3,4-dimethoxyphenyl, 3,5-dimethoxyphenyl, 2-fluoro-5-trifluoromethyl-phenyl, 2-fluoro-6-trifluoromethyl-phenyl, 2-fluoro-4-trifluoromethyl-phenyl, 2-trifluoromethoxy-phenyl, 4-pentafluoroethyl-phenyl, and 3,5-bis-trifluoromethyl-phenyl. In addition to the above-listed, further examples of $R^3$ representing aryl (especially for X being an optionally substituted —$(C_{1-4})$alkylene-) are phenyl, 2-naphthyl, 2-chlorophenyl, 2,3-dichlorophenyl, 2,4-dichlorophenyl, 2,6-dichlorophenyl, 2-chloro-4-fluorophenyl, 2-chloro-6-fluorophenyl, 2,3-dichloro-6-fluorophenyl, 2,4-dichloro-5-fluorophenyl, 2-chloro-3,6-difluorophenyl, 2-methoxyphenyl, 3-methoxyphenyl, 4-methoxyphenyl, 3-trifluoromethylphenyl, 2-chloro-3-trifluoromethylphenyl, 2,3-dichloro-6-trifluoromethylphenyl, and 2,6-dichloro-3-trifluoromethylphenyl.

Particular examples of phenylene groups as used for the group $Ar^1$ are 4-fluoro-1,3-phenylene, 1,3-phenylene, 2-chloro-1,3-phenylene, 4-chloro-1,3-phenylene, 6-chloro-1,3-phenylene, 2-methyl-1,3-phenylene, 4-methyl-1,3-phenylene, 5-methyl-1,3-phenylene, 6-methyl-1,3-phenylene, 2-methoxy-1,3-phenylene, 4-methoxy-1,3-phenylene, 5-methoxy-1,3-phenylene, and 6-methoxy-1,3-phenylene; and in addition to the above-listed: 4-ethyl-1,3-phenylene, 5-ethyl-1,3-phenylene, 6-ethyl-1,3-phenylene; wherein in the above groups the —NH—CO— group is attached in position 1.

The term "aryl-$(C_{1-4})$alkyl-" refers to an aryl group as defined before which is linked to the rest of the molecule through a $(C_{1-4})$alkylene group as defined before (especially through a methylene or ethylene group). The aryl group part of aryl-$(C_{1-4})$alkyl- is unsubstituted or substituted as explicitly defined. For the substituent $R^1$, such aryl group is unsubstituted, mono-, or di-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy (especially $(C_{1-4})$alkyl, $(C_{1-4})$alkoxy, halogen, and $(C_{1-3})$fluoroalkyl). Examples are phenyl, 1-naphthyl, 4-chlorophenyl, 3-chlorophenyl, 2-chlorophenyl, 2-methoxyphenyl, 3-methoxyphenyl, and 4-methoxyphenyl.

The term "heteroaryl", used alone or in combination, means a 5- to 10-membered monocyclic or bicyclic aromatic ring containing one to a maximum of four heteroatoms, each independently selected from oxygen, nitrogen and sulfur. Examples of such heteroaryl groups are furanyl, oxazolyl, isoxazolyl, oxadiazolyl, thiophenyl, thiazolyl, isothiazolyl, thiadiazolyl, pyrrolyl, imidazolyl, pyrazolyl, triazolyl, pyridinyl, pyrimidinyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. The above-mentioned heteroaryl groups are unsubstituted or substituted as explicitly defined.

In case $R^3$ represents "heteroaryl", the term means the above-mentioned groups. In one embodiment, the term especially refers to thiophenyl, thiazolyl, imidazolyl, pyrazolyl, pyrrolyl, isoxazolyl, pyridinyl, 1-oxy-pyridinyl, pyrimidinyl, pyridazinyl, pyrazinyl, benzofuranyl, indazolyl, indolyl, pyrrolopyridinyl (notably pyrrolo[3,2-b]pyridinyl, pyrrolo[2,3-b]pyridinyl), quinoxalinyl, naphthyridinyl, quinolinyl, isoquinolinyl, and pyrazolo[3,4-b]pyridinyl. The above-mentioned heteroaryl groups as used for the substitutent $R^3$ are unsubstituted or substituted as explicitly defined. In particular, the above-mentioned heteroaryl groups are unsubstituted, or mono-, di-, or tri-substituted, wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; cyano, $(C_{3-6})$cycloalkyl; —CO—$(C_{1-4})$alkoxy; and —NR$^6$R$^7$, wherein R$^6$ and R$^7$ independently represent hydrogen or $(C_{1-3})$alkyl, or, R$^6$ and R$^7$ together with the nitrogen atom to which they are attached to form a 5- or 6-membered ring selected from pyrrolidinyl, morpholinyl, piperidinyl and piperazinyl, optionally substituted at the vacant nitrogen atom with $(C_{1-4})$alkyl. In a sub-embodiment, it is unsubstituted, or mono-, di-, or tri-substituted (especially unsubstituted, or mono-, or di-substituted), wherein the substituents are independently selected from the group consisting of $(C_{1-4})$alkyl; $(C_{1-4})$alkoxy; $(C_{1-3})$fluoroalkyl; $(C_{1-3})$ fluoroalkoxy; halogen; and cyano. In a further sub-embodiment, substituents are selected from the group consisting of $(C_{1-4})$alkyl; $(C_{1-4})$alkoxy; $(C_{1-3})$fluoroalkyl; halogen; and cyano. In a further sub-embodiment, the substituents are selected from the group consisting of $(C_{1-4})$alkyl and halogen. Pyridine groups part of heteroaryl as used for the substitutent $R^3$ may in addition be present in form of the respective N-oxides. Particular examples of $R^3$ representing heteroaryl (especially for X being a direct bond) are thiophen-2-yl, thiophen-3-yl, 5-methyl-thiophen-2-yl, 5-chloro-thiophen-2-yl, 5-tert.butyl-thiophen-2-yl, 4-isobutyl-5-methyl-thiophen-2-yl, 2-(pyrrolidin-1-yl)-thiazol-5-yl, imidazol-2-yl, imidazol-4-yl, 1-methyl-1H-imidazol-4-yl, pyrazol-4-yl, 5-isobutyl-2-methyl-2H-pyrazol-3-yl, pyrrol-2-yl, isoxazol-5-yl, 5-methyl-isoxazol-3-yl, pyridin-2-yl, pyridin-3-yl, pyridin-4-yl, 5-fluoro-pyridin-2-yl, 5-fluoro-pyridin-3-yl, 5-chloro-pyridin-2-yl, 5-chloro-pyridin-3-yl, 6-chloro-pyridin-2-yl, 6-chloro-pyridin-3-yl, 2-chloro-pyridin-3-yl, 4-chloro-pyridin-2-yl, 3-bromo-pyridin-2-yl, 5-methyl-pyridin-3-yl, 4-methyl-pyridin-3-yl, 2-methyl-pyridin-3-yl, 3-methyl-pyridin-2-yl, 4-methyl-pyridin-2-yl, 6-methyl-pyridin-2-yl, 2-methyl-pyridin-4-yl, 6-methyl-pyridin-3-yl, 4,6-dimethyl-pyridin-2-yl, 5-ethyl-pyridin-3-yl, 2-chloro-6-methyl-pyridin-3-yl, 2,6-dichloro-pyridin-3-yl, 5,6-dichloro-pyridin-3-yl, 5-methoxy-pyridin-3-yl, 2-methoxy-pyridin-3-yl, 6-methoxy-pyridin-3-yl, 5-cyclopropyl-pyridin-3-yl, 2,6-dichloro-5-fluoro-pyridin-3-yl, 2-chloro-6-methoxy-pyridin-3-yl, 4-trifluoromethyl-pyridin-2-yl, 2-trifluoromethyl-pyridin-3-yl, 6-trifluoromethyl-pyridin-3-yl, 6-trifluoromethyl-pyridin-2-yl, 5-trifluoromethyl-pyridin-3-yl, 5-trifluoromethyl-pyridin-2-yl, 5-(pyrrolidin-1-yl)-pyridin-2-yl, 2-(morpholin-4-yl)-pyridin-3-yl, 6-(4-methyl-piperazin-1-yl)-pyridin-3-yl, 6-diethylamino-pyridine-3-yl, 2-cyclopentyl-6-methyl-pyridin-4-yl, 1-oxy-pyridin-2-yl, 5-fluoro-1-oxy-pyridin-2-yl, pyrimidin-2-yl, pyrimidin-4-yl, 4-methyl-pyrimidin-5-yl, 6-methyl-pyrimidin-4-yl, 2-methyl-pyrimidin-4-yl, 2,6-dimethoxy-pyrimidin-4-yl, 2-dimethylamino-6-methyl-pyrimidin-4-yl, pyridazin-3-yl, pyridazin-4-yl, pyrazin-2-yl, 5-methyl-pyrazin-2-yl, 3-chloro-6-methyl-pyrazin-4-yl, benzofuran-3-yl, 1H-indazole-3-yl, 1H-indole-3-yl, 1-methyl-1H-indole-3-yl, 1H-pyrrolo[3,2-b]pyridine-6-yl, 1H-pyrrolo[2,3-b]pyridine-2-yl, 1H-pyrrolo[2,3-b]pyridine-5-yl, quinoxalin-2-yl, [1,6]-naphthyridine-2-yl, quinoline-2-yl, quinoline-6-yl, quinoline-3-yl, 7-chloro-quinoline-3-yl, isoquinoline-4-yl, isoquinoline-1-yl, isoquinoline-4-yl, isoquinoline-8-yl, 1-isopropyl-6-methyl-1H-pyrazolo[3,4-b]pyridine-4-yl. In addition to the above-listed, further examples are 3-(methoxycarbonyl)-pyridin-5-yl, 1-oxy-6-trifluoromethyl-pyridin-2-yl, 1-oxy-5-trifluoromethyl-pyridin-2-yl, 5-chloro-1-oxy-pyridin-2-yl, 5-methyl-1-oxy-pyridin-3-yl, 5-methyl-pyridin-3-yl, 5-chloro-3-fluoro-pyridin-2-yl, 6-bromo-pyridin-2-yl, 5-amino-pyridin-2-yl, 6-methyl-pyridazin-4-yl, benzo[1,2,3]thiadiazol-5-yl, benzothiazol-6-yl, and 2-methyl-benzothiazol-5-yl. In addition to the above-listed, further examples of $R^3$ representing heteroaryl (especially for X being an optionally substituted —$(C_{1-4})$alkylene-) are 2,4-dimethyl-thiazol-5-yl, 2,5-dimethyl-thiazol-4-yl, pyridin-2-yl, pyrimidin-2-yl, pyrazin-2-yl, 1-methyl-1H-indol-3-yl, and benzimidazole-2-yl.

The term "5- or 6-membered heteroaryl-$(C_{1-4})$alkyl-" refers to an 5- or 6-membered heteroaryl group as defined before which is linked to the rest of the molecule through a $(C_{1-4})$alkylene group as defined before (especially through a methylene or ethylene group). The 5- or 6-membered heteroaryl group part of 5- or 6-membered heteroaryl-$(C_{1-4})$alkyl- is unsubstituted or substituted as explicitly defined. For the substituent $R^1$, such 5- or 6-membered heteroaryl group is unsubstituted, mono-, or di-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy. Examples are pyridine-2-yl, pyridine-3-yl, pyridine-4-yl, thiazol-2-yl, and 5-methyl-2-trifluoromethyl-furan-3-yl.

In case $Ar^1$ represents a 5- or 6-membered heteroarylene group, such heteroarylene group refers to a bivalent 5- or 6-membered heteroaryl group as defined before; wherein the —$CHR^4$— group and the —NH—CO—X—$R^3$ group are attached in meta arrangement (or in other words: in a 1,3-arrangement) to ring carbon atoms of such groups. Examples of such 5- or 6-membered heteroarylene groups are furane-diyl, oxazole-diyl, isoxazole-diyl, oxadiazole-diyl, thiophene-diyl, thiazole-diyl, isothiazole-diyl, thiadiazole-diyl, pyrrole-diyl, imidazole-diyl, pyrazole-diyl, [1,2,4]-triazole-diyl, pyridine-diyl, pyrimidine-diyl, pyridazine-diyl, and pyrazine-diyl. Especially, examples are thiazole-diyl (notably thiazole-2,4-diyl), thiophene-diyl (notably thiophene-2,4-diyl), pyridine-diyl (notably pyridine-2,4-diyl, pyridine-3,5-diyl), and pyrimidine-diyl (notably pyrimidine-2,4-diyl, pyrimidine-4,6-diyl).

In case $R^1$ and $R^2$ together with the nitrogen atom to which they are attached to represent an azetidine, pyrrolidine, piperidine, morpholine, or azepane ring, wherein said rings independently are unsubstituted, or substituted as explicitly defined, examples of such groups are pyrrolidine, 2-methyl-pyrrolidine, 3-fluoro-pyrrolidine, 3,3-difluoro-pyrrolidine, 3,3-dimethyl-pyrrolidine, 2,2-dimethyl-pyrrolidine, 2,5-dimethyl-pyrrolidine, piperidine, 4,4-difluoro-piperidine, and azepane.

Examples of 1,2,3,4-tetrahydronaphthalenyl or indanyl groups which are attached to the rest of the molecule through a carbon atom that is part of the non-aromatic ring, are indan-1-yl, indan-2-yl, and 1,2,3,4-tetrahydronaphthalen-1-yl.

Examples of partially aromatic bicyclic ring systems consisting of a phenyl ring which is fused to a 4- to 6-membered saturated carbocyclic ring optionally containing one or two heteroatoms independently selected from nitrogen and oxygen; wherein said ring system is optionally mono-, or di-substituted with $(C_{1-4})$alkyl or halogen, are especially unsubstituted or mono-substituted with halogen. Examples are the carbocyclic ring systems bicyclo[4.2.0]octa-1(6),2,4-triene-7-yl, indane-1-yl; as well as the heterocyclic ring systems 2,3-dihydro-1H-indole-3-yl, 2,3-dihydro-benzofuran-3-yl, and 7-chloro-2,3-dihydro-benzofuran-4-yl.

Further embodiments of the invention are presented hereinafter:

2) A second embodiment relates to compounds according to embodiment 1), wherein $Ar^1$ represents a phenylene group or a 5- or 6-membered heteroarylene group, wherein the —$CHR^4$— group and the —NH—CO—X—$R^3$ group are attached in meta arrangement to ring carbon atoms of $Ar^1$; wherein said phenylene is unsubstituted or mono-substituted, wherein the substituent is selected from the group consisting of $(C_{1-4})$alkyl, $(C_{1-4})$alkoxy, halogen, $(C_{1-3})$fluoroalkyl, and $(C_{1-3})$fluoroalkoxy (notably $(C_{1-4})$alkyl, $(C_{1-4})$alkoxy, and halogen); and said 5- or 6-membered heteroarylene independently is unsubstituted. In a sub-embodiment, said 5- or 6-membered heteroarylene is selected from the group consisting of thiazole-diyl (notably thiazole-2,4-diyl), thiophene-diyl (notably thiophene-2,4-diyl), pyridine-diyl (notably pyridine-2,4-diyl, pyridine-3,5-diyl), and pyrimidine-diyl (notably pyrimidine-2,4-diyl, pyrimidine-4,6-diyl).

3) Another embodiment relates to compounds according to embodiment 1), wherein $Ar^1$ represents a phenylene group, wherein the —$CHR^4$— group and the —NH—CO—X—$R^3$ group are attached in meta arrangement to said phenylene group; wherein said phenylene is unsubstituted or mono-substituted, wherein the substituent is selected from the group consisting of $(C_{1-4})$alkyl, $(C_{1-4})$alkoxy, halogen, $(C_{1-3})$fluoroalkyl, and $(C_{1-3})$fluoroalkoxy (notably $(C_{1-4})$alkyl, $(C_{1-4})$alkoxy, and halogen).

4) Another embodiment relates to compounds according to embodiment 1), wherein $Ar^1$ represents an unsubstituted 5- or 6-membered heteroarylene group, wherein the —$CHR^4$— group and the —NH—CO—X—$R^3$ group are attached in meta arrangement to ring carbon atoms of $Ar^1$. In a sub-embodiment, said 5- or 6-membered heteroarylene is selected from the group consisting of thiazole-diyl (notably thiazole-2,4-diyl), thiophene-diyl (notably thiophene-2,4-diyl), pyridine-diyl (notably pyridine-2,4-diyl, pyridine-3,5-diyl), and pyrimidine-diyl (notably pyrimidine-2,4-diyl, pyrimidine-4,6-diyl).

5) Another embodiment relates to compounds according to any one of embodiments 1) to 4), wherein X represents a direct bond; —$(C_{1-4})$alkylene- which is optionally mono-substituted, wherein the substituent is hydroxy; —$(C_{3-6})$cycloalkylene-; or —$CH_2$—O—, wherein the oxygen is linked to the $R^3$ group; and $R^3$ represents aryl or 5- to 10-membered heteroaryl; wherein said aryl or 5- to 10-membered heteroaryl independently is unsubstituted, mono-, di- or tri-substituted, wherein the substituents are independently selected from the group consisting of $(C_{1-4})$alkyl; $(C_{1-4})$alkoxy; $(C_{1-3})$ fluoroalkyl; $(C_{1-3})$fluoroalkoxy; halogen; cyano; $(C_{3-6})$cycloalkyl; and —$NR^6R^7$, wherein $R^6$ and $R^7$ independently represent hydrogen or $(C_{1-3})$alkyl, or $R^6$ and $R^7$ together with the nitrogen atom to which they are attached to form a 5- or 6-membered ring selected from pyrrolidinyl, morpholinyl, piperidinyl, and piperazinyl optionally substituted at the vacant nitrogen atom with $(C_{1-4})$alkyl; wherein in case said 5- to 10-membered heteroaryl is pyridine, such pyridine may additionally be present in form of the respective N-oxide; or X represents a direct bond or methylene; and $R^3$ represents a partially aromatic bicyclic ring system consisting of a phenyl ring which is fused to a 4- to 6-membered saturated carbocyclic ring optionally containing one or two heteroatoms independently selected from nitrogen and oxygen; wherein said ring system is optionally mono-, or di-substituted with $(C_{1-4})$alkyl or halogen; or X represents a direct bond or methylene; and $R^3$ represents $(C_{3-8})$cycloalkyl, wherein the cycloalkyl may optionally contain a ring oxygen atom, and wherein said cycloalkyl is optionally substituted with up to four methyl groups; or X represents a direct bond; and $R^3$ represents $(C_{2-6})$alkyl.

6) Another embodiment relates to compounds according to any one of embodiments 1) to 4), wherein X represents a direct bond; —$(C_{1-4})$alkylene- which is optionally mono-substituted, wherein the substituent is hydroxy; cyclopropylene; or —CH$_2$—O—, wherein the oxygen is linked to the R$^3$ group; and R$^3$ represents aryl (especially phenyl) which is unsubstituted, mono-, di- or tri-substituted (especially unsubstituted, or mono-, or di-substituted), wherein the substituents are independently selected from the group consisting of (C$_{1-4}$)alkyl; (C$_{1-4}$)alkoxy; (C$_{1-3}$)fluoroalkyl; (C$_{1-3}$)fluoroalkoxy; halogen; and cyano; or R$^3$ represents 5- to 10-membered heteroaryl [notably selected from the group consisting of thiophenyl, thiazolyl, imidazolyl, pyrazolyl, pyrrolyl, isoxazolyl, pyridinyl, pyrimidinyl, pyridazinyl, pyrazinyl, benzofuranyl, indazolyl, indolyl, pyrrolopyridinyl (notably pyrrolo[3,2-b]pyridinyl, pyrrolo[2,3-b]pyridinyl), quinoxalinyl, naphthyridinyl, quinolinyl, isoquinolinyl, and pyrazolo[3,4-b]pyridinyl]; which is unsubstituted, mono-, di- or tri-substituted (especially unsubstituted, or mono-, or di-substituted), wherein the substituents are independently selected from the group consisting of (C$_{1-4}$)alkyl; (C$_{1-4}$)alkoxy; (C$_{1-3}$)fluoroalkyl; halogen; (C$_{3-6}$)cycloalkyl; and —NR$^6$R$^7$, wherein R$^6$ and R$^7$ independently represent hydrogen or (C$_{1-3}$)alkyl, or R$^6$ and R$^7$ together with the nitrogen atom to which they are attached to form a 5- or 6-membered ring selected from pyrrolidinyl, morpholinyl, piperidinyl, and piperazinyl optionally substituted at the vacant nitrogen atom with (C$_{1-4}$)alkyl; wherein in case said 5- to 10-membered heteroaryl is pyridine, such pyridine may additionally be present in form of the respective N-oxide; or X represents a direct bond or methylene; and R$^3$ represents bicyclo[4.2.0]octa-1(6),2,4-triene-7-yl, indane-1-yl, 2,3-dihydro-1H-indole-3-yl, 2,3-dihydro-benzofuran-3-yl, and 7-chloro-2,3-dihydro-benzofuran-4-yl; or X represents a direct bond or methylene; and R$^3$ represents cyclopropyl, cyclobutyl, cyclopentyl, cyclohexyl, cycloheptanyl, bicyclo[2,2,1]heptan-2-yl 2,2-dimethylcyclopropyl, 2,2,3,3-tetramethylcyclopropyl, tetrahydrofuranyl or tetrahydropyranyl; or X represents a direct bond; and R$^3$ represents (C$_{2-6}$)alkyl.

7) Another embodiment relates to compounds according to any one of embodiments 1) to 4), wherein X represents a direct bond; methylene; ethylene; ethane-1,1-diyl; propane-2,2-diyl; 2-methyl-propan-1,1-diyl; —CH(OH)—; cyclopropylene; or —CH$_2$—O—, wherein the oxygen is linked to the R$^3$ group [notably X represents a direct bond or methylene]; and R$^3$ represents aryl (especially phenyl) which is unsubstituted, mono-, di- or tri-substituted (especially unsubstituted, or mono-, or di-substituted), wherein the substituents are independently selected from the group consisting of (C$_{1-4}$)alkyl; (C$_{1-4}$)alkoxy; (C$_{1-3}$)fluoroalkyl; (C$_{1-3}$)fluoroalkoxy; halogen; and cyano; or R$^3$ represents 5- to 10-membered heteroaryl [notably selected from the group consisting of thiophenyl, thiazolyl, imidazolyl, pyrazolyl, pyrrolyl, isoxazolyl, pyridinyl, pyrimidinyl, pyridazinyl, pyrazinyl, benzofuranyl, indazolyl, indolyl, pyrrolopyridinyl (especially pyrrolo[3,2-b]pyridinyl, pyrrolo[2,3-b]pyridinyl), quinoxalinyl, naphthyridinyl, quinolinyl, isoquinolinyl, and pyrazolo[3,4-b]pyridinyl]; which is unsubstituted, mono-, di- or tri-substituted (especially unsubstituted, or mono-, or di-substituted), wherein the substituents are independently selected from the group consisting of (C$_{1-4}$)alkyl; (C$_{1-4}$)alkoxy; (C$_{1-3}$)fluoroalkyl; halogen; (C$_{3-6}$)cycloalkyl; and —NR$^6$R$^7$, wherein R$^6$ and R$^7$ independently represent hydrogen or (C$_{1-3}$)alkyl, or R$^6$ and R$^7$ together with the nitrogen atom to which they are attached to form a 5- or 6-membered ring selected from pyrrolidinyl, morpholinyl, piperidinyl, and piperazinyl optionally substituted at the vacant nitrogen atom with methyl; wherein in case said 5- to 10-membered heteroaryl is pyridine, such pyridine may additionally be present in form of the respective N-oxide; or X represents a direct bond or methylene; and R$^3$ represents bicyclo[4.2.0]octa-1(6),2,4-triene-7-yl, indane-1-yl, 2,3-dihydro-1H-indole-3-yl, 2,3-dihydro-benzofuran-3-yl, and 7-chloro-2,3-dihydro-benzofuran-4-yl; or X represents a direct bond or methylene; and R$^3$ represents cyclopropyl, cyclobutyl, cyclopentyl, cyclohexyl, cycloheptanyl, bicyclo[2,2,1]heptan-2-yl 2,2-dimethylcyclopropyl, 2,2,3,3-tetramethylcyclopropyl, tetrahydrofuranyl or tetrahydropyranyl; or X represents a direct bond; and R$^3$ represents (C$_{2-6}$)alkyl.

8) Another embodiment relates to compounds according to any one of embodiments 1) to 7), wherein X represents a direct bond or methylene (especially a direct bond).

9) Another embodiment relates to compounds according to any one of embodiments 1) to 7), wherein X represents methylene; ethylene; ethane-1,1-diyl; propane-2,2-diyl; or cyclopropylene (especially methylene).

10) Another embodiment relates to compounds according to any one of embodiments 1) to 9), wherein R$^1$ represents
- (C$_{1-6}$)alkyl which is optionally mono-substituted with (C$_{1-4}$)alkoxy or hydroxy;
- (C$_{2-3}$)fluoroalkyl;
- (C$_{3-8}$)cycloalkyl; wherein the (C$_{3-8}$)cycloalkyl group optionally contains a ring oxygen atom; wherein the (C$_{3-8}$)cycloalkyl is unsubstituted, or mono- or di-substituted wherein the substituents are independently selected from the group consisting of (C$_{1-4}$)alkyl, fluoro, hydroxy-methyl, hydroxy, and cyano;
- (C$_{3-8}$)cycloalkyl-(C$_{1-3}$)alkyl; wherein the (C$_{1-3}$)alkyl group is optionally mono-substituted with hydroxy;
- aryl-(C$_{1-4}$)alkyl-, wherein the aryl is unsubstituted, mono-, or di-substituted, wherein the substituents are independently selected from the group consisting of (C$_{1-4}$)alkyl, (C$_{1-4}$)alkoxy, halogen, cyano, (C$_{1-3}$)fluoroalkyl, and (C$_{1-3}$)fluoroalkoxy (especially (C$_{1-4}$)alkyl, (C$_{1-4}$)alkoxy, halogen, and (C$_{1-3}$)fluoroalkyl);
- 5- or 6-membered heteroaryl-(C$_{1-4}$)alkyl-, wherein the 5- or 6-membered heteroaryl is unsubstituted, mono-, or di-substituted, wherein the substituents are independently selected from the group consisting of (C$_{1-4}$)alkyl, (C$_{1-4}$)alkoxy, halogen, cyano, (C$_{1-3}$)fluoroalkyl, and (C$_{1-3}$)fluoroalkoxy (especially (C$_{1-4}$)alkyl, (C$_{1-4}$)alkoxy, halogen, and (C$_{1-3}$)fluoroalkyl); or
- a 1,2,3,4-tetrahydronaphthalenyl or an indanyl group, which groups are attached to the rest of the molecule through a carbon atom that is part of the non-aromatic ring;

and R$^2$ represents hydrogen, or (C$_{1-3}$)alkyl; or

R$^1$ and R$^2$ together with the nitrogen atom to which they are attached to represent an azetidine, pyrrolidine, piperidine, morpholine, or azepane ring, wherein said rings independently are unsubstituted, or mono- or di-substituted, wherein the substituents are independently selected from the group consisting of fluorine and methyl.

11) Another embodiment relates to compounds according to any one of embodiments 1) to 9), wherein $R^1$ represents $(C_{1-6})$alkyl which is optionally mono-substituted with $(C_{1-4})$alkoxy or hydroxy;

$(C_{2-3})$fluoroalkyl;

$C_{3-8}$)cycloalkyl; wherein the $(C_{3-8})$cycloalkyl group optionally contains a ring oxygen atom; wherein the $(C_{3-8})$cycloalkyl is unsubstituted, or mono- or di-substituted wherein the substituents are independently selected from the group consisting of $(C_{1-4})$alkyl, fluoro, hydroxy-methyl, and hydroxy;

a 1,2,3,4-tetrahydronaphthalenyl or an indanyl group, which groups are attached to the rest of the molecule through a carbon atom that is part of the non-aromatic ring;

and $R^2$ represents hydrogen, methyl, or ethyl (especially hydrogen); or $R^1$ and $R^2$ together with the nitrogen atom to which they are attached to represent an azetidine, pyrrolidine, piperidine, morpholine, or azepane ring, wherein said rings independently are unsubstituted, or mono- or di-substituted, wherein the substituents are independently selected from the group consisting of fluorine and methyl.

12) Another embodiment relates to compounds according to any one of embodiments 1) to 9), wherein $R^1$ represents $(C_{1-6})$alkyl which is optionally mono-substituted with $(C_{1-4})$alkoxy or hydroxy;

$(C_{2-3})$fluoroalkyl;

$(C_{3-8})$cycloalkyl; wherein the $(C_{3-8})$cycloalkyl group optionally contains a ring oxygen atom; wherein the $(C_{3-8})$cycloalkyl is unsubstituted, or mono- or di-substituted wherein the substituents are independently selected from the group consisting of $(C_{1-4})$alkyl, fluoro, hydroxy-methyl, and hydroxy; or a 1,2,3,4-tetrahydronaphthalenyl or an indanyl group, which groups are attached to the rest of the molecule through a carbon atom that is part of the non-aromatic ring;

and $R^2$ represents hydrogen, methyl, or ethyl (especially hydrogen).

13) Another embodiment relates to compounds according to any one of embodiments 1) to 9), wherein $R^1$ represents $(C_{3-6})$alkyl; or a group selected from the group consisting of cyclopropyl, cyclobutyl, cyclopentyl, cyclohexyl, bicyclo[2,2,1]heptan-2-yl, 1-hydroxymethyl-cyclopentyl, 4-hydroxy-cyclohexyl, 4-methyl-cyclohexyl, 4-tert.butyl-cyclohexyl, 4,4-difluoro-cyclohexyl, tetrahydrofuranyl and tetrahydropyranyl (especially cyclopentyl, and cyclohexyl);

and $R^2$ represents hydrogen, methyl, or ethyl (especially hydrogen).

14) Another embodiment relates to compounds according to any one of embodiments 1) to 9), wherein $R^1$ and $R^2$ together with the nitrogen atom to which they are attached to represent an azetidine, pyrrolidine, piperidine, morpholine, or azepane ring, wherein said rings independently are unsubstituted, or mono- or di-substituted, wherein the substituents are independently selected from the group consisting of fluorine and methyl.

15) Another embodiment relates to compounds according to any one of embodiments 1) to 9), wherein $R^1$ and $R^2$ together with the nitrogen atom to which they are attached to represent pyrrolidine, 2-methyl-pyrrolidine, 3-fluoro-pyrrolidine, 3,3-difluoro-pyrrolidine, 3,3-dimethyl-pyrrolidine, 2,2-dimethyl-pyrrolidine, 2,5-dimethyl-pyrrolidine, piperidine, 4,4-difluoro-piperidine, or azepane.

16) Another embodiment relates to compounds according to any one of embodiments 1) to 15), wherein $R^4$ represents hydrogen or methyl (especially hydrogen).

17) Another embodiment relates to compounds according to any one of the embodiments 1) to 16) wherein $R^{5b}$ represents hydrogen, and $R^{5a}$ represents hydrogen, methyl, or fluorine (especially hydrogen); and p represents the integer 0, 1, or 2.

18) Another embodiment relates to compounds according to any one of the embodiments 1) to 16) wherein $R^{5a}$ represents hydrogen; $R^{5b}$ represents methyl; and p represents the integer 1.

19) Another embodiment relates to compounds according to any one of the embodiments 1) to 18) wherein p represents the integer 1.

20) Another embodiment relates to compounds according to embodiment 17) wherein p represents the integer 0.

21) Another embodiment relates to compounds according to embodiments 17) wherein p represents the integer 2.

22) The invention, thus, relates to compounds of the formula (I) as defined in embodiment 1), or to such compounds further limited by the characteristics of any one of embodiments 2) to 21), under consideration of their respective dependencies; to pharmaceutically acceptable salts thereof; and to the use of such compounds as medicaments especially in the treatment of disorders relating to a dysfunction of the CXCR7 receptor or its ligands. For avoidance of any doubt, especially the following embodiments relating to the compounds of formula (I) are thus possible and intended and herewith specifically disclosed in individualized form:

1, 2+1, 3+1, 5+1, 5+2+1, 5+3+1, 6+1, 6+2+1, 6+3+1, 7+1, 7+2+1, 7+3+1, 8+1, 8+2+1, 8+3+1, 8+5+1, 8+5+2+1, 8+5+3+1, 8+6+1, 8+6+2+1, 8+6+3+1, 8+7+1, 8+7+2+1, 8+7+3+1, 10+1, 10+2+1, 10+3+1, 10+5+1, 10+5+2+1, 10+5+3+1, 10+6+1, 10+6+2+1, 10+6+3+1, 10+7+1, 10+7+2+1, 10+7+3+1, 10+8+1, 10+8+2+1, 10+8+3+1, 10+8+5+1, 10+8+5+2+1, 10+8+5+3+1, 10+8+6+1, 10+8+6+2+1, 10+8+6+3+1, 10+8+7+1, 10+8+7+2+1, 10+8+7+3+1, 11+1, 11+2+1, 11+3+1, 11+5+1, 11+5+2+1, 11+5+3+1, 11+6+1, 11+6+2+1, 11+6+3+1, 11+7+1, 11+7+2+1, 11+7+3+1, 11+8+1, 11+8+2+1, 11+8+3+1, 11+8+5+1, 11+8+5+2+1, 11+8+5+3+1, 11+8+6+1, 11+8+6+2+1, 11+8+6+3+1, 11+8+7+1, 11+8+7+2+1, 11+8+7+3+1, 16+1, 16+2+1, 16+3+1, 16+5+1, 16+5+2+1, 16+5+3+1, 16+6+1, 16+6+2+1, 16+6+3+1, 16+7+1, 16+7+2+1, 16+7+3+1, 16+8+1, 16+8+2+1, 16+8+3+1, 16+8+5+1, 16+8+5+2+1, 16+8+5+3+1, 16+8+6+1, 16+8+6+2+1, 16+8+6+3+1, 16+8+7+1, 16+8+7+2+1, 16+8+7+3+1, 16+10+1, 16+10+2+1, 16+10+3+1, 16+10+5+1, 16+10+5+2+1, 16+10+5+3+1, 16+10+6+1, 16+10+6+2+1, 16+10+6+3+1, 16+10+7+1, 16+10+7+2+1, 16+10+7+3+1, 16+10+8+1, 16+10+8+2+1, 16+10+8+3+1, 16+10+8+5+1, 16+10+8+5+2+1, 16+10+8+5+3+1, 16+10+8+6+1, 16+10+8+6+2+1, 16+10+8+6+3+1, 16+10+8+7+1, 16+10+8+7+2+1, 16+10+8+7+3+1, 16+11+1, 16+11+2+1, 16+11+3+1, 16+11+5+1, 16+11+5+2+1, 16+11+5+3+1, 16+11+6+1, 16+11+6+2+1, 16+11+6+3+1, 16+11+7+1, 16+11+7+2+1, 16+11+7+3+1, 16+11+8+1, 16+11+8+2+1, 16+11+8+3+1, 16+11+8+5+1, 16+11+8+5+2+1, 16+11+8+5+3+1, 16+11+8+6+1, 16+11+8+6+2+1, 16+11+8+6+3+1, 16+11+8+7+1, 16+11+8+7+2+1, 16+11+8+7+3+1, 17+1, 17+2+1, 17+3+1, 17+5+1, 17+5+2+1, 17+5+3+1, 17+6+1, 17+6+2+1, 17+7+1, 17+7+2+1, 17+7+3+1, 17+8+1, 17+8+2+1, 17+8+3+1, 17+8+5+1, 17+8+5+2+1, 17+8+5+3+1, 17+8+6+1, 17+8+6+2+1, 17+8+6+3+1, 17+8+7+1, 17+8+7+2+1, 17+8+7+3+1, 17+10+1, 17+10+2+1, 17+10+

3+1, 17+10+5+1, 17+10+5+2+1, 17+10+5+3+1, 17+10+6+1, 17+10+6+2+1, 17+10+6+3+1, 17+10+7+1, 17+10+7+2+1, 17+10+7+3+1, 17+10+8+1, 17+10+8+2+1, 17+10+8+3+1, 17+10+8+5+1, 17+10+8+5+2+1, 17+10+8+5+3+1, 17+10+8+6+1, 17+10+8+6+2+1, 17+10+8+6+3+1, 17+10+8+7+1, 17+10+8+7+2+1, 17+10+8+7+3+1, 17+11+1, 17+11+2+1, 17+11+3+1, 17+11+5+1, 17+11+5+2+1, 17+11+5+3+1, 17+11+6+1, 17+11+6+2+1, 17+11+6+3+1, 17+11+7+1, 17+11+7+2+1, 17+11+7+3+1, 17+11+8+1, 17+11+8+2+1, 17+11+8+3+1, 17+11+8+5+1, 17+11+8+5+2+1, 17+11+8+5+3+1, 17+11+8+6+1, 17+11+8+6+2+1, 17+11+8+6+3+1, 17+11+8+7+1, 17+11+8+7+2+1, 17+11+8+7+3+1, 17+16+1, 17+16+2+1, 17+16+3+1, 17+16+5+1, 17+16+5+2+1, 17+16+5+3+1, 17+16+6+1, 17+16+6+2+1, 17+16+6+3+1, 17+16+7+1, 17+16+7+2+1, 17+16+7+3+1, 17+16+8+1, 17+16+8+2+1, 17+16+8+3+1, 17+16+8+5+1, 17+16+8+5+2+1, 17+16+8+5+3+1, 17+16+8+6+1, 17+16+8+6+2+1, 17+16+8+6+3+1, 17+16+8+7+1, 17+16+8+7+2+1, 17+16+8+7+3+1, 17+16+10+1, 17+16+10+2+1, 17+16+10+3+1, 17+16+10+5+1, 17+16+10+5+2+1, 17+16+10+5+3+1, 17+16+10+6+1, 17+16+10+6+2+1, 17+16+10+6+3+1, 17+16+10+7+1, 17+16+10+7+2+1, 17+16+10+7+3+1, 17+16+10+8+1, 17+16+10+8+2+1, 17+16+10+8+3+1, 17+16+10+8+5+1, 17+16+10+8+5+2+1, 17+16+10+8+5+3+1, 17+16+10+8+6+1, 17+16+10+8+6+2+1, 17+16+10+8+6+3+1, 17+16+10+8+7+1, 17+16+10+8+7+2+1, 17+16+10+8+7+3+1, 17+16+11+1, 17+16+11+2+1, 17+16+11+3+1, 17+16+11+5+1, 17+16+11+5+2+1, 17+16+11+5+3+1, 17+16+11+6+1, 17+16+11+6+2+1, 17+16+11+6+3+1, 17+16+11+7+1, 17+16+11+7+2+1, 17+16+11+7+3+1, 17+16+11+8+1, 17+16+11+8+2+1, 17+16+11+8+3+1, 17+16+11+8+5+1, 17+16+11+8+5+2+1, 17+16+11+8+5+3+1, 17+16+11+8+6+1, 17+16+11+8+6+2+1, 17+16+11+8+6+3+1, 17+16+11+8+7+1, 17+16+11+8+7+2+1, 17+16+11+8+7+3+1, 19+17+1, 19+17+2+1, 19+17+3+1, 19+17+5+1, 19+17+5+2+1, 19+17+5+3+1, 19+17+6+1, 19+17+6+2+1, 19+17+6+3+1, 19+17+7+1, 19+17+7+2+1, 19+17+7+3+1, 19+17+8+1, 19+17+8+2+1, 19+17+8+3+1, 19+17+8+5+1, 19+17+8+5+2+1, 19+17+8+5+3+1, 19+17+8+6+1, 19+17+8+6+2+1, 19+17+8+6+3+1, 19+17+8+7+1, 19+17+8+7+2+1, 19+17+8+7+3+1, 19+17+10+1, 19+17+10+2+1, 19+17+10+3+1, 19+17+10+5+1, 19+17+10+5+2+1, 19+17+10+5+3+1, 19+17+10+6+1, 19+17+10+6+2+1, 19+17+10+6+3+1, 19+17+10+7+1, 19+17+10+7+2+1, 19+17+10+7+3+1, 19+17+10+8+1, 19+17+10+8+2+1, 19+17+10+8+3+1, 19+17+10+8+5+1, 19+17+10+8+5+2+1, 19+17+10+8+5+3+1, 19+17+10+8+6+1, 19+17+10+8+6+2+1, 19+17+10+8+6+3+1, 19+17+10+8+7+1, 19+17+10+8+7+2+1, 19+17+10+8+7+3+1, 19+17+11+1, 19+17+11+2+1, 19+17+11+3+1, 19+17+11+5+1, 19+17+11+5+2+1, 19+17+11+5+3+1, 19+17+11+6+1, 19+17+11+6+2+1, 19+17+11+6+3+1, 19+17+11+7+1, 19+17+11+7+2+1, 19+17+11+7+3+1, 19+17+11+8+1, 19+17+11+8+2+1, 19+17+11+8+3+1, 19+17+11+8+5+1, 19+17+11+8+5+2+1, 19+17+11+8+5+3+1, 19+17+11+8+6+1, 19+17+11+8+6+2+1, 19+17+11+8+6+3+1, 19+17+11+8+7+1, 19+17+11+8+7+2+1, 19+17+11+8+7+3+1, 19+17+16+1, 19+17+16+2+1, 19+17+16+3+1, 19+17+16+5+1, 19+17+16+5+2+1, 19+17+16+5+3+1, 19+17+16+6+1, 19+17+16+6+2+1, 19+17+16+6+3+1, 19+17+16+7+1, 19+17+16+7+2+1, 19+17+16+7+3+1, 19+17+16+8+1, 19+17+16+8+2+1, 19+17+16+8+3+1, 19+17+16+8+5+1, 19+17+16+8+5+2+1, 19+17+16+8+5+3+1, 19+17+16+8+6+1, 19+17+16+8+6+2+1, 19+17+16+8+6+3+1, 19+17+16+8+7+1, 19+17+16+8+7+2+1, 19+17+16+8+7+3+1, 19+17+16+10+1, 19+17+16+10+2+1, 19+17+16+10+3+1, 19+17+16+10+5+1, 19+17+16+10+5+2+1, 19+17+16+10+5+3+1, 19+17+16+10+6+1, 19+17+16+10+6+2+1, 19+17+16+10+6+3+1, 19+17+16+10+7+1, 19+17+16+10+7+2+1, 19+17+16+10+7+3+1, 19+17+16+10+8+1, 19+17+16+10+8+2+1, 19+17+16+10+8+3+1, 19+17+16+10+8+5+1, 19+17+16+10+8+5+2+1, 19+17+16+10+8+5+3+1, 19+17+16+10+8+6+1, 19+17+16+10+8+6+2+1, 19+17+16+10+8+6+3+1, 19+17+16+10+8+7+1, 19+17+16+10+8+7+2+1, 19+17+16+10+8+7+3+1, 19+17+16+11+1, 19+17+16+11+2+1, 19+17+16+11+3+1, 19+17+16+11+5+1, 19+17+16+11+5+2+1, 19+17+16+11+5+3+1, 19+17+16+11+6+1, 19+17+16+11+6+2+1, 19+17+16+11+6+3+1, 19+17+16+11+7+1, 19+17+16+11+7+2+1, 19+17+16+11+7+3+1, 19+17+16+11+8+1, 19+17+16+11+8+2+1, 19+17+16+11+8+3+1, 19+17+16+11+8+5+1, 19+17+16+11+8+5+2+1, 19+17+16+11+8+5+3+1, 19+17+16+11+8+6+1, 19+17+16+11+8+6+2+1, 19+17+16+11+8+6+3+1, 19+17+16+11+8+7+1, 19+17+16+11+8+7+2+1, 19+17+16+11+8+7+3+1.

In the list above the numbers refer to the embodiments according to their numbering provided hereinabove whereas "+" indicates the dependency from another embodiment. The different individualized embodiments are separated by commas. In other words, "19+17+8+1" for example refers to embodiment 19) depending on embodiment 17), depending on embodiment 8), depending on embodiment 1), i.e. embodiment "19+17+8+1" corresponds to the compounds of formula (I) according to embodiment 1) further limited by all the features of the embodiments 8), 17), and 19).

23) Another embodiment relates to compounds according to embodiment 1) which are selected from the following compounds:

1-(5-Benzoylamino-2-chloro-benzyl)-piperidine-4-carboxylic acid cyclopentylamide;
5-Fluoro-pyridine-2-carboxylic acid [4-chloro-3-(4-cyclopentylcarbamoyl-piperidin-1-ylmethyl)-phenyl]-amide;
1-[3-(4-Fluoro-benzoylamino)-benzyl]-piperidine-4-carboxylic acid tert-butylamide;
5-Trifluoromethyl-pyridine-2-carboxylic acid [3-(4-tert-butylcarbamoyl-piperidin-1-ylmethyl)-phenyl]-amide;
5-Trifluoromethyl-pyridine-2-carboxylic acid [3-(4-cyclopentylcarbamoyl-piperidin-1-ylmethyl)-phenyl]-amide;
6-Trifluoromethyl-pyridine-2-carboxylic acid [3-(4-cyclopentylcarbamoyl-piperidin-1-ylmethyl)-phenyl]-amide;
5-Chloro-N-[4-chloro-3-(4-cyclopentylcarbamoyl-piperidin-1-ylmethyl)-phenyl]-nicotinamide;
N-[4-Chloro-3-(4-cyclopentylcarbamoyl-piperidin-1-ylmethyl)-phenyl]-5-trifluoromethyl-nicotinamide;
5-Fluoro-pyridine-2-carboxylic acid [3-(4-cyclopentylcarbamoyl-piperidin-1-ylmethyl)-phenyl]-amide;
1-[3-(4-Chloro-benzoylamino)-benzyl]-piperidine-4-carboxylic acid isopropylamide;
5-Fluoro-pyridine-2-carboxylic acid [3-(4-cyclohexylcarbamoyl-piperidin-1-ylmethyl)-phenyl]-amide;
1-{3-[(2,2,3,3-Tetramethyl-cyclopropanecarbonyl)-amino]-benzyl}-piperidine-4-carboxylic acid tert-butylamide;
1-[3-(4-Chloro-benzoylamino)-benzyl]-piperidine-4-carboxylic acid tert-butylamide;
1-[3-(4-Fluoro-benzoylamino)-benzyl]-piperidine-4-carboxylic acid cyclopentylamide;
6-Methyl-pyridine-2-carboxylic acid [3-(4-cyclohexylcarbamoyl-piperidin-1-ylmethyl)-phenyl]-amide;
1-[3-(4-Chloro-benzoylamino)-benzyl]-piperidine-4-carboxylic acid cyclopentylamide;
Quinoline-2-carboxylic acid [3-(4-tert-butylcarbamoyl-piperidin-1-ylmethyl)-phenyl]-amide;
1-[2-Chloro-5-(4-fluoro-benzoylamino)-benzyl]-piperidine-4-carboxylic acid cyclopentylamide;

1-[3-(4-Chloro-benzoylamino)-benzyl]-piperidine-4-carboxylic acid cyclobutylamide;
1-[3-(2-Methyl-2-phenyl-propionylamino)-benzyl]-piperidine-4-carboxylic acid tert-butylamide;
6-Trifluoromethyl-pyridine-2-carboxylic acid [3-(4-tert-butylcarbamoyl-piperidin-1-ylmethyl)-phenyl]-amide;
6-Trifluoromethyl-pyridine-2-carboxylic acid [3-(4-tert-butylcarbamoyl-piperidin-1-ylmethyl)-4-methyl-phenyl]-amide;
5-Chloro-pyridine-2-carboxylic acid [3-(4-cyclohexylcarbamoyl-piperidin-1-ylmethyl)-phenyl]-amide;
1-{3-[2-(2-Chloro-phenyl)-acetylamino]-benzyl}-piperidine-4-carboxylic acid tert-butylamide;
5-Trifluoromethyl-pyridine-2-carboxylic acid [4-chloro-3-(4-cyclopentylcarbamoyl-piperidin-1-ylmethyl)-phenyl]-amide;
5-Chloro-N-[3-(4-cyclopentylcarbamoyl-piperidin-1-ylmethyl)-phenyl]-nicotinamide;
1-[3-(4-Chloro-benzoylamino)-benzyl]-piperidine-4-carboxylic acid diethylamide;
6-Trifluoromethyl-pyridine-2-carboxylic acid [3-(4-cyclohexylcarbamoyl-piperidin-1-ylmethyl)-phenyl]-amide;
6-Chloro-pyridine-2-carboxylic acid [3-(4-cyclohexylcarbamoyl-piperidin-1-ylmethyl)-phenyl]-amide;
1-{3-[(1-Phenyl-cyclopropanecarbonyl)-amino]-benzyl}-piperidine-4-carboxylic acid tert-butylamide;
1-{3-[2-(2,6-Dichloro-phenyl)-acetylamino]-benzyl}-piperidine-4-carboxylic acid tert-butylamide;
3-Bromo-pyridine-2-carboxylic acid [3-(4-cyclohexylcarbamoyl-piperidin-1-ylmethyl)-phenyl]-amide;
1-[5-(4-Fluoro-benzoylamino)-2-methyl-benzyl]-piperidine-4-carboxylic acid tert-butylamide;
5-Fluoro-1-oxy-pyridine-2-carboxylic acid [3-(4-cyclopentylcarbamoyl-piperidin-1-ylmethyl)-phenyl]-amide;
6-Trifluoromethyl-pyridine-2-carboxylic acid [3-(4-propyl-carbamoyl-piperidin-1-ylmethyl)-phenyl]-amide;
1-{3-[2-(4-Chloro-phenyl)-2-methyl-propionylamino]-benzyl}-piperidine-4-carboxylic acid tert-butylamide;
Quinoline-6-carboxylic acid [4-chloro-3-(4-cyclopentylcarbamoyl-piperidin-1-ylmethyl)-phenyl]-amide;
3-Methyl-pyridine-2-carboxylic acid [3-(4-cyclohexylcarbamoyl-piperidin-1-ylmethyl)-phenyl]-amide;
Pyridine-2-carboxylic acid [3-(4-cyclohexylcarbamoyl-piperidin-1-ylmethyl)-phenyl]-amide;
1-{3-[(Bicyclo[4.2.0]octa-1(6),2,4-triene-7-carbonyl)-amino]-benzyl}-piperidine-4-carboxylic acid tert-butylamide;
N-[3-(4-tert-Butylcarbamoyl-piperidin-1-ylmethyl)-phenyl]-5-trifluoromethyl-nicotinamide;
Pyrimidine-4-carboxylic acid [2-chloro-5-(4-cyclohexylcarbamoyl-piperidin-1-ylmethyl)-phenyl]-amide;
5-Chloro-pyridine-2-carboxylic acid {3-[1-(4-cyclohexylcarbamoyl-piperidin-1-yl)-ethyl]-phenyl}-amide;
1-[3-(4-Chloro-benzoylamino)-benzyl]-piperidine-4-carboxylic acid cyclopropylamide;
6-Trifluoromethyl-pyridine-2-carboxylic acid [4-chloro-3-(4-cyclopentylcarbamoyl-piperidin-1-ylmethyl)-phenyl]-amide;
1-{3-[2-(2-Chloro-4-fluoro-phenyl)-acetylamino]-benzyl}-piperidine-4-carboxylic acid tert-butylamide;
6-Trifluoromethyl-pyridine-2-carboxylic acid [5-(4-tert-butylcarbamoyl-piperidin-1-ylmethyl)-2-methyl-phenyl]-amide;
1-{3-[2-(2-Chloro-6-fluoro-phenyl)-acetylamino]-benzyl}-piperidine-4-carboxylic acid tert-butylamide;
5-Methyl-pyrazine-2-carboxylic acid [3-(4-cyclohexylcarbamoyl-piperidin-1-ylmethyl)-phenyl]-amide;
6-Chloro-N-[3-(4-cyclohexylcarbamoyl-piperidin-1-ylmethyl)-phenyl]-nicotinamide;
1-[3-(4-Fluoro-benzoylamino)-benzyl]-piperidine-4-carboxylic acid cyclohexylamide;
6-Trifluoromethyl-pyridine-2-carboxylic acid [3-(4-tert-butylcarbamoyl-piperidin-1-ylmethyl)-4-fluoro-phenyl]-amide;
1-{3-[2-(2-Chloro-3-trifluoromethyl-phenyl)-acetylamino]-benzyl}-piperidine-4-carboxylic acid tert-butylamide;
1-[3-(4-Chloro-benzoylamino)-benzyl]-piperidine-4-carboxylic acid cyclohexylamide;
1-{3-[2-(2-Chloro-3,6-difluoro-phenyl)-acetylamino]-benzyl}-piperidine-4-carboxylic acid tert-butylamide;
1-[3-(4-Chloro-benzoylamino)-benzyl]-piperidine-4-carboxylic acid (4,4-difluoro-cyclohexyl)-amide;
1-[3-(3-Chloro-benzoylamino)-benzyl]-piperidine-4-carboxylic acid cyclohexylamide;
Pyrazine-2-carboxylic acid [3-(4-cyclohexylcarbamoyl-piperidin-1-ylmethyl)-phenyl]-amide;
N-[4-Chloro-3-(4-cyclopentylcarbamoyl-piperidin-1-ylmethyl)-phenyl]-5-methyl-nicotinamide;
[1,6]Naphthyridine-2-carboxylic acid [3-(4-tert-butylcarbamoyl-piperidin-1-ylmethyl)-phenyl]-amide;
1-(3-{[1-(2,4-Dichloro-phenyl)-cyclopropanecarbonyl]-amino}-benzyl)-piperidine-4-carboxylic acid tert-butylamide;
5-Fluoro-pyridine-2-carboxylic acid [3-(4-cyclopropylcarbamoyl-piperidin-1-ylmethyl)-phenyl]-amide;
1-(3-{[1-(4-Chloro-phenyl)-cyclopropanecarbonyl]-amino}-benzyl)-piperidine-4-carboxylic acid tert-butylamide;
1-[3-(4-Fluoro-benzoylamino)-benzyl]-piperidine-4-carboxylic acid isobutyl-methyl-amide;
1-[3-(3,4-Difluoro-benzoylamino)-benzyl]-piperidine-4-carboxylic acid cyclohexylamide;
Quinoline-3-carboxylic acid [3-(4-tert-butylcarbamoyl-piperidin-1-ylmethyl)-phenyl]-amide;
1-{3-[2-(2,5-Dimethyl-thiazol-4-yl)-acetylamino]-benzyl}-piperidine-4-carboxylic acid tert-butylamide;
1-{3-[(Indane-1-carbonyl)-amino]-benzyl}-piperidine-4-carboxylic acid tert-butylamide;
Pyrimidine-4-carboxylic acid [3-(4-cyclohexylcarbamoyl-piperidin-1-ylmethyl)-phenyl]-amide;
N-[3-(4-Cyclopentylcarbamoyl-piperidin-1-ylmethyl)-phenyl]-5-trifluoromethyl-nicotinamide;
6-Trifluoromethyl-pyridine-2-carboxylic acid [3-(4-butyl-carbamoyl-piperidin-1-ylmethyl)-phenyl]-amide;
1-[3-(2-Indan-2-yl-acetylamino)-benzyl]-piperidine-4-carboxylic acid tert-butylamide;
N-[3-(4-Cyclohexylcarbamoyl-piperidin-1-ylmethyl)-phenyl]-5-ethyl-nicotinamide;
6-Trifluoromethyl-pyridine-2-carboxylic acid [3-(4-isobutylcarbamoyl-piperidin-1-ylmethyl)-phenyl]-amide;
N-[3-(4-Cyclopentylcarbamoyl-piperidin-1-ylmethyl)-phenyl]-5-fluoro-nicotinamide;
1-[3-(3,5-Difluoro-benzoylamino)-benzyl]-piperidine-4-carboxylic acid cyclohexylamide;
1-[3-(4-Methoxy-benzoylamino)-benzyl]-piperidine-4-carboxylic acid cyclohexylamide;
1-[3-(4-Fluoro-benzoylamino)-4-methyl-benzyl]-piperidine-4-carboxylic acid tert-butylamide;
N-[3-(4-tert-Butylcarbamoyl-piperidin-1-ylmethyl)-phenyl]-5-cyclopropyl-nicotinamide;
N-[3-(4-tert-Butylcarbamoyl-piperidin-1-ylmethyl)-phenyl]-5-methyl-nicotinamide;

1-{3-[2-(2,6-Dichloro-3-trifluoromethyl-phenyl)-acetylamino]-benzyl}-piperidine-4-carboxylic acid tert-butylamide;

5-Trifluoromethyl-pyridine-2-carboxylic acid {3-[4-(isobutyl-methyl-carbamoyl)-piperidin-1-ylmethyl]-phenyl}-amide;

N-[3-(4-tert-Butylcarbamoyl-piperidin-1-ylmethyl)-4-methyl-phenyl]-5-methyl-nicotinamide;

1-[3-(4-Fluoro-3-methyl-benzoylamino)-benzyl]-piperidine-4-carboxylic acid cyclohexylamide;

6-Methyl-pyridine-2-carboxylic acid [3-(4-cyclopropylcarbamoyl-piperidin-1-ylmethyl)-phenyl]-amide;

4-Chloro-pyridine-2-carboxylic acid [3-(4-cyclohexylcarbamoyl-piperidin-1-ylmethyl)-phenyl]-amide;

1-[3-(4-Chloro-benzoylamino)-benzyl]-piperidine-4-carboxylic acid methylamide;

1-{3-[2-(2,3-Dichloro-phenyl)-acetylamino]-benzyl}-piperidine-4-carboxylic acid tert-butylamide;

1-(3-Benzoylamino-benzyl)-piperidine-4-carboxylic acid cyclohexylamide;

Quinoline-6-carboxylic acid [3-(4-cyclopentylcarbamoyl-piperidin-1-ylmethyl)-phenyl]-amide;

N-{3-[4-(1,1-Dimethyl-propylcarbamoyl)-piperidin-1-ylmethyl]-phenyl}-5-methyl-nicotinamide;

1-[5-(4-Fluoro-benzoylamino)-thiophen-3-ylmethyl]-piperidine-4-carboxylic acid tert-butylamide;

N-[3-(4-Cyclohexylcarbamoyl-piperidin-1-ylmethyl)-phenyl]-6-methoxy-nicotinamide;

1-[3-(3-Methyl-benzoylamino)-benzyl]-piperidine-4-carboxylic acid cyclohexylamide;

Quinoxaline-2-carboxylic acid [3-(4-tert-butylcarbamoyl-piperidin-1-ylmethyl)-phenyl]-amide;

1-{3-[2-(2-Chloro-phenyl)-acetylamino]-benzyl}-piperidine-4-carboxylic acid cyclohexylamide;

5-Fluoro-1-oxy-pyridine-2-carboxylic acid [3-(4-tert-butylcarbamoyl-piperidin-1-ylmethyl)-phenyl]-amide;

6-Trifluoromethyl-pyridine-2-carboxylic acid {3-[4-(2-methoxy-1-methyl-ethylcarbamoyl)-piperidin-1-ylmethyl]-phenyl}-amide;

1-[3-(2-Phenyl-propionylamino)-benzyl]-piperidine-4-carboxylic acid tert-butylamide;

1-[3-(4-Chloro-benzoylamino)-benzyl]-piperidine-4-carboxylic acid (2,2,2-trifluoro-ethyl)-amide;

1-{3-[(5-Methyl-thiophene-2-carbonyl)-amino]-benzyl}-piperidine-4-carboxylic acid cyclohexylamide;

6-Trifluoromethyl-pyridine-2-carboxylic acid [3-(4-cyclohexylcarbamoyl-piperidin-1-ylmethyl)-4-fluoro-phenyl]-amide;

1-{3-[2-(2,3-Dichloro-6-trifluoromethyl-phenyl)-acetylamino]-benzyl}-piperidine-4-carboxylic acid tert-butylamide;

1-[3-(4-Fluoro-benzoylamino)-benzyl]-piperidine-4-carboxylic acid cyclopropylamide;

Quinoline-3-carboxylic acid [3-(4-cyclopentylcarbamoyl-piperidin-1-ylmethyl)-phenyl]-amide;

6-Trifluoromethyl-pyridine-2-carboxylic acid {3-[4-(4-methyl-cyclohexylcarbamoyl)-piperidin-1-ylmethyl]-phenyl}-amide;

Quinoline-3-carboxylic acid [4-chloro-3-(4-cyclopentylcarbamoyl-piperidin-1-ylmethyl)-phenyl]-amide;

1-{3-[(Benzofuran-3-carbonyl)-amino]-benzyl}-piperidine-4-carboxylic acid cyclohexylamide;

1-[3-(3-Chloro-5-fluoro-benzoylamino)-benzyl]-piperidine-4-carboxylic acid cyclohexylamide;

1-(3-Phenylacetylamino-benzyl)-piperidine-4-carboxylic acid tert-butylamide;

1-[3-(3-Fluoro-5-methyl-benzoylamino)-benzyl]-piperidine-4-carboxylic acid cyclohexylamide;

N-[3-(4-tert-Butylcarbamoyl-piperidin-1-ylmethyl)-phenyl]-5-ethyl-nicotinamide;

1-[3-(4-Chloro-benzoylamino)-benzyl]-piperidine-4-carboxylic acid cyclopentylmethyl-amide;

6-Trifluoromethyl-pyridine-2-carboxylic acid [5-(4-tert-butylcarbamoyl-piperidin-1-ylmethyl)-2-methoxy-phenyl]-amide;

1-{3-[2-(2,3-Dichloro-6-fluoro-phenyl)-acetylamino]-benzyl}-piperidine-4-carboxylic acid tert-butylamide;

4-Methyl-pyridine-2-carboxylic acid [3-(4-cyclohexylcarbamoyl-piperidin-1-ylmethyl)-phenyl]-amide;

6-Trifluoromethyl-pyridine-2-carboxylic acid [3-(4-ethylcarbamoyl-piperidin-1-ylmethyl)-phenyl]-amide;

1-{3-[2-(2-Methoxy-phenyl)-acetylamino]-benzyl}-piperidine-4-carboxylic acid cyclohexylamide;

1-[3-(2,4-Dimethyl-benzoylamino)-benzyl]-piperidine-4-carboxylic acid cyclohexylamide;

1-[3-(4-Trifluoromethyl-benzoylamino)-benzyl]-piperidine-4-carboxylic acid tert-butylamide;

1-[4-(4-Fluoro-benzoylamino)-thiophen-2-ylmethyl]-piperidine-4-carboxylic acid tert-butylamide;

1-[3-(3-Methoxy-benzoylamino)-benzyl]-piperidine-4-carboxylic acid cyclohexylamide;

N-(3-((4-(cyclopentylcarbamoyl)piperidin-1-yl)d2methyl)phenyl)-5-methylnicotinamide;

1-{3-[(Thiophene-3-carbonyl)-amino]-benzyl}-piperidine-4-carboxylic acid cyclohexylamide;

1-[3-(3-Fluoro-4-methoxy-benzoylamino)-benzyl]-piperidine-4-carboxylic acid cyclohexylamide;

1-[3-(4-Fluoro-benzoylamino)-4-methoxy-benzyl]-piperidine-4-carboxylic acid tert-butylamide;

6-Trifluoromethyl-pyridine-2-carboxylic acid [3-(4-methylcarbamoyl-piperidin-1-ylmethyl)-phenyl]-amide;

1-{3-[2-(2,4-Dichloro-5-fluoro-phenyl)-acetylamino]-benzyl}-piperidine-4-carboxylic acid tert-butylamide;

1-[3-(3-Trifluoromethyl-benzoylamino)-benzyl]-piperidine-4-carboxylic acid tert-butylamide;

Pyridazine-3-carboxylic acid [3-(4-tert-butylcarbamoyl-piperidin-1-ylmethyl)-phenyl]-amide;

1-[3-(4-Methyl-benzoylamino)-benzyl]-piperidine-4-carboxylic acid cyclohexylamide;

1-[3-(2-Fluoro-benzoylamino)-benzyl]-piperidine-4-carboxylic acid cyclohexylamide;

N-[3-(4-Cyclohexylcarbamoyl-piperidin-1-ylmethyl)-phenyl]-5-methyl-nicotinamide;

1-[3-(4-Ethyl-benzoylamino)-benzyl]-piperidine-4-carboxylic acid cyclohexylamide;

7-Chloro-quinoline-3-carboxylic acid [3-(4-tert-butylcarbamoyl-piperidin-1-ylmethyl)-phenyl]-amide;

1-{3-[2-(2,4-Dichloro-phenyl)-acetylamino]-benzyl}-piperidine-4-carboxylic acid tert-butylamide;

N-(3-((4-(cyclohexylcarbamoyl)piperidin-1-yl)d2methyl)phenyl)-5-methylnicotinamide;

1-[3-(3-Fluoro-5-methoxy-benzoylamino)-benzyl]-piperidine-4-carboxylic acid cyclohexylamide;

1-{3-[(1H-Pyrrole-2-carbonyl)-amino]-benzyl}-piperidine-4-carboxylic acid cyclohexylamide;

1-[3-(3,4-Dichloro-benzoylamino)-benzyl]-piperidine-4-carboxylic acid cyclohexylamide;

1-[3-(2-Trifluoromethoxy-benzoylamino)-benzyl]-piperidine-4-carboxylic acid cyclohexylamide;

N-[3-(4-Cyclohexylcarbamoyl-piperidin-1-ylmethyl)-phenyl]-5-cyclopropyl-nicotinamide;

1-[3-(2,3-Difluoro-benzoylamino)-benzyl]-piperidine-4-carboxylic acid cyclohexylamide;

1-[3-(3-Trifluoromethyl-benzoylamino)-benzyl]-piperidine-4-carboxylic acid cyclohexylamide;
1-{3-[4-(2-Fluoro-ethyl)-benzoylamino]-benzyl}-piperidine-4-carboxylic acid cyclohexylamide;
1-[3-(4-Chloro-benzoylamino)-benzyl]-piperidine-4-carboxylic acid (1-hydroxymethyl-cyclopentyl)-amide;
1-{3-[(7-Chloro-2,3-dihydro-benzofuran-4-carbonyl)-amino]-benzyl}-piperidine-4-carboxylic acid cyclohexylamide;
1-[3-(4-Chloro-benzoylamino)-benzyl]-piperidine-4-carboxylic acid (2-methoxy-ethyl)-amide;
1-[3-(4-Fluoro-2-methyl-benzoylamino)-benzyl]-piperidine-4-carboxylic acid cyclohexylamide;
1-{3-[((1S*,2S*)-2-Phenyl-cyclopropanecarbonyl)-amino]-benzyl}-piperidine-4-carboxylic acid cyclohexylamide;
1-[3-(4-Chloro-2-methyl-benzoylamino)-benzyl]-piperidine-4-carboxylic acid cyclohexylamide;
N-[3-(4-Cyclohexylcarbamoyl-piperidin-1-ylmethyl)-phenyl]-5-trifluoromethyl-nicotinamide;
6-Trifluoromethyl-pyridine-2-carboxylic acid {3-[4-(3-methyl-butylcarbamoyl)-piperidin-1-ylmethyl]-phenyl}-amide;
1-[4-Chloro-3-(4-chloro-benzoylamino)-benzyl]-piperidine-4-carboxylic acid cyclohexylamide;
N-[3-(4-Cyclopentylcarbamoyl-piperidin-1-ylmethyl)-phenyl]-5-methyl-nicotinamide;
1-[3-(4-Trifluoromethyl-benzoylamino)-benzyl]-piperidine-4-carboxylic acid cyclohexylamide;
1-{3-[(5-Chloro-thiophene-2-carbonyl)-amino]-benzyl}-piperidine-4-carboxylic acid cyclohexylamide;
1-{3-[((1S,2R,4R)-Bicyclo[2.2.1]heptane-2-carbonyl)-amino]-benzyl}-piperidine-4-carboxylic acid cyclohexylamide;
5,6-Dichloro-N-[3-(4-cyclohexylcarbamoyl-piperidin-1-ylmethyl)-phenyl]-nicotinamide;
1-[3-(3-Fluoro-benzoylamino)-benzyl]-piperidine-4-carboxylic acid cyclohexylamide;
1-[3-(2,4-Dichloro-benzoylamino)-benzyl]-piperidine-4-carboxylic acid cyclohexylamide;
1-[3-(4-Chloro-benzoylamino)-benzyl]-piperidine-4-carboxylic acid (2S,4R)-bicyclo[2.2.1]hept-2-ylamide;
6-Trifluoromethyl-pyridine-2-carboxylic acid {3-[4-(2,2-dimethyl-propylcarbamoyl)-piperidin-1-ylmethyl]-phenyl}-amide;
6-Trifluoromethyl-pyridine-2-carboxylic acid {3-[4-(2-methoxy-propylcarbamoyl)-piperidin-1-ylmethyl]-phenyl}-amide;
1-{3-[(2,3-Dihydro-benzofuran-3-carbonyl)-amino]-benzyl}-piperidine-4-carboxylic acid tert-butylamide;
(S)-1-{3-[(6-Trifluoromethyl-pyridine-2-carbonyl)-amino]-benzyl}-azepane-4-carboxylic acid sec-butylamide;
1-[3-(2-Fluoro-4-methyl-benzoylamino)-benzyl]-piperidine-4-carboxylic acid cyclohexylamide;
6-Trifluoromethyl-pyridine-2-carboxylic acid {3-[4-(2-hydroxy-1,1-dimethyl-ethylcarbamoyl)-piperidin-1-ylmethyl]-phenyl}-amide;
5-Chloro-N-{3-[4-(isobutyl-methyl-carbamoyl)-piperidin-1-ylmethyl]-phenyl}-nicotinamide;
4-Trifluoromethyl-pyridine-2-carboxylic acid [3-(4-tert-butylcarbamoyl-piperidin-1-ylmethyl)-phenyl]-amide;
1-{3-[(Naphthalene-2-carbonyl)-amino]-benzyl}-piperidine-4-carboxylic acid cyclohexylamide;
N-{3-[4-(Isobutyl-methyl-carbamoyl)-piperidin-1-ylmethyl]-phenyl}-5-trifluoromethyl-nicotinamide;
1-[3-(2-Fluoro-5-methyl-benzoylamino)-benzyl]-piperidine-4-carboxylic acid cyclohexylamide;
1-[3-(4-Fluoro-benzoylamino)-2-methoxy-benzyl]-piperidine-4-carboxylic acid tert-butylamide;
6-Trifluoromethyl-pyridine-2-carboxylic acid [3-(4-tert-butylcarbamoyl-piperidin-1-ylmethyl)-4-methoxy-phenyl]-amide;
N-[5-(4-tert-Butylcarbamoyl-piperidin-1-ylmethyl)-2-methyl-phenyl]-5-methyl-nicotinamide;
5-Methyl-N-{3-[4-(methyl-propyl-carbamoyl)-piperidin-1-ylmethyl]-phenyl}-nicotinamide;
5-Methyl-N-{3-[4-(piperidine-1-carbonyl)-piperidin-1-ylmethyl]-phenyl}-nicotinamide;
1-{3-[2-(2-Chloro-phenyl)-2-hydroxy-acetylamino]-benzyl}-piperidine-4-carboxylic acid tert-butylamide;
1-{3-[(2,2-Dimethyl-cyclopropanecarbonyl)-amino]-benzyl}-piperidine-4-carboxylic acid tert-butylamide;
1-[3-(2-Fluoro-5-trifluoromethyl-benzoylamino)-benzyl]-piperidine-4-carboxylic acid cyclohexylamide;
1-[3-(3,4-Dimethyl-benzoylamino)-benzyl]-piperidine-4-carboxylic acid cyclohexylamide;
1-[3-(2-Chloro-4-fluoro-benzoylamino)-benzyl]-piperidine-4-carboxylic acid cyclohexylamide;
N-[5-(4-tert-Butylcarbamoyl-piperidin-1-ylmethyl)-2-methoxy-phenyl]-5-methyl-nicotinamide;
4-Trifluoromethyl-pyridine-2-carboxylic acid [3-(4-cyclopentylcarbamoyl-piperidin-1-ylmethyl)-phenyl]-amide;
1-{3-[(Isoxazole-5-carbonyl)-amino]-benzyl}-piperidine-4-carboxylic acid cyclohexylamide;
1-[3-(4-Chloro-2-fluoro-benzoylamino)-benzyl]-piperidine-4-carboxylic acid cyclohexylamide;
5-Fluoro-1-oxy-pyridine-2-carboxylic acid [3-(4-cyclohexylcarbamoyl-piperidin-1-ylmethyl)-phenyl]-amide;
1-(3-Phenylacetylamino-benzyl)-piperidine-4-carboxylic acid cyclohexylamide;
6-Trifluoromethyl-pyridine-2-carboxylic acid {3-[1-(4-cyclohexylcarbamoyl-piperidin-1-yl)-ethyl]-phenyl}-amide;
1-{3-[(Thiophene-2-carbonyl)-amino]-benzyl}-piperidine-4-carboxylic acid cyclohexylamide;
N-[3-(4-Cyclohexylcarbamoyl-piperidin-1-ylmethyl)-phenyl]-6-trifluoromethyl-nicotinamide;
N-[3-(4-Cyclohexylcarbamoyl-piperidin-1-ylmethyl)-phenyl]-5-fluoro-nicotinamide;
6-Methyl-pyridine-2-carboxylic acid {3-[1-(4-cyclohexylcarbamoyl-piperidin-1-yl)-ethyl]-phenyl}-amide;
1-{3-[2-(4-Chloro-phenyl)-propionylamino]-benzyl}-piperidine-4-carboxylic acid tert-butylamide;
1-[3-(2,5-Dimethyl-benzoylamino)-benzyl]-piperidine-4-carboxylic acid cyclohexylamide;
N-[3-(4-tert-Butylcarbamoyl-piperidin-1-ylmethyl)-phenyl]-5-methoxy-nicotinamide;
1-[3-(4-Cyano-benzoylamino)-benzyl]-piperidine-4-carboxylic acid cyclohexylamide;
N-{3-[4-(1-Ethyl-propylcarbamoyl)-piperidin-1-ylmethyl]-phenyl}-5-methyl-nicotinamide;
N-[3-(4-tert-Butylcarbamoyl-piperidin-1-ylmethyl)-phenyl]-4-fluoro-phenyl]-5-methyl-nicotinamide;
1-{1-[3-(4-Chloro-benzoylamino)-phenyl]-ethyl}-piperidine-4-carboxylic acid cyclohexylamide;
1-[3-(2,5-Dichloro-benzoylamino)-benzyl]-piperidine-4-carboxylic acid cyclohexylamide;
N-{3-[4-(Isobutyl-methyl-carbamoyl)-piperidin-1-ylmethyl]-phenyl}-5-methyl-nicotinamide;
1H-Pyrrolo[2,3-b]pyridine-2-carboxylic acid [3-(4-cyclohexylcarbamoyl-piperidin-1-ylmethyl)-phenyl]-amide;
1-[3-(2-Fluoro-4-trifluoromethyl-benzoylamino)-benzyl]-piperidine-4-carboxylic acid cyclohexylamide;

2-Chloro-N-[3-(4-cyclohexylcarbamoyl-piperidin-1-ylmethyl)-phenyl]-6-methoxy-isonicotinamide;
6-Trifluoromethyl-pyridine-2-carboxylic acid {3-[4-(isobutyl-methyl-carbamoyl)-piperidin-1-ylmethyl]-phenyl}-amide;
1-[3-(4-Chloro-benzoylamino)-benzyl]-piperidine-4-carboxylic acid indan-2-ylamide;
1-[3-(2-Cyclohexyl-acetylamino)-benzyl]-piperidine-4-carboxylic acid cyclohexylamide;
N-[3-(4-Cyclopentylcarbamoyl-piperidin-1-ylmethyl)-phenyl]-5-methoxy-nicotinamide;
N-[3-(4-Cyclohexylcarbamoyl-piperidin-1-ylmethyl)-phenyl]-2-methoxy-nicotinamide;
1-{3-[2-(3-Chloro-phenyl)-acetylamino]-benzyl}-piperidine-4-carboxylic acid cyclohexylamide;
1-[3-(4-Chloro-3-fluoro-benzoylamino)-benzyl]-piperidine-4-carboxylic acid cyclohexylamide;
1-[3-(4-Pentafluoroethyl-benzoylamino)-benzyl]-piperidine-4-carboxylic acid cyclohexylamide;
N-[3-(4-Cyclohexylcarbamoyl-piperidin-1-ylmethyl)-phenyl]-2-methyl-isonicotinamide;
1-[3-(Cyclohexanecarbonyl-amino)-benzyl]-piperidine-4-carboxylic acid cyclohexylamide;
1-[3-(3,5-Dimethoxy-benzoylamino)-benzyl]-piperidine-4-carboxylic acid cyclohexylamide;
N-{3-[4-(2,2-Dimethyl-pyrrolidine-1-carbonyl)-piperidin-1-ylmethyl]-phenyl}-5-methyl-nicotinamide;
1-[3-(Cycloheptanecarbonyl-amino)-benzyl]-piperidine-4-carboxylic acid cyclohexylamide;
1-{1-[3-(4-Fluoro-benzoylamino)-phenyl]-ethyl}-piperidine-4-carboxylic acid cyclohexylamide;
1-{3-[(6-Trifluoromethyl-pyridine-2-carbonyl)-amino]-benzyl}-azepane-4-carboxylic acid tert-butylamide;
N-[3-(4-Cyclohexylcarbamoyl-piperidin-1-ylmethyl)-phenyl]-5-methoxy-nicotinamide;
4,6-Dimethyl-pyridine-2-carboxylic acid [3-(4-cyclohexylcarbamoyl-piperidin-1-ylmethyl)-phenyl]-amide;
N-[3-(4-Cyclohexylcarbamoyl-piperidin-1-ylmethyl)-4-fluoro-phenyl]-5-methyl-nicotinamide;
1-[3-(2-Chloro-benzoylamino)-benzyl]-piperidine-4-carboxylic acid cyclohexylamide;
1-[3-(4-Isopropyl-benzoylamino)-benzyl]-piperidine-4-carboxylic acid cyclohexylamide;
Pyridine-2-carboxylic acid {3-[1-(4-cyclohexylcarbamoyl-piperidin-1-yl)-ethyl]-phenyl}-amide;
1-[3-(3-Cyano-benzoylamino)-benzyl]-piperidine-4-carboxylic acid cyclohexylamide;
4-Trifluoromethyl-pyridine-2-carboxylic acid [3-(4-cyclohexylcarbamoyl-piperidin-1-ylmethyl)-phenyl]-amide;
2,6-Dichloro-N-[3-(4-cyclohexylcarbamoyl-piperidin-1-ylmethyl)-phenyl]-nicotinamide;
N-[3-(4-Isopropylcarbamoyl-piperidin-1-ylmethyl)-phenyl]-5-methyl-nicotinamide;
1-[3-(4-Fluoro-benzoylamino)-5-methyl-benzyl]-piperidine-4-carboxylic acid tert-butylamide;
1-{3-[(1H-Imidazole-2-carbonyl)-amino]-benzyl}-piperidine-4-carboxylic acid cyclohexylamide;
N-[3-(4-Cyclobutylcarbamoyl-piperidin-1-ylmethyl)-phenyl]-5-methyl-nicotinamide;
6-Trifluoromethyl-pyridine-2-carboxylic acid [3-(4-tert-butylcarbamoyl-4-methyl-piperidin-1-ylmethyl)-phenyl]-amide;
N-[5-(4-tert-Butylcarbamoyl-piperidin-1-ylmethyl)-thiophen-3-yl]-5-methyl-nicotinamide;
1-[3-(3-Fluoro-2-methyl-benzoylamino)-benzyl]-piperidine-4-carboxylic acid cyclohexylamide;
1-[3-(4-Chloro-benzoylamino)-benzyl]-piperidine-4-carboxylic acid (tetrahydro-pyran-4-yl)-amide;
1-{4-Chloro-3-[(5-methyl-thiophene-2-carbonyl)-amino]-benzyl}-piperidine-4-carboxylic acid cyclohexylamide;
1-Oxy-pyridine-2-carboxylic acid [3-(4-cyclohexylcarbamoyl-piperidin-1-ylmethyl)-phenyl]-amide;
1-[4-Chloro-3-(4-methoxy-benzoylamino)-benzyl]-piperidine-4-carboxylic acid cyclohexylamide;
5-Methyl-pyrazine-2-carboxylic acid {3-[1-(4-cyclohexylcarbamoyl-piperidin-1-yl)-ethyl]-phenyl}-amide;
1-(1-{3-[(5-Isobutyl-2-methyl-2H-pyrazole-3-carbonyl)-amino]-phenyl}-ethyl)-piperidine-4-carboxylic acid cyclohexylamide;
2-Methyl-pyrimidine-4-carboxylic acid {3-[1-(4-cyclohexylcarbamoyl-piperidin-1-yl)-ethyl]-phenyl}-amide;
1-[3-(4-Methoxy-3-methyl-benzoylamino)-benzyl]-piperidine-4-carboxylic acid cyclohexylamide;
1-[3-(4-Chloro-benzoylamino)-benzyl]-piperidine-4-carboxylic acid (1-cyano-cyclopropyl)-amide;
2,3-Dihydro-1H-indole-3-carboxylic acid [3-(4-tert-butylcarbamoyl-piperidin-1-ylmethyl)-phenyl]-amide;
6-Trifluoromethyl-pyridine-2-carboxylic acid [3-(4-pentylcarbamoyl-piperidin-1-ylmethyl)-phenyl]-amide;
1-[3-(4-Chloro-benzoylamino)-benzyl]-piperidine-4-carboxylic acid 2-methoxy-benzylamide;
2,6-Dichloro-N-[3-(4-cyclohexylcarbamoyl-piperidin-1-ylmethyl)-phenyl]-5-fluoro-nicotinamide;
N-[3-(4-tert-Butylcarbamoyl-4-fluoro-piperidin-1-ylmethyl)-phenyl]-5-methyl-nicotinamide;
4-Chloro-pyridine-2-carboxylic acid [3-(4-cyclopropylcarbamoyl-piperidin-1-ylmethyl)-phenyl]-amide;
1-[3-(2-Methoxy-benzoylamino)-benzyl]-piperidine-4-carboxylic acid cyclohexylamide;
1-[3-(4-Chloro-benzoylamino)-benzyl]-piperidine-4-carboxylic acid 2-chloro-benzylamide;
1-{3-[2-(3-Methoxy-phenyl)-acetylamino]-benzyl}-piperidine-4-carboxylic acid cyclohexylamide;
1-[3-(2-Trifluoromethyl-benzoylamino)-benzyl]-piperidine-4-carboxylic acid tert-butylamide;
1-{3-[2-(1-Methyl-1H-indol-3-yl)-acetylamino]-benzyl}-piperidine-4-carboxylic acid cyclohexylamide;
Pyrazine-2-carboxylic acid {3-[1-(4-cyclohexylcarbamoyl-piperidin-1-yl)-ethyl]-phenyl}-amide;
5-Fluoro-N-{3-[4-(isobutyl-methyl-carbamoyl)-piperidin-1-ylmethyl]-phenyl}-nicotinamide;
1-{3-[(5-Methyl-isoxazole-3-carbonyl)-amino]-benzyl}-piperidine-4-carboxylic acid cyclohexylamide;
1-[3-(3-Phenyl-propionylamino)-benzyl]-piperidine-4-carboxylic acid cyclohexylamide;
1-[3-(2-Methyl-benzoylamino)-benzyl]-piperidine-4-carboxylic acid cyclohexylamide;
1-[3-(4-Fluoro-benzoylamino)-2-methyl-benzyl]-piperidine-4-carboxylic acid tert-butylamide;
1-[5-(4-Fluoro-benzoylamino)-2-methoxy-benzyl]-piperidine-4-carboxylic acid tert-butylamide;
N-{3-[4-(Azepane-1-carbonyl)-piperidin-1-ylmethyl]-phenyl}-5-methyl-nicotinamide;
1-{3-[(6-Trifluoromethyl-pyridine-2-carbonyl)-amino]-benzyl}-azepane-4-carboxylic acid (1,1-dimethyl-propyl)-amide;
N-{3-[4-(Isobutyl-methyl-carbamoyl)-piperidin-1-ylmethyl]-phenyl}-5-methoxy-nicotinamide;
N-[3-(4-Cyclohexylcarbamoyl-piperidin-1-ylmethyl)-phenyl]-6-methyl-nicotinamide;
1-[3-(4-Chloro-benzoylamino)-benzyl]-piperidine-4-carboxylic acid (pyridin-2-ylmethyl)-amide;

N-{3-[4-(Cyclopropylmethyl-carbamoyl)-piperidin-1-ylmethyl]-phenyl}-5-methyl-nicotinamide;
6-Trifluoromethyl-pyridine-2-carboxylic acid [3-(4-tert-butylcarbamoyl-4-fluoro-piperidin-1-ylmethyl)-phenyl]-amide;
1-[3-(2-Pyridin-2-yl-acetylamino)-benzyl]-piperidine-4-carboxylic acid cyclohexylamide;
1-[3-(3,5-Dimethyl-benzoylamino)-benzyl]-piperidine-4-carboxylic acid cyclohexylamide;
1-[3-(4-Chloro-benzoylamino)-benzyl]-piperidine-4-carboxylic acid indan-1-ylamide;
1-[3-(3,5-Dichloro-benzoylamino)-benzyl]-piperidine-4-carboxylic acid cyclohexylamide;
Pyrimidine-4-carboxylic acid {3-[1-(4-cyclohexylcarbamoyl-piperidin-1-yl)-ethyl]-phenyl}-amide;
1-[1-(3-Benzoylamino-phenyl)-ethyl]-piperidine-4-carboxylic acid cyclohexylamide;
N-[3-(4-Cyclohexylcarbamoyl-piperidin-1-ylmethyl)-phenyl]-nicotinamide;
2-Dimethylamino-6-methyl-pyrimidine-4-carboxylic acid [3-(4-cyclohexylcarbamoyl-piperidin-1-ylmethyl)-phenyl]-amide;
1-[2-(4-Fluoro-benzoylamino)-pyridin-4-ylmethyl]-piperidine-4-carboxylic acid cyclohexylamide;
1-[3-(3,3-Dimethyl-butyrylamino)-benzyl]-piperidine-4-carboxylic acid cyclohexylamide;
1-[3-(Cyclobutanecarbonyl-amino)-benzyl]-piperidine-4-carboxylic acid cyclohexylamide;
1-{1-[3-(4-Methoxy-benzoylamino)-phenyl]-ethyl}-piperidine-4-carboxylic acid cyclohexylamide;
1-{4-Chloro-3-[(2-phenyl-cyclopropanecarbonyl)-amino]-benzyl}-piperidine-4-carboxylic acid cyclohexylamide;
1H-Pyrrolo[2,3-b]pyridine-5-carboxylic acid [3-(4-cyclohexylcarbamoyl-piperidin-1-ylmethyl)-phenyl]-amide;
1-(1-{3-[2-(3-Trifluoromethyl-phenyl)-acetylamino]-phenyl}-ethyl)-piperidine-4-carboxylic acid cyclohexylamide;
6-Trifluoromethyl-pyridine-2-carboxylic acid {3-[4-(1-hydroxymethyl-propylcarbamoyl)-piperidin-1-ylmethyl]-phenyl}-amide;
5-Methyl-N-{3-[4-(2-methyl-pyrrolidine-1-carbonyl)-piperidin-1-ylmethyl]-phenyl}-nicotinamide;
N-{3-[4-(4,4-Difluoro-cyclohexylcarbamoyl)-piperidin-1-ylmethyl]-phenyl}-5-methyl-nicotinamide;
1-{4-[2-(2-Chloro-phenyl)-acetylamino]-thiophen-2-ylmethyl}-piperidine-4-carboxylic acid tert-butylamide;
1-[4-(4-Chloro-benzoylamino)-pyridin-2-ylmethyl]-piperidine-4-carboxylic acid cyclohexylamide;
N-[3-(3-Cyclopentylcarbamoyl-pyrrolidin-1-ylmethyl)-phenyl]-5-methyl-nicotinamide;
N-{3-[1-(4-Cyclohexylcarbamoyl-piperidin-1-yl)-ethyl]-phenyl}-5-methyl-nicotinamide;
1-[3-(Cyclopentanecarbonyl-amino)-benzyl]-piperidine-4-carboxylic acid cyclohexylamide;
6-Trifluoromethyl-pyridine-2-carboxylic acid [6-(4-tert-butylcarbamoyl-piperidin-1-ylmethyl)-pyrimidin-4-yl]-amide;
1-[3-(4-Chloro-benzoylamino)-benzyl]-piperidine-4-carboxylic acid (thiazol-2-ylmethyl)-amide;
N-{3-[1-(4-Cyclohexylcarbamoyl-piperidin-1-yl)-ethyl]-phenyl}-2-methyl-isonicotinamide;
1-{3-[(5-Methyl-pyridine-3-carbonyl)-amino]-benzyl}-azepane-4-carboxylic acid sec-butylamide;
1-{3-[(5-tert-Butyl-thiophene-2-carbonyl)-amino]-benzyl}-piperidine-4-carboxylic acid cyclohexylamide;
1-{3-[2-(4-Chloro-phenyl)-acetylamino]-benzyl}-piperidine-4-carboxylic acid cyclohexylamide;
1-[3-(4-tert-Butyl-benzoylamino)-benzyl]-piperidine-4-carboxylic acid cyclohexylamide;
1-[3-(3-Chloro-2-methyl-benzoylamino)-benzyl]-piperidine-4-carboxylic acid cyclohexylamide;
1H-Indazole-3-carboxylic acid [3-(4-cyclohexylcarbamoyl-piperidin-1-ylmethyl)-phenyl]-amide;
1-[3-(3-Methyl-2-phenyl-butyrylamino)-benzyl]-piperidine-4-carboxylic acid cyclohexylamide;
1-[3-(2-Indan-2-yl-acetylamino)-benzyl]-piperidine-4-carboxylic acid cyclohexylamide;
1-[3-(2,6-Difluoro-benzoylamino)-benzyl]-piperidine-4-carboxylic acid cyclohexylamide;
6-Trifluoromethyl-pyridine-2-carboxylic acid [3-(4-tert-butylcarbamoyl-piperidin-1-ylmethyl)-5-methyl-phenyl]-amide;
1-{3-[(6-Trifluoromethyl-pyridine-2-carbonyl)-amino]-benzyl}-azepane-4-carboxylic acid cyclopropylmethyl-amide;
1-[5-(4-Chloro-benzoylamino)-pyridin-3-ylmethyl]-piperidine-4-carboxylic acid cyclohexylamide;
Pyrimidine-2-carboxylic acid [3-(4-cyclohexylcarbamoyl-piperidin-1-ylmethyl)-phenyl]-amide;
1-{1-[3-(4-Trifluoromethyl-benzoylamino)-phenyl]-ethyl}-piperidine-4-carboxylic acid cyclohexylamide;
Isoquinoline-1-carboxylic acid [3-(4-cyclohexylcarbamoyl-piperidin-1-ylmethyl)-phenyl]-amide;
5-Pyrrolidin-1-yl-pyridine-2-carboxylic acid [3-(4-cyclohexylcarbamoyl-piperidin-1-ylmethyl)-phenyl]-amide;
1-{3-[(4-Isobutyl-5-methyl-thiophene-2-carbonyl)-amino]-benzyl}-piperidine-4-carboxylic acid cyclohexylamide;
1-[3-(4-Dimethylamino-benzoylamino)-benzyl]-piperidine-4-carboxylic acid cyclohexylamide;
1-[3-(4-Chloro-benzoylamino)-benzyl]-piperidine-4-carboxylic acid (1,2,3,4-tetrahydro-naphthalen-1-yl)-amide;
N-[3-(4-Cyclohexylcarbamoyl-piperidin-1-ylmethyl)-phenyl]-isonicotinamide;
1-[3-(2,3-Dimethyl-benzoylamino)-benzyl]-piperidine-4-carboxylic acid cyclohexylamide;
2-Chloro-N-[3-(4-cyclohexylcarbamoyl-piperidin-1-ylmethyl)-phenyl]-6-methyl-nicotinamide;
N-[3-(4-Cyclohexylcarbamoyl-piperidin-1-ylmethyl)-phenyl]-2-cyclopentyl-6-methyl-isonicotinamide;
1-{5-[2-(2-Chloro-phenyl)-acetylamino]-thiophen-3-ylmethyl}-piperidine-4-carboxylic acid tert-butylamide;
1H-Indole-3-carboxylic acid [3-(4-cyclohexylcarbamoyl-piperidin-1-ylmethyl)-phenyl]-amide;
1-[3-(4-Isobutyl-benzoylamino)-benzyl]-piperidine-4-carboxylic acid cyclohexylamide;
1-[3-(3,5-Bis-trifluoromethyl-benzoylamino)-benzyl]-piperidine-4-carboxylic acid cyclohexylamide;
2-Chloro-N-[3-(4-cyclohexylcarbamoyl-piperidin-1-ylmethyl)-phenyl]-nicotinamide;
N-[4-(4-tert-Butylcarbamoyl-piperidin-1-ylmethyl)-thiophen-2-yl]-5-methyl-nicotinamide;
6-Trifluoromethyl-pyridine-2-carboxylic acid [3-(4-tert-butylcarbamoyl-piperidin-1-ylmethyl)-2-methoxy-phenyl]-amide;
1-[3-(4-Chloro-benzoylamino)-benzyl]-piperidine-4-carboxylic acid benzylamide;
1-{3-[(Naphthalene-1-carbonyl)-amino]-benzyl}-piperidine-4-carboxylic acid cyclohexylamide;
1-[3-(4-Chloro-benzoylamino)-benzyl]-piperidine-4-carboxylic acid cyclohexylmethyl-amide;
N-[3-(4-Cyclohexylcarbamoyl-4-fluoro-piperidin-1-ylmethyl)-phenyl]-5-methyl-nicotinamide;
N-[3-(4-Cyclopropylcarbamoyl-piperidin-1-ylmethyl)-phenyl]-5-fluoro-nicotinamide;

N-[3-(4-tert-Butylcarbamoyl-piperidin-1-ylmethyl)-2-methoxy-phenyl]-5-methyl-nicotinamide; and
1-{3-[(5-Methyl-pyridine-3-carbonyl)-amino]-benzyl}-azepane-4-carboxylic acid tert-butylamide.

24) In addition to the above-listed compounds, further compounds are selected from:
5-Amino-pyridine-2-carboxylic acid [3-(4-tert-butylcarbamoyl-piperidin-1-ylmethyl)-phenyl]-amide;
5-Chloro-1-oxy-pyridine-2-carboxylic acid {3-[4-(1,1-dimethyl-propylcarbamoyl)-piperidin-1-ylmethyl]-phenyl}-amide;
5-Chloro-1-oxy-pyridine-2-carboxylic acid [3-(4-tert-butylcarbamoyl-piperidin-1-ylmethyl)-phenyl]-amide;
5-Fluoro-1-oxy-pyridine-2-carboxylic acid {3-[4-(1,1-dimethyl-propylcarbamoyl)-piperidin-1-ylmethyl]-phenyl}-amide;
5-Fluoro-pyridine-2-carboxylic acid [3-(4-tert-butylcarbamoyl-piperidin-1-ylmethyl)-phenyl]-amide;
6-Trifluoromethyl-pyridine-2-carboxylic acid [3-((2R,4R)-4-cyclohexylcarbamoyl-2-methyl-piperidin-1-ylmethyl)-phenyl]-amide;
6-Trifluoromethyl-pyridine-2-carboxylic acid [3-((2S,4S)-4-cyclohexylcarbamoyl-2-methyl-piperidin-1-ylmethyl)-phenyl]-amide;
N-[3-((2S*,4S*)-4-Cyclohexylcarbamoyl-2-methyl-piperidin-1-ylmethyl)-phenyl]-5-methyl-nicotinamide;
N-[3-((2S*,4S*)-4-tert-Butylcarbamoyl-2-methyl-piperidin-1-ylmethyl)-phenyl]-5-methyl-nicotinamide;
6-Trifluoromethyl-pyridine-2-carboxylic acid [3-((2S*,4S*)-4-tert-butylcarbamoyl-2-methyl-piperidin-1-ylmethyl)-phenyl]-amide;
6-Trifluoromethyl-pyridine-2-carboxylic acid [3-((2S*,4S*)-4-cyclohexylcarbamoyl-2-methyl-piperidin-1-ylmethyl)-phenyl]-amide;
1-{3-[2-(2-Chloro-4-fluoro-phenyl)-acetylamino]-benzyl}-pyrrolidine-3-carboxylic acid tert-butylamide;
N-[3-(3-tert-Butylcarbamoyl-pyrrolidin-1-ylmethyl)-phenyl]-5-methyl-nicotinamide;
Benzothiazole-6-carboxylic acid [3-(4-tert-butylcarbamoyl-piperidin-1-ylmethyl)-phenyl]-amide;
5-[3-(4-Cyclohexylcarbamoyl-piperidin-1-ylmethyl)-phenylcarbamoyl]-nicotinic acid methyl ester;
5-[3-(4-tert-Butylcarbamoyl-piperidin-1-ylmethyl)-phenylcarbamoyl]-nicotinic acid methyl ester;
1-Oxy-5-trifluoromethyl-pyridine-2-carboxylic acid [3-(4-tert-butylcarbamoyl-piperidin-1-ylmethyl)-phenyl]-amide;
1-Oxy-5-trifluoromethyl-pyridine-2-carboxylic acid {3-[4-(1,1-dimethyl-propylcarbamoyl)-piperidin-1-ylmethyl]-phenyl}-amide;
1-Oxy-6-trifluoromethyl-pyridine-2-carboxylic acid {3-[4-(1,1-dimethyl-propylcarbamoyl)-piperidin-1-ylmethyl]-phenyl}-amide;
1-Oxy-6-trifluoromethyl-pyridine-2-carboxylic acid [3-(4-tert-butylcarbamoyl-piperidin-1-ylmethyl)-phenyl]-amide;
6-Bromo-pyridine-2-carboxylic acid [3-(4-tert-butylcarbamoyl-piperidin-1-ylmethyl)-phenyl]-amide;
5-Chloro-3-fluoro-pyridine-2-carboxylic acid {3-[4-(1,1-dimethyl-propylcarbamoyl)-piperidin-1-ylmethyl]-phenyl}-amide;
5-Trifluoromethyl-pyridine-2-carboxylic acid {3-[4-(1,1-dimethyl-propylcarbamoyl)-piperidin-1-ylmethyl]-phenyl}-amide;
5-Chloro-3-fluoro-pyridine-2-carboxylic acid [3-(4-tert-butylcarbamoyl-piperidin-1-ylmethyl)-phenyl]-amide;
5-Chloro-pyridine-2-carboxylic acid [3-(4-tert-butylcarbamoyl-piperidin-1-ylmethyl)-phenyl]-amide;
5-Chloro-pyridine-2-carboxylic acid {3-[4-(1,1-dimethyl-propylcarbamoyl)-piperidin-1-ylmethyl]-phenyl}-amide;
1-{3-[(E)-(3-Phenyl-acryloyl)amino]-benzyl}-piperidine-4-carboxylic acid tert-butylamide;
Benzo[1,2,3]thiadiazole-5-carboxylic acid [3-(4-tert-butylcarbamoyl-piperidin-1-ylmethyl)-phenyl]-amide;
1-[3-((E)-But-2-enoylamino)-benzyl]-piperidine-4-carboxylic acid tert-butylamide;
1-[2-Ethyl-5-(4-fluoro-benzoylamino)-benzyl]-piperidine-4-carboxylic acid tert-butylamide;
6-Trifluoromethyl-pyridine-2-carboxylic acid [3-(4-tert-butylcarbamoyl-piperidin-1-ylmethyl)-4-ethyl-phenyl]-amide;
1-[4-Ethyl-3-(4-fluoro-benzoylamino)-benzyl]-piperidine-4-carboxylic acid tert-butylamide;
N-[5-(4-tert-Butylcarbamoyl-piperidin-1-ylmethyl)-2-ethyl-phenyl]-5-methyl-nicotinamide; and
6-Trifluoromethyl-pyridine-2-carboxylic acid [5-(4-tert-butylcarbamoyl-piperidin-1-ylmethyl)-2-ethyl-phenyl]-amide.

25) A second aspect of the invention are compounds of formula (I), which are also compounds of formula (I$_P$)

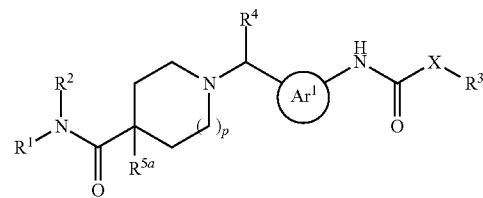

Formula (I$_P$)

wherein
Ar$^1$ represents a phenylene group or a 5- or 6-membered heteroarylene group, wherein the —CHR$^4$— group and the —NH—CO—X—R$^3$ group are attached in meta arrangement to ring carbon atoms of Ar$^1$; wherein said phenylene or 5- or 6-membered heteroarylene independently is unsubstituted or mono-substituted, wherein the substituent is selected from the group consisting of (C$_{1-4}$)alkyl, (C$_{1-4}$)alkoxy, halogen, (C$_{1-3}$)fluoroalkyl, and (C$_{1-3}$)fluoroalkoxy; (notably (C$_{1-4}$)alkyl, (C$_{1-4}$)alkoxy, and halogen);
X represents a
  direct bond (i.e. R$^3$ is attached directly to the carbonyl group);
  —(C$_{1-4}$)alkylene- which is optionally mono-substituted, wherein the substituent is hydroxy;
  —(C$_{3-6}$)cycloalkylene-; or
  —CH$_2$—O—, wherein the oxygen is linked to the R$^3$ group;
R$^3$ represents
  aryl or 5- to 10-membered heteroaryl; wherein said aryl or 5- to 10-membered heteroaryl independently is unsubstituted, mono-, di- or tri-substituted, wherein the substituents are independently selected from the group consisting of (C$_{1-4}$)alkyl; (C$_{1-4}$)alkoxy; (C$_{1-3}$)fluoroalkyl; (C$_{1-3}$)fluoroalkoxy; halogen; cyano; (C$_{3-6}$)cycloalkyl; and —NR$^6$R$^7$, wherein R$^6$ and R$^7$ independently represent hydrogen or (C$_{1-3}$)alkyl, or R$^6$ and R$^7$ together with the nitrogen atom to which they are attached to form a 5- or 6-membered ring selected from pyrrolidinyl, morpholinyl, piperidinyl and piperazinyl optionally substituted at the vacant nitrogen atom with (C$_{1-4}$)alkyl; wherein in case said 5- to 10-membered heteroaryl is pyridine, such pyridine may additionally be present in form of the respective N-oxide;

or, in case X is a direct bond or a methylene group, R$^3$ may in addition represent a partially aromatic bicyclic ring system consisting of a phenyl ring which is fused to a 4- to 6-membered saturated carbocyclic ring optionally containing one or two heteroatoms independently selected from nitrogen and oxygen; wherein said ring system is optionally mono-, or di-substituted with (C$_{1-4}$)alkyl or halogen;

(C$_{3-8}$)cycloalkyl, wherein the cycloalkyl may optionally contain a ring oxygen atom, and wherein said cycloalkyl is optionally substituted with up to four methyl groups;

or, in case X is a direct bond, R$^3$ may in addition represent (C$_{2-6}$)alkyl;

R$^1$ represents (C$_{1-6}$)alkyl which is optionally mono-substituted with (C$_{1-4}$)alkoxy or hydroxy;

(C$_{2-3}$)fluoroalkyl;

(C$_{3-8}$)cycloalkyl or (C$_{3-8}$)cycloalkyl-(C$_{1-3}$)alkyl; wherein the respective (C$_{3-8}$)cycloalkyl groups may optionally contain a ring oxygen atom; wherein the (C$_{3-8}$)cycloalkyl or (C$_{3-8}$)cycloalkyl-(C$_{1-3}$)alkyl independently is unsubstituted, or substituted as follows:

the (C$_{3-8}$)cycloalkyl group is mono- or di-substituted wherein the substituents are independently selected from the group consisting of (C$_{1-4}$)alkyl, fluoro, hydroxy-methyl, hydroxy, and cyano; or the (C$_{1-3}$)alkyl group is mono-substituted with hydroxy;

aryl-(C$_{1-4}$)alkyl-, or 5- or 6-membered heteroaryl-(C$_{1-4}$)alkyl-, wherein the aryl or 5- or 6-membered heteroaryl independently is unsubstituted, mono-, or di-substituted, wherein the substituents are independently selected from the group consisting of (C$_{1-4}$)alkyl, (C$_{1-4}$)alkoxy, halogen, cyano, (C$_{1-3}$)fluoroalkyl, and (C$_{1-3}$)fluoroalkoxy (especially (C$_{1-4}$)alkyl, (C$_{1-4}$)alkoxy, halogen, and (C$_{1-3}$)fluoroalkyl); or a 1,2,3,4-tetrahydronaphthalenyl or an indanyl group, which groups are attached to the rest of the molecule through a carbon atom that is part of the non-aromatic ring;

and R$^2$ represents hydrogen, or (C$_{1-3}$)alkyl; or

R$^1$ and R$^2$ together with the nitrogen atom to which they are attached to represent an azetidine, pyrrolidine, piperidine, morpholine, or azepane ring, wherein said rings independently are unsubstituted, or mono- or di-substituted, wherein the substituents are independently selected from the group consisting of fluorine and methyl;

R$^4$ represents hydrogen, or (C$_{1-3}$)alkyl;

R$^{5a}$ represents hydrogen, methyl, or fluorine; and p represents the integer 0, 1 or 2;

with the exception of the following compounds:

1-[1-[3-(benzoylamino)phenyl]ethyl]-N-[(4-fluorophenyl) methyl]-4-piperidinecarboxamide (CAS-Registry No. 1297116-69-8); and N-[3-[1-[4-(1-pyrrolidinylcarbonyl)-1-piperidinyl]ethyl] phenyl]-benzamide (CAS-Registry No. 1279551-37-9);

wherein the characteristics disclosed in embodiments 2) to 17), and 19) to 21), especially the embodiments listed in embodiment 22), are intended to apply mutatis mutandis also to the compounds formula (I$_P$) according to embodiment 25).

26) A third aspect of the invention are compounds of formula (I), which are also compounds of formula (III)

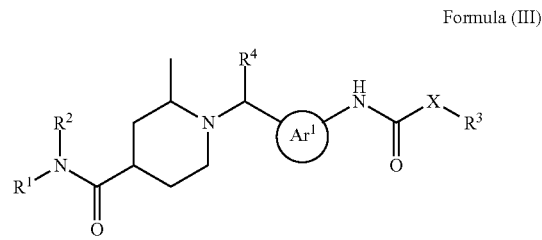

Formula (III)

wherein

Ar$^1$ represents a phenylene group or a 5- or 6-membered heteroarylene group, wherein the —CHR$^4$— group and the —NH—CO—X—R$^3$ group are attached in meta arrangement to ring carbon atoms of Ar$^1$; wherein said phenylene or 5- or 6-membered heteroarylene independently is unsubstituted or mono-substituted, wherein the substituent is selected from the group consisting of (C$_{1-4}$)alkyl, (C$_{1-4}$)alkoxy, halogen, (C$_{1-3}$)fluoroalkyl, and (C$_{1-3}$)fluoroalkoxy; (notably (C$_{1-4}$)alkyl, (C$_{1-4}$)alkoxy, and halogen);

X represents a direct bond (i.e. R$^3$ is attached directly to the carbonyl group);

—(C$_{1-4}$)alkylene- which is optionally mono-substituted, wherein the substituent is hydroxy;

—(C$_{3-6}$)cycloalkylene-;

—CH$_2$—O—, wherein the oxygen is linked to the R$^3$ group; or

—CH=CH—;

R$^3$ represents aryl or 5- to 10-membered heteroaryl; wherein said aryl or 5- to 10-membered heteroaryl independently is unsubstituted, mono-, di- or tri-substituted, wherein the substituents are independently selected from the group consisting of (C$_{1-4}$)alkyl; (C$_{1-4}$)alkoxy; (C$_{1-3}$)fluoroalkyl; (C$_{1-3}$)fluoroalkoxy; halogen; cyano; (C$_{3-6}$)cycloalkyl; —CO—(C$_{1-4}$)alkoxy; —SO$_2$—(C$_{1-4}$)alkyl; and —NR$^6$R$^7$, wherein R$^6$ and R$^7$ independently represent hydrogen or (C$_{1-3}$)alkyl, or R$^6$ and R$^7$ together with the nitrogen atom to which they are attached to form a 5- or 6-membered ring selected from pyrrolidinyl, morpholinyl, piperidinyl and piperazinyl optionally substituted at the vacant nitrogen atom with (C$_{1-4}$)alkyl; wherein in case said 5- to 10-membered heteroaryl is pyridine, such pyridine may additionally be present in form of the respective N-oxide;

or, in case X is a direct bond or a methylene group, R$^3$ may in addition represent a partially aromatic bicyclic ring system consisting of a phenyl ring which is fused to a 4- to 6-membered saturated carbocyclic ring optionally containing one or two heteroatoms independently selected from nitrogen and oxygen; wherein said ring system is optionally mono-, or di-substituted with (C$_{1-4}$)alkyl or halogen;

(C$_{3-8}$)cycloalkyl, wherein the cycloalkyl may optionally contain a ring oxygen atom, and wherein said cycloalkyl is optionally substituted with up to four methyl groups;

or, in case X is a direct bond, R$^3$ may in addition represent (C$_{2-6}$)alkyl;

or, in case X is —CH=CH—, $R^3$ may in addition represent hydrogen, $(C_{1-4})$alkyl, or (dimethylamino)methyl;

$R^1$ represents $(C_{1-6})$alkyl which is optionally mono-substituted with $(C_{1-4})$alkoxy or hydroxy;

$(C_{2-3})$fluoroalkyl;

$(C_{3-8})$cycloalkyl or $(C_{3-8})$cycloalkyl-$(C_{1-3})$alkyl; wherein the respective $(C_{3-8})$cycloalkyl groups may optionally contain a ring oxygen atom; wherein the $(C_{3-8})$cycloalkyl or $(C_{3-8})$cycloalkyl-$(C_{1-3})$alkyl independently is unsubstituted, or substituted as follows:

the $(C_{3-8})$cycloalkyl group is mono- or di-substituted wherein the substituents are independently selected from the group consisting of $(C_{1-4})$alkyl, fluoro, hydroxy-methyl, hydroxy, and cyano; or the $(C_{1-3})$alkyl group is mono-substituted with hydroxy;

aryl-$(C_{1-4})$alkyl-, or 5- or 6-membered heteroaryl-$(C_{1-4})$alkyl-, wherein the aryl or 5- or 6-membered heteroaryl independently is unsubstituted, mono-, or di-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy (especially $(C_{1-4})$alkyl, $(C_{1-4})$alkoxy, halogen, and $(C_{1-3})$fluoroalkyl); or a 1,2,3,4-tetrahydronaphthalenyl or an indanyl group, which groups are attached to the rest of the molecule through a carbon atom that is part of the non-aromatic ring;

and $R^2$ represents hydrogen, or $(C_{1-3})$alkyl; or $R^1$ and $R^2$ together with the nitrogen atom to which they are attached to represent an azetidine, pyrrolidine, piperidine, morpholine, or azepane ring, wherein said rings independently are unsubstituted, or mono- or di-substituted, wherein the substituents are independently selected from the group consisting of fluorine and methyl; and $R^4$ represents hydrogen, or $(C_{1-3})$alkyl;

wherein the characteristics disclosed in embodiments 2) to 16) are intended to apply mutatis mutandis also to the compounds formula (III) according to embodiment 26). In a sub-embodiment, especially one or more of the following characteristics may be present in the compounds of formula (III):

$Ar^1$ represents a phenylene group, wherein the —$CHR^4$— group and the —NH—CO—X—$R^3$ group are attached in meta arrangement to ring carbon atoms of $Ar^1$; wherein said phenylene is unsubstituted or mono-substituted, wherein the substituent is selected from the group consisting of $(C_{1-4})$alkyl, $(C_{1-4})$alkoxy, halogen, $(C_{1-3})$fluoroalkyl, and $(C_{1-3})$fluoroalkoxy (notably $(C_{1-4})$alkyl, $(C_{1-4})$alkoxy, and halogen); and/or X represents a direct bond or methylene; and $R^3$ represents aryl (especially phenyl) which is unsubstituted, mono-, di- or tri-substituted (especially unsubstituted, or mono-, or di-substituted), wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; and cyano; or $R^3$ represents 5- to 10-membered heteroaryl [notably selected from the group consisting of thiophenyl, thiazolyl, imidazolyl, pyrazolyl, pyrrolyl, isoxazolyl, pyridinyl, pyrimidinyl, pyridazinyl, pyrazinyl, benzofuranyl, indazolyl, indolyl, pyrrolopyridinyl (especially pyrrolo[3,2-b]pyridinyl, pyrrolo[2,3-b]pyridinyl), quinoxalinyl, naphthyridinyl, quinolinyl, isoquinolinyl, and pyrazolo[3,4-b]pyridinyl]; which is unsubstituted, mono-, di- or tri-substituted (especially unsubstituted, or mono-, or di-substituted), wherein the substituents are independently selected from the group consisting of $(C_{1-4})$alkyl; $(C_{1-4})$alkoxy; $(C_{1-3})$fluoroalkyl; halogen; $(C_{3-6})$cycloalkyl; and —$NR^6R^7$, wherein $R^6$ and $R^7$ independently represent hydrogen or $(C_{1-3})$alkyl, or $R^6$ and $R^7$ together with the nitrogen atom to which they are attached to form a 5- or 6-membered ring selected from pyrrolidinyl, morpholinyl, piperidinyl, and piperazinyl optionally substituted at the vacant nitrogen atom with methyl; wherein in case said 5- to 10-membered heteroaryl is pyridine, such pyridine may additionally be present in form of the respective N-oxide; and/or $R^1$ represents $(C_{1-6})$alkyl which is optionally mono-substituted with $(C_{1-4})$alkoxy or hydroxy;

$(C_{2-3})$fluoroalkyl;

$(C_{3-8})$cycloalkyl; wherein the $(C_{3-8})$cycloalkyl group optionally contains a ring oxygen atom; wherein the $(C_{3-8})$cycloalkyl is unsubstituted, or mono- or di-substituted wherein the substituents are independently selected from the group consisting of $(C_{1-4})$alkyl, fluoro, hydroxy-methyl, and hydroxy;

a 1,2,3,4-tetrahydronaphthalenyl or an indanyl group, which groups are attached to the rest of the molecule through a carbon atom that is part of the non-aromatic ring;

and $R^2$ represents hydrogen, methyl, or ethyl (especially hydrogen); or $R^1$ and $R^2$ together with the nitrogen atom to which they are attached to represent an azetidine, pyrrolidine, piperidine, morpholine, or azepane ring, wherein said rings independently are unsubstituted, or mono- or di-substituted, wherein the substituents are independently selected from the group consisting of fluorine and methyl; and/or $R^4$ represents hydrogen, or $(C_{1-3})$alkyl.

The compounds of formula (I) according to embodiments 1) to 26) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to embodiments 1) to 26).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5 OC.

For avoidance of any doubt, if compounds are described as useful for the prevention or treatment of certain diseases, such compounds are likewise suitable for use in the preparation of a medicament for the prevention or treatment of said diseases.

The compounds of formula (I) according to embodiments 1) to 26) are useful for the prevention or treatment of disorders relating to a dysfunction of the CXCR7 receptor or its ligands, i.e. relating to a dysfunction of the CXCR7 receptor, or dysfunction of ligands signalling through CXCR7, or dysfunction of CXCR7 ligands (CXCL12 and CXCL11) signalling through their other receptors (CXCR4 and CXCR3).

Such disorders relating to a dysfunction of the CXCR7 receptor or its ligands may in particular be defined as comprising especially cancer, as well as autoimmune disorders (notably rheumatoid arthritis, multiple sclerosis, inflammatory bowel disease, systemic lupus erythematosus, lupus nephritis, interstitial cystitis, celiac disease), inflammatory diseases (notably asthma, chronic obstructive pulmonary disorder, atherosclerosis, myocarditis, sarcoidosis), transplant rejection, and fibrosis (notably liver cirrhosis), as well as hematopoietic stem cell transplantation. Notably such disorders are cancer and autoimmune disorders.

In a further embodiment, diseases or disorders relating to a dysfunction of the CXCR7 receptor or its ligands are selected from the group consisting of cancer, notably carcinomas, leukemias, adenocarcinomas, gliomas, glioblastoma, brain metastases, multiple myelomas, renal clear cell carcinoma, prostate cancer, pancreatic adenocarcinoma, melanoma, metastatic melanoma, rhabdomyosarcoma, hepatocellular carcinoma, colon tumors, breast cancer, non-small cell lung cancer, oral tumors, gallbladder cancer, brain tumors, Ewing's sarcoma, bladder cancer, meningiomas, lymphoma, viral-induced tumors, Burkitt's lymphoma, Hodgkin's lymphoma, lymphoproliferative disease, Kaposi's sarcoma, as well as MALT lymphoma, papillary thyroid carcinoma, cervical cancer, and osteosarcoma; primary intra-ocular B-cell lymphoma; inflammation; multiple sclerosis; renal allograft rejection; rheumatoid arthritis; autoimmune encephalomyelitis; demyelinating diseases; pulmonary vascular diseases; osteoarthritis; acute renal failure; ischemia; inflammatory bowel disease; injured central nervous system; HSCs transplantation; cerebral ischemia; pulmonary hypertension; Shiga-toxin-associated heomolytic uremic syndrome; Preeclampsia; choriocarcinoma; chronic rhinosinusitis; and HIV.

In addition, further particular diseases or disorders relating to a dysfunction of the CXCR7 receptor or its ligands are selected from the group consisting of proliferative diabetic retinopathy; West Nile virus encephalitis; acute renal failure; ischemia; vascular injury; inflammatory bowel disease; injured central nervous system; HSCs transplantation; cerebral ischemia; pulmonary hypertension; AIDS; pulmonary fibrosis; angiogenesis; chemotaxis; cell adhesion; transendothelial migration; cell proliferation and/or survival; and brain and neuronal dysfunctions, such as inflammatory components of Alzheimer's disease.

In addition, further particular diseases or disorders relating to a dysfunction of the CXCR7 receptor or its ligands are selected from the group consisting of kidney dysfunction; nasal polyposis; cardiac allograft rejection; cardiac dysfunction; atherosclerosis; asthma; glomerulonephritis; contact dermatitis; inflammatory bowel disease; colitis; psoriasis; and reperfusion injury.

In addition, further particular diseases or disorders relating to a dysfunction of the CXCR7 receptor or its ligands are hematopoietic stem cell mobilizations.

Cancer may be defined as comprising all sorts of cancers such as carcinomas, leukemias, adenocarcinomas, gliomas, glioblastoma, brain metastases, multiple myelomas, renal clear cell carcinoma, prostate cancer, pancreatic adenocarcinoma, melanoma, metastatic melanoma, rhabdomyosarcoma, hepatocellular carcinoma, colon tumors, breast cancer, non-small cell lung cancer, oral tumors, colorectal cancer, gallbladder cancer, brain tumors, Ewing's sarcoma, bladder cancer, meningioma's, lymphoma, viral-induced tumors, Burkitt's lymphoma, Hodgkin's lymphoma, adult T-cell leukemia, lymphoproliferative disease, Kaposi's sarcoma, as well as MALT lymphoma, papillary thyroid carcinoma, cervical cancer, and osteosarcoma; primary intraocular B-cell lymphoma; and diseases involving CXCR7 and/or CXCL12 and/or CXCL11 mediated metastasis. In addition, cancer furthermore comprises mesotheliomas, ovarian cancer, cervical cancer, head and neck cancer, small cell lung cancer, cancer of the esophagus, stomach cancer, hepatobiliary cancer, cancer of the small intestine, recta cancer, kidney cancer, bladder cancer, penile cancer, urethral cancer, testicular cancer, cervical cancer, vaginal cancer, uterine cancer, thyroid cancer, parathyroid cancer, adrenal cancer, pancreatic endocrine cancer, carcinoid cancer, bone cancer, skin cancer, retinoblastomas, non-Hodgkin's lymphoma, multicentric Castleman's disease or AIDS-associated cancer, primary effusion lymphoma, and neuroectodermal tumors.

Autoimmune disorders may be defined as comprising rheumatoid arthritis (RA); multiple sclerosis (MS); autoimmune encephalomyelitis; and inflammatory bowel disease (IBD, especially comprising Crohn's disease and ulcerative colitis). In addition, autoimmune diseases further comprise disorders such as systemic lupus erythematosus (SLE); psoriasis; psoriatic arthritis; lupus nephritis; interstitial cystitis; celiac disease; antiphospholipid syndrome; thyroiditis such as Hashimoto's thyroiditis; lymphocytic thyroiditis; myasthenia gravis; type I diabetes; uveitis; episcleritis; scleritis; Kawasaki's disease; uveo-retinitis; posterior uveitis; uveitis associated with Behcet's disease; uveomeningitis syndrome; allergic encephalomyelitis; atopic diseases such as rhinitis, conjunctivitis, dermatitis; and post-infectious autoimmune diseases including rheumatic fever and post-infectious glomerulonephritis. In a sub-embodiment, autoimmune disorders include rheumatoid arthritis (RA); multiple sclerosis (MS); and inflammatory bowel disease (comprising Crohn's disease and ulcerative colitis); as well as systemic lupus erythematosus (SLE); lupus nephritis; interstitial cystitis; celiac disease; and type I diabetes.

Inflammatory diseases may be defined as comprising especially chronic rhinusitis as well as asthma, chronic obstructive pulmonary disorder (COPD), atherosclerosis, myocarditis, dry eye disease, sarcoidosis, and inflammatory myopathies, as well as acute lung injury.

Transplant rejection may be defined as comprising rejection of transplanted organs such as kidney, liver, heart, lung, pancreas, cornea, and skin; graft-versus-host diseases brought about by stem cell transplantation; chronic allograft rejection and chronic allograft vasculopathy.

Fibrosis may be defined as comprising especially liver cirrhosis, as well as idiopathic pulmonary fibrosis, renal fibrosis, endomyocardial fibrosis, and arthrofibrosis.

The compounds of formula (I) according to embodiments 1) to 26) are also useful in method of treating tumors comprising administering an effective amount of the compound of formula (I) wherein said effective amount leads to a change of tumor properties, and wherein said modification is achieved by modulating the CXCL12 receptor pathway.

The compounds of formula (I) according to embodiments 1) to 26) are also useful in method of modulating an immune response comprising the administration of an effective amount of the compound of formula (I) wherein said effective amount modulates an inflammatory disease and wherein said response is mediated by the CXCL12 receptor pathway.

Preparation of Compounds of Formula (I)

The compounds of formula (I) can be prepared by the methods given below, by the methods given in the experimental part below or by analogous methods. Optimum reaction conditions may vary with the particular reactants or solvents used, but such conditions can be determined by a person skilled in the art by routine optimisation procedures. In some cases the final product may be further modified, for example, by manipulation of substituents to give a new final product. These manipulations may include, but are not limited to, reduction, oxidation, alkylation, acylation, and hydrolysis reactions which are commonly known to those skilled in the art. In some cases the order of carrying out the following reaction schemes, and/or reaction steps, may be varied to facilitate the reaction or to avoid unwanted reaction products.

Compounds of formula (I) of the present invention can be prepared according to the general sequence of reactions outlined below wherein X, $Ar^1$, $R^1$, $R^2$, $R^3$, $R^4$, $R^{5a}$, $R^{5b}$ and p are as defined for formula (I).

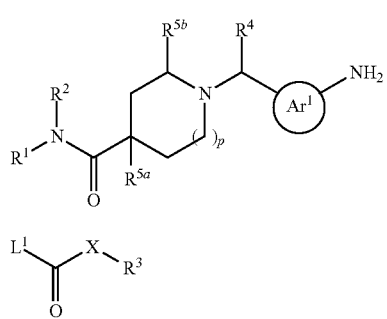

Compounds of formula (I) are prepared by reaction of an amine of Structure 1, or a salt such as a HCl salt thereof, with an acid of Structure 2 ($L^1$=OH) in the presence of an amide-coupling reagent such as TBTU, HATU, COMU, EDC, DCC or PyBOP and a base like DIPEA or TEA in a solvent such as MeCN or DMF; or the corresponding acyl chloride ($L_1$=Cl) and a base like DIPEA or TEA in a solvent like DCM.

Compounds of Structure 1 may be prepared by one of the synthetic pathways described below.

Compounds of Structure 1 may be prepared by the procedure illustrated in Reaction Scheme A. A Boc-protected amino aryl or heteroaryl aldehyde or ketone derivative A-1, either commercially available or prepared following the procedure described by Schadendorf T et al., Tetrahedron Letters (2007), 48(51), 9044-9047, can be aminated by treatment with an amino ester in the presence of a reductive reagent like $NaBH_4$, $NaBH_3CN$, $NaBH(OAc)_3$ in a solvent like DCM, MeOH, THF; and in the case of $R^4$=alkyl, in the presence of a titanium salt like $TiCl_4$ or tetraisopropyl-orthotitanate, to give the aminoester A-2. The ester A-2 can be saponified by treatment with a base like LiOH in a mixture of water/THF or water/MeOH to deliver the acid A-3. Condensation of the acid A-3 with an amine $HNR^1R^2$ after activation of the acid with $POCl_3$/pyridine or oxalyl chloride in DCM gives the amide A-4. The amide A-4 is Boc-deprotected by treatment with 4M HCl in dioxane or with TFA to give the corresponding amine 1.

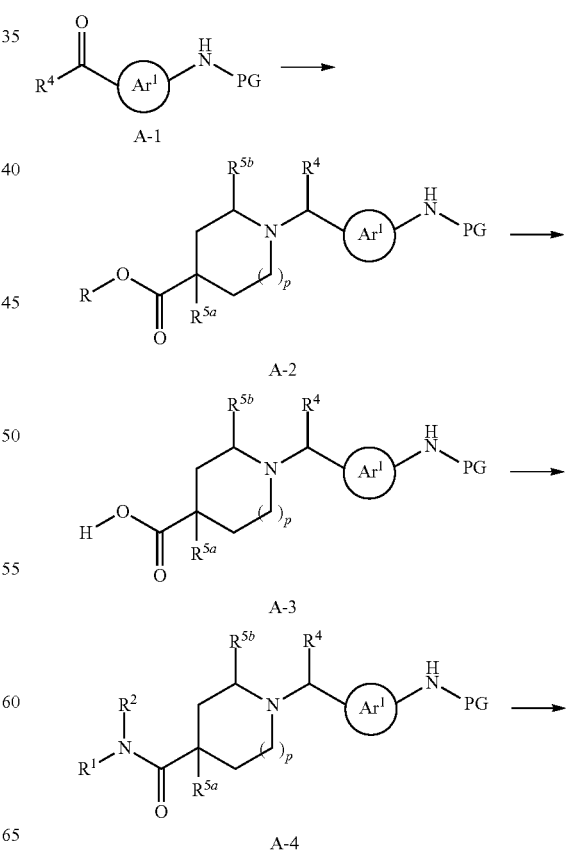

Reaction Scheme A

-continued

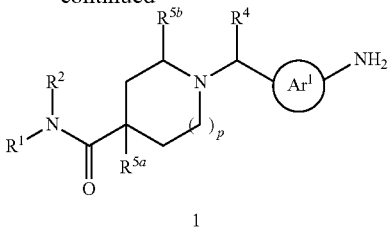

1

Reaction Scheme B

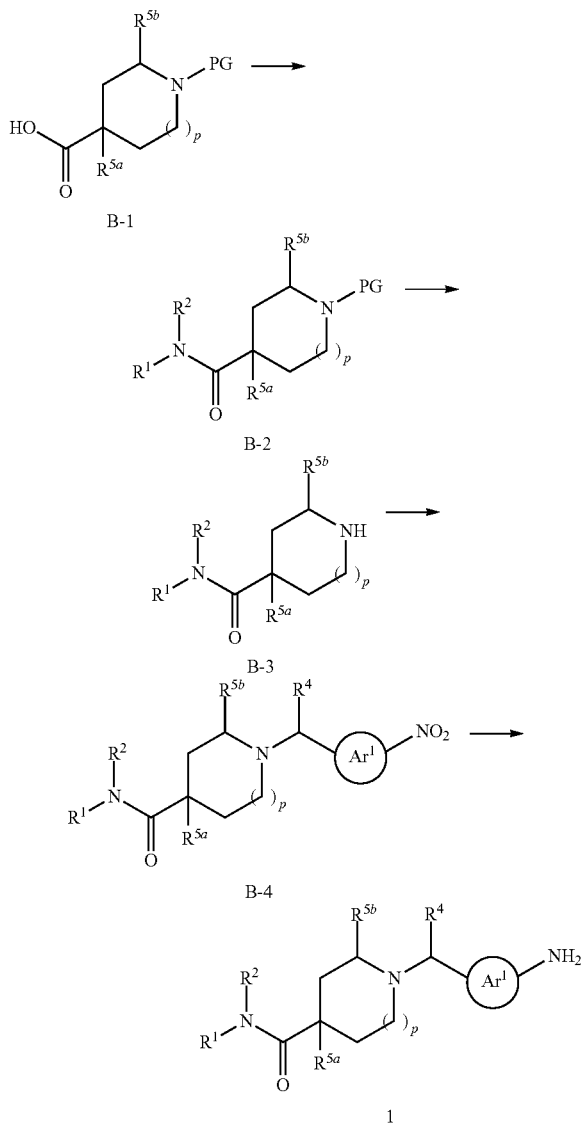

Compounds of Structure 1 may alternatively be prepared as illustrated in Reaction Scheme B. Amidation of acid B-1 with an amine HNR¹R² in the presence of EDC hydrochloride and DMAP in a solvent like DCM gives the corresponding amide B-2 which can be Boc-deprotected under standard conditions to furnish intermediates of type B-3. Reductive amination of B-3 can be achieved by treatment with a nitro-aldehyde or- ketone in the presence of a reductive reagent like NaBH$_4$, NaBH$_3$CN, NaBH(OAc)$_3$ in a solvent like DCM, MeOH or THF. The nitro derivative B-4 can be transformed into compounds of structure 1 by reduction with stannous chloride in an alcohol, preferably MeOH.

Reaction Scheme C

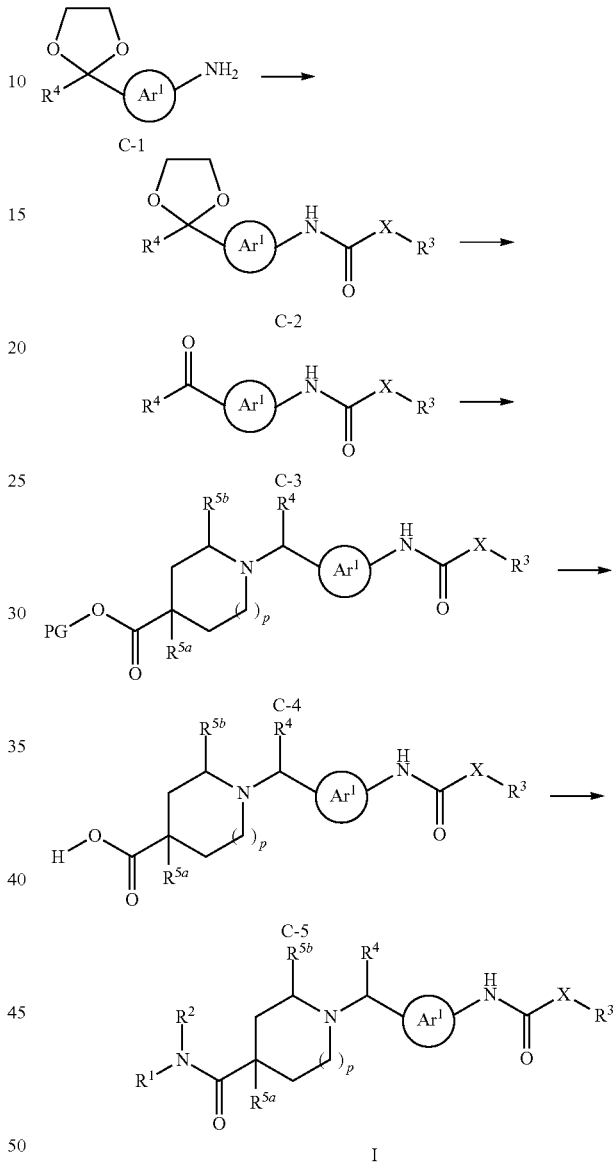

Compounds of Structure I may alternatively be prepared as illustrated in Reaction Scheme C. Intermediate C-1 can be acylated with the corresponding acid chlorides in presence of a base like TEA or DIPEA in DCM or by acylation with the corresponding acid activated with an amide-coupling reagent such as COMU, TBTU, HATU, EDC, DCC or PyBOP and a base like DIPEA or TEA in a solvent such as DCM, MeCN or DMF to deliver the acylated ketal or acetal C-2. Deprotection of the ketal or acetal carried out in the presence of an acid like aq. HCl or p-toluene sulfonic acid in a dioxane water mixture gives the corresponding aldehyde or ketone C-3. Reductive amination with an amino ester in the presence of a reductive reagent like NaBH$_4$, NaBH$_3$CN, NaBH(OAc)$_3$ in a solvent like DCM, MeOH or THF delivers the ester intermediate C-4 which can saponified by treatment with a base like LiOH in a mixture of water/THF or water/MeOH to deliver the acid C-5. Condensation of the acid C-5 with an amine HNR¹R² after activation of the acid with POCl₃/pyridine or oxalyl chloride in DCM gives the product I. Amidation of the acid C-5 with an amine HNR¹R² can also be done in the presence of an amide-coupling reagent such as TBTU, HATU, COMU, EDC, DCC, si-DCC or PyBOP and a base like DIPEA or TEA in a solvent such as MeCN or DMF to deliver compound of structure 1.

Reaction Scheme D

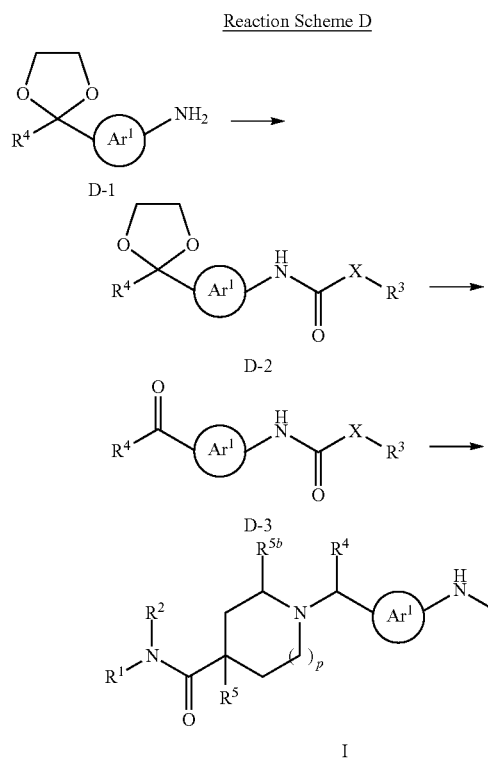

Compounds of Structure I may also be prepared as illustrated in Reaction Scheme D. Intermediate D-1 can be acylated from the corresponding acid chlorides in presence of a base like TEA or DIPEA in DCM or by acylation with the corresponding acid activated with an amide-coupling reagent such as COMU, TBTU, HATU, EDC, DCC or PyBOP and a base like DIPEA or TEA in a solvent such as DCM, MeCN or DMF to deliver the acylated ketal or acetal D-2. Deprotection of the ketal or acetal carried out in the presence of an acid like aqueous HCl or p-toluene sulfonic acid in a dioxane water mixture gives the corresponding aldehyde or ketone D-3. Reductive amination with an amine of type B-3 in the presence of a reductive reagent like NaBH₄, NaBH₃CN, NaBH(OAc)₃ in a solvent like DCM, MeOH or THF delivers the product I.

Reaction Scheme E

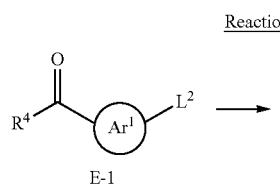

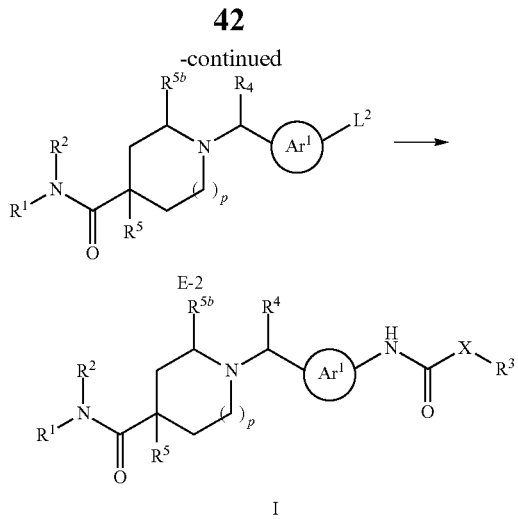

Final compounds of the present invention may be prepared as illustrated in Reaction Scheme E. For example, intermediate E-2 can be prepared from an aldehyde or ketone of general formula E-1, with L²=halogen like Cl, Br, I by reductive amination with an amine of type B-3 in the presence of a reductive reagent like NaBH₄, NaBH₃CN, NaBH(OAc)₃ in a solvent like DCM, MeOH or THF. Condensation of E-2 with a carboxamide of type H₂NCO—X—R³ can be accomplished by metal catalysed conditions employing for example copper catalysts in the presence of diamines like N,N'-dimethylethylendiamine, or palladium catalysts in the presence of a strong base like sodium t-butoxyde in toluene, THF or dioxane at temperatures between 60° C. and 110° C. to give final compounds of type I.

Reaction Scheme F

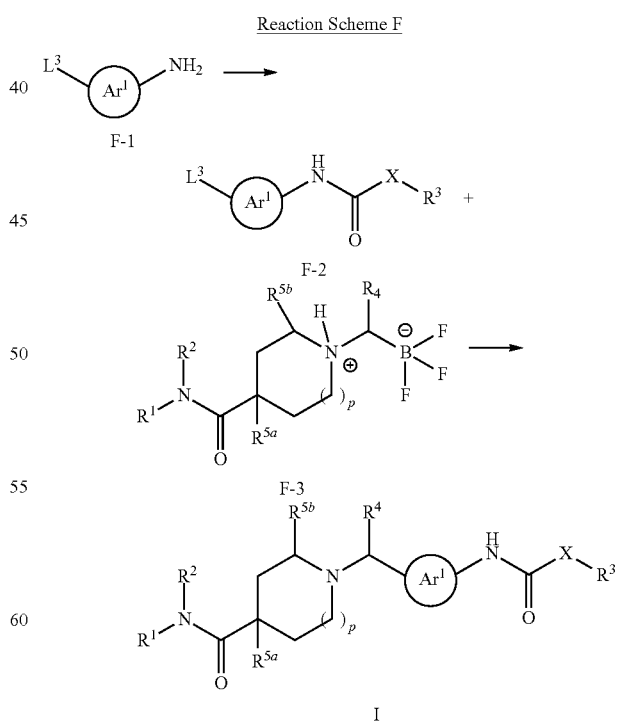

Final compounds of the present invention may be prepared as illustrated in Reaction Scheme E. For example, intermediate F-2 can be prepared from an halogenated amino derivative of general formula F-1, with $L^3$=halogen like Cl, Br, I by acylation of it with the corresponding acid chlorides in presence of a base like TEA or DIPEA in DCM or by acylation with the corresponding acid activated with an amide-coupling reagent such as COMU, TBTU, HATU, EDC, DCC or PyBOP and a base like DIPEA or TEA in a solvent such as DCM, MeCN or DMF. Substitution of $L^3$ on F-2 with an ammoniomethyltrifluoroborate derivative of type F-3, itself obtained by condensation of the amine of type B-3 with potassium chloromethyltrifluoroborate in THF, or a mixture of THF/n-BuOH at 80° C., can be accomplished under Suzuki-Miyaura cross-coupling reaction conditions in the presence of a palladium salt, like $Pd(OAc)_2$, a phosphine ligand, preferentially XPhos in the presence of a base like $Cs_2CO_3$ in THF, dioxane or a mixture of THF/$H_2O$ 10:1 at 80-100° C. ° C. to give the final compound I.

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm), IC (5 μm) or AD-H (5 μm) column. Typical conditions of chiral HPLC are an isocratic mixture of eluent A (EtOH or EtOAc, in presence or absence of an amine such as triethylamine or diethylamine) and eluent B (heptane, in presence or absence of an amine such as triethylamine or diethylamine), at a flow rate of 0.8 to 150 mL/min.

The following examples are provided to illustrate the invention. These examples are illustrative only and should not be construed as limiting the invention in any way.

EXPERIMENTAL PART

I. Chemistry

All temperatures are stated in ° C. Commercially available starting materials were used as received without further purification. Unless otherwise specified, all reactions were carried out in oven-dried glassware under an atmosphere of nitrogen. Compounds were purified by flash column chromatography on silica gel or by preparative HPLC. Compounds described in the invention are characterised by LC-MS data (retention time $t_R$ is given in min; molecular weight obtained from the mass spectrum is given in g/mol) using the conditions listed below. In cases where compounds of the present invention appear as a mixture of conformational isomers, particularly visible in their LC-MS spectra, the retention time of the most abundant conformer is given.
LC-MS with Acidic Conditions
Method A:
Agilent 1100 series with mass spectrometry detection (MS: Finnigan single quadrupole). Column: Zorbax SB-aq (3.5 μm, 4.6×50 mm). Conditions: MeCN [eluent A]; water+0.04% TFA [eluent B]. Gradient: 95% B→5% B over 1.5 min (flow: 4.5 mL/min). Detection: UV/Vis+MS.
Method B:
Agilent 1100 series with mass spectrometry detection (MS: Finnigan single quadrupole). Column: Waters XBridge C18 (2.5 μm, 4.6×30 mm). Conditions: MeCN [eluent A]; water+0.04% TFA [eluent B]. Gradient: 95% B→5% B over 1.5 min (flow: 4.5 mL/min). Detection: UV/Vis+MS.

Method C:
Waters Acquity Binary, Solvent Manager, MS: Waters SQ Detector, DAD: Acquity UPLC PDA Detector, ELSD: Acquity UPLC ELSD. Column: Acquity UPLC BEH C18 1.7 um 2.1×50 mm from Waters, thermostated in the Acquity UPLC Column Manager at 60° C. Eluents: $H_2O$+0.05% TFA; B2: MeCN+0.045% TFA. Method: Gradient: 2% B 98% B over 2.0 min. Flow: 1.2 mL/min. Detection: UV 214 nm and ELSD, and MS, tR is given in min.
LC-MS with Basic Conditions
Method D:
Dionex Ultimate 3000 Series with MS Detection (Dionex MSQ), Column: Ascentis 2.1*50 mm 5 um, Eluents: A:$H_2O$+0.05% $NH_4OH$, B: MeCN, Method: 5% B to 95% B in 1.1 min, Flow 1.8 ml/min, Detection UV: 214 nm
Preparative HPLC with Basic Conditions
Method E:
Gilson HPLC system, equipped with a Gilson 215 autosampler, Gilson 333/334 pumps, Dionex MSQ Plus detector system, and a Dionex UVD340U (or Dionex DAD-3000) UV detector. Column: Waters XBridge (10 μm, 75×30 mm). Conditions: MeCN [eluent A]; water+0.5% $NH_4OH$ (25% aq.) [eluent B]; Gradient: 90% B→5% B over 6.5 min (flow: 75 mL/min). Detection: UV/Vis+MS
Method F:
Waters system, equipped with a binary gradient module (2545), a HPLC pump (515), a photodiode array detector (2998) and a mass detector (3100). Column: Waters X-Bridge column (Prep C18, 5 μm OBD, 19×50 mm). The two elution solvents were as follows: solvent A=water+0.1% $NH_4OH$; solvent B=acetonitrile+0.1% $NH_4OH$. The eluent flow rate was 40 mL/min and the characteristics of the eluting mixture proportion in function of the time t from start of the elution are summarized in the tables below (a linear gradient being used between two consecutive time points):

| | t (min) | | | | | | |
|---|---|---|---|---|---|---|---|
| | 0 | 0.2 | 0.3 | 3.2 | 3.3 | 4.3 | 4.4 |
| Solvent A (%) | 90 | 90 | 80 | 50 | 5 | 5 | 95 |
| Solvent B (%) | 10 | 10 | 20 | 50 | 95 | 95 | 5 |

Chiral HPLC with Basic Conditions
Method G:
Analytical LC performed with a binary HPLC pump Dionex HPG-3200SD, Auto sampler: Dionex WPS-3000, Column compartment: Dionex TCC-3200, Column compartment: Dionex TCC-3200, Diode array detector: Dionex DAD-3000, 4-Channel Degasser: Dionex SRD-3400, Valve actuator: Gilson Valvemate II and a Valve actuator Gilson Valvemate II; Column: Daicel Chiralpak IA (5 μm, 250×4.6 mm). Conditions: 90 EtOAc with 0.02% DEA [eluent A], 10% Heptane with 0.05% DEA [eluent B], flow 1.0 ml/min, Detection: UV/Vis.
Method H:
Preparative LC performed with Preparative Pump: Varian SD-1, preparative Pump: Varian SD-1, Auto sampler: Gilson 215 Liquid Handler, Injection Module: Gilson 819, Valve actuator: Gilson Valvemate II, DAD Detector: Dionex DAD-3000, Analog-to-digital converter: Dionex UCI-100 Universal Chromatography Interface, Solvent valve: Gilson Vici Valve system; Column: Daicel ChiralPak IA, (5 μm, 20×250 mm). Conditions: 90 EtOAc with 0.02% DEA [eluent A]10% Heptane [Eluent B], flow 20.0 ml/min. Detection: UV/Vis.

ABBREVIATIONS

As Used Hereinbefore or Hereinafter aq. aqueous
atm atmosphere
BSA bovine serum albumin
Boc butyloxycarbonyl
CDI carbonyl diimidazole
COMU 1-Cyano-2-ethoxy-2-oxoethylidenaminooxy)dimethylamino-morpholino-carbenium hexafluorophosphate
d days
dba dibenzylidene acetone
DCC dicyclohexyl carbodiimide
DCM dichloromethane
DIPEA diisopropyl-ethylamine, Hünig's base, ethyl-diisopropylamine
DMAP 4-dimethylaminopyridne
DMF dimethylformamide
DMSO dimethylsulfoxide
dppf 1,1'-bis(diphenylphosphino)ferrocene
EDC N-(3-dimethylaminopropyl)-N'-ethyl-carbodiimide
eq. equivalent(s)
Et ethyl
EtOAc ethyl acetate
Ex. example(s)
h hour(s)
HATU 2-(7-Aza-1H-benzotriazole-1-yl)-1,1,3,3-tetramethyluronium hexafluorophosphate
HBTU O-(benzotriazol-1-yl)-N,N,N',N'-tetramethyluronium hexafluorophosphate
HOBt 1-hydroxybenzotriazole
HOAT 7-Aza-1-hydroxybenzotriazole
HPLC high performance liquid chromatography
HV high vacuum conditions
$^{i}$Bu isobutyl
$^{i}$Pr isopropyl
KO$^{t}$Bu potassium tert-butoxide
LC-MS liquid chromatography-mass spectrometry
Lit. Literature
Me methyl
MeCN acetonitrile
MeOH methanol
mL milliliter
MTBE methyl-tert-butyl ether
min minute(s)
NaOAc sodium acetate
$^{n}$Pr n-propyl
OAc acetate
Pd(dppf)Cl$_2$.DCM [1,1'-bis(diphenylphosphino)-ferrocene] dichloropalladium (II) complex with dichloromethane
Ph phenyl
PPh$_3$ triphenyl phosphine
POCl$_3$ Phosphorous oxychloride
PL-DETA PL-DETA Resin (diethylenetriamine)
PL-NCO PL-NCO Resin (isocyanate)
prep. Preparative
PyBOP benzotriazol-1-yl-oxy-tris-pyrrolidino-phosphonium-hexafluoro-phosphate
rac racemic
RT room temperature
s second(s)
sat. Saturated
si-DCC SiliaBond Carbodiimide
soln. solution
tBu tert-butyl=tertiary butyl
TBTU 2-(1H-benzotriazole-1-yl)-1,2,3,3-tetramethyluronium tetrafluoroborate
TEA triethylamine
TFA trifluoroacetic acid
THF tetrahydrofuran
TLC thin layer chromatography
$t_R$ retention time
XPhos 2-Dicyclohexylphosphino-2',4',6'-triisopropylbiphenyl General Method A for the Synthesis of piperidine-4-carboxamide of Structure (I)

Buildings Blocks

Preparation of Building Blocks of General Formula 1

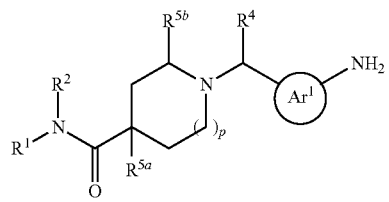

1-(3-Amino-benzyl)-piperidine-4-carboxylic acid cyclohexylamide BB-1

(1.001a): 1-(3-tert-Butoxycarbonylamino-benzyl)-piperidine-4-carboxylic acid ethyl ester A mixture of (3-formyl-phenyl)-carbamic acid tert-butyl ester (Schadendorf T et al., Tetrahedron Letters (2007), 48(51), 9044-9047), (1 g, 4.52 mmol), ethyl isonipecotate (800 mg, 5.09 mmol) and TEA (0.7 mL, 5 mmol) in MeOH (50 mL) is treated with acetic acid (1.03 mL, 18 mmol) and stirred at RT for 2 h. Sodium cyanoborohydride (398 mg, 6.33 mmol) is added at once and the reaction mixture is stirred for 18 h at RT. Water (5 mL) is added to the mixture and the solvents are evaporated. The residue is partitioned between diethyl ether (50 mL) and aqueous 0.1N HCl (50 mL). The aqueous phase is separated, washed twice with diethyl ether (25 mL) and basified with 1N NaOH solution (10 mL). The aqueous phase is extracted three times with DCM (3×50 mL). The combined organic phases are dried over MgSO$_4$ and evaporated. The title compound is obtained as a thick oil; LC-MS A: $t_R$=0.71 min; [M+H]$^+$=363.48.

(1.001b): 1-(3-tert-Butoxycarbonylamino-benzyl)-piperidine-4-carboxylic acid

A solution of 1-(3-tert-butoxycarbonylamino-benzyl)-piperidine-4-carboxylic acid ethyl ester (7.6 g, 21.4 mmol) in a mixture of water (90 mL) and MeOH (90 mL) at RT is treated at once with LiOH mono hydrate (922 mg, 22 mmol). The mixture is stirred at RT for 18 h then HCl 1N (22 mmol, 22 mL) is added and the reaction mixture is stirred at RT for 30 min. The solvents are removed under reduce pressure and the crude acid is dried under high vacuum. The crude title compound containing LiCl is used for the next step. LC-MS A: $t_R$=0.56 min; [M+H]$^+$=335.26.

(1.001c): [3-(4-Cyclohexylcarbamoyl-piperidin-1-ylmethyl)-phenyl]-carbamic acid tert-butyl ester A suspension of crude 1-(3-tert-butoxycarbonylamino-benzyl)-piperidine-4-carboxylic acid (6.7 g, 20 mmol) in DCM (250 mL) and DMF (0.2 mL) is treated with oxalyl chloride (25 mmol, 2.21 mL) dropwise at 0° C. during 20 min. under nitrogen. The reaction mixture is stirred at RT for 2 h. Then the solvent is evaporated under reduced pressure and dried under high vacuum. The crude acid chloride is dissolved in DCM (250 mL) and treated with DIPEA (20 mmol, 3.42 mL) and cooled down to 0° C. A solution of cyclohexylamine (2.18 g, 22 mmol) in DCM (20 mL) is added dropwise over 15 min. and the resulting mixture is stirred for 2 h. at RT. The reaction mixture is washed twice with aq. sat. NaHCO$_3$ (100 mL) and dried over MgSO4. After evaporation of the solvent, the crude residue is purified by flash chromatography on silica gel using a mixture of DCM/MeOH 9:1. After concentration of the product containing fractions, the title compound (2.44 g, 29%) is obtained as a beige powder: LC-MS A: $t_R$=0.66 min; $[M+H]^+$=416.2.

1.001d): 1-(3-Amino-benzyl)-piperidine-4-carboxylic acid cyclohexylamide BB-1

A solution of [3-(4-cyclohexylcarbamoyl-piperidin-1-ylmethyl)-phenyl]-carbamic acid tert-butyl ester (4.6 g, 11.1 mmol) in 1,4-dioxane (110 mL) is cooled down to 0° C. and treated with a 4N HCl solution in 1,4-dioxane (24.9 mL, 99.6 mmol). The reaction mixture is heated to 60° C. for 1 h. The reaction mixture is cooled down to RT and treated with aqueous 2N sodium hydroxide. After evaporation of 1,4-dioxane under reduced pressure the reaction mixture is extracted twice with DCM (110 mL). The combined organic phases are dried over MgSO$_4$ and evaporated to yield the title compound as a yellowish powder: LC-MS A: $t_R$=0.50 min; $[M+H]^+$=316.32.

Preparation of Building Blocks of Substituted 1-(3-Amino-benzyl)-piperidine-4-carboxylic acid alkyl amides of General Formula (1) Used as Intermediates in the Preparation of Examples 1.004-1.291

In analogy to example 1.001d the following amides are prepared:

1-(3-Amino-benzyl)-piperidine-4-carboxylic acid cyclopropylamide BB-2

1[3-(4-Cyclopropylcarbamoyl-piperidin-1-ylmethyl)-phenyl]-carbamic acid tert-butyl ester The title compound is prepared according to the reaction 1.001a described above using (3-formyl-phenyl)-carbamic acid tert-butyl ester and piperidine-4-carboxylic acid cyclopropylamide: LC-MS B: $t_R$=0.53 min; $[M+H]^+$=374.33.

1-(3-Amino-benzyl)-piperidine-4-carboxylic acid cyclopropylamide

The title compound is prepared according to the reaction 1.001d described above by deprotection of 1[3-(4-cyclopropylcarbamoyl-piperidin-1-ylmethyl)-phenyl]-carbamic acid tert-butyl ester; LC-MS B: $t_R$=0.21 min; $[M+H]^+$=274.07.

1-(3-amino-benzyl)-piperidine-4-carboxylic acid cyclopentylamide BB-3

The title compound is prepared according to the reactions 1.001a and 1.001d described above using (3-formyl-phenyl)-carbamic acid tert-butyl ester and piperidine-4-carboxylic acid cyclopentylamide: LC-MS A: $t_R$=0.45 min; $[M+H]^+$=302.40.

1-(3-amino-benzyl)-piperidine-4-carboxylic acid tert-butylamide BB-4

The title compound is prepared according to the reaction 1.001a and 1.001d described above using (3-formyl-phenyl)-carbamic acid tert-butyl ester and piperidine-4-carboxylic acid tert-butylamide: LC-MS A: $t_R$=0.44 min; $[M+H]^+$=289.92.

rac-1-[1-(3-Amino-phenyl)-ethyl]-piperidine-4-carboxylic acid cyclohexylamide BB-5 rac-1-[1-(3-Nitro-phenyl)-ethyl]-piperidine-4-carboxylic acid cyclohexylamide Piperidine-4-carboxylic acid cyclohexylamide (1.5 g 7.132 mmol) and 3-nitroacetophenone (1.77 g, 10.7 mmol) are dissolved in MeOH (40 mL). Tetraisopropyl-orthotitanate (3.167 mL, 10.7 mmol) is added and the mixture is stirred at RT for 18 h. NaBH$_4$ (539.6 mg, 14.3 mmol) is added carefully. The mixture is evaporated under reduced pressure. DCM (25 mL) and water (25 mL) are added, following by 1 M NaOH solution (50 mL). The organic phase is separated and the aqueous phase is extracted with DCM (25 mL). The combined organic phases are dried over MgSO$_4$, filtered and concentrated. The crude residue is purified by flash chromatography on silica gel using a gradient of heptane/EtOAc 4:1 to EtOAc 100%. After concentration of the product-containing fractions, the title compound (0.375 g, 15%) is obtained as a colorless solid LC-MS A: $t_R$=0.64 min; $[M+H]^+$=360.26.

rac-1-[1-(3-Amino-phenyl)-ethyl]-piperidine-4-carboxylic acid cyclohexylamide A solution of rac-1-[1-(3-nitro-phenyl)-ethyl]-piperidine-4-carboxylic acid cyclohexylamide (375 mg, 1.04 mmol) in MeOH (15 mL) is treated with anhydrous stannous chloride (908 mg, 4.7 mmol). The mixture is heated at reflux overnight. The mixture is let to cool to RT and MeOH is evaporated under reduced pressure. Water (25 mL) is added to the residue, followed by saturated NaHCO$_3$ solution (25 mL). The mixture is extracted twice with DCM (25 mL), the organic phases are washed with water (25 mL), brine (25 mL) and dried over MgSO$_4$. The crude product (0.35 g, 99%) is isolated after evaporation under reduced pressure as a colorless oil: LC-MS A: $t_R$=0.51 min; $[M+H]^+$=330.31.

1-(3-Amino-2-chloro-benzyl)-piperidine-4-carboxylic acid cyclohexylamide BB-6

The title compound is prepared according to the reactions described above starting from 2-chloro-3-nitro-benzaldehyde and piperidine-4-carboxylic acid cyclohexylamide giving after reductive amination 1-(2-chloro-3-nitro-benzyl)-piperidine-4-carboxylic acid cyclohexylamide LC-MS B:

$t_R$=0.57 min; [M+H]$^+$=380.14 and reduction with stannous chloride the title compound LC-MS A: $t_R$=0.50 min; [M+H]$^+$=350.20.

1-(3-Amino-4-chloro-benzyl)-piperidine-4-carboxylic acid cyclohexylamide BB-7

The title compound is prepared according to the reactions described above starting from 4-chloro-3-nitro-benzaldehyde and piperidine-4-carboxylic acid cyclohexylamide yielding after reductive amination 1-(4-Chloro-3-nitro-benzyl)-piperidine-4-carboxylic acid cyclohexylamide LC-MS A: $t_R$=0.67 min; [M+H]$^+$=380.03 and reduction with stannous chloride the title compound LC-MS A: $t_R$=0.63 min; [M+H]$^+$=350.21.

1-(5-Amino-2-chloro-benzyl)-piperidine-4-carboxylic acid cyclopentylamide BB-8

The title compound is prepared according to the reactions described above starting from 2-chloro-5-nitro-benzaldehyde and piperidine-4-carboxylic acid cyclopentylamide yielding after reductive amination 1-(2-chloro-5-nitro-benzyl)-piperidine-4-carboxylic acid cyclopentylamide LC-MS A: $t_R$=0.61 min; [M+H]$^+$=366.35 and reduction with stannous chloride the title compound LC-MS A: $t_R$=0.55 min; [M+H]$^+$=336.39.

1-(3-Amino-benzyl)-piperidine-4-carboxylic acid isobutyl-methyl-amide BB-9

The title compound is prepared according to the reactions described above starting from 3-nitro-benzaldehyde and piperidine-4-carboxylic acid isobutyl-methyl-amide yielding after reductive amination 1-(3-nitro-benzyl)-piperidine-4-carboxylic acid isobutyl-methyl-amide; LC-MS A: $t_R$=0.61 min; [M+H]$^+$=366.35 followed by reduction with stannous chloride the title compound LC-MS A: $t_R$=0.48 min; [M+H]$^+$=304.24.

1-(3-Amino-5-bromo-benzyl)-piperidine-4-carboxylic acid tert-butylamide BB-10

The title compound is prepared according to the reactions described above starting from 3-bromo-5-nitro-benzaldehyde and piperidine-4-carboxylic acid tert-butylamide yielding after reductive amination BB-10a; LC-MS A: $t_R$=0.65 min; [M+H]$^+$=398.00 followed by reduction with stannous chloride the title compound; LC-MS A: $t_R$=0.60 min; [M+H]$^+$=369.67.

1-(4-Amino-pyrimidin-2-ylmethyl)-piperidine-4-carboxylic acid tert-butylamide BB-11

A solution of 2-chloromethyl-pyrimidin-4-ylamine (Imperial Chemical Industries PLC Patent: U.S. Pat. No. 4,447,441 A1, 1984; 300 mg, 2.1 mmol) in methanol (25 mL) is treated with piperidine-4-carboxylic acid tert-butylamide (404 mg, 2.19 mmol) and TEA (0.872 mL, 6.27 mmol). The resulting mixture is heated at reflux overnight. DCM (25 mL) and water (25 mL) are added followed by NaOH 1M to adjust at pH 10. The organic phase is separated. The aqueous phase is extracted with DCM (25 mL). The combined organic phases are dried over MgSO$_4$, filtered and evaporated. Evaporation of the solvent yields the crude product (0.57 g, 94%) as a brownish solid; LC-MS A: $t_R$=0.40 min; [M+H]$^+$=292.14.

1-(4-Amino-pyrimidin-2-ylmethyl)-piperidine-4-carboxylic acid cyclohexylamide BB-12

The title compound is prepared according to the reactions described above starting from 2-chloromethyl-pyrimidin-4-ylamine and piperidine-4-carboxylic acid cyclohexylamide; LC-MS A: $t_R$=0.47 min; [M+H]$^+$=318.12.

1-(2-Amino-thiazol-4-ylmethyl)-piperidine-4-carboxylic acid cyclopentylamide BB-13 (4-Formyl-thiazol-2-yl)-carbamic acid tert-butyl ester A solution of (4-hydroxymethyl-thiazol-2-yl)-carbamic acid tert-butyl ester (0.302 g, 1.31 mmol) in dry DCM (15 mL) is treated with manganese dioxide (1.14 g, 13.1 mmol). The mixture is stirred at RT overnight. The reaction mixture is filtered over celite. The celite cake is washed with DCM (15 mL) and MeOH (15 mL). The filtrate is evaporated under reduced pressure and dried under HV for 1 h to deliver the title compound (0.225 g, 75%) as a colorless solid; LC-MS A: $t_R$=0.71 min; [M+H]$^+$=229.12.

[4-(4-Cyclopentylcarbamoyl-piperidin-1-ylmethyl)-thiazol-2-yl]-carbamic acid tert-butyl ester The title compound is prepared according to the reactions described above starting from (4-formyl-thiazol-2-yl)-carbamic acid tert-butyl ester and piperidine-4-carboxylic acid cyclopentylamide J-4 yielding after reductive amination [4-(4-cyclopentylcarbamoyl-piperidin-1-ylmethyl)-thiazol-2-yl]-carbamic acid tert-butyl ester; LC-MS A: $t_R$=0.66 min; [M+H]$^+$=409.13.

1-(2-Amino-thiazol-4-ylmethyl)-piperidine-4-carboxylic acid cyclopentylamide The title compound is prepared according to the reaction 1.001d described above by deprotection of [4-(4-cyclopentylcarbamoyl-piperidin-1-ylmethyl)-thiazol-2-yl]-carbamic acid tert-butyl ester); LC-MS A: $t_R$=0.47 min; [M+H]$^+$=309.22.

1-(5-Amino-2-methyl-benzyl)-piperidine-4-carboxylic acid tert-butylamide BB-14

The title compound is prepared according to the reactions described for BB-5 above starting from 2-methyl-5-nitro-benzaldehyde and piperidine-4-carboxylic acid tert-butylamide yielding after reductive amination 1-(2-methyl-5-nitro-benzyl)-piperidine-4-carboxylic acid tert-butylamide; LC-MS A: $t_R$=0.62 min; [M+H]$^+$=334.21 followed by reduction with stannous chloride the title compound; LC-MS A: $t_R$=0.44 min; [M+H]$^+$=304.28.

1-(5-Amino-2-methoxy-benzyl)-piperidine-4-carboxylic acid tert-butylamide BB-15

The title compound is prepared according to the reactions described for BB-5 above starting from 2-methoxy-5-nitro-benzaldehyde and piperidine-4-carboxylic acid tert-butylamide yielding after reductive amination 1-(2-methoxy-5-nitro-benzyl)-piperidine-4-carboxylic acid tert-butylamide; LC-MS A: $t_R$=0.61 min; [M+H]$^+$=350.18 followed by reduction with stannous chloride the title compound; LC-MS A: $t_R$=0.42 min; [M+H]$^+$=320.24.

1-(3-Amino-4-methyl-benzyl)-piperidine-4-carboxylic acid tert-butylamide BB-16

The title compound is prepared according to the reactions described for BB-5 above starting from 4-methyl-3-nitro-benzaldehyde and piperidine-4-carboxylic acid tert-butylamide yielding after reductive amination 1-(4-methyl-3-nitro-benzyl)-piperidine-4-carboxylic acid tert-butylamide; LC-MS A: $t_R$=0.63 min; [M+H]$^+$=334.25 followed by reduction with stannous chloride the title compound; LC-MS A: $t_R$=0.49 min; [M+H]$^+$=304.26.

1-(3-Amino-4-methoxy-benzyl)-piperidine-4-carboxylic acid tert-butylamide BB-17

The title compound is prepared according to the reactions described for BB-5 above starting from 4-methoxy-3-nitro-benzaldehyde and piperidine-4-carboxylic acid tert-butylamide yielding after reductive amination 1-(4-methoxy-3-nitro-benzyl)-piperidine-4-carboxylic acid tert-butylamide; LC-MS A: $t_R$=0.60 min; [M+H]$^+$=350.22 followed by reduction with stannous chloride the title compound; LC-MS A: $t_R$=0.47 min; [M+H]$^+$=320.26.

1-(3-Amino-2-methyl-benzyl)-piperidine-4-carboxylic acid tert-butylamide BB-18

The title compound is prepared according to the reactions described for BB-5 above starting from 2-methyl-3-nitro-benzaldehyde and piperidine-4-carboxylic acid tert-butylamide yielding after reductive amination 1-(2-methyl-3-nitro-benzyl)-piperidine-4-carboxylic acid tert-butylamide; LC-MS A: $t_R$=0.62 min; [M+H]$^+$=334.32 followed by reduction with stannous chloride the title compound; LC-MS A: $t_R$=0.45 min; [M+H]$^+$=304.32.

1-(3-Amino-2-methoxy-benzyl)-piperidine-4-carboxylic acid tert-butylamide BB-19

The title compound is prepared according to the reactions described for BB-5 above starting from 2-methoxy-3-nitro-benzaldehyde and piperidine-4-carboxylic acid tert-butylamide yielding after reductive amination 1-(2-methoxy-3-nitro-benzyl)-piperidine-4-carboxylic acid tert-butylamide; LC-MS A: $t_R$=0.61 min; [M+H]$^+$=350.22 followed by reduction with stannous chloride the title compound; LC-MS A: $t_R$=0.52 min; [M+H]$^+$=320.27.

1-(3-Amino-5-methoxy-benzyl)-piperidine-4-carboxylic acid tert-butylamide BB-20

The title compound is prepared according to the reactions described for BB-5 above starting from 3-methoxy-5-nitro-benzaldehyde and piperidine-4-carboxylic acid tert-butylamide yielding after reductive amination 1-(3-methoxy-5-nitro-benzyl)-piperidine-4-carboxylic acid tert-butylamide; LC-MS A: $t_R$=0.63 min; [M+H]$^+$=350.14 followed by reduction with stannous chloride the title compound; LC-MS A: $t_R$=0.50 min; [M+H]$^+$=320.19.

rac-1-[1-(3-Amino-phenyl)-propyl]-piperidine-4-carboxylic acid cyclohexylamide BB-21 rac-1-[1-(3-Nitro-phenyl)-propyl]-piperidine-4-carboxylic acid cyclohexylamide A solution of α-ethyl-3-nitro-benzenemethanol (0.54 g, 2.98 mmol) in DCM (10 mL) is treated with PPh$_3$ (1.6 g, 6.1 mmol).) and CBr$_4$ (2 g, 6.03 mmol). The yellowish solution is stirred at RT for 2 h 30. Piperidine-4-carboxylic acid cyclohexylamide hydrochloride J-1 (0.82 g) is added at once, as well as DIPEA (2 mL). The RM is stirred at RT overnight then heated to 70° C. for 1H. The RM is evaporated under reduced pressure. The residue is partitioned between DCM (25 mL) and sat. aq. NaHCO$_3$ (25 mL). The organic layer is washed twice with sat. aq. NaHCO$_3$, dried over MgSO4 and evaporated under reduced pressure. The crude residue is purified by flash chromatography on silica gel using a gradient of DCM/MeOH/NH$_4$OH 95:5:1 to 90:10:1. After concentration of the product-containing fractions, the title compound (0.173 g, 16%) is obtained as a colorless solid LC-MS A: $t_R$=0.68 min; [M+H]$^+$=374.21.

rac-1-[1-(3-Amino-phenyl)-propyl]-piperidine-4-carboxylic acid cyclohexylamide The title compound is prepared according to the reaction described above by reduction of rac-1-[1-(3-nitro-phenyl)-propyl]-piperidine-4-carboxylic acid cyclohexylamide with stannous chloride; LC-MS A: $t_R$=0.58 min; [M+H]$^+$=344.27.

1-(3-Amino-5-methyl-benzyl)-piperidine-4-carboxylic acid tert-butylamide BB-22

1-(3-Methyl-5-nitro-benzyl)-piperidine-4-carboxylic acid tert-butylamide BB-22a Methylboronic acid (23.2 mg, 0.377 mmol) and a solution of 2 M Na$_2$CO$_3$ (0.088 mL, 0.502 mmol) is added to a solution of 1-(3-bromo-5-nitro-benzyl)-piperidine-4-carboxylic acid tert-butylamide BB-10a (100 mg, 0.251 mmol) in anhydrous toluene (3 mL) The mixture is purged under argon for 15 min. Tetrakis(triphenylphosphine)palladium (0) (58 mg, 0.0502 mmol) is added and the mixture is heated to 100° C. overnight. Water (10 mL) and AcOEt (10 mL) are added and the aqueous phase is extracted twice with AcOEt (10 mL). The combined organic phases are dried over MgSO4, filtered and concentrated under reduced pressure. The title compound is obtained by prep. LC-MS F as a colorless powder (61 mg, 73%); LC-MS A: $t_R$=0.63 min; [M+H]$^+$=334.24.

1-(3-Amino-5-methyl-benzyl)-piperidine-4-carboxylic acid tert-butylamide BB-22

The title compound is prepared according to the reaction described above by reduction of 1-(3-methyl-5-nitro-benzyl)-piperidine-4-carboxylic acid tert-butylamide BB-22a with stannous chloride; LC-MS A: $t_R$=0.47 min; [M+H]$^+$=304.24.

1-(3-Amino-4-ethyl-benzyl)-piperidine-4-carboxylic acid tert-butylamide BB-23

The title compound is prepared according to the reactions described for BB-5 above starting from 4-ethyl-3-nitro-benzaldehyde and piperidine-4-carboxylic acid tert-butylamide yielding after reductive amination 1-(4-ethyl-3-nitro-benzyl)-piperidine-4-carboxylic acid tert-butylamide; LC-MS A: $t_R$=0.67 min; [M+H]$^+$=348.18 followed by reduction with stannous chloride the title compound; LC-MS A: $t_R$=0.53 min; [M+H]$^+$=318.22.

1-(3-Amino-5-ethyl-benzyl)-piperidine-4-carboxylic acid tert-butylamide BB-24

The title compound is prepared according to the reactions described for BB-22 above starting from 1-(3-bromo-5- nitro-benzyl)-piperidine-4-carboxylic acid tert-butylamide BB-10a by treatment with ethylboronic acid to yield 1-(3-ethyl-5-nitro-benzyl)-piperidine-4-carboxylic acid tert-butylamide; LC-MS A: $t_R$=0.68 min; [M+H]$^+$=348.17, followed by reduction with stannous chloride the title compound; LC-MS A: $t_R$=0.51 min; [M+H]$^+$=318.28.

1-(5-Amino-2-ethyl-benzyl)-piperidine-4-carboxylic acid tert-butylamide BB-25

The title compound is prepared according to the reactions described above starting from 2-bromo-5-nitro-benzaldehyde and piperidine-4-carboxylic acid tert-butylamide yielding after reductive amination 1-(2-bromo-5-nitro-benzyl)-piperidine-4-carboxylic acid tert-butylamide; LC-MS A: $t_R$=0.62 min; [M+H]$^+$=397.99; followed by alkylation with ethylboronic acid yielding 1-(2-ethyl-5-nitro-benzyl)-piperidine-4-carboxylic acid tert-butylamide; LC-MS A: $t_R$=0.66 min; [M+H]$^+$=348.34, followed by reduction with stannous chloride the title compound; LC-MS A: $t_R$=0.49 min; [M+H]$^+$=318.21.

1-(3-Amino-benzyl)-piperidine-4-carboxylic acid (1,1-dimethyl-propyl)-amide BB-26

The title compound is prepared according to the reaction 1.001a and 1.001d described above using (3-formyl-phenyl)-carbamic acid tert-butyl ester and piperidine-4-carboxylic acid (1,1-dimethyl-propyl)-amide: LC-MS A: $t_R$=0.48 min; [M+H]$^+$=304.23.

Preparation of Building Blocks of General Formula 2

1-Oxy-6-trifluoromethyl-pyridine-2-carboxylic acid CC-1

6-Trifluoromethylpyridine-2-carboxylic acid (500 mg, 2.62 mmol) Is added to a solution obtained form trifluoroacetic acid 98% (4 mL) and aqueous hydrogen peroxide 35% (8 mL). The mixture is stirred overnight at 100° C. The RM is evaporated to dryness. The title compound is obtained as a yellowish solid LC-MS A: $t_R$=0.57 min; [M+H]$^+$=208.20.

1-Oxy-5-trifluoromethyl-pyridine-2-carboxylic acid CC-2

The title compound is prepared according to the preparation of CC-1 described above using 5-trifluoromethylpyridine-2-carboxylic acid as starting material: LC-MS A: $t_R$=0.50 min; [M+H]$^+$=208.04.

Example 1.001

1-[3-(4-Chloro-benzoylamino)-benzyl]-piperidine-4-carboxylic acid cyclohexylamide Method A
A solution of 1-(3-Amino-benzyl)-piperidine-4-carboxylic acid cyclohexylamide BB-1 (80 mg, 0.25 mmol) in DCM (3 mL) is treated with DIPEA (33 mg, 43 µl, 0.25 mmol) under argon and cooled to 0° C. A solution of 4-chlorobenzoylchloride (49 mg, 0.28 mmol) in DCM (1 mL) is added and the resulting solution is stirred at 0° C. for 2 h. The mixture is diluted with DCM (25 mL) and washed twice with aq. sat. NaHCO$_3$ (25 mL). The solvent is evaporated and the title compound is obtained by prep. LC-MS F as a colorless powder: LC-MS A: $t_R$=0.81 min; [M+H]$^+$=454.4. $^1$H-NMR (DMSO-d$_6$): δ 1-1.3 (m, 6H), 1.5-1.7 (m, 9H), 1.8-2.1 (m, 3H), 2.8-2.9 (m, 2H), 3.4-3.5 (m, 3H), 7.03 (d, J=8, 1H), 7.29 (t, J=8, 1H), 7.5-7.7 (m, 5H), 7.98 (d, J=8, 1H), 10.2 (s, 1H).

Example 1.002

6-Trifluoromethyl-pyridine-2-carboxylic acid [3-(4-cyclohexylcarbamoyl-piperidin-1-ylmethyl)-phenyl]-amide Method B
A solution of 6-trifluoromethylpyridine-2-carboxylic acid (19.1 mg, 0.1 mmol) in DMF (0.5 mL) is treated successively with a solution of 1-(3-Amino-benzyl)-piperidine-4-carboxylic acid cyclohexylamide BB-1 (36.3 mg, 0.1 mmol) in DMF (0.5 mL) and with POCl$_3$ (0.01 mL, 0.11 mmol) at RT. The resulting solution is stirred at RT for 30 min and heated at 80° C. for 1 h. The reaction mixture is treated with water (0.2 mL) and evaporated under HV. The title compound is obtained by prep. HPLC F as a colorless powder: LC-MS B: $t_R$=1.21 min; [M+H]$^+$=440.1. $^1$H-NMR (CDCl3): δ 1-1.3 (m, 6H), 1.5-2.1 (m, 12H), 2.3-2.4 (m, 1H), 3.0-3.1 (m, 2H), 3.4-3.5 (m, 1H) 5.4 (s broad, 1H), 7.16 (d, J=7, 1H), 7.37 (t, J=7, 1H), 7.67 (s, 1H), 7.79 (d, J=7.5, 1H), 7.90 (d, J=7.5, 1H), 8.15 (t, J=8, 1H), 8.53 (d, J=8, 1H) 9.81 (s, 1H).

Example 1.003

N-[3-(4-Cyclohexylcarbamoyl-piperidin-1-ylmethyl)-phenyl]-nicotinamide

Method C
To a solution of 1-(3-amino-benzyl)-piperidine-4-carboxylic acid cyclohexylamide BB-1 (200 mg, 0.57 mmol) in DCM (5 mL) are added successively nicotinic acid (70 mg, 0.57 mmol), HOBT (154 mg, 1.14 mmol), DMAP (14 mg, 0.11 mmol) and DIPEA (0.29 mL, 1.7 mmol). A solution of EDC hydrochloride (163 mg, 0.85 mmol) in DCM (2 mL) is added and the reaction mixture is stirred for 4 days at RT. The mixture is diluted with DCM (10 mL) and washed twice with sat.aq. NaHCO$_3$ (20 mL). The combined organic phases are dried over MgSO$_4$ and filtered. The solvent is evaporated under reduced pressure. The residue is dissolved in acetonitrile and purified by prep. HPLC E. LCMS C: $t_R$=0.56 min; [M+H]$^+$=421.4. $^1$H-NMR (DMSO-d$_6$): δ 1.1-1.3 (m, 5H), 1.5-1.7 (m, 9H), 1.8-1.9 (m, 2H), 2.0-2.1 (m, 1H), 2.84 (d, J=9, 2H), 3.4-3.5 (m, 3H), 7.03 (d, J=7, 1H), 7.30 (t, J=7, 1H), 7.5-7.8 (m, 4H), 8.29 (d, J=8, 1H), 8.7-8.8 (m, 1H), 9.11 (s, 1H), 10.4 (s, 1H).

Compounds of Examples 1.004-1.355 listed in Table 1 below are prepared by applying either one of the above-mentioned methods A, B or C described for Example 1.001, 1.002 or 1.003 to the building blocks BB-1-BB-26 coupled with commercially available acids or acid chlorides or with acids CC-1 and CC-2 of general formula 2.

TABLE 1

Examples 1.004-1.355

| Example | Compound | $t_R$ [min] (LC-MS Method) | MS Data m/z [M + H]$^+$ |
|---|---|---|---|
| 1.004 | 1-{3-[(4-Isobutyl-5-methyl-thiophene-2-carbonyl)-amino]-benzyl}-piperidine-4-carboxylic acid cyclohexylamide | 0.96 (LC-C) | 496.4 |
| 1.005 | 1-{3-[(5-Methyl-isoxazole-3-carbonyl)-amino]-benzyl}-piperidine-4-carboxylic acid cyclohexylamide | 0.69 (LC-C) | 425.4 |
| 1.006 | Pyrimidine-4-carboxylic acid [3-(4-cyclohexylcarbamoyl-piperidin-1-ylmethyl)-phenyl]-amide | 0.62 (LC-C) | 422.4 |
| 1.007 | 1-{3-[(Naphthalene-2-carbonyl)-amino]-benzyl}-piperidine-4-carboxylic acid cyclohexylamide | 0.85 (LC-C) | 470.4 |
| 1.008 | 1H-Indazole-3-carboxylic acid [3-(4-cyclohexylcarbamoyl-piperidin-1-ylmethyl)-phenyl]-amide | 0.75 (LC-C) | 460.3 |
| 1.009 | 1-[3-(2-Methoxy-benzoylamino)-benzyl]-piperidine-4-carboxylic acid cyclohexylamide | 0.77 (LC-C) | 450.4 |
| 1.010 | Isoquinoline-8-carboxylic acid [3-(4-cyclohexylcarbamoyl-piperidin-1-ylmethyl)-phenyl]amide | 0.54 (LC-5) | 471.4 |
| 1.011 | 1-(3-Phenylacetylamino-benzyl)-piperidine-4-carboxylic acid cyclohexylamide | 0.75 (LC-C) | 434.4 |
| 1.012 | 1-{3-[(Thiophene-3-carbonyl)-amino]-benzyl}-piperidine-4-carboxylic acid cyclohexylamide | 0.71 (LC-C) | 426.3 |
| 1.013 | 1-[3-(2-Pyridin-2-yl-acetylamino)-benzyl]-piperidine-4-carboxylic acid cyclohexylamide | 0.51 (LC-C) | 435.4 |
| 1.014 | 1-(3-Benzoylamino-benzyl)-piperidine-4-carboxylic acid cyclohexylamide | 0.73 (LC-C) | 420.4 |
| 1.015 | 1-[3-(2-Naphthalen-2-yl-acetylamino)-benzyl]-piperidine-4-carboxylic acid cyclohexylamide | 0.84 (LC-C) | 484.4 |
| 1.016 | 1-(3-Isobutyrylamino-benzyl)-piperidine-4-carboxylic acid cyclohexylamide | 0.67 (LC-C) | 386.4 |
| 1.017 | 1-[3-(Cyclopentanecarbonyl-amino)-benzyl]-piperidine-4-carboxylic acid cyclohexylamide | 0.75 (LC-C) | 412.4 |
| 1.018 | Rac-1-{3-[((1S,2R,4R)-Bicyclo[2.2.1]heptane-2-carbonyl)-amino]-benzyl}-piperidine-4-carboxylic acid cyclohexylamide | 0.81 (LC-C) | 438.4 |
| 1.019 | 1-[3-(3,5-Difluoro-benzoylamino)-benzyl]-piperidine-4-carboxylic acid cyclohexylamide | 0.79 (LC-C) | 456.4 |
| 1.020 | 1-[3-(3,3-Dimethyl-butyrylamino)-benzyl]-piperidine-4-carboxylic acid cyclohexylamide | 0.77 (LC-C) | 414.4 |
| 1.021 | Isoquinoline-1-carboxylic acid [3-(4-cyclohexylcarbamoyl-piperidin-1-ylmethyl)-phenyl]amide | 0.81 (LC-C) | 471.4 |
| 1.022 | Isoquinoline-4-carboxylic acid [3-(4-cyclohexylcarbamoyl-piperidin-1-ylmethyl)-phenyl]amide | 0.62 (LC-C) | 471.4 |
| 1.023 | 1-[3-(3-Methoxy-benzoylamino)-benzyl]-piperidine-4-carboxylic acid cyclohexylamide | 0.75 (LC-C) | 450.4 |
| 1.024 | 1-{3-[2-(3-Chloro-phenyl)-acetylamine]-benzyl}-piperidine-4-carboxylic acid cyclohexylamide | 0.82 (LC-C) | 468.3 |
| 1.025 | 1-{3-[2-(2-Chloro-phenyl)-acetylamine]-benzyl}-piperidine-4-carboxylic acid cyclohexylamide | 0.79 (LC-C) | 468.4 |
| 1.026 | 1-Methyl-1H-indole-3-carboxylic acid [3-(4-cyclohexylcarbamoyl-piperidin-1-ylmethyl)-phenyl]amide | 0.80 (LC-C) | 473.4 |
| 1.027 | 1H-Indole-3-carboxylic acid [3-(4-cyclohexylcarbamoyl-piperidin-1-ylmethyl)-phenyl]amide | 0.74 (LC-C) | 459.4 |
| 1.028 | 1-{3-[(Benzofuran-3-carbonyl)-amino]-benzyl}-piperidine-4-carboxylic acid cyclohexylamide | 0.81 (LC-C) | 460.4 |
| 1.029 | rac-1-{3-[(-2-Phenyl-cyclopropanecarbonyl)-amino]-benzyl}-piperidine-4-carboxylic acid cyclohexylamide | 0.83 (LC-C) | 460.4 |
| 1.030 | 1-{3-[2-(1-Methyl-1H-indol-3-yl)-acetylamino]-benzyl}-piperidine-4-carboxylic acid cyclohexylamide | 0.82 (LC-C) | 487.4 |
| 1.031 | 1-[3-(4-Methoxy-benzoylamino)-benzyl]-piperidine-4-carboxylic acid cyclohexylamide | 0.74 (LC-C) | 450.4 |
| 1.032 | 1-[3-(4-tert-Butyl-benzoylamino)-benzyl]-piperidine-4-carboxylic acid cyclohexylamide | 0.92 (LC-C) | 476.5 |
| 1.033 | 1-[3-(3-Chloro-benzoylamino)-benzyl]-piperidine-4-carboxylic acid cyclohexylamide | 0.81 (LC-C) | 454.3 |
| 1.034 | 1-[3-(3-Phenyl-propionylamino)-benzyl]-piperidine-4-carboxylic acid cyclohexylamide | 0.79 (LC-C) | 448.4 |
| 1.035 | 1-{3-[2-(2-Methoxy-phenyl)-acetylamino]-benzyl}-piperidine-4-carboxylic acid cyclohexylamide | 0.77 (LC-C) | 464.4 |
| 1.036 | rac-1-[3-(3-Methyl-2-phenyl-butyrylamino)-benzyl]-piperidine-4-carboxylic acid cyclohexylamide | 0.88 (LC-C) | 476.5 |
| 1.037 | 1-{3-[2-(4-Chloro-phenyl)-acetylamine]-benzyl}-piperidine-4-carboxylic acid cyclohexylamide | 0.82 (LC-C) | 468.4 |
| 1.038 | 1-{3-[(1H-Imidazole-2-carbonyl)-amino]-benzyl}-piperidine-4-carboxylic acid cyclohexylamide | 0.58 (LC-C) | 410.3 |
| 1.039 | Pyridine-2-carboxylic acid [3-(4-cyclohexylcarbamoyl-piperidin-1-ylmethyl)-phenyl]-amide | 0.70 (LC-C) | 421.4 |
| 1.040 | 1-{3-[(3H-Imidazole-4-carbonyl)-amino]-benzyl}-piperidine-4-carboxylic acid cyclohexylamide | 0.52 (LC-C) | 410.4 |

TABLE 1-continued

Examples 1.004-1.355

| Example | Compound | $t_R$ [min] (LC-MS Method) | MS Data m/z [M + H]$^+$ |
|---|---|---|---|
| 1.041 | 1-[3-(4-Isobutyl-benzoylamino)-benzyl]-piperidine-4-carboxylic acid cyclohexylamide | 0.94 (LC-C) | 476.4 |
| 1.042 | 1-{3-[2-(4-Methoxy-phenyl)-acetylamino]-benzyl}-piperidine-4-carboxylic acid cyclohexylamide | 0.75 (LC-C) | 464.5 |
| 1.043 | 1-[3-(2-Cyclohexyl-acetylamino)-benzyl]-piperidine-4-carboxylic acid cyclohexylamide | 0.85 (LC-C) | 440.4 |
| 1.044 | 1-{3-[(1H-Pyrazole-4-carbonyl)-amino]-benzyl}-piperidine-4-carboxylic acid cyclohexylamide | 0.57 (LC-C) | 410.3 |
| 1.045 | 1-[3-(3-1H-Benzoimidazol-2-yl-propionylamino)-benzyl]-piperidine-4-carboxylic acid cyclohexylamide | 0.57 (LC-C) | 488.5 |
| 1.046 | 1-{3-[(1H-Pyrrole-2-carbonyl)-amino]-benzyl}-piperidine-4-carboxylic acid cyclohexylamide | 0.66 (LC-C) | 409.4 |
| 1.047 | 1-{3-[2-(3-Methoxy-phenyl)-acetylamino]-benzyl}-piperidine-4-carboxylic acid cyclohexylamide | 0.76 (LC-C) | 464.4 |
| 1.048 | 1-{3-[(Naphthalene-1-carbonyl)-amino]-benzyl}-piperidine-4-carboxylic acid cyclohexylamide | 0.82 (LC-C) | 470.4 |
| 1.049 | 1-{3-[(Isoxazole-5-carbonyl)-amino]-benzyl}-piperidine-4-carboxylic acid cyclohexylamide | 0.63 (LC-C) | 411.4 |
| 1.050 | 1-[3-(2-Chloro-benzoylamino)-benzyl]-piperidine-4-carboxylic acid cyclohexylamide | 0.75 (LC-C) | 454.3 |
| 1.051 | 1-{3-[(1-Methyl-1H-imidazole-4-carbonyl)-amino]-benzyl}-piperidine-4-carboxylic acid cyclohexylamide | 0.55 (LC-C) | 424.3 |
| 1.052 | 1-[3-(2-Indan-2-yl-acetylamino)-benzyl]-piperidine-4-carboxylic acid cyclohexylamide | 0.86 (LC-C) | 474.4 |
| 1.053 | N-[3-(4-Cyclohexylcarbamoyl-piperidin-1-ylmethyl)-phenyl]-isonicotinamide | 0.55 (LC-C) | 421.4 |
| 1.054 | N-[3-(4-Cyclohexylcarbamoyl-piperidin-1-ylmethyl)-phenyl]-2-cyclopentyl-6-methyl-isonicotinamide | 0.65 (LC-C) | 503.5 |
| 1.055 | N-[3-(4-Cyclohexylcarbamoyl-piperidin-1-ylmethyl)-phenyl]-2-methyl-isonicotinamide | 0.54 (LC-C) | 435.4 |
| 1.056 | N-[3-(4-Cyclohexylcarbamoyl-piperidin-1-ylmethyl)-phenyl]-5-fluoro-nicotinamide | 0.67 (LC-C) | 439.4 |
| 1.057 | 5-Fluoro-pyridine-2-carboxylic acid [3-(4-cyclohexylcarbamoyl-piperidin-1-ylmethyl)-phenyl]-amide | 0.70 (LC-C) | 439.37 |
| 1.058 | N-[3-(4-Cyclohexylcarbamoyl-piperidin-1-ylmethyl)-phenyl]-5-trifluoromethyl-nicotinamide | 0.77 (LC-C) | 489.4 |
| 1.059 | N-[3-(4-Cyclohexylcarbamoyl-piperidin-1-ylmethyl)-phenyl]-2-trifluoromethyl-nicotinamide | 0.72 (LC-C) | 489.3 |
| 1.060 | N-[3-(4-Cyclohexylcarbamoyl-piperidin-1-ylmethyl)-phenyl]-5-methyl-nicotinamide) | 0.59 (LC-C) | 435.4 |
| 1.061 | 3-Methyl-pyridine-2-carboxylic acid [3-(4-cyclohexylcarbamoyl-piperidin-1-ylmethyl)-phenyl]-amide | 0.76 (LC-C) | 435.4 |
| 1.062 | 2,6-Dimethoxy-pyrimidine-4-carboxylic acid [3-(4-cyclohexylcarbamoyl-piperidin-1-ylmethyl)-phenyl]-amide | 0.82 (LC-C) | 482.4 |
| 1.063 | N-[3-(4-Cyclohexylcarbamoyl-piperidin-1-ylmethyl)-phenyl]-4-methyl-nicotinamide | 0.56 (LC-C) | 435.4 |
| 1.064 | N-[3-(4-Cyclohexylcarbamoyl-piperidin-1-ylmethyl)-phenyl]-6-methyl-nicotinamide | 0.56 (LC-C) | 435.4 |
| 1.065 | N-[3-(4-Cyclohexylcarbamoyl-piperidin-1-ylmethyl)-phenyl]-2-methyl-nicotinamide | 0.54 (LC-C) | 435.4 |
| 1.066 | 2-Chloro-N-[3-(4-cyclohexylcarbamoyl-piperidin-1-ylmethyl)-phenyl]-nicotinamide | 0.67 (LC-C) | 455.4 |
| 1.067 | 6-Chloro-N-[3-(4-cyclohexylcarbamoyl-piperidin-1-ylmethyl)-phenyl]-nicotinamide | 0.73 (LC-C) | 455.3 |
| 1.068 | N-[3-(4-Cyclohexylcarbamoyl-piperidin-1-ylmethyl)-phenyl]-6-trifluoromethyl-nicotinamide | 0.8 (LC-C) | 489.4 |
| 1.069 | N-[3-(4-Cyclohexylcarbamoyl-piperidin-1-ylmethyl)-phenyl]-2-methoxy-nicotinamide | 0.75 (LC-C) | 451.4 |
| 1.070 | 2-Chloro-N-[3-(4-cyclohexylcarbamoyl-piperidin-1-ylmethyl)-phenyl]-6-methyl-nicotinamide | 0.71 (LC-C) | 469.4 |
| 1.071 | N-[3-(4-Cyclohexylcarbamoyl-piperidin-1-ylmethyl)-phenyl]-6-diethylamino-nicotinamide | 0.62 (LC-C) | 492.5 |
| 1.072 | N-[3-(4-Cyclohexylcarbamoyl-piperidin-1-ylmethyl)-phenyl]-6-(4-methyl-piperazin-1-yl)-nicotinamide | 0.56 (LC-C) | 519.44 |
| 1.073 | N-[3-(4-Cyclohexylcarbamoyl-piperidin-1-ylmethyl)-phenyl]-2-morpholin-4-yl-nicotinamide | 0.65 (LC-C) | 506.4 |
| 1.074 | 3-Chloro-N-[3-(4-cyclohexylcarbamoyl-piperidin-1-ylmethyl)-phenyl]-isonicotinamide | 0.67 (LC-C) | 455.3 |
| 1.075 | 2-Chloro-N-[3-(4-cyclohexylcarbamoyl-piperidin-1-ylmethyl)-phenyl]-6-methoxy-isonicotinamide | 0.84 (LC-C) | 485.4 |
| 1.076 | 1H-Pyrrolo[2,3-b]pyridine-5-carboxylic acid [3-(4-cyclohexylcarbamoyl-piperidin-1-ylmethyl)-phenyl]-amide | 0.66 (LC-C) | 460.4 |
| 1.077 | 4-Chloro-pyridine-2-carboxylic acid [3-(4-cyclohexylcarbamoyl-piperidin-1-ylmethyl)-phenyl]-amide | 0.81 (LC-C) | 455.4 |

TABLE 1-continued

Examples 1.004-1.355

| Example | Compound | $t_R$ [min] (LC-MS Method) | MS Data m/z [M + H]+ |
|---|---|---|---|
| 1.078 | 6-Chloro-pyridine-2-carboxylic acid [3-(4-cyclohexylcarbamoyl-piperidin-1-ylmethyl)-phenyl]-amide | 0.8 (LC-C) | 455.4 |
| 1.079 | rac-1-[3-(2-Phenyl-propionylamino)-benzyl]-piperidine-4-carboxylic acid tert-butylamide | 0.75 (LC-C) | 422.5 |
| 1.080 | 1-Oxy-pyridine-2-carboxylic acid [3-(4-cyclohexylcarbamoyl-piperidin-1-ylmethyl)-phenyl]amide | 0.64 (LC-C) | 437.4 |
| 1.081 | 6-Methyl-pyridine-2-carboxylic acid [3-(4-cyclohexylcarbamoyl-piperidin-1-ylmethyl)-phenyl]amide | 0.78 (LC-C) | 435.4 |
| 1.082 | 4-Methyl-pyridine-2-carboxylic acid [3-(4-cyclohexylcarbamoyl-piperidin-1-ylmethyl)-phenyl]amide | 0.77 (LC-C) | 435.4 |
| 1.083 | 4,6-Dimethyl-pyridine-2-carboxylic acid [3-(4-cyclohexylcarbamoyl-piperidin-1-ylmethyl)-phenyl]amide | 0.82 (LC-C) | 449.4 |
| 1.084 | 5-Pyrrolidin-1-yl-pyridine-2-carboxylic acid [3-(4-cyclohexylcarbamoyl-piperidin-1-ylmethyl)-phenyl]amide | 0.85 (LC-C) | 490.5 |
| 1.085 | 3-Bromo-pyridine-2-carboxylic acid [3-(4-cyclohexylcarbamoyl-piperidin-1-ylmethyl)-phenyl]amide | 0.73 (LC-C) | 499.3 |
| 1.086 | 4-Methyl-pyrimidine-5-carboxylic acid [3-(4-cyclohexylcarbamoyl-piperidin-1-ylmethyl)-phenyl]amide | 0.61 (LC-C) | 436.4 |
| 1.087 | Pyrimidine-2-carboxylic acid [3-(4-cyclohexylcarbamoyl-piperidin-1-ylmethyl)-phenyl]amide | 0.61 (LC-C) | 422.4 |
| 1.088 | 2-Dimethylamino-6-methyl-pyrimidine-4-carboxylic acid [3-(4-cyclohexylcarbamoyl-piperidin-1-ylmethyl)-phenyl]amide | 0.84 (LC-C) | 479.4 |
| 1.089 | 2,6-Dichloro-N-[3-(4-cyclohexylcarbamoyl-piperidin-1-ylmethyl)-phenyl]-5-fluoro-nicotinamide | 0.83 (LC-C) | 507.3 |
| 1.090 | 5,6-Dichloro-N-[3-(4-cyclohexylcarbamoyl-piperidin-1-ylmethyl)-phenyl]-nicotinamide | 0.83 (LC-C) | 489.3 |
| 1.091 | 2,6-Dichloro-N-[3-(4-cyclohexylcarbamoyl-piperidin-1-ylmethyl)-phenyl]-nicotinamide | 0.78 (LC-C) | 489.3 |
| 1.092 | N-[3-(4-Cyclohexylcarbamoyl-piperidin-1-ylmethyl)-phenyl]-6-methoxy-nicotinamide | 0.72 (LC-C) | 451.4 |
| 1.093 | 1H-Pyrrolo[3,2-b]pyridine-6-carboxylic acid [3-(4-cyclohexylcarbamoyl-piperidin-1-ylmethyl)-phenyl]-amide | 0.54 (LC-C) | 460.4 |
| 1.094 | 5-Chloro-pyridine-2-carboxylic acid [3-(4-cyclohexylcarbamoyl-piperidin-1-ylmethyl)-phenyl]-amide | 0.82 (LC-C) | 455.3 |
| 1.095 | 1-[3-(2-Trifluoromethoxy-benzoylamino)-benzyl]-piperidine-4-carboxylic acid cyclohexylamide | 0.83 (LC-C) | 504.4 |
| 1.096 | 1-[3-(4-Dimethylamino-benzoylamino)-benzyl]-piperidine-4-carboxylic acid cyclohexylamide | 0.78 (LC-C) | 463.5 |
| 1.097 | 1-[3-(4-Ethyl-benzoylamino)-benzyl]-piperidine-4-carboxylic acid cyclohexylamide | 0.87 (LC-C) | 448.4 |
| 1.098 | 1-[3-(4-Isopropyl-benzoylamino)-benzyl]-piperidine-4-carboxylic acid cyclohexylamide | 0.92 (LC-C) | 462.4 |
| 1.099 | 1-[3-(2-Methyl-benzoylamino)-benzyl]-piperidine-4-carboxylic acid cyclohexylamide | 0.78 (LC-C) | 434.4 |
| 1.100 | 1-[3-(3-Methyl-benzoylamino)-benzyl]-piperidine-4-carboxylic acid cyclohexylamide | 0.81 (LC-C) | 434.4 |
| 1.101 | 1-[3-(4-Methyl-benzoylamino)-benzyl]-piperidine-4-carboxylic acid cyclohexylamide | 0.81 (LC-C) | 434.4 |
| 1.102 | 1-[3-(2-Fluoro-benzoylamino)-benzyl]-piperidine-4-carboxylic acid cyclohexylamide | 0.75 (LC-C) | 438.4 |
| 1.103 | 1-[3-(3-Fluoro-benzoylamino)-benzyl]-piperidine-4-carboxylic acid cyclohexylamide | 0.78 (LC-C) | 546.4 |
| 1.104 | 1-[3-(3-Trifluoromethyl-benzoylamino)-benzyl]-piperidine-4-carboxylic acid cyclohexylamide | 0.88 (LC-C) | 488.4 |
| 1.105 | 1-[3-(4-Trifluoromethyl-benzoylamino)-benzyl]-piperidine-4-carboxylic acid cyclohexylamide | 0.88 (LC-C) | 488.3 |
| 1.106 | 1-[3-(3-Cyano-benzoylamino)-benzyl]-piperidine-4-carboxylic acid cyclohexylamide | 0.74 (LC-C) | 445.4 |
| 1.107 | 1-[3-(4-Cyano-benzoylamino)-benzyl]-piperidine-4-carboxylic acid cyclohexylamide | 0.74 (LC-C) | 445.4 |
| 1.108 | 1-[3-(2,6-Dimethyl-benzoylamino)-benzyl]-piperidine-4-carboxylic acid cyclohexylamide | 0.8 (LC-C) | 448.4 |
| 1.109 | 1-[3-(2,3-Dimethyl-benzoylamino)-benzyl]-piperidine-4-carboxylic acid cyclohexylamide | 0.82 (LC-C) | 448.4 |
| 1.110 | 1-[3-(2,5-Dimethyl-benzoylamino)-benzyl]-piperidine-4-carboxylic acid cyclohexylamide | 0.83 (LC-C) | 448.4 |
| 1.111 | 1-[3-(2,4-Dimethyl-benzoylamino)-benzyl]-piperidine-4-carboxylic acid cyclohexylamide | 0.83 (LC-C) | 448.4 |
| 1.112 | 1-[3-(3,5-Dimethyl-benzoylamino)-benzyl]-piperidine-4-carboxylic acid cyclohexylamide | 0.87 (LC-C) | 448.4 |
| 1.113 | 1-[3-(3,4-Dimethyl-benzoylamino)-benzyl]-piperidine-4-carboxylic acid cyclohexylamide | 0.86 (LC-C) | 448.4 |
| 1.114 | 1-[3-(3-Fluoro-2-methyl-benzoylamino)-benzyl]-piperidine-4-carboxylic acid cyclohexylamide | 0.8 (LC-C) | 452.4 |

TABLE 1-continued

Examples 1.004-1.355

| Example | Compound | $t_R$ [min] (LC-MS Method) | MS Data m/z [M + H]+ |
|---|---|---|---|
| 1.115 | 1-[3-(4-Fluoro-2-methyl-benzoylamino)-benzyl]-piperidine-4-carboxylic acid cyclohexylamide | 0.8 (LC-C) | 452.4 |
| 1.116 | 1-[3-(2-Fluoro-5-methyl-benzoylamino)-benzyl]-piperidine-4-carboxylic acid cyclohexylamide | 0.82 (LC-C) | 452.4 |
| 1.117 | 1-[3-(3-Fluoro-5-methyl-benzoylamino)-benzyl]-piperidine-4-carboxylic acid cyclohexylamide | 0.84 (LC-C) | 452.4 |
| 1.118 | 1-[3-(4-Fluoro-3-methyl-benzoylamino)-benzyl]-piperidine-4-carboxylic acid cyclohexylamide | 0.83 (LC-C) | 452.4 |
| 1.119 | 1-[3-(2-Fluoro-4-methyl-benzoylamino)-benzyl]-piperidine-4-carboxylic acid cyclohexylamide | 0.82 (LC-C) | 452.4 |
| 1.120 | 1-[3-(3-Chloro-2-methyl-benzoylamino)-benzyl]-piperidine-4-carboxylic acid cyclohexylamide | 0.85 (LC-C) | 468.3 |
| 1.121 | 1-[3-(4-Chloro-2-methyl-benzoylamino)-benzyl]-piperidine-4-carboxylic acid cyclohexylamide | 0.86 (LC-C) | 468.3 |
| 1.122 | 1-[3-(4-Methoxy-3-methyl-benzoylamino)-benzyl]-piperidine-4-carboxylic acid cyclohexylamide | 0.84 (LC-C) | 464.4 |
| 1.123 | 1-[3-(3-Fluoro-4-methoxy-benzoylamino)-benzyl]-piperidine-4-carboxylic acid cyclohexylamide | 0.79 (LC-C) | 468.4 |
| 1.124 | 1-[3-(3-Fluoro-5-methoxy-benzoylamino)-benzyl]-piperidine-4-carboxylic acid cyclohexylamide | 0.82 (LC-C) | 468.3 |
| 1.125 | 1-[3-(3,5-Dimethoxy-benzoylamino)-benzyl]-piperidine-4-carboxylic acid cyclohexylamide | 0.81 (LC-C) | 480.4 |
| 1.126 | 1-[3-(3,4-Dimethoxy-benzoylamino)-benzyl]-piperidine-4-carboxylic acid cyclohexylamide | 0.74 (LC-C) | 480.4 |
| 1.127 | 1-[3-(2,6-Difluoro-benzoylamino)-benzyl]-piperidine-4-carboxylic acid cyclohexylamide | 0.75 (LC-C) | 456.4 |
| 1.128 | 1-[3-(2,3-Difluoro-benzoylamino)-benzyl]-piperidine-4-carboxylic acid cyclohexylamide | 0.78 (LC-C) | 456.4 |
| 1.129 | 1-[3-(3,4-Difluoro-benzoylamino)-benzyl]-piperidine-4-carboxylic acid cyclohexylamide | 0.8 (LC-C) | 456.4 |
| 1.130 | 1-[3-(4-Chloro-2-fluoro-benzoylamino)-benzyl]-piperidine-4-carboxylic acid cyclohexylamide | 0.83 (LC-C) | 472.3 |
| 1.131 | 1-[3-(3-Chloro-5-fluoro-benzoylamino)-benzyl]-piperidine-4-carboxylic acid cyclohexylamide | 0.87 (LC-C) | 472.3 |
| 1.132 | 1-[3-(4-Chloro-3-fluoro-benzoylamino)-benzyl]-piperidine-4-carboxylic acid cyclohexylamide | 0.86 (LC-C) | 472.3 |
| 1.133 | 1-[3-(2-Chloro-4-fluoro-benzoylamino)-benzyl]-piperidine-4-carboxylic acid cyclohexylamide | 0.8 (LC-C) | 472.3 |
| 1.134 | 1-[3-(2-Fluoro-4-trifluoromethyl-benzoylamino)-benzyl]-piperidine-4-carboxylic acid cyclohexylamide | 0.88 (LC-C) | 506.4 |
| 1.135 | 1-[3-(2-Fluoro-5-trifluoromethyl-benzoylamino)-benzyl]-piperidine-4-carboxylic acid cyclohexylamide | 0.87 (LC-C) | 506.4 |
| 1.136 | 1-[3-(3,5-Bis-trifluoromethyl-benzoylamino)-benzyl]-piperidine-4-carboxylic acid cyclohexylamide | 0.98 (LC-C) | 556.4 |
| 1.137 | 1-[3-(2,5-Dichloro-benzoylamino)-benzyl]-piperidine-4-carboxylic acid cyclohexylamide | 0.84 (LC-C) | 488.3 |
| 1.138 | 1-[3-(2,4-Dichloro-benzoylamino)-benzyl]-piperidine-4-carboxylic acid cyclohexylamide | 0.85 (LC-C) | 488.4 |
| 1.139 | 1-[3-(3,5-Dichloro-benzoylamino)-benzyl]-piperidine-4-carboxylic acid cyclohexylamide | 0.92 (LC-C) | 488.3 |
| 1.140 | 1-[3-(3,4-Dichloro-benzoylamino)-benzyl]-piperidine-4-carboxylic acid cyclohexylamide | 0.9 (LC-C) | 488.3 |
| 1.141 | Pyrazine-2-carboxylic acid [3-(4-cyclohexylcarbamoyl-piperidin-1-ylmethyl)-phenyl]-amide | 0.65 (LC-C) | 422.4 |
| 1.142 | 5-Methyl-pyrazine-2-carboxylic acid [3-(4-cyclohexylcarbamoyl-piperidin-1-ylmethyl)-phenyl]-amide | 0.68 (LC-C) | 436.4 |
| 1.143 | 1-{3-[(7-Chloro-2,3-dihydro-benzofuran-4-carbonyl)-amino]-benzyl}-piperidine-4-carboxylic acid cyclohexylamide | 0.86 (LC-C) | 496.3 |
| 1.144 | 1-[3-(3-Dimethylamino-benzoylamino)-benzyl]-piperidine-4-carboxylic acid cyclohexylamide | 0.68 (LC-C) | 463.4 |
| 1.145 | 1-[3-(2-Fluoro-6-trifluoromethyl-benzoylamino)-benzyl]-piperidine-4-carboxylic acid cyclohexylamide | 0.81 (LC-C) | 506.4 |
| 1.146 | 1H-Pyrrolo[2,3-b]pyridine-2-carboxylic acid [3-(4-cyclohexylcarbamoyl-piperidin-1-ylmethyl)-phenyl]-amide | 0.64 (LC-C) | 460.4 |
| 1.147 | N-[3-(4-Cyclohexylcarbamoyl-piperidin-1-ylmethyl)-phenyl]-5-cyclopropyl-nicotinamide | 0.64 (LC-C) | 461.4 |
| 1.148 | 1-{3-[4-(2-Fluoro-ethyl)-benzoylamino]-benzyl}-piperidine-4-carboxylic acid cyclohexylamide | 0.78 (LC-C) | 466.4 |
| 1.149 | 1-[3-(Cyclopropanecarbonyl-amino)-benzyl]-piperidine-4-carboxylic acid cyclohexylamide | 0.66 (LC-C) | 384.4 |
| 1.150 | 1-[3-(Cyclobutanecarbonyl-amino)-benzyl]-piperidine-4-carboxylic acid cyclohexylamide | 0.7 (LC-C) | 398.4 |
| 1.151 | 1-[3-(Cyclohexanecarbonyl-amino)-benzyl]-piperidine-4-carboxylic acid cyclohexylamide | 0.8 (LC-C) | 426.4 |

TABLE 1-continued

Examples 1.004-1.355

| Example | Compound | $t_R$ [min] (LC-MS Method) | MS Data m/z [M + H]+ |
|---|---|---|---|
| 1.152 | 1-[3-(Cycloheptanecarbonyl-amino)-benzyl]-piperidine-4-carboxylic acid cyclohexylamide | 0.85 (LC-C) | 440.4 |
| 1.153 | 1-[3-(4-Pentafluoroethyl-benzoylamino)-benzyl]-piperidine-4-carboxylic acid cyclohexylamide | 0.81 (LC-C) | 538.0 |
| 1.154 | N-[3-(4-Cyclohexylcarbamoyl-piperidin-1-ylmethyl)-phenyl]-5-ethyl-nicotinamide | 0.62 (LC-C) | 449.4 |
| 1.155 | 4-Trifluoromethyl-pyridine-2-carboxylic acid [3-(4-cyclohexylcarbamoyl-piperidin-1-ylmethyl)-phenyl]-amide | 0.84 (LC-C) | 489.4 |
| 1.156 | 1-[3-(4-Fluoro-benzoylamino)-benzyl]-piperidine-4-carboxylic acid cyclohexylamide | 0.77 (LC-C) | 438.4 |
| 1.157 | Pyrimidine-4-carboxylic acid [2-chloro-5-(4-cyclohexylcarbamoyl-piperidin-1-ylmethyl)-phenyl]-amide | 0.74 (LC-C) | 456.4 |
| 1.158 | 1-{4-Chloro-3-[(5-methyl-thiophene-2-carbonyl)-amino]-benzyl}-piperidine-4-carboxylic acid cyclohexylamide | 0.85 (LC-C) | 474.3 |
| 1.159 | 1-[4-Chloro-3-(4-methoxy-benzoylamino)-benzyl]-piperidine-4-carboxylic acid cyclohexylamide | 0.83 (LC-C) | 484.4 |
| 1.160 | 1-[4-Chloro-3-(4-chloro-benzoylamino)-benzyl]-piperidine-4-carboxylic acid cyclohexylamide | 0.88 LC-2) | 488.3 |
| 1.161 | 1-{4-Chloro-3-[(2-phenyl-cyclopropanecarbonyl)-amino]-benzyl}-piperidine-4-carboxylic acid cyclohexylamide | 0.84 (LC-C) | 489.4 |
| 1.162 | 1-[2-Chloro-3-(4-chloro-benzoylamino)-benzyl]-piperidine-4-carboxylic acid cyclohexylamide | 0.83 (LC-C) | 488.3 |
| 1.163 | 1-{2-Chloro-3-[(5-methyl-thiophene-2-carbonyl)-amino]-benzyl}-piperidine-4-carboxylic acid cyclohexylamide | 0.78 (LC-C) | 474.3 |
| 1.164 | 1-{1-[3-(4-Chloro-benzoylamino)-phenyl]-ethyl}-piperidine-4-carboxylic acid cyclohexylamide | 0.84 (LC-C) | 468.3 |
| 1.165 | 1-[1-(3-Benzoylamino-phenyl)-ethyl]-piperidine-4-carboxylic acid cyclohexylamide | 0.76 (LC-C) | 434.4 |
| 1.166 | 1-{1-[3-(4-Fluoro-benzoylamino)-phenyl]-ethyl}-piperidine-4-carboxylic acid cyclohexylamide | 0.79 (LC-C) | 452.4 |
| 1.167 | 1-{1-[3-(4-Methoxy-benzoylamino)-phenyl]-ethyl}-piperidine-4-carboxylic acid cyclohexylamide | 0.77 (LC-C) | 464.4 |
| 1.168 | rac-5-Chloro-pyridine-2-carboxylic acid {3-[1-(4-cyclohexylcarbamoyl-piperidin-1-yl)-ethyl]-phenyl}-amide | 0.82 (LC-C) | 469.3 |
| 1.169 | rac-Pyridine-2-carboxylic acid {3-[1-(4-cyclohexylcarbamoyl-piperidin-1-yl)-ethyl]-phenyl}-amide | 0.74 (LC-C) | 435.4 |
| 1.170 | rac-Pyrazine-2-carboxylic acid {3-[1-(4-cyclohexylcarbamoyl-piperidin-1-yl)-ethyl]-phenyl}-amide | 0.66 (LC-C) | 436.4 |
| 1.171 | rac-N-{3-[1-(4-Cyclohexylcarbamoyl-piperidin-1-yl)-ethyl]-phenyl}-nicotinamide | 0.58 (LC-C) | 435.4 |
| 1.172 | rac-N-{3-[1-(4-Cyclohexylcarbamoyl-piperidin-1-yl)-ethyl]-phenyl}-5-methyl-nicotinamide | 0.59 (LC-C) | 449.4 |
| 1.173 | rac-1-(1-{3-[2-(3-Trifluoromethyl-phenyl)-acetylamino]-phenyl}-ethyl)-piperidine-4-carboxylic acid cyclohexylamide | 0.89 (LC-C) | 516.4 |
| 1.174 | rac-3-Chloro-N-{3-[1-(4-cyclohexylcarbamoyl-piperidin-1-yl)-ethyl]-phenyl}-isonicotinamide | 0.68 (LC-C) | 469.4 |
| 1.175 | rac-1-(1-{3-[2-(4-Methoxy-phenoxy)-acetylamino]-phenyl}-ethyl)-piperidine-4-carboxylic acid cyclohexylamide | 0.81 (LC-C) | 494.4 |
| 1.176 | rac-N-{3-[1-(4-Cyclohexylcarbamoyl-piperidin-1-yl)-ethyl]-phenyl}-isonicotinamide | 0.56 (LC-C) | 435.4 |
| 1.177 | rac-1-{1-[3-(4-Trifluoromethyl-benzoylamino)-phenyl]-ethyl}-piperidine-4-carboxylic acid cyclohexylamide | 0.88 (LC-C) | 502.4 |
| 1.178 | rac-1-{1-[3-(4-Cyano-benzoylamino)-phenyl]-ethyl}-piperidine-4-carboxylic acid cyclohexylamide | 0.74 (LC-C) | 459.4 |
| 1.179 | rac-1-{1-[3-(3-Cyano-benzoylamino)-phenyl]-ethyl}-piperidine-4-carboxylic acid cyclohexylamide | 0.75 (LC-C) | 459.4 |
| 1.180 | rac-4-Chloro-pyridine-2-carboxylic acid {3-[1-(4-cyclohexylcarbamoyl-piperidin-1-yl)-ethyl]-phenyl}-amide | 0.82 (LC-C) | 469.3 |
| 1.181 | rac-N-{3-[1-(4-Cyclohexylcarbamoyl-piperidin-1-yl)-ethyl]-phenyl}-6-methyl-nicotinamide | 0.57 (LC-C) | 449.4 |
| 1.182 | rac-6-Methyl-pyridine-2-carboxylic acid {3-[1-(4-cyclohexylcarbamoyl-piperidin-1-yl)-ethyl]-phenyl}-amide | 0.79 (LC-C) | 449.4 |
| 1.183 | rac-N-{3-[1-(4-Cyclohexylcarbamoyl-piperidin-1-yl)-ethyl]-phenyl}-6-trifluoromethyl-nicotinamide | 0.81 (LC-C) | 503.4 |
| 1.184 | rac-N-{3-[1-(4-Cyclohexylcarbamoyl-piperidin-1-yl)-ethyl]-phenyl}-2-methyl-isonicotinamide | 0.55 (LC-C) | 449.4 |
| 1.185 | rac-5-Methyl-pyrazine-2-carboxylic acid {3-[1-(4-cyclohexylcarbamoyl-piperidin-1-yl)-ethyl]-phenyl}-amide | 0.7 (LC-C) | 450.4 |
| 1.186 | rac-1-Isopropyl-6-methyl-1H-pyrazolo[3,4-b]pyridine-4-carboxylic acid {3-[1-(4-cyclohexylcarbamoyl-piperidin-1-yl)-ethyl]-phenyl}-amide | 0.86 (LC-C) | 531.4 |
| 1.187 | rac-6-Trifluoromethyl-pyridine-2-carboxylic acid {3-[1-(4-cyclohexylcarbamoyl-piperidin-1-yl)-ethyl]-phenyl}-amide | 0.86 (LC-C) | 503.4 |
| 1.188 | rac-5-Pyrrolidin-1-yl-pyridine-2-carboxylic acid {3-[1-(4-cyclohexylcarbamoyl-piperidin-1-yl)-ethyl]-phenyl}-amide | 0.85 (LC-C) | 504.4 |

TABLE 1-continued

Examples 1.004-1.355

| Example | Compound | $t_R$ [min] (LC-MS Method) | MS Data m/z [M + H]+ |
|---|---|---|---|
| 1.189 | rac-1-(1-{3-[(5-Isobutyl-2-methyl-2H-pyrazole-3-carbonyl)-amino]-phenyl}-ethyl)-piperidine-4-carboxylic acid cyclohexylamide | 0.86 (LC-C) | 494.5 |
| 1.190 | rac-1H-Pyrrolo[2,3-b]pyridine-5-carboxylic acid {3-[1-(4-cyclohexylcarbamoyl-piperidin-1-yl)-ethyl]-phenyl}-amide | 0.66 (LC-C) | 474.4 |
| 1.191 | rac-4-Methyl-pyridine-2-carboxylic acid {3-[1-(4-cyclohexylcarbamoyl-piperidin-1-yl)-ethyl]-phenyl}-amide | 0.79 (LC-C) | 449.4 |
| 1.192 | rac-4,6-Dimethyl-pyridine-2-carboxylic acid {3-[1-(4-cyclohexylcarbamoyl-piperidin-1-yl)-ethyl]-phenyl}-amide | 0.83 (LC-C) | 463.4 |
| 1.193 | rac-Pyrimidine-4-carboxylic acid {3-[1-(4-cyclohexylcarbamoyl-piperidin-1-yl)-ethyl]-phenyl}-amide | 0.65 (LC-C) | 436.4 |
| 1.194 | rac-1-(1-{3-[(2-Pyrrolidin-1-yl-thiazole-5-carbonyl)-amino]-phenyl}-ethyl)-piperidine-4-carboxylic acid cyclohexylamide | 0.70 (LC-C) | 510.4 |
| 1.195 | rac-Pyrimidine-2-carboxylic acid {3-[1-(4-cyclohexylcarbamoyl-piperidin-1-yl)-ethyl]-phenyl}-amide | 0.62 (LC-C) | 436.4 |
| 1.196 | rac-N-{3-[1-(4-Cyclohexylcarbamoyl-piperidin-1-yl)-ethyl]-phenyl}-6-diethylamino-nicotinamide | 0.62 (LC-C) | 506.5 |
| 1.197 | rac-2-Methyl-pyrimidine-4-carboxylic acid {3-[1-(4-cyclohexylcarbamoyl-piperidin-1-yl)-ethyl]-phenyl}-amide | 0.69 (LC-C) | 460.4 |
| 1.198 | rac-6-Methyl-pyrimidine-4-carboxylic acid {3-[1-(4-cyclohexylcarbamoyl-piperidin-1-yl)-ethyl]-phenyl}-amide | 0.69 (LC-C) | 450.4 |
| 1.199 | 1-[3-(4-Fluoro-benzoylamino)-benzyl]-piperidine-4-carboxylic acid cyclopropylamide | 0.61 (LC-C) | 396.3 |
| 1.200 | 4-Chloro-pyridine-2-carboxylic acid [3-(4-cyclopropylcarbamoyl-piperidin-1-ylmethyl)-phenyl]-amide | 0.65 (LC-C) | 413.3 |
| 1.201 | 6-Methyl-pyridine-2-carboxylic acid [3-(4-cyclopropylcarbamoyl-piperidin-1-ylmethyl)-phenyl]-amide | 0.62 (LC-C) | 393.3 |
| 1.202 | N-[3-(4-Cyclopropylcarbamoyl-piperidin-1-ylmethyl)-phenyl]-6-methyl-nicotinamide | 0.41 (LC-C) | 399.3 |
| 1.203 | N-[3-(4-Cyclopropylcarbamoyl-piperidin-1-ylmethyl)-phenyl]-2-methyl-isonicotinamide | 0.45 (LC-C) | 393.29 |
| 1.204 | N-[3-(4-Cyclopropylcarbamoyl-piperidin-1-ylmethyl)-phenyl]-5-fluoro-nicotinamide | 0.51 (LC-C) | 397.3 |
| 1.205 | 5-Fluoro-pyridine-2-carboxylic acid [3-(4-cyclopropylcarbamoyl-piperidin-1-ylmethyl)-phenyl]-amide | 0.59 (LC-C) | 397.3 |
| 1.206 | 1-[3-(4-Fluoro-benzoylamino)-benzyl]-piperidine-4-carboxylic acid cyclopentylamide | 0.71 (LC-C) | 424.4 |
| 1.207 | 5-Fluoro-pyridine-2-carboxylic acid [3-(4-cyclopentylcarbamoyl-piperidin-1-ylmethyl)-phenyl]-amide | 0.69 (LC-C) | 425.3 |
| 1.208 | 6-Trifluoromethyl-pyridine-2-carboxylic acid [3-(4-cyclopentylcarbamoyl-piperidin-1-ylmethyl)-phenyl]-amide | 0.79 (LC-C) | 475.4 |
| 1.209 | 5-Chloro-N-[3-(4-cyclopentylcarbamoyl-piperidin-1-ylmethyl)-phenyl]-nicotinamide | 0.66 (LC-C) | 441.3 |
| 1.210 | 5-Trifluoromethyl-pyridine-2-carboxylic acid [3-(4-cyclopentylcarbamoyl-piperidin-1-ylmethyl)-phenyl]-amide | 0.8 (LC-C) | 475.3 |
| 1.211 | Quinoline-3-carboxylic acid [3-(4-cyclopentylcarbamoyl-piperidin-1-ylmethyl)-phenyl]-amide | 0.64 (LC-C) | 457.4 |
| 1.212 | N-[3-(4-Cyclopentylcarbamoyl-piperidin-1-ylmethyl)-phenyl]-5-trifluoromethyl-nicotinamide | 0.72 (LC-C) | 475.4 |
| 1.213 | Quinoline-6-carboxylic acid [3-(4-cyclopentylcarbamoyl-piperidin-1-ylmethyl)-phenyl]-amide | 0.55 (LC-C) | 457.4 |
| 1.214 | N-[3-(4-Cyclopentylcarbamoyl-piperidin-1-ylmethyl)-phenyl]-2-trifluoromethyl-nicotinamide | 0.66 (LC-C) | 475.4 |
| 1.215 | N-[3-(4-Cyclopentylcarbamoyl-piperidin-1-ylmethyl)-phenyl]-5-fluoro-nicotinamide | 0.61 (LC-C) | 425.4 |
| 1.216 | 4-Trifluoromethyl-pyridine-2-carboxylic acid [3-(4-cyclopentylcarbamoyl-piperidin-1-ylmethyl)-phenyl]-amide | 0.8 (LC-C) | 475.3 |
| 1.217 | 1-(5-Benzoylamino-2-chloro-benzyl)-piperidine-4-carboxylic acid cyclopentylamide | 0.73 (LC-C) | 440.3 |
| 1.218 | 6-Trifluoromethyl-pyridine-2-carboxylic acid [4-chloro-3-(4-cyclopentylcarbamoyl-piperidin-1-ylmethyl)-phenyl]-amide | 0.83 LC-2) | 509.3 |
| 1.219 | 1-[2-Chloro-5-(4-fluoro-benzoylamino)-benzyl]-piperidine-4-carboxylic acid cyclopentylamide | 0.75 (LC-C) | 458.3 |
| 1.220 | 5-Trifluoromethyl-pyridine-2-carboxylic acid [4-chloro-3-(4-cyclopentylcarbamoyl-piperidin-1-ylmethyl)-phenyl]-amide | 0.76 (LC-C) | 509.3 |
| 1.221 | Quinoline-6-carboxylic acid [4-chloro-3-(4-cyclopentylcarbamoyl-piperidin-1-ylmethyl)-phenyl]-amide | 0.6 (LC-C) | 491.3 |
| 1.222 | Quinoline-3-carboxylic acid [4-chloro-3-(4-cyclopentylcarbamoyl-piperidin-1-ylmethyl)-phenyl]-amide | 0.68 (LC-C) | 491.3 |
| 1.223 | 1-[3-(4-Fluoro-benzoylamino)-benzyl]-piperidine-4-carboxylic acid tert-butylamide | 0.71 (LC-C) | 412.3 |
| 1.224 | 5-Fluoro-pyridine-2-carboxylic acid [4-chloro-3-(4-cyclopentylcarbamoyl-piperidin-1-ylmethyl)-phenyl]-amide | 0.73 (LC-C) | 459.3 |
| 1.225 | N-[4-Chloro-3-(4-cyclopentylcarbamoyl-piperidin-1-ylmethyl)-phenyl]-5-trifluoromethyl-nicotinamide | 0.76 (LC-C) | 509.3 |

TABLE 1-continued

Examples 1.004-1.355

| Example | Compound | $t_R$ [min] (LC-MS Method) | MS Data m/z [M + H]+ |
|---|---|---|---|
| 1.226 | N-[4-Chloro-3-(4-cyclopentylcarbamoyl-piperidin-1-ylmethyl)-phenyl]-5-methyl-nicotinamide | 0.58 (LC-C) | 455.3 |
| 1.227 | 5-Chloro-N-[4-chloro-3-(4-cyclopentylcarbamoyl-piperidin-1-ylmethyl)-phenyl]-nicotinamide | 0.71 (LC-C) | 455.3 |
| 1.228 | 6-Trifluoromethyl-pyridine-2-carboxylic acid [3-(4-tert-butylcarbamoyl-piperidin-1-ylmethyl)-phenyl]-amide | 0.79 (LC-C) | 463.4 |
| 1.229 | 5-Trifluoromethyl-pyridine-2-carboxylic acid [3-(4-tert-butylcarbamoyl-piperidin-1-ylmethyl)-phenyl]-amide | 0.8 (LC-C) | 463.4 |
| 1.230 | N-[3-(4-tert-Butylcarbamoyl-piperidin-1-ylmethyl)-phenyl]-5-trifluoromethyl-nicotinamide | 0.72 (LC-C) | 463.4 |
| 1.231 | N-[3-(4-tert-Butylcarbamoyl-piperidin-1-ylmethyl)-phenyl]-2-trifluoromethyl-nicotinamide | 0.66 (LC-C) | 463.3 |
| 1.232 | Quinoxaline-2-carboxylic acid [3-(4-tert-butylcarbamoyl-piperidin-1-ylmethyl)-phenyl]-amide | 0.74 (LC-C) | 446.4 |
| 1.233 | Quinoline-3-carboxylic acid [3-(4-tert-butylcarbamoyl-piperidin-1-ylmethyl)-phenyl]-amide | 0.64 (LC-C) | 445.4 |
| 1.234 | [1,6]Naphthyridine-2-carboxylic acid [3-(4-tert-butylcarbamoyl-piperidin-1-ylmethyl)-phenyl]-amide | 0.58 (LC-C) | 446.4 |
| 1.235 | Quinoline-2-carboxylic acid [3-(4-tert-butylcarbamoyl-piperidin-1-ylmethyl)-phenyl]-amide | 0.82 (LC-C) | 445.4 |
| 1.236 | 7-Chloro-quinoline-3-carboxylic acid [3-(4-tert-butylcarbamoyl-piperidin-1-ylmethyl)-phenyl]-amide | 0.77 (LC-C) | 479.3 |
| 1.237 | 1-[3-(3-Trifluoromethyl-benzoylamino)-benzyl]-piperidine-4-carboxylic acid tert-butylamide | 0.83 (LC-C) | 462.4 |
| 1.238 | 1-[3-(4-Trifluoromethyl-benzoylamino)-benzyl]-piperidine-4-carboxylic acid tert-butylamide | 0.83 (LC-C) | 462.3 |
| 1.239 | 1-[3-(2-Trifluoromethyl-benzoylamino)-benzyl]-piperidine-4-carboxylic acid tert-butylamide | 0.75 (LC-C) | 462.3 |
| 1.240 | N-[3-(4-tert-Butylcarbamoyl-piperidin-1-ylmethyl)-phenyl]-5-cyclopropyl-nicotinamide | 0.59 (LC-C) | 435.4 |
| 1.241 | N-[3-(4-tert-Butylcarbamoyl-piperidin-1-ylmethyl)-phenyl]-5-ethyl-nicotinamide | 0.57 (LC-C) | 423.4 |
| 1.242 | 4-Trifluoromethyl-pyridine-2-carboxylic acid [3-(4-tert-butylcarbamoyl-piperidin-1-ylmethyl)-phenyl]-amide | 0.81 (LC-C) | 463.3 |
| 1.244 | 1-{3-[2-(2,4-Dichloro-phenyl)-acetylamino]-benzyl}-piperidine-4-carboxylic acid tert-butylamide | 0.85 (LC-C) | 476.3 |
| 1.245 | 1-{3-[2-(2,6-Dichloro-phenyl)-acetylamino]-benzyl}-piperidine-4-carboxylic acid tert-butylamide | 0.81 (LC-C) | 476.3 |
| 1.246 | 1-{3-[2-(2,3-Dichloro-phenyl)-acetylamino]-benzyl}-piperidine-4-carboxylic acid tert-butylamide | 0.82 (LC-C) | 476.3 |
| 1.247 | 1-{3-[2-(2-Chloro-6-fluoro-phenyl)-acetylamino]-benzyl}-piperidine-4-carboxylic acid tert-butylamide | 0.77 (LC-C) | 460.3 |
| 1.248 | 1-{3-[2-(2-Chloro-4-fluoro-phenyl)-acetylamino]-benzyl}-piperidine-4-carboxylic acid tert-butylamide | 0.78 (LC-C) | 460.3 |
| 1.249 | 1-{3-[2-(2-Chloro-3-trifluoromethyl-phenyl)-acetylamino]-benzyl}-piperidine-4-carboxylic acid tert-butylamide | 0.86 (LC-C) | 510.3 |
| 1.250 | 1-{3-[2-(2,6-Dichloro-3-trifluoromethyl-phenyl)-acetylamino]-benzyl}-piperidine-4-carboxylic acid tert-butylamide | 0.89 (LC-C) | 544.3 |
| 1.251 | 1-{3-[2-(2,3-Dichloro-6-trifluoromethyl-phenyl)-acetylamino]-benzyl}-piperidine-4-carboxylic acid tert-butylamide | 0.89 (LC-C) | 544.3 |
| 1.252 | 1-{3-[2-(2,4-Dichloro-5-fluoro-phenyl)-acetylamino]-benzyl}-piperidine-4-carboxylic acid tert-butylamide | 0.86 (LC-C) | 494.3 |
| 1.253 | 1-{3-[2-(2,3-Dichloro-6-fluoro-phenyl)-acetylamino]-benzyl}-piperidine-4-carboxylic acid tert-butylamide | 0.83 (LC-C) | 494.3 |
| 1.254 | 1-{3-[2-(2-Chloro-3,6-difluoro-phenyl)-acetylamino]-benzyl}-piperidine-4-carboxylic acid tert-butylamide | 0.78 (LC-C) | 478.3 |
| 1.255 | 1-[3-(2-Tetrahydro-pyran-4-yl-acetylamino)-benzyl]-piperidine-4-carboxylic acid tert-butylamide | 0.59 (LC-C) | 416.4 |
| 1.256 | rac-1-{3-[(Tetrahydro-furan-3-carbonyl)-amino]-benzyl}-piperidine-4-carboxylic acid tert-butylamide | 0.55 (LC-C) | 388.4 |
| 1.257 | rac-1-{3-[(2,2-Dimethyl-cyclopropanecarbonyl)-amino]-benzyl}-piperidine-4-carboxylic acid tert-butylamide | 0.72 (LC-C) | 386.4 |
| 1.258 | 1-{3-[2-(2-Chloro-phenyl)-acetylamino]-benzyl}-piperidine-4-carboxylic acid tert-butylamide | 0.76 (LC-C) | 442.4 |
| 1.259 | 1-(3-Phenylacetylamino-benzyl)-piperidine-4-carboxylic acid tert-butylamide | 0.71 (LC-C) | 408.4 |
| 1.260 | 1-{3-[(2,2,3,3-Tetramethyl-cyclopropanecarbonyl)-amino]-benzyl}-piperidine-4-carboxylic acid tert-butylamide | 0.86 (LC-C) | 414.4 |
| 1.261 | 1-{3-[2-(2,5-Dimethyl-thiazol-4-yl)-acetylamino]-benzyl}-piperidine-4-carboxylic acid tert-butylamide | 0.61 (LC-C) | 443.3 |
| 1.262 | 1-{3-[2-(2,4-Dimethyl-thiazol-5-yl)-acetylamino]-benzyl}-piperidine-4-carboxylic acid tert-butylamide | 0.52 (LC-C) | 443.3 |
| 1.263 | 1-[3-(2-Pyrazin-2-yl-acetylamino)-benzyl]-piperidine-4-carboxylic acid tert-butylamide | 0.54 (LC-C) | 410.4 |

TABLE 1-continued

Examples 1.004-1.355

| Example | Compound | $t_R$ [min] (LC-MS Method) | MS Data m/z [M + H]$^+$ |
|---|---|---|---|
| 1.264 | 1-[3-(2-Pyrimidin-2-yl-acetylamino)-benzyl]-piperidine-4-carboxylic acid tert-butylamide | 0.53 (LC-C) | 410.4 |
| 1.265 | rac-2,3-Dihydro-1H-indole-3-carboxylic acid [3-(4-tert-butylcarbamoyl-piperidin-1-ylmethyl)-phenyl]-amide | 0.53 (LC-C) | 435.4 |
| 1.266 | rac-1-{3-[(2,3-Dihydro-benzofuran-3-carbonyl)-amino]-benzyl}-piperidine-4-carboxylic acid tert-butylamide | 0.71 (LC-C) | 436.4 |
| 1.267 | rac-1-{3-[(Indane-1-carbonyl)-amino]-benzyl}-piperidine-4-carboxylic acid tert-butylamide | 0.78 (LC-C) | 434.4 |
| 1.268 | 1-(3-{[1-(2,4-Dichloro-phenyl)-cyclopropanecarbonyl]-amino}-benzyl)-piperidine-4-carboxylic acid tert-butylamide | 0.91 (LC-C) | 502.3 |
| 1.269 | 1-{3-[2-(4-Chloro-phenyl)-2-methyl-propionylamino]-benzyl}-piperidine-4-carboxylic acid tert-butylamide | 0.76 (LC-C) | 471.3 |
| 1.270 | rac-1-{3-[2-(2-Chloro-phenyl)-2-hydroxy-acetylamino]-benzyl}-piperidine-4-carboxylic acid tert-butylamide | 0.69 (LC-C) | 458.3 |
| 1.271 | rac-1-{3-[(Bicyclo[4.2.0]octa-1(6),2,4-triene-7-carbonyl)-amino]-benzyl}-piperidine-4-carboxylic acid tert-butylamide | 0.75 (LC-C) | 420.4 |
| 1.272 | 1-[3-(2-Indan-2-yl-acetylamino)-benzyl]-piperidine-4-carboxylic acid tert-butylamide | 0.83 (LC-C) | 448.4 |
| 1.273 | 1-[3-(4-Fluoro-benzoylamino)-benzyl]-piperidine-4-carboxylic acid isobutyl-methyl-amide | 0.75 (LC-C) | 426.4 |
| 1.274 | 6-Trifluoromethyl-pyridine-2-carboxylic acid {3-[4-(isobutyl-methyl-carbamoyl)-piperidin-1-ylmethyl]-phenyl}-amide | 0.83 (LC-C) | 477.3 |
| 1.275 | 5-Trifluoromethyl-pyridine-2-carboxylic acid {3-[4-(isobutyl-methyl-carbamoyl)-piperidin-1-ylmethyl]-phenyl}-amide | 0.84 (LC-C) | 477.4 |
| 1.276 | N-{3-[4-(Isobutyl-methyl-carbamoyl)-piperidin-1-ylmethyl]-phenyl}-5-trifluoromethyl-nicotinamide | 0.76 (LC-C) | 477.4 |
| 1.277 | 5-Fluoro-N-{3-[4-(isobutyl-methyl-carbamoyl)-piperidin-1-ylmethyl]-phenyl}-nicotinamide | 0.65 (LC-C) | 427.4 |
| 1.278 | 5-Chloro-N-{3-[4-(isobutyl-methyl-carbamoyl)-piperidin-1-ylmethyl]-phenyl}-nicotinamide | 0.7 (LC-C) | 443.3 |
| 1.279 | 6-Trifluoromethyl-pyridine-2-carboxylic acid [3-bromo-5-(4-tert-butylcarbamoyl-piperidin-1-ylmethyl)-phenyl]-amide | 0.87 (LC-C) | 541.3 |
| 1.280 | 1-[3-(4-Fluoro-benzoylamino)-5-methoxy-benzyl]-piperidine-4-carboxylic acid tert-butylamide | 0.73 (LC-C) | 442.4 |
| 1.281 | 1-{3-[(5-Methyl-thiophene-2-carbonyl)-amino]-benzyl}-piperidine-4-carboxylic acid cyclohexylamide | 0.77 (LC-C) | 440.4 |
| 1.282 | 1-{3-[(5-Chloro-thiophene-2-carbonyl)-amino]-benzyl}-piperidine-4-carboxylic acid cyclohexylamide | 0.82 (LC-C) | 460.3 |
| 1.283 | 1-{3-[(5-tert-Butyl-thiophene-2-carbonyl)-amino]-benzyl}-piperidine-4-carboxylic acid cyclohexylamide | 0.91 (LC-C) | 482.4 |
| 1.284 | 6-Trifluoromethyl-pyridine-2-carboxylic acid [2-(4-cyclohexylcarbamoyl-piperidin-1-ylmethyl)-pyrimidin-4-yl]-amide | 0.78 (LC-C) | 491.4 |
| 1.285 | N-[2-(4-Cyclohexylcarbamoyl-piperidin-1-ylmethyl)-pyrimidin-4-yl]-5-methyl-nicotinamide | 0.59 (LC-C) | 437.1 |
| 1.286 | 6-Trifluoromethyl-pyridine-2-carboxylic acid [2-(4-tert-butylcarbamoyl-piperidin-1-ylmethyl)-pyrimidin-4-yl]-amide | 0.74 (LC-C) | 465.3 |
| 1.287 | rac-1-{3-[(5-Methyl-pyridine-3-carbonyl)-amino]-benzyl}-azepane-4-carboxylic acid ethylamide | 0.45 (LC-C) | 395.3 |
| 1.288 | Rac-1-{3-[(5-Methyl-pyridine-3-carbonyl)-amino]-benzyl}-azepane-4-carboxylic acid sec-butylamide | 0.54 (LC-C) | 423.4 |
| 1.289 | rac-1-{3-[(5-Methyl-pyridine-3-carbonyl)-amino]-benzyl}-azepane-4-carboxylic acid isopropylamide | 0.5 (LC-C) | 409.4 |
| 1.290 | rac-1-{3-[(5-Methyl-pyridine-3-carbonyl)-amino]-benzyl}-azepane-4-carboxylic acid tert-butylamide | 0.56 (LC-C) | 423.4 |
| 1.291 | rac-1-{3-[(5-Methyl-pyridine-3-carbonyl)-amino]-benzyl}-azepane-4-carboxylic acid cyclohexylamide | 0.62 (LC-C) | 449.4 |
| 1.293 | 1-[2-(4-Chloro-benzoylamino)-thiazol-4-ylmethyl]-piperidine-4-carboxylic acid cyclopentylamide | 0.75 (LC-C) | 447.3 |
| 1.294 | N-[4-(4-Cyclopentylcarbamoyl-piperidin-1-ylmethyl)-thiazol-2-yl]-5-methyl-nicotinamide | 0.54 (LC-C) | 428.4 |
| 1.295 | 6-Trifluoromethyl-pyridine-2-carboxylic acid [3-(4-tert-butylcarbamoyl-piperidin-1-ylmethyl)-4-methyl-phenyl]-amide | 0.69 (LC-C) | 463.3 |
| 1.296 | 6-Trifluoromethyl-pyridine-2-carboxylic acid [3-(4-tert-butylcarbamoyl-piperidin-1-ylmethyl)-4-methoxy-phenyl]-amide | 0.80 (LC-C) | 493.4 |
| 1.297 | N-[3-(4-tert-Butylcarbamoyl-piperidin-1-ylmethyl)-4-methoxy-phenyl]-5-methyl-nicotinamide | 0.53 (LC-C) | 439.4 |
| 1.298 | 1-[5-(4-Fluoro-benzoylamino)-2-methoxy-benzyl]-piperidine-4-carboxylic acid tert-butylamide | 0.71 (LC-C) | 442.4 |
| 1.299 | N-[3-(4-tert-Butylcarbamoyl-piperidin-1-ylmethyl)-4-methyl-phenyl]-5-methyl-nicotinamide | 0.54 (LC-C) | 423.5 |
| 1.300 | 1-[5-(4-Fluoro-benzoylamino)-2-methyl-benzyl]-piperidine-4-carboxylic acid tert-butylamide | 0.73 (LC-C) | 426.4 |
| 1.301 | 6-Trifluoromethyl-pyridine-2-carboxylic acid [5-(4-tert-butylcarbamoyl-piperidin-1-ylmethyl)-2-methyl-phenyl]-amide | 0.84 (LC-C) | 477.4 |

TABLE 1-continued

Examples 1.004-1.355

| Example | Compound | $t_R$ [min] (LC-MS Method) | MS Data m/z [M + H]+ |
|---|---|---|---|
| 1.302 | N-[5-(4-tert-Butylcarbamoyl-piperidin-1-ylmethyl)-2-methyl-phenyl]-5-methyl-nicotinamide | 0.53 (LC-C) | 423.4 |
| 1.303 | 1-[3-(4-Fluoro-benzoylamino)-4-methyl-benzyl]-piperidine-4-carboxylic acid tert-butylamide | 0.72 (LC-C) | 426.4 |
| 1.304 | 6-Trifluoromethyl-pyridine-2-carboxylic acid [5-(4-tert-butylcarbamoyl-piperidin-1-ylmethyl)-2-methoxy-phenyl]-amide | 0.85 (LC-C) | 493.3 |
| 1.305 | N-[5-(4-tert-Butylcarbamoyl-piperidin-1-ylmethyl)-2-methoxy-phenyl]-5-methyl-nicotinamide | 0.54 (LC-C) | 439.4 |
| 1.306 | 1-[3-(4-Fluoro-benzoylamino)-4-methoxy-benzyl]-piperidine-4-carboxylic acid tert-butylamide | 0.75 (LC-C) | 442.4 |
| 1.307 | rac-N-{3-[1-(4-Cyclohexylcarbamoyl-piperidin-1-yl)-propyl]-phenyl}-5-methyl-nicotinamide | 0.61 (LC-C) | 463.4 |
| 1.308 | rac-6-Trifluoromethyl-pyridine-2-carboxylic acid {3-[1-(4-cyclohexylcarbamoyl-piperidin-1-yl)-propyl]-phenyl}-amide | 0.88 (LC-C) | 517.4 |
| 1.309 | 1-{3-[(1-Phenyl-cyclopropanecarbonyl)-amino]-benzyl}-piperidine-4-carboxylic acid tert-butylamide | 0.79 (LC-C) | 434.4 |
| 1.310 | 1-(3-{[1-(4-Chloro-phenyl)-cyclopropanecarbonyl]-amino}-benzyl)-piperidine-4-carboxylic acid tert-butylamide | 0.87 (LC-C) | 468.4 |
| 1.311 | 1-[3-(2-Methyl-2-phenyl-propionylamino)-benzyl]-piperidine-4-carboxylic acid tert-butylamide | 0.79 LC-C) | 436.4 |
| 1.312 | 1-{3-[2-(4-Chloro-phenyl)-propionylamino]-benzyl}-piperidine-4-carboxylic acid tert-butylamide | 0.83 (LC-C) | 456.4 |
| 1.313 | 1-[3-(4-Fluoro-benzoylamino)-2-methyl-benzyl]-piperidine-4-carboxylic acid tert-butylamide | 0.68 (LC-C) | 426.5 |
| 1.314 | N-[3-(4-tert-Butylcarbamoyl-piperidin-1-ylmethyl)-2-methyl-phenyl]-5-methyl-nicotinamide | 0.50 (LC-C) | 423.4 |
| 1.315 | 6-Trifluoromethyl-pyridine-2-carboxylic acid [3-(4-tert-butylcarbamoyl-piperidin-1-ylmethyl)-2-methyl-phenyl]-amide | 0.77 (LC-C) | 477.4 |
| 1.316 | 6-Trifluoromethyl-pyridine-2-carboxylic acid [3-(4-tert-butylcarbamoyl-piperidin-1-ylmethyl)-5-methyl-phenyl]-amide | 0.83 (LC-C) | 477.4 |
| 1.317 | N-[3-(4-tert-Butylcarbamoyl-piperidin-1-ylmethyl)-5-methyl-phenyl]-5-methyl-nicotinamide | 0.55 (LC-C) | 423.4 |
| 1.318 | 1-[3-(4-Fluoro-benzoylamino)-5-methyl-benzyl]-piperidine-4-carboxylic acid tert-butylamide | 0.75 (LC-C) | 426.4 |
| 1.319 | 6-Trifluoromethyl-pyridine-2-carboxylic acid [3-(4-tert-butylcarbamoyl-piperidin-1-ylmethyl)-2-methoxy-phenyl]-amide | 0.81 (LC-C) | 493.4 |
| 1.320 | N-[3-(4-tert-Butylcarbamoyl-piperidin-1-ylmethyl)-2-methoxy-phenyl]-5-methyl-nicotinamide | 0.52 (LC-C) | 439.4 |
| 1.321 | 1-[3-(4-Fluoro-benzoylamino)-2-methoxy-benzyl]-piperidine-4-carboxylic acid tert-butylamide | 0.70 (LC-C) | 442.4 |
| 1.322 | Pyridazine-3-carboxylic acid [3-(4-tert-butylcarbamoyl-piperidin-1-ylmethyl)-phenyl]-amide | 0.55 LC-C) | 396.4 |
| 1.323 | Pyridazine-4-carboxylic acid [3-(4-tert-butylcarbamoyl-piperidin-1-ylmethyl)-phenyl]-amide | 0.51 (LC-C) | 396.4 |
| 1.324 | 3-Chloro-6-methyl-pyridazine-4-carboxylic acid [3-(4-tert-butylcarbamoyl-piperidin-1-ylmethyl)-phenyl]-amide | 0.58 (LC-C) | 444.3 |
| 1.325 | 6-Trifluoromethyl-pyridine-2-carboxylic acid [3-(4-tert-butylcarbamoyl-piperidin-1-ylmethyl)-5-methoxy-phenyl]-amide | 0.80 (LC-C) | 493.4 |
| 1.326 | 6-Trifluoromethyl-pyridine-2-carboxylic acid [5-(4-tert-butylcarbamoyl-piperidin-1-ylmethyl)-2-ethyl-phenyl]-amide | 0.94 (LC-C) | 491.4 |
| 1.327 | N-[5-(4-tert-Butylcarbamoyl-piperidin-1-ylmethyl)-2-ethyl-phenyl]-5-methyl-nicotinamide | 0.61 (LC-C) | 437.5 |
| 1.328 | 1-[4-Ethyl-3-(4-fluoro-benzoylamino)-benzyl]-piperidine-4-carboxylic acid tert-butylamide | 0.82 (LC-C) | 440.4 |
| 1.329 | 6-Trifluoromethyl-pyridine-2-carboxylic acid [3-(4-tert-butylcarbamoyl-piperidin-1-ylmethyl)-5-ethyl-phenyl]-amide | 0.93 (LC-C) | 491.4 |
| 1.330 | N-[3-(4-tert-Butylcarbamoyl-piperidin-1-ylmethyl)-5-ethyl-phenyl]-5-methyl-nicotinamide | 0.64 (LC-C) | 437.5 |
| 1.331 | 1-[3-Ethyl-5-(4-fluoro-benzoylamino)-benzyl]-piperidine-4-carboxylic acid tert-butylamide | 0.85 (LC-C) | 440.4 |
| 1.332 | 6-Trifluoromethyl-pyridine-2-carboxylic acid [3-(4-tert-butylcarbamoyl-piperidin-1-ylmethyl)-4-ethyl-phenyl]-amide | 0.91 (LC-C) | 491.4 |
| 1.333 | N-[3-(4-tert-Butylcarbamoyl-piperidin-1-ylmethyl)-4-ethyl-phenyl]-5-methyl-nicotinamide | 0.63 (LC-C) | 437.5 |
| 1.334 | 1-[2-Ethyl-5-(4-fluoro-benzoylamino)-benzyl]-piperidine-4-carboxylic acid tert-butylamide | 0.83 (LC-C) | 440.4 |
| 1.335 | 1-[3-((E)-But-2-enoylamino)-benzyl]-piperidine-4-carboxylic acid tert-butylamide | 0.65 (LC-C) | 358.4 |
| 1.336 | 1-(3-Acryloylamino-benzyl)-piperidine-4-carboxylic acid tert-butylamide | 0.60 (LC-C) | 344.4 |
| 1.337 | 1-{3-[((E)-(3-Phenyl-acryloyl)amino]-benzyl}-piperidine-4-carboxylic acid tert-butylamide | 0.81 (LC-C) | 420.4 |
| 1.338 | 5-Chloro-pyridine-2-carboxylic acid {3-[4-(1,1-dimethyl-propylcarbamoyl)-piperidin-1-ylmethyl]-phenyl}-amide | 0.84 (LC-C) | 443.4 |

TABLE 1-continued

Examples 1.004-1.355

| Example | Compound | $t_R$ [min] (LC-MS Method) | MS Data m/z [M + H]⁺ |
|---|---|---|---|
| 1.339 | 5-Chloro-pyridine-2-carboxylic acid [3-(4-tert-butylcarbamoyl-piperidin-1-ylmethyl)-phenyl]-amide | 0.79 (LC-C) | 429.4 |
| 1.340 | 5-Chloro-3-fluoro-pyridine-2-carboxylic acid [3-(4-tert-butylcarbamoyl-piperidin-1-ylmethyl)-phenyl]-amide | 0.76 (LC-C) | 447.4 |
| 1.341 | 5-Trifluoromethyl-pyridine-2-carboxylic acid {3-[4-(1,1-dimethyl-propylcarbamoyl)-piperidin-1-ylmethyl]-phenyl}-amide | 0.88 (LC-C) | 477.4 |
| 1.342 | 1-[3-((E)-4-Dimethylamino-but-2-enoylamino)-benzyl]-piperidine-4-carboxylic acid tert-butylamide | 0.49 (LC-C) | 401.4 |
| 1.343 | 5-Chloro-3-fluoro-pyridine-2-carboxylic acid {3-[4-(1,1-dimethyl-propylcarbamoyl)-piperidin-1-ylmethyl]-phenyl}-amide | 0.81 (LC-C) | 461.4 |
| 1.344 | 6-Bromo-pyridine-2-carboxylic acid [3-(4-tert-butylcarbamoyl-piperidin-1-ylmethyl)-phenyl]-amide | 0.79 (LC-C) | 473.3 |
| 1.345 | 1-Oxy-6-trifluoromethyl-pyridine-2-carboxylic acid [3-(4-tert-butylcarbamoyl-piperidin-1-ylmethyl)-phenyl]-amide | 0.77 (LC-C) | 479.4 |
| 1.346 | 1-Oxy-6-trifluoromethyl-pyridine-2-carboxylic acid {3-[4-(1,1-dimethyl-propylcarbamoyl)-piperidin-1-ylmethyl]-phenyl}-amide | 0.82 (LC-C) | 493.4 |
| 1.347 | 1-Oxy-5-trifluoromethyl-pyridine-2-carboxylic acid {3-[4-(1,1-dimethyl-propylcarbamoyl)-piperidin-1-ylmethyl]-phenyl}-amide | 0.81 (LC-C) | 493.4 |
| 1.348 | 1-Oxy-5-trifluoromethyl-pyridine-2-carboxylic acid [3-(4-tert-butylcarbamoyl-piperidin-1-ylmethyl)-phenyl]-amide | 0.76 (LC-C) | 479.4 |
| 1.349 | 5-[3-(4-tert-Butylcarbamoyl-piperidin-1-ylmethyl)-phenylcarbamoyl]-nicotinic acid methyl ester | 0.67 (LC-C) | 453.4 |
| 1.350 | 5-[3-(4-Cyclohexylcarbamoyl-piperidin-1-ylmethyl)-phenylcarbamoyl]-nicotinic acid methyl ester | 0.72 (LC-C) | 479.4 |
| 1.351 | 1-[3-(4-Methanesulfonyl-benzoylamino)-benzyl]-piperidine-4-carboxylic acid tert-butylamide | 0.65 (LC-C) | 472.4 |
| 1.352 | 1-[3-(3-Methanesulfonyl-benzoylamino)-benzyl]-piperidine-4-carboxylic acid tert-butylamide | 0.66 (LC-C) | 472.4 |
| 1.353 | Benzothiazole-6-carboxylic acid [3-(4-tert-butylcarbamoyl-piperidin-1-ylmethyl)-phenyl]-amide | 0.69 (LC-C) | 451.4 |
| 1.354 | 2-Methyl-benzothiazole-5-carboxylic acid [3-(4-tert-butylcarbamoyl-piperidin-1-ylmethyl)-phenyl]-amide | 0.76 (LC-C) | 465.4 |
| 1.355 | Benzo[1,2,3]thiadiazole-5-carboxylic acid [3-(4-tert-butylcarbamoyl-piperidin-1-ylmethyl)-phenyl]-amide | 0.74 (LC-C) | 452.4 |

General Method B for the Synthesis of piperidine-4-carboxamide of Structure (I)

Buildings Blocks

Preparation of Building Blocks of General Formula C-5

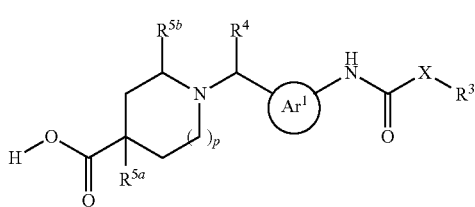

C-5

[3-(4-Chloro-benzoylamino)-benzyl]-piperidine-4-carboxylic acid I-1

(2.001a): 4-Chloro-N-(3-[1,3]dioxolan-2-yl-phenyl)-benzamide

A solution of 3-aminobenzaldehyde ethylene acetal (10 g, 60.5 mmol) and TEA (7.35 g, 72.6 mmol) in ethyl acetate (100 mL) at 0° C. is treated dropwise with 4-chlorobenzoyl chloride (9.44 mL, 72.6 mmol) during 30 min. The reaction mixture is stirred at RT for 3 h before dilution with EtOAc. The medium is washed twice with sat. aq. NaHCO₃ (100 mL) and once with brine (100 mL). The organic layer is dried over MgSO₄, filtered and evaporated. The residual oil is triturated with ethyl acetate and the resulting crystalline material is filtered to give the title compound (14.33 g, 78%) as a slightly pink solid; LC-MS B: $t_R$=0.86 min; [M+H]⁺ =304.03.

(2.001 b): 4-Chloro-N-(3-formyl-phenyl)-benzamide

A solution of 4-chloro-N-(3-[1,3]dioxolan-2-yl-phenyl)-benzamide (14.33 g, 47.2 mmol) in 1,4-dioxane (120 mL) is treated with 1N aq. HCl (120 mL) at RT for 1 h then at 60° C. for 30 min. The reaction mixture is cooled down to RT and diluted with ethyl acetate (100 mL). The organic phase is separated and the aqueous phase is extracted twice with ethyl acetate (100 mL). The combined organic phases are washed with brine (200 mL) and dried over MgSO₄. After evaporation of the organic solvents the residue is triturated with diethyl ether to give the title compound (10.34 g, 84%) as a beige powder; LC-MS B: $t_R$=0.83 min; [M+H]⁺=259.82.

(2.001c): 1-[3-(4-Chloro-benzoylamino)-benzyl]-piperidine-4-carboxylic acid ethyl ester A mixture of 4-chloro-N-(3-formyl-phenyl)-benzamide (2.1 g, 8.09 mmol), ethyl isonipecotate (1.53 g, 9.55 mmol) in DCM (45 mL) is treated with sodium triacetoxy borohydride (2.5 g, 11.2 mmol) in 5 portions over 20 min. and the reaction mixture is stirred for 18 h at RT. Aq. sat. NaHCO₃

(20 mL) is added and the mixture is stirred for 30 min. The phases are separated and the aqueous phase is extracted twice with DCM (50 ml). The combined organic phases are dried over $MgSO_4$ and evaporated. The title compound is obtained as a colorless solid (3.24 g, 98%); LC-MS A: $t_R$=0.72 min; $[M+H]^+$=401.01.

(2.001d): [3-(4-Chloro-benzoylamino)-benzyl]-piperidine-4-carboxylic acid I-1

A solution of 1-[3-(4-chloro-benzoylamino)-benzyl]-piperidine-4-carboxylic acid ethyl ester (1.65 g, 4.12 mmol) in a mixture of THF (20 mL) water (10 mL) and MeOH (10 mL) is treated with lithium hydroxide monohydrate (190 mg, 4.53 mmol) at RT for 2 h. Aq. 2N HCl (2.3 mL) is added and the resulting solution is lyophilized to yield the crude title compound (1.41 g) containing one equivalent LiCl. LC-MS A: $t_R$=0.64 min; $[M+H]^+$=372.93.

In analogy to example I-1, the following building blocks I-2-I-6 are prepared.

1-{3-[(Thiophene-2-carbonyl)-amino]-benzyl}-piperidine-4-carboxylic acid I-2

The title compound is prepared according to the reaction sequence 2.001a-2.001d described above using 2-thiophene carbonyl chloride instead of 4-chlorobenzoyl chloride as in 2.001a: LC-MS A: $t_R$=0.56 min; $[M+H]^+$=345.43.

1-{3-[(5-Methyl-pyridine-3-carbonyl)-amino]-benzyl}-piperidine-4-carboxylic acid I-3

The title compound is prepared according to the reaction sequence 2.001a-2.001d described above using 5-methylnicotinoyl chloride instead of 4-chlorobenzoyl chloride as in 2.001a: LC-MS A: $t_R$=0.46 min; $[M+H]^+$=353.99.

1-{3-[(6-Trifluoromethyl-pyridine-2-carbonyl)-amino]-benzyl}-piperidine-4-carboxylic acid I-4

The title compound is prepared according to the reaction sequence 2.001a-2.001d described above using 6-(trifluoromethyl)picolinoyl chloride instead of 4-chlorobenzoyl chloride as in 2.001a: LC-MS A: $t_R$=0.65 min; $[M+H]^+$=408.38.

rac-1-{3-[(5-Methyl-pyridine-3-carbonyl)-amino]-benzyl}-azepane-4-carboxylic acid I-5

The title compound is prepared according to the reaction sequence 2.001a-2.001d described above using 5-methylnicotinoyl chloride instead of 4-chlorobenzoyl chloride as in 2.001a and rac-methyl azepane-4-carboxylate instead of ethyl isonipecotate as in 2.001c: LC-MS A: $t_R$=0.48 min; $[M+H]^+$=368.14.

rac-1-{3-[(5-Methyl-pyridine-3-carbonyl)-amino]-benzyl}-pyrrolidine-3-carboxylic acid I-6

The title compound is prepared according to the reaction sequence 2.001a-2.001d described above using 5-methylnicotinoyl chloride instead of 4-chlorobenzoyl chloride as in 2.001a and methyl pyrrolidine-3-carboxylate instead of ethyl isonipecotate as in 2.001c: LC-MS A: $t_R$=0. 45 min; $[M+H]^+$=340.14.

rac-1-{3-[2-(2-Chloro-4-fluoro-phenyl)-acetylamino]-benzyl}-pyrrolidine-3-carboxylic acid I-7

The title compound is prepared according to the reaction sequence 2.001a-2.001d described above using 2-(2-chloro-4-fluorophenyl)acetyl chloride instead of 4-chlorobenzoyl chloride as in 2.001a and methyl pyrrolidine-3-carboxylate instead of ethyl isonipecotate as in 2.001c: LC-MS A: $t_R$=0.63 min; $[M+H]^+$=391.01.

rac-1-{3-[(6-Trifluoromethyl-pyridine-2-carbonyl)-amino]-benzyl}-pyrrolidine-3-carboxylic acid I-8

The title compound is prepared according to the reaction sequence 2.001a-2.001d described above using 6-(trifluoromethyl)picolinoyl chloride instead of 4-chlorobenzoyl chloride as in 2.001a and methyl pyrrolidine-3-carboxylate instead of ethyl isonipecotate as in 2.001c: LC-MS A: $t_R$=0.64 min; $[M+H]^+$=394.00.

rac-(2S*,4S*)-2-Methyl-1-{3-[(6-trifluoromethyl-pyridine-2-carbonyl)-amino]-benzyl}-piperidine-4-carboxylic acid I-9

The title compound is prepared according to the reaction sequence 2.001a-2.001d described above using 6-(trifluoromethyl)picolinoyl chloride instead of 4-chlorobenzoyl chloride as in 2.001a and rac-(2S*,4S*)-methyl 2-methyl-piperidine-4-carboxylate instead of ethyl isonipecotate as in 2.001c: LC-MS A: $t_R$=0.49 min; $[M+H]^+$=368.07.

rac-(2S*,4S*)-2-Methyl-1-{3-[(5-methyl-pyridine-3-carbonyl)-amino]-benzyl}-piperidine-4-carboxylic acid I-10

The title compound is prepared according to the reaction sequence 2.001a-2.001d described above using 5-methylnicotinoyl chloride instead of 4-chlorobenzoyl chloride as in 2.001a and rac-(2S*,4S*)-methyl 2-methylpiperidine-4-carboxylate instead of ethyl isonipecotate as in 2.001c: LC-MS A: $t_R$=0.67 min; $[M+H]^+$=422.08.

Example 2.001

1-[3-(4-Chloro-benzoylamino)-benzyl]-piperidine-4-carboxylic acid cyclopentylamide Method A 1-Cyclopentylamine (10.7 mg, 0.124 mmol) is added to a solution of [3-(4-chloro-benzoylamino)-benzyl]-piperidine-4-carboxylic acid (35.4 mg, 0.095 mmol) in DMF (0.5 mL). The resulting solution is treated with a solution of HOAT (15.5 mg, 0.114 mmol) in DMF (0.5 mL) followed by si-DCC (200 mg, 0.95 mmol/g, 0.19 mmol), and DIPEA (0.033 mL, 0.19 mmol). The mixture is stirred at 50° C. overnight. PI-DETA (7.99 mmol/g, 0.3 mmol, 37 mg) is added to the solution in order to scavenge the acid, PI-NCO (2.24 mmol/g, 0.3 mmol, 130 mg) is added to scavenge the amine in excess and the mixture is stirred for 1 h. The resin is filtered and washed with a mixture of MeOH/DCM 1:1, (4×1 mL). The resulting solution is evaporated under HV. The title compound is obtained by prep. HPLC F as a colourless powder: LC-MS A: $t_R$=1.21 min; $[M+H]^+$=440.1.

Compounds of Examples 2.002-2.104 listed in Table 2 below are prepared by applying either one of the abovementioned methods described under Method A for Example 2.01 to the building blocks I-1-I-10 coupled with commercially available amines of general formula $HNR_1R_2$.

TABLE 2

Examples 2.002-2.104

| Example | Compound | $t_R$ [min] (LC-MS Method) | MS Data m/z [M + H]+ |
|---|---|---|---|
| 2.002 | 1-[3-(4-Chloro-benzoylamino)-benzyl]-piperidine-4-carboxylic acid methylamide | 0.63 (LC-C) | 386.3 |
| 2.003 | 1-[3-(4-Chloro-benzoylamino)-benzyl]-piperidine-4-carboxylic acid isopropylamide | 0.7 (LC-C) | 414.3 |
| 2.004 | 1-[3-(4-Chloro-benzoylamino)-benzyl]-piperidine-4-carboxylic acid tert-butylamide | 0.76 (LC-C) | 428.3 |
| 2.005 | 1-[3-(4-Chloro-benzoylamino)-benzyl]-piperidine-4-carboxylic acid (2-methoxy-ethyl)-amide | 0.65 (LC-C) | 430.3 |
| 2.006 | 1-[3-(4-Chloro-benzoylamino)-benzyl]-piperidine-4-carboxylic acid cyclopropylamide | 0.67 (LC-C) | 412.3 |
| 2.007 | 1-[3-(4-Chloro-benzoylamino)-benzyl]-piperidine-4-carboxylic acid cyclobutylamide | 0.72 (LC-C) | 426.3 |
| 2.008 | Rac-1-[3-(4-Chloro-benzoylamino)-benzyl]-piperidine-4-carboxylic acid-bicyclo[2.2.1]hept-2-ylamide | 0.82 (LC-C) | 466.3 |
| 2.009 | 1-[3-(4-Chloro-benzoylamino)-benzyl]-piperidine-4-carboxylic acid diethylamide | 0.75 (LC-C) | 428.3 |
| 2.010 | 1-[3-(4-Chloro-benzoylamino)-benzyl]-piperidine-4-carboxylic acid cyclopentylmethyl-amide | 0.82 (LC-C) | 454.3 |
| 2.011 | 1-[3-(4-Chloro-benzoylamino)-benzyl]-piperidine-4-carboxylic acid (4-hydroxy-cyclohexyl)-amide | 0.64 (LC-C) | 470.3 |
| 2.012 | 1-[3-(4-Chloro-benzoylamino)-benzyl]-piperidine-4-carboxylic acid (4-tert-butyl-cyclohexyl)-amide | 0.99 (LC-C) | 510.4 |
| 2.013 | 1-[3-(4-Chloro-benzoylamino)-benzyl]-piperidine-4-carboxylic acid (tetrahydro-pyran-4-yl)-amide | 0.66 (LC-C) | 466.3 |
| 2.014 | 1-[3-(4-Chloro-benzoylamino)-benzyl]-piperidine-4-carboxylic acid (4,4-difluoro-cyclohexyl)-amide | 0.78 (LC-C) | 490.3 |
| 2.015 | 1-[3-(4-Chloro-benzoylamino)-benzyl]-piperidine-4-carboxylic acid cyclohexylmethyl-amide | 0.86 (LC-C) | 468.3 |
| 2.016 | rac-1-[3-(4-Chloro-benzoylamino)-benzyl]-piperidine-4-carboxylic acid (1-cyclohexyl-ethyl)-amide | 0.9 (LC-C) | 482.4 |
| 2.017 | 1-[3-(4-Chloro-benzoylamino)-benzyl]-piperidine-4-carboxylic acid (1-methyl-1-phenyl-ethyl)-amide | 0.85 (LC-C) | 490.3 |
| 2.018 | rac-1-[3-(4-Chloro-benzoylamino)-benzyl]-piperidine-4-carboxylic acid (1-naphthalen-1-yl-ethyl)-amide | 0.9 (LC-C) | 526.4 |
| 2.019 | rac-1-[3-(4-Chloro-benzoylamino)-benzyl]-piperidine-4-carboxylic acid (1,2,3,4-tetrahydro-naphthalen-1-yl)-amide | 0.87 (LC-C) | 502.4 |
| 2.020 | rac-1-[3-(4-Chloro-benzoylamino)-benzyl]-piperidine-4-carboxylic acid indan-1-ylamide | 0.83 (LC-C) | 488.4 |
| 2.021 | 1-[3-(4-Chloro-benzoylamino)-benzyl]-piperidine-4-carboxylic acid (pyridin-4-ylmethyl)-amide | 0.56 (LC-C) | 463.3 |
| 2.022 | 1-[3-(4-Chloro-benzoylamino)-benzyl]-piperidine-4-carboxylic acid (pyridin-2-ylmethyl)-amide | 0.57 (LC-C) | 463.3 |
| 2.023 | 1-[3-(4-Chloro-benzoylamino)-benzyl]-piperidine-4-carboxylic acid (pyridin-3-ylmethyl)-amide | 0.56 (LC-C) | 463.4 |
| 2.024 | 1-[3-(4-Chloro-benzoylamino)-benzyl]-piperidine-4-carboxylic acid (thiazol-2-ylmethyl)-amide | 0.67 (LC-C) | 469.3 |
| 2.025 | 1-[3-(4-Chloro-benzoylamino)-benzyl]-piperidine-4-carboxylic acid 2-chloro-benzylamide | 0.83 (LC-C) | 496.3 |
| 2.026 | 1-[3-(4-Chloro-benzoylamino)-benzyl]-piperidine-4-carboxylic acid 2-methoxy-benzylamide | 0.8 (LC-C) | 492.3 |
| 2.027 | 1-[3-(4-Chloro-benzoylamino)-benzyl]-piperidine-4-carboxylic acid 3-chloro-benzylamide | 0.84 (LC-C) | 496.3 |
| 2.028 | 1-[3-(4-Chloro-benzoylamino)-benzyl]-piperidine-4-carboxylic acid 3-methoxy-benzylamide | 0.79 (LC-C) | 492.4 |
| 2.029 | 1-[3-(4-Chloro-benzoylamino)-benzyl]-piperidine-4-carboxylic acid 4-chloro-benzylamide | 0.85 (LC-C) | 496.2 |
| 2.030 | 1-[3-(4-Chloro-benzoylamino)-benzyl]-piperidine-4-carboxylic acid 4-methoxy-benzylamide | 0.78 (LC-C) | 492.3 |
| 2.031 | 1-[3-(4-Chloro-benzoylamino)-benzyl]-piperidine-4-carboxylic acid (2,2,2-trifluoro-ethyl)-amide | 0.75 (LC-C) | 454.3 |
| 2.032 | 1-[3-(4-Chloro-benzoylamino)-benzyl]-piperidine-4-carboxylic acid (1-hydroxymethyl-cyclopentyl)-amide | 0.75 (LC-C) | 470.3 |
| 2.033 | 1-[3-(4-Chloro-benzoylamino)-benzyl]-piperidine-4-carboxylic acid indan-2-ylamide | 0.86 (LC-C) | 488.3 |
| 2.034 | 1-[3-(4-Chloro-benzoylamino)-benzyl]-piperidine-4-carboxylic acid (5-methyl-2-trifluoromethyl-furan-3-ylmethyl)-amide | 0.91 (LC-C) | 534.3 |
| 2.035 | 1-[3-(4-Chloro-benzoylamino)-benzyl]-piperidine-4-carboxylic acid benzylamide | 0.81 (LC-C) | 462.4 |
| 2.036 | 1-[3-(4-Chloro-benzoylamino)-benzyl]-piperidine-4-carboxylic acid (1-cyano-cyclopropyl)-amide | 0.81 LC-2) | 462.4 |
| 2.037 | N-[3-(4-Cyclopropylcarbamoyl-piperidin-1-ylmethyl)-phenyl]-5-methyl-nicotinamide | 0.43 (LC-C) | 393.3 |
| 2.038 | N-[3-(4-Isopropylcarbamoyl-piperidin-1-ylmethyl)-phenyl]-5-methyl-nicotinamide | 0.47 (LC-C) | 395.4 |

TABLE 2-continued

Examples 2.002-2.104

| Example | Compound | $t_R$ [min] (LC-MS Method) | MS Data m/z [M + H]+ |
|---|---|---|---|
| 2.039 | N-[3-(4-tert-Butylcarbamoyl-piperidin-1-ylmethyl)-phenyl]-5-methyl-nicotinamide | 0.53 (LC-C) | 409.4 |
| 2.040 | N-{3-[4-(1-Ethyl-propylcarbamoyl)-piperidin-1-ylmethyl]-phenyl}-5-methyl-nicotinamide | 0.55 (LC-C) | 423.4 |
| 2.041 | N-[3-(4-Cyclobutylcarbamoyl-piperidin-1-ylmethyl)-phenyl]-5-methyl-nicotinamide | 0.49 (LC-C) | 407.4 |
| 2.042 | N-[3-(4-Cyclopentylcarbamoyl-piperidin-1-ylmethyl)-phenyl]-5-methyl-nicotinamide | 0.53 (LC-C) | 421.4 |
| 2.043 | N-{3-[4-(Cyclopropylmethyl-carbamoyl)-piperidin-1-ylmethyl]-phenyl}-5-methyl-nicotinamide | 0.48 (LC-C) | 407.4 |
| 2.044 | N-{3-[4-(4,4-Difluoro-cyclohexylcarbamoyl)-piperidin-1-ylmethyl]-phenyl}-5-methyl-nicotinamide | 0.55 (LC-C) | 471.4 |
| 2.045 | N-{3-[4-(1-Cyano-cyclopropylcarbamoyl)-piperidin-1-ylmethyl]-phenyl}-5-methyl-nicotinamide | 0.43 (LC-C) | 418.3 |
| 2.046 | 5-Methyl-N-{3-[4-(piperidine-1-carbonyl)-piperidin-1-ylmethyl]-phenyl}-nicotinamide | 0.52 (LC-C) | 421.4 |
| 2.047 | 5-Methyl-N-{3-[4-(pyrrolidine-1-carbonyl)-piperidin-1-ylmethyl]-phenyl}-nicotinamide | 0.47 (LC-C) | 407.4 |
| 2.048 | N-{3-[4-(Azepane-1-carbonyl)-piperidin-1-ylmethyl]-phenyl}-5-methyl-nicotinamide | 0.56 (LC-C) | 435.4 |
| 2.049 | N-{3-[4-(4,4-Difluoro-piperidine-1-carbonyl)-piperidin-1-ylmethyl]-phenyl}-5-methyl-nicotinamide | 0.53 (LC-C) | 457.4 |
| 2.050 | Rac-5-Methyl-N-{3-[4-(2-methyl-pyrrolidine-1-carbonyl)-piperidin-1-ylmethyl]-phenyl}-nicotinamide | 0.51 (LC-C) | 421.4 |
| 2.051 | N-{3-[4-(2,5-Dimethyl-pyrrolidine-1-carbonyl)-piperidin-1-ylmethyl]-phenyl}-5-methyl-nicotinamide | 0.57 (LC-C) | 435.4 |
| 2.052 | N-{3-[4-((R)-3-Fluoro-pyrrolidine-1-carbonyl)-piperidin-1-ylmethyl]-phenyl}-5-methyl-nicotinamide | 0.45 (LC-C) | 425.4 |
| 2.053 | N-{3-[4-((S)-3-Fluoro-pyrrolidine-1-carbonyl)-piperidin-1-ylmethyl]-phenyl}-5-methyl-nicotinamide | 0.45 (LC-C) | 425.4 |
| 2.054 | N-{3-[4-(3,3-Difluoro-pyrrolidine-1-carbonyl)-piperidin-1-ylmethyl]-phenyl}-5-methyl-nicotinamide | 0.49 (LC-C) | 443.3 |
| 2.055 | N-[3-(4-Dimethylcarbamoyl-piperidin-1-ylmethyl)-phenyl]-5-methyl-nicotinamide | 0.42 (LC-C) | 381.3 |
| 2.056 | 5-Methyl-N-{3-[4-(methyl-propyl-carbamoyl)-piperidin-1-ylmethyl]-phenyl}-nicotinamide | 0.51 (LC-C) | 409.4 |
| 2.057 | N-{3-[4-(Isobutyl-methyl-carbamoyl)-piperidin-1-ylmethyl]-phenyl}-5-methyl-nicotinamide | 0.56 (LC-C) | 423.4 |
| 2.058 | N-(3-{4-[(2-Methoxy-ethyl)-methyl-carbamoyl]-piperidin-1-ylmethyl}-phenyl)-5-methyl-nicotinamide | 0.46 (LC-C) | 425.4 |
| 2.059 | N-{3-[4-(1,1-Dimethyl-propylcarbamoyl)-piperidin-1-ylmethyl]-phenyl}-5-methyl-nicotinamide | 0.57 (LC-C) | 423.4 |
| 2.060 | N-{3-[4-(2,2-Dimethyl-pyrrolidine-1-carbonyl)-piperidin-1-ylmethyl]-phenyl}-5-methyl-nicotinamide | 0.57 (LC-C) | 435.4 |
| 2.061 | N-{3-[4-(3,3-Dimethyl-pyrrolidine-1-carbonyl)-piperidin-1-ylmethyl]-phenyl}-5-methyl-nicotinamide | 0.56 (LC-C) | 435.4 |
| 2.062 | N-[3-(3-Cyclopentylcarbamoyl-pyrrolidin-1-ylmethyl)-phenyl]-5-methyl-nicotinamide | 0.54 (LC-C) | 407.4 |
| 2.063 | N-[3-(3-Cyclohexylcarbamoyl-pyrrolidin-1-ylmethyl)-phenyl]-5-methyl-nicotinamide | 0.59 (LC-C) | 421.4 |
| 2.064 | rac-6-Trifluoromethyl-pyridine-2-carboxylic acid {3-[4-(1-hydroxymethyl-2-methyl-propylcarbamoyl)-piperidin-1-ylmethyl]-phenyl}-amide | 0.72 (LC-C) | 493.4 |
| 2.065 | 6-Trifluoromethyl-pyridine-2-carboxylic acid {3-[4-(1-hydroxymethyl-propylcarbamoyl)-piperidin-1-ylmethyl]-phenyl}-amide | 0.69 (LC-C) | 479.3 |
| 2.066 | 6-Trifluoromethyl-pyridine-2-carboxylic acid {3-[4-((S)-1-cyclohexyl-2-hydroxy-ethylcarbamoyl)-piperidin-1-ylmethyl]-phenyl}-amide | 0.81 (LC-C) | 533.4 |
| 2.067 | 6-Trifluoromethyl-pyridine-2-carboxylic acid {3-[4-((S)-1-hydroxymethyl-2,2-dimethyl-propylcarbamoyl)-piperidin-1-ylmethyl]-phenyl}-amide | 0.76 (LC-C) | 507.4 |
| 2.068 | 6-Trifluoromethyl-pyridine-2-carboxylic acid [3-(4-methylcarbamoyl-piperidin-1-ylmethyl)-phenyl]-amide | 0.66 (LC-C) | 421.3 |
| 2.069 | 6-Trifluoromethyl-pyridine-2-carboxylic acid [3-(4-ethylcarbamoyl-piperidin-1-ylmethyl)-phenyl]-amide | 0.69 (LC-C) | 435.3 |
| 2.070 | 6-Trifluoromethyl-pyridine-2-carboxylic acid {3-[4-(2,2-dimethyl-propylcarbamoyl)-piperidin-1-ylmethyl]-phenyl}-amide | 0.83 (LC-C) | 477.4 |
| 2.071 | 6-Trifluoromethyl-pyridine-2-carboxylic acid [3-(4-isobutylcarbamoyl-piperidin-1-ylmethyl)-phenyl]-amide | 0.78 (LC-C) | 463.3 |
| 2.072 | 1-{3-[(Thiophene-2-carbonyl)-amino]-benzyl}-piperidine-4-carboxylic acid methylamide | 0.51 (LC-C) | 358.2 |
| 2.073 | 1-{3-[(Thiophene-2-carbonyl)-amino]-benzyl}-piperidine-4-carboxylic acid dimethylamide | 0.55 (LC-C) | 372.3 |
| 2.074 | 1-{3-[(Thiophene-2-carbonyl)-amino]-benzyl}-piperidine-4-carboxylic acid diethylamide | 0.64 (LC-C) | 400.4 |
| 2.075 | 1-{3-[(Thiophene-2-carbonyl)-amino]-benzyl}-piperidine-4-carboxylic acid cyclohexylamide | 0.71 (LC-C) | 426.4 |

TABLE 2-continued

Examples 2.002-2.104

| Example | Compound | $t_R$ [min] (LC-MS Method) | MS Data m/z [M + H]+ |
|---|---|---|---|
| 2.076 | 1-{3-[(Thiophene-2-carbonyl)-amino]-benzyl}-piperidine-4-carboxylic acid benzylamide | 0.68 (LC-C) | 434.3 |
| 2.077 | 1-{3-[(Thiophene-2-carbonyl)-amino]-benzyl}-piperidine-4-carboxylic acid cyclohexyl-methyl-amide | 0.77 (LC-C) | 440.3 |
| 2.078 | 6-Trifluoromethyl-pyridine-2-carboxylic acid [3-(4-hexylcarbamoyl-piperidin-1-ylmethyl)-phenyl]-amide | 0.89 (LC-C) | 491.4 |
| 2.079 | 6-Trifluoromethyl-pyridine-2-carboxylic acid {3-[4-(hexyl-methyl-carbamoyl)-piperidin-1-ylmethyl]-phenyl}-amide | 0.93 (LC-C) | 505.3 |
| 2.080 | 6-Trifluoromethyl-pyridine-2-carboxylic acid [3-(4-pentylcarbamoyl-piperidin-1-ylmethyl)-phenyl]-amide | 0.72 (LC-C) | 426.4 |
| 2.081 | 6-Trifluoromethyl-pyridine-2-carboxylic acid {3-[4-(3-methyl-butylcarbamoyl)-piperidin-1-ylmethyl]-phenyl}-amide | 0.82 (LC-C) | 477.4 |
| 2.082 | 6-Trifluoromethyl-pyridine-2-carboxylic acid {3-[4-(3,3-dimethyl-butylcarbamoyl)-piperidin-1-ylmethyl]-phenyl}-amide | 0.86 8LC-C) | 491.4 |
| 2.083 | 6-Trifluoromethyl-pyridine-2-carboxylic acid {3-[4-(4-methyl-cyclohexylcarbamoyl)-piperidin-1-ylmethyl]-phenyl}-amide | 0.88 (LC-C) | 503.4 |
| 2.084 | rac-1-{3-[(5-Methyl-pyridine-3-carbonyl)-amino]-benzyl}-azepane-4-carboxylic acid cyclopropylmethyl-amide | 0.50 (LC-C) | 421.4 |
| 2.085 | rac-1-{3-[(5-Methyl-pyridine-3-carbonyl)-amino]-benzyl}-azepane-4-carboxylic acid (1,1-dimethyl-propyl)-amide | 0.60 (LC-C) | 437.5 |
| 2.086 | rac-1-{3-[(6-Trifluoromethyl-pyridine-2-carbonyl)-amino]-benzyl}-azepane-4-carboxylic acid tert-butylamide | 0.84 (LC-C) | 477.4 |
| 2.087 | rac-1-{3-[(6-Trifluoromethyl-pyridine-2-carbonyl)-amino]-benzyl}-azepane-4-carboxylic acid sec-butylamide | 0.81 (LC-C) | 477.3 |
| 2.088 | rac-1-{3-[(6-Trifluoromethyl-pyridine-2-carbonyl)-amino]-benzyl}-azepane-4-carboxylic acid (1,1-dimethyl-propyl)-amide | 0.88 (LC-C) | 491.4 |
| 2.089 | rac-1-{3-[(6-Trifluoromethyl-pyridine-2-carbonyl)-amino]-benzyl}-azepane-4-carboxylic acid cyclopropylmethyl-amide | 0.77 (LC-C) | 475.4 |
| 2.091 | 6-Trifluoromethyl-pyridine-2-carboxylic acid {3-[4-(2-hydroxy-1,1-dimethyl-ethylcarbamoyl)-piperidin-1-ylmethyl]-phenyl}-amide | 0.66 (LC-A) | 479.14 |
| 2.092 | 6-Trifluoromethyl-pyridine-2-carboxylic acid {3-[4-(2-methoxy-1-methyl-ethylcarbamoyl)-piperidin-1-ylmethyl]-phenyl}-amide | 0.70 (LC-C) | 479.4 |
| 2.093 | 6-Trifluoromethyl-pyridine-2-carboxylic acid {3-[4-(2-methoxy-propylcarbamoyl)-piperidin-1-ylmethyl]-phenyl}-amide | 0.69 (LC-C) | 479.3 |
| 2.094 | 6-Trifluoromethyl-pyridine-2-carboxylic acid [3-(4-propylcarbamoyl-piperidin-1-ylmethyl)-phenyl]-amide | 0.70 (LC-A) | 449.16 |
| 2.095 | 6-Trifluoromethyl-pyridine-2-carboxylic acid [3-(4-butylcarbamoyl-piperidin-1-ylmethyl)-phenyl]-amide | 0.73 (LC-A) | 463.33 |
| 2.096 | rac-N-[3-(3-tert-Butylcarbamoyl-pyrrolidin-1-ylmethyl)-phenyl]-5-methyl-nicotinamide | 0.57 (LC-C) | 395.3 |
| 2.097 | rac-1-{3-[2-(2-Chloro-4-fluoro-phenyl)-acetylamino]-benzyl}-pyrrolidine-3-carboxylic acid tert-butylamide | 0.84 (LC-C) | 446.4 |
| 2.098 | rac-6-Trifluoromethyl-pyridine-2-carboxylic acid [3-(3-isobutylcarbamoyl-pyrrolidin-1-ylmethyl)-phenyl]-amide | 0.84 (LC-C) | 449.4 |
| 2.099 | rac-6-Trifluoromethyl-pyridine-2-carboxylic acid [3-(3-cyclohexylcarbamoyl-pyrrolidin-1-ylmethyl)-phenyl]-amide | 0.89 (LC-C) | 475.4 |
| 2.100 | rac-1-{3-[2-(2-Chloro-4-fluoro-phenyl)-acetylamino]-benzyl}-pyrrolidine-3-carboxylic acid cyclohexylamide | 0.88 (LC-C) | 472.4 |
| 2.101 | rac-6-Trifluoromethyl-pyridine-2-carboxylic acid [3-((2S*,4S*)-4-cyclohexylcarbamoyl-2-methyl-piperidin-1-ylmethyl)-phenyl]-amide | 0.89 (LC-C) | 505.5 |
| 2.102 | rac-6-Trifluoromethyl-pyridine-2-carboxylic acid [3-((2S*,4S*)-4-tert-butylcarbamoyl-2-methyl-piperidin-1-ylmethyl)-phenyl]-amide | 0.85 LC-C) | 477.4 |
| 2.103 | rac-N-[3-((2S*,4S*)-4-tert-Butylcarbamoyl-2-methyl-piperidin-1-ylmethyl)-phenyl]-5-methyl-nicotinamide | 0.57 (LC-C) | 423.5 |
| 2.104 | rac-N-[3-((2S*,4S*)-4-Cyclohexylcarbamoyl-2-methyl-piperidin-1-ylmethyl)-phenyl]-5-methyl-nicotinamide | 0.63 (LC-C) | 449.5 |

The two enantiomers of rac-6-trifluoromethyl-pyridine-2-carboxylic acid [3-((2S*,4S*)-4-cyclohexylcarbamoyl-2-methyl-piperidin-1-ylmethyl)-phenyl]-amide (Example 2.102) are separated by chiral prep. LC-MS (H). Conditions: Daicel ChiralPak IA column, Eluent: 90% EtOAc with 0.2% DEA, 10% Heptane.

Example 2.105

6-Trifluoromethyl-pyridine-2-carboxylic acid [3-((2S,4S)-4-cyclohexylcarbamoyl-2-methyl-piperidin-1-ylmethyl)-phenyl]-amide or 6-trifluoromethyl-pyridine-2-carboxylic acid [3-((2R,4R)-4-cyclohexylcarbamoyl-2-methyl-piperidin-1-ylmethyl)-phenyl]-amide LC-MS G: $t_R$=12.0 min; LC-MS C $t_R$=0.89 min; [M+H]+=503.5

Example 2.106

6-Trifluoromethyl-pyridine-2-carboxylic acid [3-((2R,4R)-4-cyclohexylcarbamoyl-2-methyl-piperidin-1-ylmethyl)-phenyl]-amide or 6-trifluoromethyl-pyridine-2-carboxylic acid [3-((2S,4S)-4-cyclohexylcarbamoyl-2-methyl-piperidin-1-ylmethyl)-phenyl]-amide LC-MS G: $t_R$=8.5 min; LC-MS C $t_R$=0.89 min; [M+H]+=503.4

General Method C for the Synthesis of piperidine-4-carboxamide of Structure (I)

Buildings Blocks

Preparation of Building Blocks of General Formula B-3

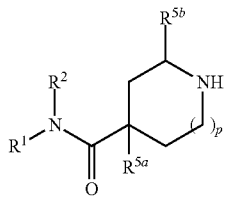

B-3

Piperidine-4-carboxylic acid cyclohexylamide hydrochloride J-1

(3.01a): 4-Cyclohexylcarbamoyl-piperidine-1-carboxylic acid tert-butyl ester

A solution of 1-(tert-butoxycarbonyl)-piperidine-4-carboxylic acid (20 g, 0.087 mmol) in DCM (200 mL) is treated successively with cyclohexylamine (9.99 ml, 0.087 mmol), EDC hydrochloride (21.74 g, 0.113 mmol) and DMAP (1.599 g, 0.013 mmol). After stirring for 18 h at RT water (200 mL) is added to the mixture. The organic phase is separated and the aqueous phase extracted twice with DCM (100 mL). The combined organic phases are washed with brine (200 mL) and dried over $MgSO_4$ and evaporated. The resulting solid compound is triturated with diethylether, filtered and dried in vacuo to yield the subtitle compound (21.11 g, 78%) as a colorless powder. LC-MS A: $t_R$=0.83 min; $[M+H]^+$=311.27.

(3.01 b): Piperidine-4-carboxylic acid cyclohexylamide hydrochloride J-1

A solution of 4-cyclohexylcarbamoyl-piperidine-1-carboxylic acid tert-butyl ester (21.11 g, 68 mmol) in dioxane (250 mL) is treated with a 4M HCl solution in dioxane (51 ml, 204 mmol) at 0° C. for 1 h. The reaction mixture is stirred at 50° C. for 4 h. The resulting suspension is cooled down to RT and the product filtered, washed with cold dioxane (50 mL) and dried under HV. The subtitle compound (16.64 g, 99%) is obtained as a white powder; LC-MS A: $t_R$=0.46 min; $[M+H]^+$=211.20.

The following Piperidine-4-carboxylic acid amides are prepared in analogy to example 3.01a-b.

Piperidine-4-carboxylic acid tert-butylamide hydrochloride J-2

The title compound is prepared according to the reaction sequence 3.01a-2.01b described above using tert-butylamine instead of cyclohexylamine as in 3.01a: LC-MS A: $t_R$=0.39 min; $[M+H]^+$=185.39.

Piperidine-4-carboxylic acid cyclopropylamide hydrochloride J-3

The title compound is prepared according to the reaction sequence 3.01a-2.01b described above using cyclopropylamine instead of cyclohexylamine as in 3.01a: LC-MS B: $t_R$=0.15 min; $[M+H]^+$=169.05.

Piperidine-4-carboxylic acid cyclopentylamide hydrochloride J-4

The title compound is prepared according to the reaction sequence 3.01a-2.01b described above using cyclopentylamine instead of cyclohexylamine as in 3.01a: LC-MS B: $t_R$=0.15 min; $[M+H]^+$=169.05.

4-Fluoro-piperidine-4-carboxylic acid tert-butylamide J-5

The title compound is prepared according to the reaction sequence 3.01a-2.01b described above using 1-(tert-butoxycarbonyl)-4-fluoropiperidine-4-carboxylic acid instead of 1-(tert-butoxycarbonyl)-piperidine-4-carboxylic acid and cyclopropylamine instead of cyclohexylamine as in 3.01a: LC-MS A: $t_R$=0.41 min; $[M+H]^+$=197.35.

4-Fluoro-piperidine-4-carboxylic acid cyclohexylamide J-6

The title compound is prepared according to the reaction sequence 3.01a-2.01b described above using 1-(tert-butoxycarbonyl)-4-fluoropiperidine-4-carboxylic acid instead of 1-(tert-butoxycarbonyl)-piperidine-4-carboxylic acid and cyclohexylamine as in 3.01a: LC-MS A: $t_R$=0.49 min; $[M+H]^+$=229.25.

Piperidine-4-carboxylic acid isobutyl-methyl-amide hydrochloride J-7

The title compound is prepared according to the reaction sequence 3.01a-2.01b described above using N-methyl-isobutylamine instead of cyclohexylamine as in 3.01a: LC-MS A: $t_R$=0.42 min; $[M+H]^+$=199.31.

Piperidine-4-carboxylic acid (1,1-dimethyl-propyl)-amide hydrochloride J-8

The title compound is prepared according to the reaction sequence 3.01a-2.01b described above using tert-amylamine instead of cyclohexylamine as in 3.01a: LC-MS A: $t_R$=0.46 min; $[M+H]^+$=199.37.

4-Methyl-piperidine-4-carboxylic acid tert-butylamide hydrochloride J-9

The title compound is prepared according to the reaction sequence 3.01a-2.01b described above using 1-(tert-butoxycarbonyl)-4-methylpiperidine-4-carboxylic acid instead of 1-(tert-butoxycarbonyl)-piperidine-4-carboxylic acid and tert-butylamine instead of cyclohexylamine as in 3.01a: LC-MS A: $t_R$=0.44 min; $[M+H]^+$=199.24.

4-Methyl-piperidine-4-carboxylic acid cyclohexylamide J-10

The title compound is prepared according to the reaction sequence 3.01a-2.01b described above using 1-(tert-butoxycarbonyl)-4-methylpiperidine-4-carboxylic acid instead of 1-(tert-butoxycarbonyl)-piperidine-4-carboxylic acid and cyclohexylamine instead of cyclohexylamine as in 3.01a: LC-MS A: $t_R$=0.50 min; $[M+H]^+$=225.17.

Preparation of Building Blocks of General Formula E-2

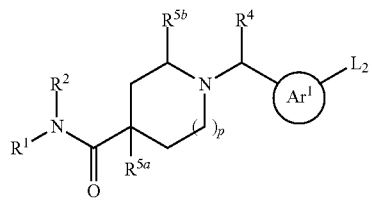

E-2

1-(2-Bromo-pyridin-4-ylmethyl)-piperidine-4-carboxylic acid cyclohexylamide K-1

A mixture of 2-bromo-4-formylpyridine (1 g, 5.38 mmol), piperidine-4-carboxylic acid cyclohexylamide hydrochloride J-1 (1.327 g, 5.38 mmol) and DIPEA (2.78 mL, 16.13 mmol) in DCM (25 mL) is treated with sodium triacetoxy borohydride (2.28 g, 10.75 mmol) in 5 portions over 20 min. and the reaction mixture is stirred for 18 h at RT. Aq. sat. NaHCO$_3$ (25 mL) is added and the mixture is stirred for 30 min. The phases are separated and the aqueous phase is extracted twice with DCM (25 mL). The combined organic phases are dried over MgSO$_4$ and evaporated. The crude residue is purified by flash chromatography on silica gel using a gradient of heptane and EtOAc 1:4 to EtOAc 100%. After concentration of the product-containing fractions, the title compound (1.18 g, 58%) is obtained as a colorless solid LC-MS A: $t_R$=0.59 min; [M+H]$^+$=382.15.

In analogy to example 3.01c the following derivatives are prepared 1-(6-Bromo-pyridin-2-ylmethyl)-piperidine-4-carboxylic acid cyclohexylamide K-2

The title compound is prepared according to the reaction 3.01c described above using 6-bromo-pyridine-2-carboxaldehyde and piperidine-4-carboxylic acid cyclohexylamide hydrochloride as in 3.01c: LC-MS A: $t_R$=0.61 min; [M+H]$^+$=382.20.

1-(5-Bromo-pyridin-3-ylmethyl)-piperidine-4-carboxylic acid cyclohexylamide K-3

The title compound is prepared according to the reaction 3.01c described above using 5-bromo-pyridine-3-carboxaldehyde and piperidine-4-carboxylic acid cyclohexylamide hydrochloride as in 3.01c: LC-MS A: $t_R$=0.58 min; [M+H]$^+$=380.19.

1-(4-Chloro-pyridin-2-ylmethyl)-piperidine-4-carboxylic acid cyclohexylamide K-4

The title compound is prepared according to the reaction 3.01c described above using 4-chloro-pyridine-2-carboxaldehyde and piperidine-4-carboxylic acid cyclohexylamide hydrochloride as in 3.01c: LC-MS A: $t_R$=0.58 min; [M+H]$^+$=380.19.

1-(5-Bromo-thiophen-3-ylmethyl)-piperidine-4-carboxylic acid tert-butylamide K-5

The title compound is prepared according to the reaction 3.01c described above using 5-bromo-thiophene-3-carbaldehyde and piperidine-4-carboxylic acid tert-butylamide hydrochloride as in 3.01c: LC-MS A: $t_R$=0.64 min; [M+H]$^+$=360.95.

1-(4-Bromo-thiophen-2-ylmethyl)-piperidine-4-carboxylic acid tert-butylamide K-6

The title compound is prepared according to the reaction 3.01c described above using 4-bromo-thiophene-2-carbaldehyde and piperidine-4-carboxylic acid tert-butylamide hydrochloride as in 3.01c: LC-MS A: $t_R$=0.65 min; [M+H]$^+$=360.95.

Example 3.001

1-[2-(4-Fluoro-benzoylamino)-pyridin-4-ylmethyl]-piperidine-4-carboxylic acid cyclohexylamide A suspension of 1-(2-chloro-pyridin-4-ylmethyl)-piperidine-4-carboxylic acid cyclohexylamide (50 mg, 0.15 mol), 4-fluoro-benzamide (20 mg, 0.15 mmol) and Cs$_2$CO$_3$ (5 mg, 0.16 mmol) in degassed dioxane (3 mL) is treated with 4,5-bis(diphenylphosphino)-9,9-dimethylxanthene (Xantphos) (17 mg, 0.030 mmol) and tris(dibenzylideneacetone)dipalladium(0) (6.8 mg, 0.007 mmol). The reaction mixture is heated overnight at 100° C. The mixture is filtered, evaporated, dissolved in MeCN (1 mL) and purified by prep HPLC E. The product is dissolved in 2 ml HCl 1.25 N in MeOH and re-evaporated at HV, delivering the title compound hydrochloride as a slightly yellow powder, LC-MS A: $t_R$=0.67 min; [M+H]$^+$=439.3.

Compounds of Examples 3.02-3.13 listed in Table 3 below are prepared by applying either one of the above-mentioned methods described for Example 3.01.

TABLE 3

Examples 3.002-3.013

| Example | Compound | $t_R$ [min] (LC-MS Method) | MS Data m/z [M + H]$^+$ |
|---|---|---|---|
| 3.002 | 1-[2-(4-Chloro-benzoylamino)-pyridin-4-ylmethyl]-piperidine-4-carboxylic acid cyclohexylamide | 0.78 (LC-C) | 455.4 |
| 3.003 | 1-[6-(4-Fluoro-benzoylamino)-pyridin-2-ylmethyl]-piperidine-4-carboxylic acid cyclohexylamide | 0.76 (LC-C) | 439.4 |
| 3.004 | 1-[5-(4-Chloro-benzoylamino)-pyridin-3-ylmethyl]-piperidine-4-carboxylic acid cyclohexylamide | 0.73 (LC-C) | 455.3 |
| 3.005 | 1-[5-(4-Fluoro-benzoylamino)-pyridin-3-ylmethyl]-piperidine-4-carboxylic acid cyclohexylamide | 0.68 (LC-C) | 439.4 |
| 3.006 | 1-[4-(4-Fluoro-benzoylamino)-pyridin-2-ylmethyl]-piperidine-4-carboxylic acid cyclohexylamide | 0.72 (LC-C) | 439.3 |

TABLE 3-continued

Examples 3.002-3.013

| Example | Compound | $t_R$ [min] (LC-MS Method) | MS Data m/z [M + H]+ |
|---|---|---|---|
| 3.007 | 1-[4-(4-Chloro-benzoylamino)-pyridin-2-ylmethyl]-piperidine-4-carboxylic acid cyclohexylamide | 0.79 (LC-C) | 455.3 |
| 3.008 | 1-[5-(4-Fluoro-benzoylamino)-thiophen-3-ylmethyl]-piperidine-4-carboxylic acid tert-butylamide | 0.69 (LC-C) | 418.4 |
| 3.009 | 1-[4-(4-Fluoro-benzoylamino)-thiophen-2-ylmethyl]-piperidine-4-carboxylic acid tert-butylamide | 0.68 (LC-C) | 418.3 |
| 3.010 | 1-{5-[2-(2-Chloro-phenyl)-acetylamino]-thiophen-3-ylmethyl}-piperidine-4-carboxylic acid tert-butylamide | 0.74 (LC-C) | 448.3 |
| 3.011 | 1-{4-[2-(2-Chloro-phenyl)-acetylamino]-thiophen-2-ylmethyl}-piperidine-4-carboxylic acid tert-butylamide | 0.72 (LC-C) | 448.3 |
| 3.012 | N-[4-(4-tert-Butylcarbamoyl-piperidin-1-ylmethyl)-thiophen-2-yl]-5-methyl-nicotinamide | 0.53 (LC-C) | 415.4 |
| 3.013 | N-[5-(4-tert-Butylcarbamoyl-piperidin-1-ylmethyl)-thiophen-3-yl]-5-methyl-nicotinamide | 0.50 (LC-C) | 415.4 |

General Method D for the Synthesis of piperidine-4-carboxamide of Structure (I)

Buildings Blocks

Preparation of Building Blocks of General Formula D-3

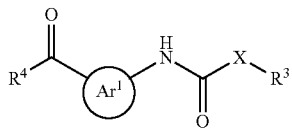

D-3

N-(3-Formyl-phenyl)-5-methyl-nicotinamide L-1

(4.01a): N-(3-[1,3]Dioxolan-2-yl-phenyl)-5-methyl-nicotinamide

A solution of EDC hydrochloride (6.3 g, 32.81 mmol) in DCM (20 mL) is added over 5 min. to a solution of 3-aminobenzaldehyde ethylene acetal (3,614 g, 21.9 mmol), 5-methylnicotinic acid (3 g, 21.9 mmol), HOBt (6.7 g, 43.75 mmol), DMAP (534.5 mg, 4.38 mmol) and DIPEA (11.2 mL, 65.63 mmol) in DCM (30 mL) at RT under argon. The mixture is stirred at RT for 18 h. The mixture is diluted with DCM (50 mL) and washed twice with aq. sat. NaHCO$_3$ (50 mL). The organic phase is separated and the aq. phase extracted twice with DCM (100 mL). The combined organic phases are washed with brine (200 mL), dried over MgSO$_4$ and evaporated. The crude product is purified by flash chromatography on silica gel using a gradient of heptane and EtOAc 1:1 to heptane/EtOAc 1:4. After concentration of the product-containing fractions, the title compound (6.14 g, 99%) is obtained as a colorless solid LC-MS A: $t_R$=0.58 min; [M+H]+=285.22.

(4.01b): N-(3-Formyl-phenyl)-5-methyl-nicotinamide L-1

A solution of N-(3-[1,3]dioxolan-2-yl-phenyl)-5-methyl-nicotinamide (3.0 g, 10.55 mmol) in dioxane (50 mL) is treated with a 4M HCl in 1,4-dioxane (30 mL). The mixture is heated at 60° C. for 3 h. Water (100 mL) is added to the mixture followed by NaOH 2M (70 mL) solution to get pH 10. The mixture is extracted twice with EtOAc (100 mL). The combined organic phases are dried over MgSO$_4$, filtered and evaporated. The crude title compound is obtained as a brownish solid (1.744 g, 69%) LC-MS A: $t_R$=0.58 min; [M+H]+=241.24.

Preparation of N-(3-Formyl-phenyl)-arylamides L-2-L-7

In analogy to example 4.01a-b the following 3-formyl aryl amides are prepared

4-Chloro-N-(3-formyl-phenyl)-benzamide L-2

The title compound is prepared according to the reaction 4.01a-b described above using 4-chloro-benzoyl chloride: LC-MS A: $t_R$=0.84 min; [M+H]+=260.00.

6-Trifluoromethyl-pyridine-2-carboxylic acid (3-formyl-phenyl)-amide L-3

The title compound is prepared according to the reaction 4.01a-b described above using 6-(trifluoromethyl)picolinoyl chloride: LC-MS A: $t_R$=0.88 min; [M+H]+=295.03.

N-(3-Formyl-phenyl)-5-methoxy-nicotinamide L-4

The title compound is prepared according to the reaction 4.01a-b described above using 5-methoxynicotinoyl chloride: LC-MS A: $t_R$=0.66 min; [M+H]+=257.18.

6-Trifluoromethyl-pyridine-2-carboxylic acid (4-fluoro-3-formyl-phenyl)-amide L-5

The title compound is prepared according to the reaction 4.01a described above using 6-(trifluoromethyl)picolinoyl chloride and (5-amino-2-fluorophenyl)methanol, followed by the oxidation of the alcohol intermediate 6-trifluoromethyl-pyridine-2-carboxylic acid (4-fluoro-3-hydroxymethyl-phenyl)-amide: LC-MS A: $t_R$=0.80 min; [M+H]+=315.06.

The crude alcohol (1.41 g, 4.5 mmol) dissolved in acetonitrile (20 ml) is treated with manganese dioxide (1.37 g, 15.8 mmol) and stirred at RT for 18 h. The manganese dioxide is filtered through a pad of decalite and after evaporation of the solvent the crude aldehyde is obtained as a light brown solid (1.34 g, 96%): LC-MS A: $t_R$=0.80 min; [M+H]$^+$=no mass.

N-(4-Fluoro-3-formyl-phenyl)-5-methyl-nicotinamide L-6

The title compound is prepared according to the reaction sequence described above using 5-methylnicotinoyl chloride and (5-amino-2-fluorophenyl)methanol followed by oxidation of the crude alcohol: LC-MS A: $t_R$=0.60 min; [M+H]$^+$=258.88.

5-Fluoro-1-oxy-pyridine-2-carboxylic acid (3-formyl-phenyl)-amide L-7

5-Fluoro-pyridine-2-carboxylic acid (3-[1,3]dioxolan-2-yl-phenyl)-amide

The subtitle compound is prepared according to the reaction 4.01a described above using 5-fluoropicolinoyl chloride: LC-MS A: $t_R$=0.89 min; [M+H]$^+$=289.29.

5-Fluoro-1-oxy-pyridine-2-carboxylic acid (3-[1,3]dioxolan-2-yl-phenyl)-amide A solution of 5-fluoro-pyridine-2-carboxylic acid (3-[1,3]dioxolan-2-yl-phenyl)-amide (0.37 g, 1.28 mmol) in DCM (8 ml) is treated with m-chloro-perbenzoic acid 75% (1.6 g, 6.4 mmol) at RT for 18 h. The mixture is diluted with DCM (20 mL) and washed successively twice with a 10% aq. sodium thiosulfate solution (25 mL), sat. aq. Na$_2$CO$_3$ solution (25 mL) and brine (25 mL). The organic phase is dried over MgSO$_4$ and evaporated. The crude product is purified by flash chromatography on silica gel using a gradient of heptane/EtOAc 4:1 to heptane/EtOAc 1:1. After concentration of the product-containing fractions, the title compound (0.158 g, 65%) is obtained as a colorless solid LC-MS A: $t_R$=0.72 min; [M+H]$^+$=305.26.

5-Fluoro-1-oxy-pyridine-2-carboxylic acid (3-formyl-phenyl)-amide

A solution of 5-fluoro-1-oxy-pyridine-2-carboxylic acid (3-[1,3]dioxolan-2-yl-phenyl)-amide (0.155 g, 0.51 mmol) in dioxane (3 mL) is treated with a solution of 10% aq. HCl (1.3 mL). The resulting suspension is heated to 60° C. for 30 min. The mixture is let to cool to RT. A white suspension is obtained. It is partitioned between EtOAc (20 mL) and sat. aq.NaHCO$_3$ (20 mL). The phases are separated. The water layer is extracted twice with EtOAc. The combined organic phases are dried over MgSO$_4$ and evaporated under reduced pressure, yielding the product as a white solid (0.104 g, 79%). LC-MS A: $t_R$=0.72 min; [M+H]$^+$=261.17.

5-Fluoro-pyridine-2-carboxylic acid (3-formyl-phenyl)-amide L-8

The title compound is prepared by treatment with HCl 10% of 5-fluoro-pyridine-2-carboxylic acid (3-[1,3]dioxolan-2-yl-phenyl)-amide: LC-MS A: $t_R$=0.79 min; [M+H]$^+$=245.05.

N-(3-Formyl-phenyl)-5-methyl-1-oxy-nicotinamide L-9

The title compound is prepared according to the reaction sequence described above starting from N-(3-[1,3]dioxolan-2-yl-phenyl)-5-methyl-nicotinamide 4.01a which is treated with m-chloro-perbenzoic acid to deliver N-(3-[1,3]dioxolan-2-yl-phenyl)-5-methyl-1-oxy-nicotinamide; LC-MS A: $t_R$=0.61 min; [M+H]$^+$=301.09, then deprotected with HCl 10% to yield N-(3-formyl-phenyl)-5-methyl-1-oxy-nicotinamide: LC-MS A: $t_R$=0.60 min; [M+H]$^+$=257.06.

5-Chloro-1-oxy-pyridine-2-carboxylic acid (3-formyl-phenyl)-amide L-10

The title compound is prepared according to the reaction sequence described above for L-7 starting from 5-chloro-pyridine-2-carboxylic acid and 3-aminobenzaldehyde ethylene acetal to yield 5-chloro-pyridine-2-carboxylic acid (3-[1,3]dioxolan-2-yl-phenyl)-amide; LC-MS A: $t_R$=0.84 min; [M+H]$^+$=305.13 which is treated with m-chloro-perbenzoic acid to deliver 5-chloro-1-oxy-pyridine-2-carboxylic acid (3-[1,3]dioxolan-2-yl-phenyl)-amide; LC-MS A: $t_R$=0.77 min; [M+H]$^+$=321.02, then deprotected with HCl 10% to yield 5-chloro-1-oxy-pyridine-2-carboxylic acid (3-formyl-phenyl)-amide LC-MS A: $t_R$=0.72 min; [M+H]$^+$=277.01.

Example 4.001

N-[3-(4-Cyclohexylcarbamoyl-4-fluoro-piperidin-1-ylmethyl)-phenyl]-5-methyl-nicotinamide A solution of N-(3-formyl-phenyl)-5-methyl-nicotinamide L-1 (60 mg, 0.25 mmol) and 4-fluoro-piperidine-4-carboxylic acid cyclohexylamide hydrochloride (66 mg, 0.25 mmol) in DCM (3 mL) is treated with DIPEA (0.128 mL, 0.75 mmol). Sodium triacetoxyborohydride (132 mg, 0.62 mmol) is added at once and the mixture is stirred at RT for 18 h. The mixture is diluted with DCM (5 mL) and washed twice with aq. sat. NaHCO$_3$ (5 mL). The organic phase is dried over MgSO$_4$ and evaporated. The residue is dissolved in acetonitrile and purified by prep HPLC E, delivering the title compound as a colorless powder, LC-MS A: $t_R$=0.62 min; [M+H]$^+$=453.4. $^1$H-NMR (CDCl3): δ 1-1.4 (m, 5H), 1.6-1.8 (m, 6H), 1.9-2.1 (m, 2H), 2.2-2.4 (m, 4H), 3.45 (s, 3H), 2.7-2.8 (m, 2H), 3.7-3.8 (m, 1H), 6.28 (t, J=6.5, 1H), 7.15 (d, J=8, 1H), 7.35 (t, J=8, 1H), 7.55 (s, 1H), 7.73 (d, J=8, 1H), 8.05 (s, 1H), 8.12 (s, 1H), 8.61 (s, 1H), 8.93 (s, 1H).

Compounds of Examples 4.002-4.025 listed in Table 4 below are prepared by applying the method described for Example 4.001.

TABLE 4

Examples 4.002-4.025

| Example | Compound | $t_R$ [min] (LC-MS Method) | MS Data m/z [M + H]$^+$ |
| --- | --- | --- | --- |
| 4.002 | N-[3-(4-tert-Butylcarbamoyl-4-fluoro-piperidin-1-ylmethyl)-phenyl]-5-methyl-nicotinamide | 0.56 (LC-C) | 427.4 |

TABLE 4-continued

Examples 4.002-4.025

| Example | Compound | $t_R$ [min] (LC-MS Method) | MS Data m/z [M + H]+ |
|---|---|---|---|
| 4.003 | N-[3-(4-Cyclohexylcarbamoyl-4-methyl-piperidin-1-ylmethyl)-phenyl]-5-methyl-nicotinamide | 0.62 (LC-C) | 449.4 |
| 4.004 | N-[3-(4-tert-Butylcarbamoyl-4-methyl-piperidin-1-ylmethyl)-phenyl]-5-methyl-nicotinamide | 0.59 (LC-C) | 423.0 |
| 4.005 | 5-Fluoro-1-oxy-pyridine-2-carboxylic acid [3-(4-cyclohexylcarbamoyl-piperidin-1-ylmethyl)-phenyl]-amide | 0.67 (LC-C) | 455.4 |
| 4.006 | 5-Fluoro-1-oxy-pyridine-2-carboxylic acid [3-(4-cyclopentylcarbamoyl-piperidin-1-ylmethyl)-phenyl]-amide | 0.62 (LC-C) | 441.4 |
| 4.007 | 5-Fluoro-1-oxy-pyridine-2-carboxylic acid [3-(4-tert-butylcarbamoyl-piperidin-1-ylmethyl)-phenyl]-amide | 0.62 (LC-C) | 429.3 |
| 4.008 | 6-Trifluoromethyl-pyridine-2-carboxylic acid [3-(4-cyclohexylcarbamoyl-4-fluoro-piperidin-1-ylmethyl)-phenyl]-amide | 0.88 (LC-C) | 507.3 |
| 4.009 | 6-Trifluoromethyl-pyridine-2-carboxylic acid [3-(4-tert-butylcarbamoyl-4-fluoro-piperidin-1-ylmethyl)-phenyl]-amide | 0.83 (LC-C) | 481.4 |
| 4.010 | 6-Trifluoromethyl-pyridine-2-carboxylic acid [3-(4-cyclohexylcarbamoyl-4-methyl-piperidin-1-ylmethyl)-phenyl]-amide | 0.88 (LC-C) | 503.4 |
| 4.011 | 6-Trifluoromethyl-pyridine-2-carboxylic acid [3-(4-tert-butylcarbamoyl-4-methyl-piperidin-1-ylmethyl)-phenyl]-amide | 0.84 (LC-C) | 477.4 |
| 4.012 | N-[3-(4-Cyclohexylcarbamoyl-piperidin-1-ylmethyl)-phenyl]-5-methoxy-nicotinamide | 0.63 (LC-C) | 451.4 |
| 4.013 | N-[3-(4-Cyclopentylcarbamoyl-piperidin-1-ylmethyl)-phenyl]-5-methoxy-nicotinamide | 0.58 (LC-C) | 437.4 |
| 4.014 | N-[3-(4-tert-Butylcarbamoyl-piperidin-1-ylmethyl)-phenyl]-5-methoxy-nicotinmide | 0.57 (LC-C) | 427.4 |
| 4.015 | N-{3-[4-(Isobutyl-methyl-carbamoyl)-piperidin-1-ylmethyl]-phenyl}-5-methoxy-nicotinamide | 0.61 (LC-C) | 439.4 |
| 4.016 | 6-Trifluoromethyl-pyridine-2-carboxylic acid [3-(4-cyclohexylcarbamoyl-piperidin-1-ylmethyl)-4-fluoro-phenyl]-amide | 0.83 (LC-C) | 507.3 |
| 4.017 | 6-Trifluoromethyl-pyridine-2-carboxylic acid [3-(4-tert-butylcarbamoyl-piperidin-1-ylmethyl)-4-fluoro-phenyl]-amide | 0.79 (LC-C) | 481.3 |
| 4.018 | N-[3-(4-Cyclohexylcarbamoyl-piperidin-1-ylmethyl)-4-fluoro-phenyl]-5-methyl-nicotinamide | 0.6 (LC-C) | 453.4 |
| 4.019 | N-[3-(4-tert-Butylcarbamoyl-piperidin-1-ylmethyl)-4-fluoro-phenyl]-5-methyl-nicotinamide | 0.54 (LC-C) | 427.3 |
| 4.020 | 5-Fluoro-pyridine-2-carboxylic acid [3-(4-tert-butylcarbamoyl-piperidin-1-ylmethyl)-phenyl]-amide | 0.73 (LC-C) | 413.4 |
| 4.021 | 5-Fluoro-1-oxy-pyridine-2-carboxylic acid {3-[4-(1,1-dimethyl-propylcarbamoyl)-piperidin-1-ylmethyl]-phenyl}amide | 0.70 (LC-C) | 443.4 |
| 4.022 | N-[3-(4-tert-Butylcarbamoyl-piperidin-1-ylmethyl)-phenyl]-5-methyl-1-oxy-nicotinamide | 0.56 (LC-C) | 425.4 |
| 4.023 | N-{3-[4-(1,1-Dimethyl-propylcarbamoyl)-piperidin-1-ylmethyl]-phenyl}-5-methyl-1-oxy-nicotinamide | 0.61 (LC-C) | 439.5 |
| 4.024 | 5-Chloro-1-oxy-pyridine-2-carboxylic acid [3-(4-tert-butylcarbamoyl-piperidin-1-ylmethyl)-phenyl]-amide | 0.7 (LC-C) | 445.4 |
| 4.025 | 5-Chloro-1-oxy-pyridine-2-carboxylic acid {3-[4-(1,1-dimethyl-propylcarbamoyl)-piperidin-1-ylmethyl]-phenyl}amide | 0.75 (LC-C) | 459.4 |

Example 5.001

6-Trifluoromethyl-pyridine-2-carboxylic acid [6-(4-tert-butylcarbamoyl-piperidin-1-ylmethyl)-pyrimidin-4-yl]-amide (5.001a): ((4-(tert-butylcarbamoyl)piperidin-1-yl)methyl)trifluoroborate To a solution of piperidine-4-carboxylic acid tert-butyl-amide (65 mg, 0.353 mmol) in a mixture of THF/t-BuOH 3:1 (3 mL) is added potassium (bromomethyl)trifluoroborate (70.8 mg, 0.353 mmol). The mixture is heated at 80° C. for 18 h. The mixture is let to cool down. The solvent is evaporated under reduced pressure. The residue is dried at hV for 24 h and directly engaged in step 5.01c; LC-MS A: $t_R$=0.49 min; [M-F]+=247.23.

(5.001b): 6-Trifluoromethyl-pyridine-2-carboxylic acid (6-chloro-pyrimidin-4-yl)-amide To a solution of 4-amino-6-chloropyrimidine (230 mg, 1.78 mmol) in DCM (15 mL) is added 6-(trifluoromethyl) picolinoyl chloride (276 mg, 1.78 mmol) and DIPEA (0.912 ml, 5.33 mmol). The mixture is stirred overnight at RT. The mixture is diluted with DCM (10 mL), washed with saturated $NaHCO_3$ solution (25 mL). The organic layer is dried over $MgSO_4$ and evaporated under reduced pressure. The residue is purified by prep HPLC E, delivering the title compound as a yellowish solid (102 mg, 19%); LC-MS A: $t_R$=0.89 min; [M+H]+=302.92.

(5.001c): 6-Trifluoromethyl-pyridine-2-carboxylic acid [6-(4-tert-butylcarbamoyl-piperidin-1-ylmethyl)-pyrimidin-4-yl]-amide To a solution of ((4-(tert-butylcarbamoyl)piperidin-1-yl) methyl)trifluoroborate (45 mg, 0.169 mmol) in THF/water 4:1 (3 mL) are added 6-trifluoromethyl-pyridine-2-carboxylic acid (6-chloro-pyrimidin-4-yl)-amide (51.2 mg, 0.169 mmol), palladium (II) acetate, (0.949 mg, 0.00423 mmol,), X-Phos, (2-dicyclohexylphosphino-2',4',6'-triisopropylbiphenyl) (4.84 mg, 0.0101 mmol) and $Cs_2CO_3$, (165 mg, 0.507 mmol). The mixture is purged with argon and is stirred overnight in a sealed tube at 80° C. The mixture is let to cool down. Water (3 mL) and AcOEt (5 mL) are added and the aqueous phase is extracted with AcOEt (10 mL). The organic phase is dried over $MgSO_4$, filtered and evaporated. The residue is purified by prep HPLC E delivering the title compound (27 mg, 30%) as a white powder, LC-MS A: $t_R$=0.74 min; $[M+H]^+$=465.4.

Example 6.001

N-(3-((4-(cyclohexylcarbamoyl)piperidine-1-yl) d$_2$methyl)phenyl)-5-methylnicotinamide (6.001a): 5-amino-benzene-1',1'-d$_2$-methanol A solution of methyl 3-aminobenzoate (8.09 g, 51.9 mmol), dissolved in THF (30 mL) is added to a stirred suspension of lithium aluminium deuteride (3.27 g, 77.9 mmol) in THF (100 mL). THF (70 mL) is added to solubilize the suspension. The mixture is stirred overnight at RT and then 1 h at refluxing temperature. $D_2O$ (11.3 mL, 623 mmol) are added dropwise under stirring. The reaction is stirred overnight at RT. The mixture is filtered off and evaporated to dryness under vacuum. The crude product (5.97 g, 92%) is used as such in the next step; LC-MS D: $t_R$=0.19 min; $[M+H]^+$=126.3.

(6.001b): N-(3-((hydroxy) d$_2$methyl)phenyl-5-methylnicotinamide

5-Amino-benzene-1',1'-d$_2$-methanol (1.97 g, 15.8 mmol), 5-methylnicotinic acid (3.24 g, 23.6 mmol), DIPEA (6.745 mL, 39.4 mmol) are dissolved in DCM/DMF: 3/1 (60 mL). A solution of HATU (6.292 g, 16.55 mmol) dissolved in DMF (10 mL) is added. The reaction is stirred 70 h at RT. The mixture is diluted with DCM (50 mL) and washed twice with sat. aq. $NaHCO_3$ (50 mL). The combined organic phases are dried over MgSO4 and filtered. The solvent is evaporated under reduced pressure. The residue is purified by flash chromatography on silica gel using a mixture of DCM/MeOH 97:3. After concentration of the product containing fractions, the title compound (2.496 g, 65%) is obtained as a beige powder: LC-MS D: $t_R$=0.44 min; $[M+H]^+$=245.17.

(6.001c): N-(3-((4-(cyclohexylcarbamoyl)piperidin-1-yl)d$_2$methyl)phenyl)-5-methylnicotinamide N-(3-(d$_2$(hydroxy)methyl)phenyl-5-methylnicotinamide (48.8 mg, 0.2 mmol) is dissolved in DCM (5 mL). Et3N (36.2 µl, 0.26 mmol) is added followed by methanesulfonyl chloride (20.4 µl, 0.26 mmol) at 0° C. The mixture is allowed to warm to RT and then stirred for 1 h. The mixture is washed with an aq. Sol. of 5% $NaHCO_3$ (5 mL). The organic layer is separated, dried over $MgSO_4$ and evaporated to dryness. The crude methane sulfonate derivative is dissolved in dry DMF (1 mL) and treated with a solution of piperidine-4-carboxylic acid cyclohexylamide hydrochloride (49.3 mg, 0.2 mmol) in DMF (1 mL). DIPEA (43 µl, 0.25 mmol) is added, and the mixture is stirred at 70° C. overnight. The mixture is diluted with DCM (10 mL) and washed twice with sat. aq. $NaHCO_3$ (50 mL). The aqueous phase is extracted twice with DCM (2×10 mL). The combined organic layers are dried over $MgSO_4$ and filtered. The solvent is evaporated under reduced pressure. The residue is purified by rep HPLC F delivering the title compound (32 mg, 36%) as a white powder, LC-MS D: $t_R$=0.49 min; $[M+H]^+$=439.25.

Example 6.002

N-(3-((4-(cyclopentylcarbamoyl)piperidin-1-yl) d$_2$methyl)phenyl)-5-methylnicotinamide The subtitle compound is prepared according to the reaction 6.011c described above using piperidine-4-carboxylic acid cyclopentylamide hydrochloride: LC-MS D: $t_R$=0.46 min; $[M+H]^+$=423.36.

Example 7.001

6-Methyl-pyridazine-4-carboxylic acid [3-(4-tert-butylcarbamoyl-piperidin-1-ylmethyl)-phenyl]-amide (7.001a): 3-Chloro-6-methyl-pyridazine-4-carboxylic acid [3-(4-tert-butylcarbamoyl-piperidin-1-ylmethyl)-phenyl]-amide A solution of 1-(3-amino-benzyl)-piperidine-4-carboxylic acid tert-butylamide BB-4 (400 mg, 1.4 mmol) in DCM (15 mL) is treated successively with 3-chloro-6-methyl-pyridazine-4-carboxylic acid (239 mg, 1.4 mmol), EDC (344 mg, 1.8 mmol) and DMAP (25.3 mg, 0.207 mmol) at RT overnight. The reaction mixture is washed twice with sat.aq. $NaHCO_3$ (15 mL). The aqueous phase is extracted twice with DCM (2×10 mL). The combined organic layers are dried over $MgSO_4$ and filtered. The solvent is evaporated under reduced pressure. The residue is purified by prep HPLC E delivering the title compound (53 mg, 36%) as a light brownish powder, LC-MS A: $t_R$=0.60 min; $[M+H]^+$=444.12.

(7.001 b): 6-Methyl-pyridazine-4-carboxylic acid [3-(4-tert-butylcarbamoyl-piperidin-1-ylmethyl)-phenyl]-amide A solution of 3-chloro-6-methyl-pyridazine-4-carboxylic acid [3-(4-tert-butylcarbamoyl-piperidin-1-ylmethyl)-phenyl]-amide (53 mg, 0.119 mmol) in methanol (5 mL) is treated with palladium 10 wt % on activated carbon wet (50% water) (5.1 mg, 0.048 mmol, 0.4 eq) and AcOH (0.00683 ml, 0.119 mmol). The mixture is stirred under hydrogen atmosphere for 4 h. The suspension is filtered over celite and the solvent is evaporated. The residue is purified by prep HPLC E delivering the title compound (7 mg, 14%) as a light yellowish powder, LC-MS A: $t_R$=0.58 min; $[M+H]^+$=410.4.

Example 8.001

5-Amino-pyridine-2-carboxylic acid [3-(4-tert-butylcarbamoyl-piperidin-1-ylmethyl)-phenyl]-amide (8.001a): {6-[3-(4-tert-Butylcarbamoyl-piperidin-1-ylmethyl)-phenylcarbamoyl]-pyridin-3-yl}-carbamic acid tert-butyl ester A solution of 5-[[(1,1-dimethylethoxy)carbonyl]amino]-2-pyridinecarboxylic acid (1 g, 4.11 mmol) in DCM (30 mL)

is treated successively with 1-(3-amino-benzyl)-piperidine-4-carboxylic acid tert-butylamide (1.309 g, 4.525 mmol), EDC-HCl (1.577 g, 8.227 mmol), DMAP (75 mg, 0.62 mmol). The RM is stirred at RT for 18 h. DCM (10 mL) and aq. sat. NaHCO3 solution (30 mL) are added and the organic phase is extracted twice with DCM (2×20 mL). The combined organic layers are dried over MgSO$_4$, filtered and evaporated. The residue is purified by flash chromatography on silica gel using a gradient of DCM/MeOH from DCM to DCM/MeOH 9:1. After concentration of the product containing fractions, the title compound (1.21 g, 58%) is obtained as a beige powder LC-MS A: $t_R$=0.75 min; [M+H]$^+$=510.23.

(8.001 b): 5-Amino-pyridine-2-carboxylic acid [3-(4-tert-butylcarbamoyl-piperidin-1-ylmethyl)-phenyl]-amide A solution of {6-[3-(4-tert-butylcarbamoyl-piperidin-1-ylmethyl)-phenylcarbamoyl]-pyridin-3-yl}-carbamic acid tert-butyl ester (1.21 g, 2.37 mmol) in dioxane (15 mL) is cooled to 0° C. and HCl 4M in dioxane (2.4 mL, 9.497 mmol) is added. The RM is stirred at RT for 1 h and then heated at 60° C. overnight. The red mixture is cooled down to RT and filtered. The filtercake is washed with dioxane (15 mL). The red solid residue is partitioned between DCM (15 mL) and aq.sat.NaHCO3 (15 mL). The aqueous phase is extracted twice with DCM (2×20 mL). The combined org phase are dried over MgSO4, filtered and concentrated until dryness. The title compound is obtained as a yellowish foam LC-MS C: $t_R$=0.61 min; [M+H]$^+$=410.4.

II. Biological Assays

In Vitro Assay

The CXCl12 receptor and CXCR7 agonistic activities of the compounds of formula (I) are determined in accordance with the following experimental method.

The assay is using the PathHunter™ CHO-K1 CXCR7 b-arrestin cell line from DiscoverX. The system is based on the Enzyme Fragment Complementation Technology. Two complementing fragments of the b-galactosidase enzyme are expressed within stably transfected cells. The larger portion of b-gal, termed EA for Enzyme Acceptor, is fused to the C-terminus of b-arrestin 2. The smaller fragment, termed ProLink™ tag, is fused to CXCR7 at the C-terminus. Upon activation, b-arrestin is recruited which forces the interaction of ProLink and EA, allowing complementation of the two fragments of b-gal and the formation of a functional enzyme which is capable of hydrolysing the substrate and generating a chemiluminescent signal.

CHO-K1 CXCR7 b-arrestin cells are detached from culture dishes with a cell dissociation buffer (Invitrogen, #13151-014) and collected in growing medium (F12 HAMS 90% (v/v)/FCS 10% (v/v), Penicilin/streptomycin 1% (v/v)). 5000 cells per well (in 20 µl) are seeded in a 384 well plate (white-walled, clear bottom; BD Falcon #353274). The plate is incubated at 37° C./5% CO$_2$ for 24 hours. Medium is then replaced by 20 µl OPTIMEM (Invitrogen #31985) for 3 to 4 hours. Test compounds are dissolved at 10 mM in DMSO and serially diluted in DMSO to 200× of the final concentration for dose response curves. Compounds are then diluted 1:33.3 in HBSS1×. 5 µl/well of HBSS1×/20 mM HEPES/0.2% BSA are added to the assay plate followed by addition of 5 µl/well of diluted compounds. CXCL12 (Peprotech #300-28A) may be used as a reference agonist. The plate is incubated for 90 minutes at 37° C. 12 µl of detection reagent (Path Hunter Detection Kit, DiscoveRx, #93-0001) is transferred to the assay plate and to the plate is incubated for 1 hour at room temperature. Luminescent signal is read in a microplate reader (FLUOstar Optima, bmg). The calculated EC$_{50}$ values may fluctuate depending on the daily cellular assay performance. Fluctuations of this kind are known to those skilled in the art. Average EC$_{50}$ values from several measurements are given as geometric mean values.

Agonistic activities of exemplified compounds are displayed in Table 5:

TABLE 5

| Example | EC$_{50}$ [nM] | Example | EC$_{50}$ [nM] | Example | EC$_{50}$ [nM] | Example | EC$_{50}$ [nM] |
|---|---|---|---|---|---|---|---|
| 1.001 | 2 | 1.033 | 2 | 1.065 | 59 | 1.097 | 5 |
| 1.002 | 1 | 1.034 | 18 | 1.066 | 44 | 1.098 | 12 |
| 1.003 | 23 | 1.035 | 4 | 1.067 | 2 | 1.099 | 19 |
| 1.004 | 40 | 1.036 | 35 | 1.068 | 7 | 1.100 | 3 |
| 1.005 | 18 | 1.037 | 34 | 1.069 | 10 | 1.101 | 4 |
| 1.006 | 2 | 1.038 | 13 | 1.070 | 40 | 1.102 | 4 |
| 1.007 | 6 | 1.039 | 1 | 1.071 | 182 | 1.103 | 6 |
| 1.008 | 35 | 1.040 | 1260 | 1.072 | 471 | 1.104 | 5 |
| 1.009 | 17 | 1.041 | 43 | 1.073 | 371 | 1.105 | 5 |
| 1.010 | 68 | 1.042 | 79 | 1.074 | 60 | 1.106 | 12 |
| 1.011 | 7 | 1.043 | 9 | 1.075 | 9 | 1.107 | 8 |
| 1.012 | 4 | 1.044 | 1240 | 1.076 | 26 | 1.108 | 633 |
| 1.013 | 20 | 1.045 | 2490 | 1.077 | 3 | 1.109 | 40 |
| 1.014 | 3 | 1.046 | 5 | 1.078 | 1 | 1.110 | 8 |
| 1.015 | 78 | 1.047 | 17 | 1.079 | 3 | 1.111 | 4 |
| 1.016 | 121 | 1.048 | 46 | 1.080 | 14 | 1.112 | 21 |
| 1.017 | 29 | 1.049 | 7 | 1.081 | 0.9 | 1.113 | 7 |
| 1.018 | 5 | 1.050 | 12 | 1.082 | 4 | 1.114 | 13 |
| 1.019 | 2 | 1.051 | 130 | 1.083 | 11 | 1.115 | 5 |
| 1.020 | 25 | 1.052 | 36 | 1.084 | 39 | 1.116 | 6 |
| 1.021 | 39 | 1.053 | 40 | 1.085 | 1 | 1.117 | 4 |
| 1.022 | 97 | 1.054 | 41 | 1.086 | 527 | 1.118 | 3 |
| 1.023 | 4 | 1.055 | 10 | 1.087 | 36 | 1.119 | 6 |
| 1.024 | 10 | 1.056 | 7 | 1.088 | 24 | 1.120 | 35 |
| 1.025 | 3 | 1.057 | 0.8 | 1.089 | 15 | 1.121 | 5 |
| 1.026 | 182 | 1.058 | 5 | 1.090 | 6 | 1.122 | 15 |
| 1.027 | 42 | 1.059 | 393 | 1.091 | 12 | 1.123 | 4 |
| 1.028 | 4 | 1.060 | 4 | 1.092 | 3 | 1.124 | 5 |
| 1.029 | 5 | 1.061 | 1 | 1.093 | 149 | 1.125 | 10 |
| 1.030 | 18 | 1.062 | 57 | 1.094 | 1 | 1.126 | 70 |
| 1.031 | 2 | 1.063 | 237 | 1.095 | 5 | 1.127 | 36 |
| 1.032 | 34 | 1.064 | 19 | 1.096 | 40 | 1.128 | 5 |
| 1.129 | 2 | 1.162 | 2780 | 1.195 | 176 | 1.228 | 1 |
| 1.130 | 7 | 1.163 | 386 | 1.196 | 491 | 1.229 | 0.5 |
| 1.131 | 4 | 1.164 | 8 | 1.197 | 15 | 1.230 | 1 |
| 1.132 | 10 | 1.165 | 23 | 1.198 | 92 | 1.231 | 99 |
| 1.133 | 7 | 1.166 | 10 | 1.199 | 3 | 1.232 | 3 |
| 1.134 | 8 | 1.167 | 25 | 1.200 | 16 | 1.233 | 2 |
| 1.135 | 7 | 1.168 | 2 | 1.201 | 3 | 1.234 | 2 |
| 1.136 | 43 | 1.169 | 12 | 1.202 | 145 | 1.235 | 0.9 |
| 1.137 | 8 | 1.170 | 18 | 1.203 | 56 | 1.236 | 5 |
| 1.138 | 6 | 1.171 | 150 | 1.204 | 47 | 1.237 | 4 |
| 1.139 | 22 | 1.172 | 28 | 1.205 | 2 | 1.238 | 4 |
| 1.140 | 5 | 1.173 | 26 | 1.206 | 0.9 | 1.239 | 17 |
| 1.141 | 2 | 1.174 | 559 | 1.207 | 0.8 | 1.240 | 3 |
| 1.142 | 2 | 1.175 | 181 | 1.208 | 0.6 | 1.241 | 4 |
| 1.143 | 5 | 1.176 | 173 | 1.209 | 1 | 1.242 | 6 |
| 1.144 | 73 | 1.177 | 37 | 1.210 | 0.6 | 1.244 | 5 |
| 1.145 | 425 | 1.178 | 64 | 1.211 | 3 | 1.245 | 1 |
| 1.146 | 8 | 1.179 | 78 | 1.212 | 2 | 1.246 | 3 |
| 1.147 | 5 | 1.180 | 51 | 1.213 | 3 | 1.247 | 2 |
| 1.148 | 5 | 1.181 | 148 | 1.214 | 109 | 1.248 | 2 |
| 1.149 | 81 | 1.182 | 7 | 1.215 | 2 | 1.249 | 2 |
| 1.150 | 25 | 1.183 | 98 | 1.216 | 7 | 1.250 | 3 |
| 1.151 | 10 | 1.184 | 33 | 1.217 | 0.4 | 1.251 | 3 |
| 1.152 | 10 | 1.185 | 15 | 1.218 | 2 | 1.252 | 4 |
| 1.153 | 10 | 1.186 | 86 | 1.219 | 0.9 | 1.253 | 4 |
| 1.154 | 2 | 1.187 | 7 | 1.220 | 1 | 1.254 | 2 |
| 1.155 | 12 | 1.188 | 215 | 1.221 | 1 | 1.255 | 137 |
| 1.156 | 2 | 1.189 | 15 | 1.222 | 3 | 1.256 | 222 |
| 1.157 | 2 | 1.190 | 134 | 1.223 | 0.5 | 1.257 | 7 |
| 1.158 | 14 | 1.191 | 64 | 1.224 | 0.4 | 1.258 | 1 |

TABLE 5-continued

| Example | EC$_{50}$ [nM] | Example | EC$_{50}$ [nM] | Example | EC$_{50}$ [nM] | Example | EC$_{50}$ [nM] |
|---|---|---|---|---|---|---|---|
| 1.159 | 14 | 1.192 | 102 | 1.225 | 0.8 | 1.259 | 4 |
| 1.160 | 5 | 1.193 | 23 | 1.226 | 2 | 1.260 | 0.9 |
| 1.161 | 26 | 1.194 | 303 | 1.227 | 0.6 | 2.035 | 45 |
| 1.261 | 2 | 1.294 | 408 | 2.002 | 3 | 2.036 | 15 |
| 1.262 | 120 | 1.295 | 1 | 2.003 | 0.8 | 2.037 | 82 |
| 1.263 | 143 | 1.296 | 6 | 2.004 | 1 | 2.038 | 12 |
| 1.264 | 90 | 1.297 | 98 | 2.005 | 5 | 2.039 | 3 |
| 1.265 | 15 | 1.298 | 19 | 2.006 | 2 | 2.040 | 8 |
| 1.266 | 6 | 1.299 | 3 | 2.007 | 1 | 2.041 | 13 |
| 1.267 | 2 | 1.300 | 1 | 2.008 | 6 | 2.042 | 5 |
| 1.268 | 2 | 1.301 | 2 | 2.009 | 1 | 2.043 | 20 |
| 1.269 | 1 | 1.302 | 6 | 2.010 | 4 | 2.044 | 27 |
| 1.270 | 6 | 1.303 | 3 | 2.011 | 241 | 2.045 | 402 |
| 1.271 | 1 | 1.304 | 4 | 2.012 | 1050 | 2.046 | 6 |
| 1.272 | 2 | 1.305 | 7 | 2.013 | 13 | 2.047 | 67 |
| 1.273 | 2 | 1.306 | 4 | 2.014 | 2 | 2.048 | 19 |
| 1.274 | 9 | 1.307 | 350 | 2.015 | 46 | 2.049 | 300 |
| 1.275 | 3 | 1.308 | 87 | 2.016 | 134 | 2.050 | 26 |
| 1.276 | 6 | 1.309 | 1 | 2.017 | 219 | 2.051 | 96 |
| 1.277 | 18 | 1.310 | 2 | 2.018 | 349 | 2.052 | 121 |
| 1.278 | 6 | 1.311 | 1 | 2.019 | 40 | 2.053 | 195 |
| 1.279 | 420 | 1.312 | 8 | 2.020 | 21 | 2.054 | 109 |
| 1.280 | 409 | 1.313 | 19 | 2.021 | 218 | 2.055 | 60 |
| 1.281 | 3 | 1.314 | 145 | 2.022 | 20 | 2.056 | 6 |
| 1.282 | 5 | 1.315 | 193 | 2.023 | 162 | 2.057 | 8 |
| 1.283 | 34 | 1.316 | 36 | 2.024 | 32 | 2.058 | 224 |
| 1.284 | 223 | 1.317 | 76 | 2.025 | 17 | 2.059 | 3 |
| 1.285 | 199 | 1.318 | 13 | 2.026 | 15 | 2.060 | 10 |
| 1.286 | 265 | 1.319 | 45 | 2.027 | 442 | 2.061 | 64 |
| 1.287 | 181 | 1.320 | 48 | 2.028 | 394 | 2.062 | 28 |
| 1.288 | 33 | 1.321 | 6 | 2.029 | 433 | 2.063 | 92 |
| 1.289 | 113 | 1.322 | 4 | 2.030 | 832 | 2.064 | 87 |
| 1.290 | 49 | 1.323 | 66 | 2.031 | 3 | 2.065 | 26 |
| 1.291 | 134 | 1.324 | 51 | 2.032 | 5 | 2.066 | 431 |
| 1.293 | 81 | 1.325 | 262 | 2.033 | 9 | 2.067 | 406 |
| 2.068 | 4 | 2.001 | 0.9 | 2.034 | 533 | 4.007 | 3 |
| 2.069 | 4 | 2.084 | 304 | 3.005 | 57 | 4.008 | 71 |
| 2.070 | 6 | 2.085 | 68 | 3.006 | 56 | 4.009 | 20 |
| 2.071 | 2 | 2.086 | 10 | 3.007 | 28 | 4.010 | 57 |
| 2.072 | 188 | 2.087 | 6 | 3.008 | 3 | 4.011 | 13 |
| 2.073 | 155 | 2.088 | 19 | 3.009 | 4 | 4.012 | 10 |
| 2.074 | 70 | 2.089 | 36 | 3.010 | 41 | 4.013 | 9 |
| 2.075 | 7 | 2.091 | 6 | 3.011 | 28 | 4.014 | 8 |
| 2.076 | 780 | 2.092 | 3 | 3.012 | 44 | 4.015 | 19 |
| 2.077 | 87 | 2.093 | 6 | 3.013 | 13 | 4.016 | 3 |
| 2.078 | 257 | 2.094 | 1 | 4.001 | 46 | 4.017 | 2 |
| 2.079 | 226 | 2.095 | 2 | 4.002 | 16 | 4.018 | 11 |
| 2.080 | 15 | 3.001 | 24 | 4.003 | 197 | 4.019 | 8 |
| 2.081 | 5 | 3.002 | 57 | 4.004 | 59 | 5.001 | 29 |
| 2.082 | 121 | 3.003 | 167 | 4.005 | 4 | 6.001 | 5 |
| 2.083 | 3 | 3.004 | 36 | 4.006 | 1 | 6.002 | 4 |
| 1.326 | 2 | 1.339 | 0.6 | 1.352 | 71 | 2.104 | 4 |
| 1.327 | 28 | 1.340 | 0.7 | 1.353 | 3 | 2.105 | 3 |
| 1.328 | 8 | 1.341 | 1 | 1.354 | 108 | 2.106 | 49 |
| 1.329 | 159 | 1.342 | 216 | 1.355 | 3 | 4.020 | 0.6 |
| 1.330 | 285 | 1.343 | 1 | 2.096 | 28 | 4.021 | 2 |
| 1.331 | 62 | 1.344 | 0.9 | 2.097 | 37 | 4.022 | 234 |
| 1.332 | 16 | 1.345 | 1 | 2.098 | 193 | 4.023 | 173 |
| 1.333 | 57 | 1.346 | 1 | 2.099 | 60 | 4.024 | 3 |
| 1.334 | 17 | 1.347 | 16 | 2.100 | 161 | 4.025 | 2 |
| 1.335 | 21 | 1.348 | 8 | 2.101 | 5 | 7.001 | 62 |
| 1.336 | 83 | 1.349 | 34 | 2.102 | 4 | 8.001 | 4 |
| 1.337 | 8 | 1.350 | 29 | 2.103 | 17 | | |
| 1.338 | 0.8 | 1.351 | 176 | | | | |

Compounds of the present invention may be further characterized with regard to their general pharmacokinetic and pharmacological properties using conventional assays well known in the art such as angiogenesis assays or tumor growth inhibition assays, or for example relating to their bioavailablility in different species (such as rat or dog); or for their properties with regard to drug safety and/or toxicological properties using conventional assays well known in the art, for example relating to cytochrome P450 enzyme inhibition and time dependent inhibition, pregnane X receptor (PXR) activation, glutathione binding, or phototoxic behavior.

The invention claimed is:
1. A compound of formula (I)

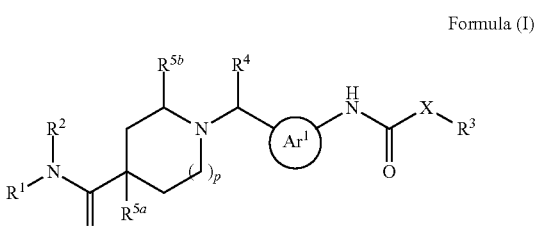

Formula (I)

wherein

Ar$^1$ represents a phenylene group or a 5- or 6-membered heteroarylene group, wherein the —CHR$^4$— group and the —NH—CO—X—R$^3$ group are attached in meta arrangement to ring carbon atoms of Ar$^1$; wherein said phenylene or 5- or 6-membered heteroarylene independently is unsubstituted or mono-substituted, wherein the substituent is selected from the group consisting of (C$_{1-4}$)alkyl, (C$_{1-4}$)alkoxy, halogen, (C$_{1-3}$)fluoroalkyl, and (C$_{1-3}$)fluoroalkoxy;

X represents a
  direct bond between R$^3$ and the carbonyl group;
  (C$_{1-4}$)alkylene which is unsubstituted, or mono-substituted with hydroxy;
  (C$_{3-6}$)cycloalkylene-;
  CH$_2$—O—, wherein the oxygen is linked to the R$^3$ group; or
  —CH=CH—;

R$^3$ represents
  aryl or 5- to 10-membered heteroaryl; wherein said aryl or 5- to 10-membered heteroaryl independently is unsubstituted, mono-, di- or tri-substituted, wherein the substituents are independently selected from the group consisting of (C$_{1-4}$)alkyl; (C$_{1-4}$)alkoxy; (C$_{1-3}$)fluoroalkyl; (C$_{1-3}$)fluoroalkoxy; halogen; cyano; (C$_{3-6}$)cycloalkyl; —CO—(C$_{1-4}$)alkoxy; —SO$_2$—(C$_{1-4}$)alkyl; and NR$^6$R$^7$, wherein R$^6$ and R$^7$ independently represent hydrogen or (C$_{1-3}$)alkyl, or R$^6$ and R$^7$ together with the nitrogen atom to which they are attached to form a 5- or 6-membered ring selected from pyrrolidinyl, morpholinyl, piperidinyl and piperazinyl optionally substituted at the vacant nitrogen atom with (C$_{1-4}$)alkyl; wherein in case said 5- to 10-membered heteroaryl is pyridine, such pyridine may additionally be present in form of the respective N-oxide;

or, in case X is a direct bond or a methylene group, R$^3$ may in addition represent
    a partially aromatic bicyclic ring system consisting of a phenyl ring which is fused to a 4- to 6-membered saturated carbocyclic ring optionally containing one or two heteroatoms independently selected from nitrogen and oxygen; wherein said ring system is optionally mono-, or di-substituted with (C$_{1-4}$)alkyl or halogen; or
    (C$_{3-8}$)cycloalkyl, wherein the cycloalkyl may optionally contain a ring oxygen atom, and wherein said cycloalkyl is optionally substituted with up to four methyl groups;

or, in case X is a direct bond, $R^3$ may in addition represent $(C_{2-6})$alkyl;

or, in case X is —CH=CH—, $R^3$ may in addition represent hydrogen, $(C_{1-4})$alkyl, or (dimethylamino) methyl;

$R^1$ represents
- $(C_{1-6})$alkyl which is unsubstituted, or mono-substituted with $(C_{1-4})$alkoxy or hydroxy;
- $(C_{2-3})$fluoroalkyl;
- $(C_{3-8})$cycloalkyl or $(C_{3-8})$cycloalkyl-$(C_{1-3})$alkyl; wherein the respective $(C_{3-8})$cycloalkyl groups may optionally contain a ring oxygen atom; wherein the $(C_{3-8})$cycloalkyl or $(C_{3-8})$cycloalkyl $(C_{1-3})$alkyl independently is unsubstituted, or substituted as follows:
  - the $(C_{3-8})$cycloalkyl group is mono- or di-substituted wherein the substituents are independently selected from the group consisting of $(C_{1-4})$alkyl, fluoro, hydroxy-methyl, hydroxy, and cyano; or
  - the $(C_{1-3})$alkyl group is mono-substituted with hydroxy;
- aryl-$(C_{1-4})$alkyl-, or 5- or 6-membered heteroaryl-$(C_{1-4})$alkyl-, wherein the aryl or 5- or 6-membered heteroaryl independently is unsubstituted, mono-, or di-substituted, wherein the substituents are independently selected from the group consisting of $(C_{1-4})$alkyl, $(C_{1-4})$alkoxy, halogen, cyano, $(C_{1-3})$fluoroalkyl, and $(C_{1-3})$fluoroalkoxy; or
- a 1,2,3,4-tetrahydronaphthalenyl or an indanyl group, which groups are attached to the rest of the molecule through a carbon atom that is part of the non-aromatic ring;

and $R^2$ represents hydrogen, or $(C_{1-3})$alkyl; or $R^1$ and $R^2$ together with the nitrogen atom to which they are attached to represent an azetidine, pyrrolidine, piperidine, morpholine, or azepane ring, wherein said rings independently are unsubstituted, or mono- or di-substituted, wherein the substituents are independently selected from the group consisting of fluorine and methyl;

$R^4$ represents hydrogen, or $(C_{1-3})$alkyl; and $R^{5a}$ represents hydrogen, methyl, or fluorine; $R^{5b}$ represents hydrogen; and p represents the integer 0, 1 or 2; or $R^{5a}$ represents hydrogen; $R^{5b}$ represents methyl; and p represents the integer 1;

or a pharmaceutically acceptable salt thereof;

wherein said compound of formula (I) is not:
1-[1-[3-(benzoylamino)phenyl]ethyl]-N-[(4-fluorophenyl)methyl]-4-piperidinecarboxamide; or
N-[3-[1-[4-(1-pyrrolidinylcarbonyl)-1-piperidinyl]ethyl]phenyl]-benzamide.

2. The compound according to claim 1; wherein $Ar^1$ represents a phenylene group, wherein the —$CHR^4$— group and the —NH—CO—X—$R^3$ group are attached in meta arrangement to said phenylene group; wherein said phenylene is unsubstituted or mono-substituted, wherein the substituent is selected from the group consisting of $(C_{1-4})$alkyl, $(C_{1-4})$alkoxy, halogen, $(C_{1-3})$fluoroalkyl, and $(C_{1-3})$fluoroalkoxy;

or a pharmaceutically acceptable salt thereof.

3. The compound according to claim 2; wherein

X represents a direct bond; —$(C_{1-4})$alkylene- which is unsubstituted, or mono-substituted with hydroxy; —$(C_{3-6})$cycloalkylene-; or —$CH_2$—O—, wherein the oxygen is linked to the $R^3$ group; and $R^3$ represents aryl or 5- to 10-membered heteroaryl; wherein said aryl or 5- to 10-membered heteroaryl independently is unsubstituted, mono-, di- or tri-substituted, wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; cyano; $(C_{3-6})$cycloalkyl; and $NR^6R^7$, wherein $R^6$ and $R^7$ independently represent hydrogen or $(C_{1-3})$alkyl, or $R^6$ and $R^7$ together with the nitrogen atom to which they are attached to form a 5- or 6-membered ring selected from pyrrolidinyl, morpholinyl, piperidinyl, and piperazinyl optionally substituted at the vacant nitrogen atom with $(C_{1-4})$alkyl; wherein in case said 5- to 10-membered heteroaryl is pyridine, such pyridine may additionally be present in form of the respective N-oxide; or X represents a direct bond or methylene; and $R^3$ represents a partially aromatic bicyclic ring system consisting of a phenyl ring which is fused to a 4- to 6-membered saturated carbocyclic ring optionally containing one or two heteroatoms independently selected from nitrogen and oxygen; wherein said ring system is optionally mono-, or di-substituted with $(C_{1-4})$alkyl or halogen; or X represents a direct bond or methylene; and $R^3$ represents $(C_{3-8})$cycloalkyl, wherein the cycloalkyl may optionally contain a ring oxygen atom, and wherein said cycloalkyl is optionally substituted with up to four methyl groups; or X represents a direct bond; and $R^3$ represents $(C_{2-6})$alkyl; or a pharmaceutically acceptable salt thereof.

4. The compound according to claim 1; wherein

X represents a direct bond; methylene; ethylene; ethane-1,1-diyl; propane-2,2-diyl; 2-methyl-propan-1,1-diyl; —CH(OH)—; cyclopropylene; or —$CH_2$—O—, wherein the oxygen is linked to the $R^3$ group; and $R^3$ represents aryl which is unsubstituted, mono-, di- or tri-substituted, wherein the substituents are independently selected from the group consisting of $(C_{1-4})$alkyl; $(C_{1-4})$alkoxy; $(C_{1-3})$fluoroalkyl; $(C_{1-3})$fluoroalkoxy; halogen; and cyano; or $R^3$ represents 5- to 10-membered heteroaryl; which is unsubstituted, mono-, di- or tri-substituted, wherein the substituents are independently selected from the group consisting of $(C_{1-4})$alkyl; $(C_{1-4})$alkoxy; $(C_{1-3})$fluoroalkyl; halogen; $(C_{3-6})$cycloalkyl; and $NR^6R^7$, wherein $R^6$ and $R^7$ independently represent hydrogen or $(C_{1-3})$alkyl, or $R^6$ and $R^7$ together with the nitrogen atom to which they are attached to form a 5- or 6-membered ring selected from pyrrolidinyl, morpholinyl, piperidinyl, and piperazinyl optionally substituted at the vacant nitrogen atom with methyl; wherein in case said 5- to 10-membered heteroaryl is pyridine, such pyridine may additionally be present in form of the respective N-oxide; or X represents a direct bond or methylene; and $R^3$ represents bicyclo[4.2.0]octa-1(6),2,4-triene-7-yl, indane-1-yl, 2,3-dihydro-1H-indole-3-yl, 2,3-dihydro-benzofuran-3-yl, or 7-chloro-2,3-dihydro-benzofuran-4-yl; or X represents a direct bond or methylene; and $R^3$ represents cyclopropyl, cyclobutyl, cyclopentyl, cyclohexyl, cycloheptanyl, bicyclo[2,2,1]heptan-2-yl 2,2-dimethylcyclopropyl, 2,2,3,3-tetramethylcyclopropyl, tetrahydrofuranyl or tetrahydropyranyl; or X represents a direct bond; and $R^3$ represents $(C_{2-6})$alkyl; or a pharmaceutically acceptable salt thereof.

5. The compound according to claim 1; wherein X represents a direct bond or methylene;

or a pharmaceutically acceptable salt thereof.

6. The compound according to claim 1; wherein $R^1$ represents
- $(C_{1-6})$alkyl which is unsubstituted, or mono-substituted with $(C_{1-4})$alkoxy or hydroxy;
- $(C_{2-3})$fluoroalkyl;
- $(C_{3-8})$cycloalkyl; wherein the $(C_{3-8})$cycloalkyl group optionally contains a ring oxygen atom; wherein the $(C_{3-8})$cycloalkyl is unsubstituted, or mono- or di-substituted wherein the substituents are independently selected from the group consisting of $(C_{1-4})$alkyl, fluoro, hydroxy-methyl, and hydroxy;
- a 1,2,3,4-tetrahydronaphthalenyl or an indanyl group, which groups are attached to the rest of the molecule through a carbon atom that is part of the non-aromatic ring;

and $R^2$ represents hydrogen, methyl, or ethyl; or
$R^1$ and $R^2$ together with the nitrogen atom to which they are attached to represent an azetidine, pyrrolidine, piperidine, morpholine, or azepane ring, wherein said rings independently are unsubstituted, or mono- or di-substituted, wherein the substituents are independently selected from the group consisting of fluorine and methyl;
or a pharmaceutically acceptable salt thereof.

7. The compound according to claim 1; wherein $R^4$ represents hydrogen or methyl;
or a pharmaceutically acceptable salt thereof.

8. The compound according to claim 7; wherein
$R^{5a}$ represents hydrogen, methyl, or fluorine; $R^{5b}$ represents hydrogen; and p represents the integer 1; or
$R^{5a}$ represents hydrogen; $R^{5b}$ represents methyl; and p represents the integer 1;
or a pharmaceutically acceptable salt thereof.

9. The compound according to claim 1; wherein $R^{5a}$ represents hydrogen, methyl, or fluorine; $R^{5b}$ represents hydrogen; and p represents the integer 1;
or a pharmaceutically acceptable salt thereof.

10. The compound according to claim 1 selected from the group consisting of:
- 1-(5-Benzoylamino-2-chloro-benzyl)-piperidine-4-carboxylic acid cyclopentylamide;
- 5-Fluoro-pyridine-2-carboxylic acid [4-chloro-3-(4-cyclopentylcarbamoyl-piperidin-1-ylmethyl)-phenyl]-amide;
- 1-[3-(4-Fluoro-benzoylamino)-benzyl]-piperidine-4-carboxylic acid tert-butylamide;
- 5-Trifluoromethyl-pyridine-2-carboxylic acid [3-(4-tert-butylcarbamoyl-piperidin-1-ylmethyl)-phenyl]-amide;
- 5-Trifluoromethyl-pyridine-2-carboxylic acid [3-(4-cyclopentylcarbamoyl-piperidin-1-ylmethyl)-phenyl]-amide;
- 6-Trifluoromethyl-pyridine-2-carboxylic acid [3-(4-cyclopentylcarbamoyl-piperidin-1-ylmethyl)-phenyl]-amide;
- 5-Chloro-N-[4-chloro-3-(4-cyclopentylcarbamoyl-piperidin-1-ylmethyl)-phenyl]-nicotinamide;
- N-[4-Chloro-3-(4-cyclopentylcarbamoyl-piperidin-1-ylmethyl)-phenyl]-5-trifluoromethyl-nicotinamide;
- 5-Fluoro-pyridine-2-carboxylic acid [3-(4-cyclopentylcarbamoyl-piperidin-1-ylmethyl)-phenyl]-amide;
- 1-[3-(4-Chloro-benzoylamino)-benzyl]-piperidine-4-carboxylic acid isopropylamide;
- 5-Fluoro-pyridine-2-carboxylic acid [3-(4-cyclohexylcarbamoyl-piperidin-1-ylmethyl)-phenyl]-amide;
- 1-{3-[(2,2,3,3-Tetramethyl-cyclopropanecarbonyl)-amino]-benzyl}-piperidine-4-carboxylic acid tert-butylamide;
- 1-[3-(4-Chloro-benzoylamino)-benzyl]-piperidine-4-carboxylic acid tert-butylamide;
- 1-[3-(4-Fluoro-benzoylamino)-benzyl]-piperidine-4-carboxylic acid cyclopentylamide;
- 6-Methyl-pyridine-2-carboxylic acid [3-(4-cyclohexylcarbamoyl-piperidin-1-ylmethyl)-phenyl]-amide;
- 1-[3-(4-Chloro-benzoylamino)-benzyl]-piperidine-4-carboxylic acid cyclopentylamide;
- Quinoline-2-carboxylic acid [3-(4-tert-butylcarbamoyl-piperidin-1-ylmethyl)-phenyl]-amide;
- 1-[2-Chloro-5-(4-fluoro-benzoylamino)-benzyl]-piperidine-4-carboxylic acid cyclopentylamide;
- 1-[3-(4-Chloro-benzoylamino)-benzyl]-piperidine-4-carboxylic acid cyclobutylamide;
- 1-[3-(2-Methyl-2-phenyl-propionylamino)-benzyl]-piperidine-4-carboxylic acid tert-butylamide;
- 6-Trifluoromethyl-pyridine-2-carboxylic acid [3-(4-tert-butylcarbamoyl-piperidin-1-ylmethyl)-phenyl]-amide;
- 6-Trifluoromethyl-pyridine-2-carboxylic acid [3-(4-tert-butylcarbamoyl-piperidin-1-ylmethyl)-4-methyl-phenyl]-amide;
- 5-Chloro-pyridine-2-carboxylic acid [3-(4-cyclohexylcarbamoyl-piperidin-1-ylmethyl)-phenyl]-amide;
- 1-{3-[2-(2-Chloro-phenyl)-acetylamino]-benzyl}-piperidine-4-carboxylic acid tert-butylamide;
- 5-Trifluoromethyl-pyridine-2-carboxylic acid [4-chloro-3-(4-cyclopentylcarbamoyl-piperidin-1-ylmethyl)-phenyl]-amide;
- 5-Chloro-N-[3-(4-cyclopentylcarbamoyl-piperidin-1-ylmethyl)-phenyl]-nicotinamide;
- 1-[3-(4-Chloro-benzoylamino)-benzyl]-piperidine-4-carboxylic acid diethylamide;
- 6-Trifluoromethyl-pyridine-2-carboxylic acid [3-(4-cyclohexylcarbamoyl-piperidin-1-ylmethyl)-phenyl]-amide;
- 6-Chloro-pyridine-2-carboxylic acid [3-(4-cyclohexylcarbamoyl-piperidin-1-ylmethyl)-phenyl]-amide;
- 1-{3-[(1-Phenyl-cyclopropanecarbonyl)-amino]-benzyl}-piperidine-4-carboxylic acid tert-butylamide;
- 1-{3-[2-(2,6-Dichloro-phenyl)-acetylamino]-benzyl}-piperidine-4-carboxylic acid tert-butylamide;
- 3-Bromo-pyridine-2-carboxylic acid [3-(4-cyclohexylcarbamoyl-piperidin-1-ylmethyl)-phenyl]-amide;
- 1-[5-(4-Fluoro-benzoylamino)-2-methyl-benzyl]-piperidine-4-carboxylic acid tert-butylamide;
- 5-Fluoro-1-oxy-pyridine-2-carboxylic acid [3-(4-cyclopentylcarbamoyl-piperidin-1-ylmethyl)-phenyl]-amide;
- 6-Trifluoromethyl-pyridine-2-carboxylic acid [3-(4-propylcarbamoyl-piperidin-1-ylmethyl)-phenyl]-amide;
- 1-{3-[2-(4-Chloro-phenyl)-2-methyl-propionylamino]-benzyl}-piperidine-4-carboxylic acid tert-butylamide;
- Quinoline-6-carboxylic acid [4-chloro-3-(4-cyclopentylcarbamoyl-piperidin-1-ylmethyl)-phenyl]-amide;
- 3-Methyl-pyridine-2-carboxylic acid [3-(4-cyclohexylcarbamoyl-piperidin-1-ylmethyl)-phenyl]-amide;
- Pyridine-2-carboxylic acid [3-(4-cyclohexylcarbamoyl-piperidin-1-ylmethyl)-phenyl]-amide;
- 1-{3-[(Bicyclo[4.2.0]octa-1(6),2,4-triene-7-carbonyl)-amino]-benzyl}-piperidine-4-carboxylic acid tert-butylamide;
- N-[3-(4-tert-Butylcarbamoyl-piperidin-1-ylmethyl)-phenyl]-5-trifluoromethyl-nicotinamide;
- Pyrimidine-4-carboxylic acid [2-chloro-5-(4-cyclohexylcarbamoyl-piperidin-1-ylmethyl)-phenyl]-amide;
- 5-Chloro-pyridine-2-carboxylic acid {3-[1-(4-cyclohexylcarbamoyl-piperidin-1-yl)-ethyl]-phenyl}-amide;

1-[3-(4-Chloro-benzoylamino)-benzyl]-piperidine-4-carboxylic acid cyclopropylamide;
6-Trifluoromethyl-pyridine-2-carboxylic acid [4-chloro-3-(4-cyclopentylcarbamoyl-piperidin-1-ylmethyl)-phenyl]-amide;
1-{3-[2-(2-Chloro-4-fluoro-phenyl)-acetylamino]-benzyl}-piperidine-4-carboxylic acid tert-butylamide;
6-Trifluoromethyl-pyridine-2-carboxylic acid [5-(4-tert-butylcarbamoyl-piperidin-1-ylmethyl)-2-methyl-phenyl]-amide;
1-{3-[2-(2-Chloro-6-fluoro-phenyl)-acetylamino]-benzyl}-piperidine-4-carboxylic acid tert-butylamide;
5-Methyl-pyrazine-2-carboxylic acid [3-(4-cyclohexylcarbamoyl-piperidin-1-ylmethyl)-phenyl]-amide;
6-Chloro-N-[3-(4-cyclohexylcarbamoyl-piperidin-1-ylmethyl)-phenyl]-nicotinamide;
1-[3-(4-Fluoro-benzoylamino)-benzyl]-piperidine-4-carboxylic acid cyclohexylamide;
6-Trifluoromethyl-pyridine-2-carboxylic acid [3-(4-tert-butylcarbamoyl-piperidin-1-ylmethyl)-4-fluoro-phenyl]-amide;
1-{3-[2-(2-Chloro-3-trifluoromethyl-phenyl)-acetylamino]-benzyl}-piperidine-4-carboxylic acid tert-butylamide;
1-[3-(4-Chloro-benzoylamino)-benzyl]-piperidine-4-carboxylic acid cyclohexylamide;
1-{3-[2-(2-Chloro-3,6-difluoro-phenyl)-acetylamino]-benzyl}-piperidine-4-carboxylic acid tert-butylamide;
1-[3-(4-Chloro-benzoylamino)-benzyl]-piperidine-4-carboxylic acid (4,4-difluoro-cyclohexyl)-amide;
1-[3-(3-Chloro-benzoylamino)-benzyl]-piperidine-4-carboxylic acid cyclohexylamide;
Pyrazine-2-carboxylic acid [3-(4-cyclohexylcarbamoyl-piperidin-1-ylmethyl)-phenyl]-amide;
N-[4-Chloro-3-(4-cyclopentylcarbamoyl-piperidin-1-ylmethyl)-phenyl]-5-methyl-nicotinamide;
[1,6]Naphthyridine-2-carboxylic acid [3-(4-tert-butylcarbamoyl-piperidin-1-ylmethyl)-phenyl]-amide;
1-(3-{[1-(2,4-Dichloro-phenyl)-cyclopropanecarbonyl]-amino}-benzyl)-piperidine-4-carboxylic acid tert-butylamide;
5-Fluoro-pyridine-2-carboxylic acid [3-(4-cyclopropylcarbamoyl-piperidin-1-ylmethyl)-phenyl]-amide;
1-(3-{[1-(4-Chloro-phenyl)-cyclopropanecarbonyl]-amino}-benzyl)-piperidine-4-carboxylic acid tert-butylamide;
1-[3-(4-Fluoro-benzoylamino)-benzyl]-piperidine-4-carboxylic acid isobutyl-methyl-amide;
1-[3-(3,4-Difluoro-benzoylamino)-benzyl]-piperidine-4-carboxylic acid cyclohexylamide;
Quinoline-3-carboxylic acid [3-(4-tert-butylcarbamoyl-piperidin-1-ylmethyl)-phenyl]-amide;
1-{3-[2-(2,5-Dimethyl-thiazol-4-yl)-acetylamino]-benzyl}-piperidine-4-carboxylic acid tert-butylamide;
1-{3-[(Indane-1-carbonyl)-amino]-benzyl}-piperidine-4-carboxylic acid tert-butylamide;
Pyrimidine-4-carboxylic acid [3-(4-cyclohexylcarbamoyl-piperidin-1-ylmethyl)-phenyl]-amide;
N-[3-(4-Cyclopentylcarbamoyl-piperidin-1-ylmethyl)-phenyl]-5-trifluoromethyl-nicotinamide;
6-Trifluoromethyl-pyridine-2-carboxylic acid [3-(4-butylcarbamoyl-piperidin-1-ylmethyl)-phenyl]-amide;
1-[3-(2-Indan-2-yl-acetylamino)-benzyl]-piperidine-4-carboxylic acid tert-butylamide;
N-[3-(4-Cyclohexylcarbamoyl-piperidin-1-ylmethyl)-phenyl]-5-ethyl-nicotinamide;
6-Trifluoromethyl-pyridine-2-carboxylic acid [3-(4-isobutylcarbamoyl-piperidin-1-ylmethyl)-phenyl]-amide;
N-[3-(4-Cyclopentylcarbamoyl-piperidin-1-ylmethyl)-phenyl]-5-fluoro-nicotinamide;
1-[3-(3,5-Difluoro-benzoylamino)-benzyl]-piperidine-4-carboxylic acid cyclohexylamide;
1-[3-(4-Methoxy-benzoylamino)-benzyl]-piperidine-4-carboxylic acid cyclohexylamide;
1-[3-(4-Fluoro-benzoylamino)-4-methyl-benzyl]-piperidine-4-carboxylic acid tert-butylamide;
N-[3-(4-tert-Butylcarbamoyl-piperidin-1-ylmethyl)-phenyl]-5-cyclopropyl-nicotinamide;
N-[3-(4-tert-Butylcarbamoyl-piperidin-1-ylmethyl)-phenyl]-5-methyl-nicotinamide;
1-{3-[2-(2,6-Dichloro-3-trifluoromethyl-phenyl)-acetylamino]-benzyl}-piperidine-4-carboxylic acid tert-butylamide;
5-Trifluoromethyl-pyridine-2-carboxylic acid {3-[4-(isobutyl-methyl-carbamoyl)-piperidin-1-ylmethyl]-phenyl}-amide;
N-[3-(4-tert-Butylcarbamoyl-piperidin-1-ylmethyl)-4-methyl-phenyl]-5-methyl-nicotinamide;
1-[3-(4-Fluoro-3-methyl-benzoylamino)-benzyl]-piperidine-4-carboxylic acid cyclohexylamide;
6-Methyl-pyridine-2-carboxylic acid [3-(4-cyclopropylcarbamoyl-piperidin-1-ylmethyl)-phenyl]-amide;
4-Chloro-pyridine-2-carboxylic acid [3-(4-cyclohexylcarbamoyl-piperidin-1-ylmethyl)-phenyl]-amide;
1-[3-(4-Chloro-benzoylamino)-benzyl]-piperidine-4-carboxylic acid methylamide;
1-{3-[2-(2,3-Dichloro-phenyl)-acetylamino]-benzyl}-piperidine-4-carboxylic acid tert-butylamide;
1-(3-Benzoylamino-benzyl)-piperidine-4-carboxylic acid cyclohexylamide;
Quinoline-6-carboxylic acid [3-(4-cyclopentylcarbamoyl-piperidin-1-ylmethyl)-phenyl]-amide;
N-{3-[4-(1,1-Dimethyl-propylcarbamoyl)-piperidin-1-ylmethyl]-phenyl}-5-methyl-nicotinamide;
1-[5-(4-Fluoro-benzoylamino)-thiophen-3-ylmethyl]-piperidine-4-carboxylic acid tert-butylamide;
N-[3-(4-Cyclohexylcarbamoyl-piperidin-1-ylmethyl)-phenyl]-6-methoxy-nicotinamide;
1-[3-(3-Methyl-benzoylamino)-benzyl]-piperidine-4-carboxylic acid cyclohexylamide;
Quinoxaline-2-carboxylic acid [3-(4-tert-butylcarbamoyl-piperidin-1-ylmethyl)-phenyl]-amide;
1-{3-[2-(2-Chloro-phenyl)-acetylamino]-benzyl}-piperidine-4-carboxylic acid cyclohexylamide;
5-Fluoro-1-oxy-pyridine-2-carboxylic acid [3-(4-tert-butylcarbamoyl-piperidin-1-ylmethyl)-phenyl]-amide;
6-Trifluoromethyl-pyridine-2-carboxylic acid {3-[4-(2-methoxy-1-methyl-ethylcarbamoyl)-piperidin-1-ylmethyl]-phenyl}-amide;
1-[3-(2-Phenyl-propionylamino)-benzyl]-piperidine-4-carboxylic acid tert-butylamide;
1-[3-(4-Chloro-benzoylamino)-benzyl]-piperidine-4-carboxylic acid (2,2,2-trifluoro-ethyl)-amide;
1-{3-[(5-Methyl-thiophene-2-carbonyl)-amino]-benzyl}-piperidine-4-carboxylic acid cyclohexylamide;
6-Trifluoromethyl-pyridine-2-carboxylic acid [3-(4-cyclohexylcarbamoyl-piperidin-1-ylmethyl)-4-fluoro-phenyl]-amide;
1-{3-[2-(2,3-Dichloro-6-trifluoromethyl-phenyl)-acetylamino]-benzyl}-piperidine-4-carboxylic acid tert-butylamide;

1-[3-(4-Fluoro-benzoylamino)-benzyl]-piperidine-4-carboxylic acid cyclopropylamide;
Quinoline-3-carboxylic acid [3-(4-cyclopentylcarbamoyl-piperidin-1-ylmethyl)-phenyl]-amide;
6-Trifluoromethyl-pyridine-2-carboxylic acid {3-[4-(4-methyl-cyclohexylcarbamoyl)-piperidin-1-ylmethyl]-phenyl}-amide;
Quinoline-3-carboxylic acid [4-chloro-3-(4-cyclopentylcarbamoyl-piperidin-1-ylmethyl)-phenyl]-amide;
1-{3-[(Benzofuran-3-carbonyl)-amino]-benzyl}-piperidine-4-carboxylic acid cyclohexylamide;
1-[3-(3-Chloro-5-fluoro-benzoylamino)-benzyl]-piperidine-4-carboxylic acid cyclohexylamide;
1-(3-Phenylacetylamino-benzyl)-piperidine-4-carboxylic acid tert-butylamide;
1-[3-(3-Fluoro-5-methyl-benzoylamino)-benzyl]-piperidine-4-carboxylic acid cyclohexylamide;
N-[3-(4-tert-Butylcarbamoyl-piperidin-1-ylmethyl)-phenyl]-5-ethyl-nicotinamide;
1-[3-(4-Chloro-benzoylamino)-benzyl]-piperidine-4-carboxylic acid cyclopentylmethyl-amide;
6-Trifluoromethyl-pyridine-2-carboxylic acid [5-(4-tert-butylcarbamoyl-piperidin-1-ylmethyl)-2-methoxy-phenyl]-amide;
1-{3-[2-(2,3-Dichloro-6-fluoro-phenyl)-acetylamino]-benzyl}-piperidine-4-carboxylic acid tert-butylamide;
4-Methyl-pyridine-2-carboxylic acid [3-(4-cyclohexylcarbamoyl-piperidin-1-ylmethyl)-phenyl]-amide;
6-Trifluoromethyl-pyridine-2-carboxylic acid [3-(4-ethylcarbamoyl-piperidin-1-ylmethyl)-phenyl]-amide;
1-{3-[2-(2-Methoxy-phenyl)-acetylamino]-benzyl}-piperidine-4-carboxylic acid cyclohexylamide;
1-[3-(2,4-Dimethyl-benzoylamino)-benzyl]-piperidine-4-carboxylic acid cyclohexylamide;
1-[3-(4-Trifluoromethyl-benzoylamino)-benzyl]-piperidine-4-carboxylic acid tert-butylamide;
1-[4-(4-Fluoro-benzoylamino)-thiophen-2-ylmethyl]-piperidine-4-carboxylic acid tert-butylamide;
1-[3-(3-Methoxy-benzoylamino)-benzyl]-piperidine-4-carboxylic acid cyclohexylamide;
N-(3-((4-(cyclopentylcarbamoyl)piperidin-1-yl)d2methyl)phenyl)-5-methylnicotinamide;
1-{3-[(Thiophene-3-carbonyl)-amino]-benzyl}-piperidine-4-carboxylic acid cyclohexylamide;
1-[3-(3-Fluoro-4-methoxy-benzoylamino)-benzyl]-piperidine-4-carboxylic acid cyclohexylamide;
1-[3-(4-Fluoro-benzoylamino)-4-methoxy-benzyl]-piperidine-4-carboxylic acid tert-butylamide;
6-Trifluoromethyl-pyridine-2-carboxylic acid [3-(4-methylcarbamoyl-piperidin-1-ylmethyl)-phenyl]-amide;
1-{3-[2-(2,4-Dichloro-5-fluoro-phenyl)-acetylamino]-benzyl}-piperidine-4-carboxylic acid tert-butylamide;
1-[3-(3-Trifluoromethyl-benzoylamino)-benzyl]-piperidine-4-carboxylic acid tert-butylamide;
Pyridazine-3-carboxylic acid [3-(4-tert-butylcarbamoyl-piperidin-1-ylmethyl)-phenyl]-amide;
1-[3-(4-Methyl-benzoylamino)-benzyl]-piperidine-4-carboxylic acid cyclohexylamide;
1-[3-(2-Fluoro-benzoylamino)-benzyl]-piperidine-4-carboxylic acid cyclohexylamide;
N-[3-(4-Cyclohexylcarbamoyl-piperidin-1-ylmethyl)-phenyl]-5-methyl-nicotinamide;
1-[3-(4-Ethyl-benzoylamino)-benzyl]-piperidine-4-carboxylic acid cyclohexylamide;
7-Chloro-quinoline-3-carboxylic acid [3-(4-tert-butylcarbamoyl-piperidin-1-ylmethyl)-phenyl]-amide;
1-{3-[2-(2,4-Dichloro-phenyl)-acetylamino]-benzyl}-piperidine-4-carboxylic acid tert-butylamide;
N-(3-((4-(cyclohexylcarbamoyl)piperidin-1-yl)d2methyl)phenyl)-5-methylnicotinamide;
1-[3-(3-Fluoro-5-methoxy-benzoylamino)-benzyl]-piperidine-4-carboxylic acid cyclohexylamide;
1-{3-[(1H-Pyrrole-2-carbonyl)-amino]-benzyl}-piperidine-4-carboxylic acid cyclohexylamide;
1-[3-(3,4-Dichloro-benzoylamino)-benzyl]-piperidine-4-carboxylic acid cyclohexylamide;
1-[3-(2-Trifluoromethoxy-benzoylamino)-benzyl]-piperidine-4-carboxylic acid cyclohexylamide;
N-[3-(4-Cyclohexylcarbamoyl-piperidin-1-ylmethyl)-phenyl]-5-cyclopropyl-nicotinamide;
1-[3-(2,3-Difluoro-benzoylamino)-benzyl]-piperidine-4-carboxylic acid cyclohexylamide;
1-[3-(3-Trifluoromethyl-benzoylamino)-benzyl]-piperidine-4-carboxylic acid cyclohexylamide;
1-{3-[4-(2-Fluoro-ethyl)-benzoylamino]-benzyl}-piperidine-4-carboxylic acid cyclohexylamide;
1-[3-(4-Chloro-benzoylamino)-benzyl]-piperidine-4-carboxylic acid (1-hydroxymethyl-cyclopentyl)-amide;
1-{3-[(7-Chloro-2, 3-dihydro-benzofuran-4-carbonyl)-amino]-benzyl}-piperidine-4-carboxylic acid cyclohexylamide;
1-[3-(4-Chloro-benzoylamino)-benzyl]-piperidine-4-carboxylic acid (2-methoxy-ethyl)-amide;
1-[3-(4-Fluoro-2-methyl-benzoylamino)-benzyl]-piperidine-4-carboxylic acid cyclohexylamide;
1-{3-[((1S*,2S*)-2-Phenyl-cyclopropanecarbonyl)-amino]-benzyl}-piperidine-4-carboxylic acid cyclohexylamide;
1-[3-(4-Chloro-2-methyl-benzoylamino)-benzyl]-piperidine-4-carboxylic acid cyclohexylamide;
N-[3-(4-Cyclohexylcarbamoyl-piperidin-1-ylmethyl)-phenyl]-5-trifluoromethyl-nicotinamide;
6-Trifluoromethyl-pyridine-2-carboxylic acid {3-[4-(3-methyl-butylcarbamoyl)-piperidin-1-ylmethyl]-phenyl}-amide;
1-[4-Chloro-3-(4-chloro-benzoylamino)-benzyl]-piperidine-4-carboxylic acid cyclohexylamide;
N-[3-(4-Cyclopentylcarbamoyl-piperidin-1-ylmethyl)-phenyl]-5-methyl-nicotinamide;
1-[3-(4-Trifluoromethyl-benzoylamino)-benzyl]-piperidine-4-carboxylic acid cyclohexylamide;
1-{3-[(5-Chloro-thiophene-2-carbonyl)-amino]-benzyl}-piperidine-4-carboxylic acid cyclohexylamide;
1-{3-[((1S,2R,4R)-Bicyclo[2.2.1]heptane-2-carbonyl)-amino]-benzyl}-piperidine-4-carboxylic acid cyclohexylamide;
5, 6-Dichloro-N-[3-(4-cyclohexylcarbamoyl-piperidin-1-ylmethyl)-phenyl]-nicotinamide;
1-[3-(3-Fluoro-benzoylamino)-benzyl]-piperidine-4-carboxylic acid cyclohexylamide;
1-[3-(2,4-Dichloro-benzoylamino)-benzyl]-piperidine-4-carboxylic acid cyclohexylamide;
1-[3-(4-Chloro-benzoylamino)-benzyl]-piperidine-4-carboxylic acid (2S,4R)-bicyclo[2.2.1]hept-2-ylamide;
6-Trifluoromethyl-pyridine-2-carboxylic acid {3-[4-(2,2-dimethyl-propylcarbamoyl)-piperidin-1-ylmethyl]-phenyl}-amide;
6-Trifluoromethyl-pyridine-2-carboxylic acid {3-[4-(2-methoxy-propylcarbamoyl)-piperidin-1-ylmethyl]-phenyl}-amide;
1-{3-[(2,3-Dihydro-benzofuran-3-carbonyl)-amino]-benzyl}-piperidine-4-carboxylic acid tert-butylamide;

(S)-1-{3-[(6-Trifluoromethyl-pyridine-2-carbonyl)-amino]-benzyl}-azepane-4-carboxylic acid sec-butylamide;
1-[3-(2-Fluoro-4-methyl-benzoylamino)-benzyl]-piperidine-4-carboxylic acid cyclohexylamide;
6-Trifluoromethyl-pyridine-2-carboxylic acid {3-[4-(2-hydroxy-1, 1-dimethyl-ethylcarbamoyl)-piperidin-1-ylmethyl]-phenyl}-amide;
5-Chloro-N-{3-[4-(isobutyl-methyl-carbamoyl)-piperidin-1-ylmethyl]-phenyl}-nicotinamide;
4-Trifluoromethyl-pyridine-2-carboxylic acid [3-(4-tert-butylcarbamoyl-piperidin-1-ylmethyl)-phenyl]-amide;
1-{3-[(Naphthalene-2-carbonyl)-amino]-benzyl}-piperidine-4-carboxylic acid cyclohexylamide;
N-{3-[4-(Isobutyl-methyl-carbamoyl)-piperidin-1-ylmethyl]-phenyl}-5-trifluoromethyl-nicotinamide;
1-[3-(2-Fluoro-5-methyl-benzoylamino)-benzyl]-piperidine-4-carboxylic acid cyclohexylamide;
1-[3-(4-Fluoro-benzoylamino)-2-methoxy-benzyl]-piperidine-4-carboxylic acid tert-butylamide;
6-Trifluoromethyl-pyridine-2-carboxylic acid [3-(4-tert-butylcarbamoyl-piperidin-1-ylmethyl)-4-methoxy-phenyl]-amide;
N-[5-(4-tert-Butylcarbamoyl-piperidin-1-ylmethyl)-2-methyl-phenyl]-5-methyl-nicotinamide;
5-Methyl-N-{3-[4-(methyl-propyl-carbamoyl)-piperidin-1-ylmethyl]-phenyl}-nicotinamide;
5-Methyl-N-{3-[4-(piperidine-1-carbonyl)-piperidin-1-ylmethyl]-phenyl}-nicotinamide;
1-{3-[2-(2-Chloro-phenyl)-2-hydroxy-acetylamino]-benzyl}-piperidine-4-carboxylic acid tert-butylamide;
1-{3-[(2,2-Dimethyl-cyclopropanecarbonyl)-amino]-benzyl}-piperidine-4-carboxylic acid tert-butylamide;
1-[3-(2-Fluoro-5-trifluoromethyl-benzoylamino)-benzyl]-piperidine-4-carboxylic acid cyclohexylamide;
1-[3-(3,4-Dimethyl-benzoylamino)-benzyl]-piperidine-4-carboxylic acid cyclohexylamide;
1-[3-(2-Chloro-4-fluoro-benzoylamino)-benzyl]-piperidine-4-carboxylic acid cyclohexylamide;
N-[5-(4-tert-Butylcarbamoyl-piperidin-1-ylmethyl)-2-methoxy-phenyl]-5-methyl-nicotinamide;
4-Trifluoromethyl-pyridine-2-carboxylic acid [3-(4-cyclopentylcarbamoyl-piperidin-1-ylmethyl)-phenyl]-amide;
1-{3-[(Isoxazole-5-carbonyl)-amino]-benzyl}-piperidine-4-carboxylic acid cyclohexylamide;
1-[3-(4-Chloro-2-fluoro-benzoylamino)-benzyl]-piperidine-4-carboxylic acid cyclohexylamide;
5-Fluoro-1-oxy-pyridine-2-carboxylic acid [3-(4-cyclohexylcarbamoyl-piperidin-1-ylmethyl)-phenyl]-amide;
1-(3-Phenylacetylamino-benzyl)-piperidine-4-carboxylic acid cyclohexylamide;
6-Trifluoromethyl-pyridine-2-carboxylic acid {3-[1-(4-cyclohexylcarbamoyl-piperidin-1-yl)-ethyl]-phenyl}-amide;
1-{3-[(Thiophene-2-carbonyl)-amino]-benzyl}-piperidine-4-carboxylic acid cyclohexylamide;
N-[3-(4-Cyclohexylcarbamoyl-piperidin-1-ylmethyl)-phenyl]-6-trifluoromethyl-nicotinamide;
N-[3-(4-Cyclohexylcarbamoyl-piperidin-1-ylmethyl)-phenyl]-5-fluoro-nicotinamide;
6-Methyl-pyridine-2-carboxylic acid {3-[1-(4-cyclohexylcarbamoyl-piperidin-1-yl)-ethyl]-phenyl}-amide;
1-{3-[2-(4-Chloro-phenyl)-propionyl amino]-benzyl}-piperidine-4-carboxylic acid tert-butylamide;
1-[3-(2,5-Dimethyl-benzoylamino)-benzyl]-piperidine-4-carboxylic acid cyclohexylamide;
N-[3-(4-tert-Butylcarbamoyl-piperidin-1-ylmethyl)-phenyl]-5-methoxy-nicotinamide;
1-[3-(4-Cyano-benzoylamino)-benzyl]-piperidine-4-carboxylic acid cyclohexylamide;
N-{3-[4-(1-Ethyl-propylcarbamoyl)-piperidin-1-ylmethyl]-phenyl}-5-methyl-nicotinamide;
N-[3-(4-tert-Butylcarbamoyl-piperidin-1-ylmethyl)-4-fluoro-phenyl]-5-methyl-nicotinamide;
1-{1-[3-(4-Chloro-benzoylamino)-phenyl]-ethyl}-piperidine-4-carboxylic acid cyclohexylamide;
1-[3-(2,5-Dichloro-benzoylamino)-benzyl]-piperidine-4-carboxylic acid cyclohexylamide;
N-{3-[4-(Isobutyl-methyl-carbamoyl)-piperidin-1-ylmethyl]-phenyl}-5-methyl-nicotinamide;
1H-Pyrrolo[2,3-b]pyridine-2-carboxylic acid [3-(4-cyclohexylcarbamoyl-piperidin-1-ylmethyl)-phenyl]-amide;
1-[3-(2-Fluoro-4-trifluoromethyl-benzoylamino)-benzyl]-piperidine-4-carboxylic acid cyclohexylamide;
2-Chloro-N-[3-(4-cyclohexylcarbamoyl-piperidin-1-ylmethyl)-phenyl]-6-methoxy-isonicotinamide;
6-Trifluoromethyl-pyridine-2-carboxylic acid {3-[4-(isobutyl-methyl-carbamoyl)-piperidin-1-ylmethyl]-phenyl}-amide;
1-[3-(4-Chloro-benzoylamino)-benzyl]-piperidine-4-carboxylic acid indan-2-ylamide;
1-[3-(2-Cyclohexyl-acetylamino)-benzyl]-piperidine-4-carboxylic acid cyclohexylamide;
N-[3-(4-Cyclopentylcarbamoyl-piperidin-1-ylmethyl)-phenyl]-5-methoxy-nicotinamide;
N-[3-(4-Cyclohexylcarbamoyl-piperidin-1-ylmethyl)-phenyl]-2-methoxy-nicotinamide;
1-{3-[2-(3-Chloro-phenyl)-acetylamino]-benzyl}-piperidine-4-carboxylic acid cyclohexylamide;
1-[3-(4-Chloro-3-fluoro-benzoylamino)-benzyl]-piperidine-4-carboxylic acid cyclohexylamide;
1-[3-(4-Pentafluoroethyl-benzoylamino)-benzyl]-piperidine-4-carboxylic acid cyclohexylamide;
N-[3-(4-Cyclohexylcarbamoyl-piperidin-1-ylmethyl)-phenyl]-2-methyl-isonicotinamide;
1-[3-(Cyclohexanecarbonyl-amino)-benzyl]-piperidine-4-carboxylic acid cyclohexylamide;
1-[3-(3,5-Dimethoxy-benzoylamino)-benzyl]-piperidine-4-carboxylic acid cyclohexylamide;
N-{3-[4-(2,2-Dimethyl-pyrrolidine-1-carbonyl)-piperidin-1-ylmethyl]-phenyl}-5-methyl-nicotinamide;
1-[3-(Cycloheptanecarbonyl-amino)-benzyl]-piperidine-4-carboxylic acid cyclohexylamide;
1-{1-[3-(4-Fluoro-benzoylamino)-phenyl]-ethyl}-piperidine-4-carboxylic acid cyclohexylamide;
1-{3-[(6-Trifluoromethyl-pyridine-2-carbonyl)-amino]-benzyl}-azepane-4-carboxylic acid tert-butylamide;
N-[3-(4-Cyclohexylcarbamoyl-piperidin-1-ylmethyl)-phenyl]-5-methoxy-nicotinamide;
4,6-Dimethyl-pyridine-2-carboxylic acid [3-(4-cyclohexylcarbamoyl-piperidin-1-ylmethyl)-phenyl]-amide;
N-[3-(4-Cyclohexylcarbamoyl-piperidin-1-ylmethyl)-4-fluoro-phenyl]-5-methyl-nicotinamide;
1-[3-(2-Chloro-benzoylamino)-benzyl]-piperidine-4-carboxylic acid cyclohexylamide;
1-[3-(4-Isopropyl-benzoylamino)-benzyl]-piperidine-4-carboxylic acid cyclohexylamide;
Pyridine-2-carboxylic acid {3-[1-(4-cyclohexylcarbamoyl-piperidin-1-yl)-ethyl]-phenyl}-amide;
1-[3-(3-Cyano-benzoylamino)-benzyl]-piperidine-4-carboxylic acid cyclohexylamide;

4-Trifluoromethyl-pyridine-2-carboxylic acid [3-(4-cyclohexylcarbamoyl-piperidin-1-ylmethyl)-phenyl]-amide;
2,6-Dichloro-N-[3-(4-cyclohexylcarbamoyl-piperidin-1-ylmethyl)-phenyl]-nicotinamide;
N-[3-(4-Isopropylcarbamoyl-piperidin-1-ylmethyl)-phenyl]-5-methyl-nicotinamide;
1-[3-(4-Fluoro-benzoylamino)-5-methyl-benzyl]-piperidine-4-carboxylic acid tert-butylamide;
1-{3-[(1H-Imidazole-2-carbonyl)-amino]-benzyl}-piperidine-4-carboxylic acid cyclohexylamide;
N-[3-(4-Cyclobutylcarbamoyl-piperidin-1-ylmethyl)-phenyl]-5-methyl-nicotinamide;
6-Trifluoromethyl-pyridine-2-carboxylic acid [3-(4-tert-butylcarbamoyl-4-methyl-piperidin-1-ylmethyl)-phenyl]-amide;
N-[5-(4-tert-Butylcarbamoyl-piperidin-1-ylmethyl)-thiophen-3-yl]-5-methyl-nicotinamide;
1-[3-(3-Fluoro-2-methyl-benzoylamino)-benzyl]-piperidine-4-carboxylic acid cyclohexylamide;
1-[3-(4-Chloro-benzoylamino)-benzyl]-piperidine-4-carboxylic acid (tetrahydro-pyran-4-yl)-amide;
1-{4-Chloro-3-[(5-methyl-thiophene-2-carbonyl)-amino]-benzyl}-piperidine-4-carboxylic acid cyclohexylamide;
1-Oxy-pyridine-2-carboxylic acid [3-(4-cyclohexylcarbamoyl-piperidin-1-ylmethyl)-phenyl]-amide;
1-[4-Chloro-3-(4-methoxy-benzoylamino)-benzyl]-piperidine-4-carboxylic acid cyclohexylamide;
5-Methyl-pyrazine-2-carboxylic acid {3-[1-(4-cyclohexylcarbamoyl-piperidin-1-yl)-ethyl]-phenyl}-amide;
1-(1-{3-[(5-Isobutyl-2-methyl-2H-pyrazole-3-carbonyl)-amino]-phenyl}-ethyl)-piperidine-4-carboxylic acid cyclohexylamide;
2-Methyl-pyrimidine-4-carboxylic acid {3-[1-(4-cyclohexylcarbamoyl-piperidin-1-yl)-ethyl]-phenyl}-amide;
1-[3-(4-Methoxy-3-methyl-benzoylamino)-benzyl]-piperidine-4-carboxylic acid cyclohexylamide;
1-[3-(4-Chloro-benzoylamino)-benzyl]-piperidine-4-carboxylic acid (1-cyano-cyclopropyl)-amide;
2,3-Dihydro-1H-indole-3-carboxylic acid [3-(4-tert-butylcarbamoyl-piperidin-1-ylmethyl)-phenyl]-amide;
6-Trifluoromethyl-pyridine-2-carboxylic acid [3-(4-pentylcarbamoyl-piperidin-1-ylmethyl)-phenyl]-amide;
1-[3-(4-Chloro-benzoylamino)-benzyl]-piperidine-4-carboxylic acid 2-methoxy-benzylamide;
2,6-Dichloro-N-[3-(4-cyclohexylcarbamoyl-piperidin-1-ylmethyl)-phenyl]-5-fluoro-nicotinamide;
N-[3-(4-tert-Butylcarbamoyl-4-fluoro-piperidin-1-ylmethyl)-phenyl]-5-methyl-nicotinamide;
4-Chloro-pyridine-2-carboxylic acid [3-(4-cyclopropylcarbamoyl-piperidin-1-ylmethyl)-phenyl]-amide;
1-[3-(2-Methoxy-benzoylamino)-benzyl]-piperidine-4-carboxylic acid cyclohexylamide;
1-[3-(4-Chloro-benzoylamino)-benzyl]-piperidine-4-carboxylic acid 2-chloro-benzylamide;
1-{3-[2-(3-Methoxy-phenyl)-acetylamino]-benzyl}-piperidine-4-carboxylic acid cyclohexylamide;
1-[3-(2-Trifluoromethyl-benzoylamino)-benzyl]-piperidine-4-carboxylic acid tert-butylamide;
1-{3-[2-(1-Methyl-1H-indol-3-yl)-acetylamino]-benzyl}-piperidine-4-carboxylic acid cyclohexylamide;
Pyrazine-2-carboxylic acid {3-[1-(4-cyclohexylcarbamoyl-piperidin-1-yl)-ethyl]-phenyl}-amide;
5-Fluoro-N-{3-[4-(isobutyl-methyl-carbamoyl)-piperidin-1-ylmethyl]-phenyl}-nicotinamide;
1-{3-[(5-Methyl-isoxazole-3-carbonyl)-amino]-benzyl}-piperidine-4-carboxylic acid cyclohexylamide;
1-[3-(3-Phenyl-propionylamino)-benzyl]-piperidine-4-carboxylic acid cyclohexylamide;
1-[3-(2-Methyl-benzoylamino)-benzyl]-piperidine-4-carboxylic acid cyclohexylamide;
1-[3-(4-Fluoro-benzoylamino)-2-methyl-benzyl]-piperidine-4-carboxylic acid tert-butylamide;
1-[5-(4-Fluoro-benzoylamino)-2-methoxy-benzyl]-piperidine-4-carboxylic acid tert-butylamide;
N-{3-[4-(Azepane-1-carbonyl)-piperidin-1-ylmethyl]-phenyl}-5-methyl-nicotinamide;
1-{3-[(6-Trifluoromethyl-pyridine-2-carbonyl)-amino]-benzyl}-azepane-4-carboxylic acid (1,1-dimethyl-propyl)-amide;
N-{3-[4-(Isobutyl-methyl-carbamoyl)-piperidin-1-ylmethyl]-phenyl}-5-methoxy-nicotinamide;
N-[3-(4-Cyclohexylcarbamoyl-piperidin-1-ylmethyl)-phenyl]-6-methyl-nicotinamide;
1-[3-(4-Chloro-benzoylamino)-benzyl]-piperidine-4-carboxylic acid (pyridin-2-ylmethyl)-amide;
N-{3-[4-(Cyclopropylmethyl-carbamoyl)-piperidin-1-ylmethyl]-phenyl}-5-methyl-nicotinamide;
6-Trifluoromethyl-pyridine-2-carboxylic acid [3-(4-tert-butylcarbamoyl-4-fluoro-piperidin-1-ylmethyl)-phenyl]-amide;
1-[3-(2-Pyridin-2-yl-acetylamino)-benzyl]-piperidine-4-carboxylic acid cyclohexylamide;
1-[3-(3,5-Dimethyl-benzoylamino)-benzyl]-piperidine-4-carboxylic acid cyclohexylamide;
1-[3-(4-Chloro-benzoylamino)-benzyl]-piperidine-4-carboxylic acid indan-1-ylamide;
1-[3-(3,5-Dichloro-benzoylamino)-benzyl]-piperidine-4-carboxylic acid cyclohexylamide;
Pyrimidine-4-carboxylic acid {3-[1-(4-cyclohexylcarbamoyl-piperidin-1-yl)-ethyl]-phenyl}-amide;
1-[1-(3-Benzoylamino-phenyl)-ethyl]piperidine-4-carboxylic acid cyclohexylamide;
N-[3-(4-Cyclohexylcarbamoyl-piperidin-1-ylmethyl)-phenyl]-nicotinamide;
2-Dimethylamino-6-methyl-pyrimidine-4-carboxylic acid [3-(4-cyclohexylcarbamoyl-piperidin-1-ylmethyl)-phenyl]-amide;
1-[2-(4-Fluoro-benzoylamino)-pyridin-4-ylmethyl]-piperidine-4-carboxylic acid cyclohexylamide;
1-[3-(3,3-Dimethyl-butyrylamino)-benzyl]-piperidine-4-carboxylic acid cyclohexylamide;
1-[3-(Cyclobutanecarbonyl-amino)-benzyl]-piperidine-4-carboxylic acid cyclohexylamide;
1-{1-[3-(4-Methoxy-benzoylamino)-phenyl]-ethyl}-piperidine-4-carboxylic acid cyclohexylamide;
1-{4-Chloro-3-[(2-phenyl-cyclopropanecarbonyl)-amino]-benzyl}-piperidine-4-carboxylic acid cyclohexylamide;
1H-Pyrrolo[2,3-b]pyridine-5-carboxylic acid [3-(4-cyclohexylcarbamoyl-piperidin-1-ylmethyl)-phenyl]-amide;
1-(1-{3-[2-(3-Trifluoromethyl-phenyl)-acetylamino]-phenyl}-ethyl)-piperidine-4-carboxylic acid cyclohexylamide;
6-Trifluoromethyl-pyridine-2-carboxylic acid {3-[4-(1-hydroxymethyl-propylcarbamoyl)-piperidin-1-ylmethyl]-phenyl}-amide;
5-Methyl-N-{3-[4-(2-methyl-pyrrolidine-1-carbonyl)-piperidin-1-ylmethyl]-phenyl}-nicotinamide;
N-{3-[4-(4,4-Difluoro-cyclohexylcarbamoyl)-piperidin-1-ylmethyl]-phenyl}-5-methyl-nicotinamide;

1-{4-[2-(2-Chloro-phenyl)-acetylamino]-thiophen-2-yl-methyl}-piperidine-4-carboxylic acid tert-butylamide;
1-[4-(4-Chloro-benzoylamino)-pyridin-2-ylmethyl]-piperidine-4-carboxylic acid cyclohexylamide;
N-[3-(3-Cyclopentylcarbamoyl-pyrrolidin-1-ylmethyl)-phenyl]-5-methyl-nicotinamide;
N-{3-[1-(4-Cyclohexylcarbamoyl-piperidin-1-yl)-ethyl]-phenyl}-5-methyl-nicotinamide;
1-[3-(Cyclopentanecarbonyl-amino)-benzyl]-piperidine-4-carboxylic acid cyclohexylamide;
6-Trifluoromethyl-pyridine-2-carboxylic acid [6-(4-tert-butylcarbamoyl-piperidin-1-ylmethyl)-pyrimidin-4-yl]-amide;
1-[3-(4-Chloro-benzoylamino)-benzyl]-piperidine-4-carboxylic acid (thiazol-2-ylmethyl)-amide;
N-{3-[1-(4-Cyclohexylcarbamoyl-piperidin-1-yl)-ethyl]-phenyl}-2-methyl-isonicotinamide;
1-{3-[(5-Methyl-pyridine-3-carbonyl)-amino]-benzyl}-azepane-4-carboxylic acid sec-butylamide;
1-{3-[(5-tert-Butyl-thiophene-2-carbonyl)-amino]-benzyl}-piperidine-4-carboxylic acid cyclohexylamide;
1-{3-[2-(4-Chloro-phenyl)-acetylamino]-benzyl}-piperidine-4-carboxylic acid cyclohexylamide;
1-[3-(4-tert-Butyl-benzoylamino)-benzyl]-piperidine-4-carboxylic acid cyclohexylamide;
1-[3-(3-Chloro-2-methyl-benzoylamino)-benzyl]-piperidine-4-carboxylic acid cyclohexylamide;
1H-Indazole-3-carboxylic acid [3-(4-cyclohexylcarbamoyl-piperidin-1-ylmethyl)-phenyl]-amide;
1-[3-(3-Methyl-2-phenyl-butyrylamino)-benzyl]-piperidine-4-carboxylic acid cyclohexylamide;
1-[3-(2-Indan-2-yl-acetylamino)-benzyl]-piperidine-4-carboxylic acid cyclohexylamide;
1-[3-(2,6-Difluoro-benzoylamino)-benzyl]-piperidine-4-carboxylic acid cyclohexylamide;
6-Trifluoromethyl-pyridine-2-carboxylic acid [3-(4-tert-butylcarbamoyl-piperidin-1-ylmethyl)-5-methyl-phenyl]-amide;
1-{3-[(6-Trifluoromethyl-pyridine-2-carbonyl)-amino]-benzyl}-azepane-4-carboxylic acid cyclopropylmethyl-amide;
1-[5-(4-Chloro-benzoylamino)-pyridin-3-ylmethyl]-piperidine-4-carboxylic acid cyclohexylamide;
Pyrimidine-2-carboxylic acid [3-(4-cyclohexylcarbamoyl-piperidin-1-ylmethyl)-phenyl]-amide;
1-{1-[3-(4-Trifluoromethyl-benzoylamino)-phenyl]-ethyl}-piperidine-4-carboxylic acid cyclohexylamide;
Isoquinoline-1-carboxylic acid [3-(4-cyclohexylcarbamoyl-piperidin-1-ylmethyl)-phenyl]-amide;
5-Pyrrolidin-1-yl-pyridine-2-carboxylic acid [3-(4-cyclohexylcarbamoyl-piperidin-1-ylmethyl)-phenyl]-amide;
1-{3-[(4-Isobutyl-5-methyl-thiophene-2-carbonyl)-amino]-benzyl}-piperidine-4-carboxylic acid cyclohexylamide;
1-[3-(4-Dimethyl amino-benzoylamino)-benzyl]-piperidine-4-carboxylic acid cyclohexylamide;
1-[3-(4-Chloro-benzoylamino)-benzyl]-piperidine-4-carboxylic acid (1,2,3,4-tetrahydro-naphthalen-1-yl)-amide;
N-[3-(4-Cyclohexylcarbamoyl-piperidin-1-ylmethyl)-phenyl]-isonicotinamide;
1-[3-(2,3-Dimethyl-benzoylamino)-benzyl]-piperidine-4-carboxylic acid cyclohexylamide;
2-Chloro-N-[3-(4-cyclohexylcarbamoyl-piperidin-1-ylmethyl)-phenyl]-6-methyl-nicotinamide;
N-[3-(4-Cyclohexylcarbamoyl-piperidin-1-ylmethyl)-phenyl]-2-cyclopentyl-6-methyl-isonicotinamide;
1-{5-[2-(2-Chloro-phenyl)-acetylamino]-thiophen-3-yl-methyl}-piperidine-4-carboxylic acid tert-butylamide;
1H-Indole-3-carboxylic acid [3-(4-cyclohexylcarbamoyl-piperidin-1-ylmethyl)-phenyl]-amide;
1-[3-(4-Isobutyl-benzoylamino)-benzyl]-piperidine-4-carboxylic acid cyclohexylamide;
1-[3-(3,5-Bis-trifluoromethyl-benzoylamino)-benzyl]-piperidine-4-carboxylic acid cyclohexylamide;
2-Chloro-N-[3-(4-cyclohexylcarbamoyl-piperidin-1-ylmethyl)-phenyl]-nicotinamide;
N-[4-(4-tert-Butylcarbamoyl-piperidin-1-ylmethyl)-thiophen-2-yl]-5-methyl-nicotinamide;
6-Trifluoromethyl-pyridine-2-carboxylic acid [3-(4-tert-butylcarbamoyl-piperidin-1-ylmethyl)-2-methoxy-phenyl]-amide;
1-[3-(4-Chloro-benzoylamino)-benzyl]-piperidine-4-carboxylic acid benzylamide;
1-{3-[(Naphthalene-1-carbonyl)-amino]-benzyl}-piperidine-4-carboxylic acid cyclohexylamide;
1-[3-(4-Chloro-benzoylamino)-benzyl]-piperidine-4-carboxylic acid cyclohexylmethyl-amide;
N-[3-(4-Cyclohexylcarbamoyl-4-fluoro-piperidin-1-ylmethyl)-phenyl]-5-methyl-nicotinamide;
N-[3-(4-Cyclopropylcarbamoyl-piperidin-1-ylmethyl)-phenyl]-5-fluoro-nicotinamide;
N-[3-(4-tert-Butylcarbamoyl-piperidin-1-ylmethyl)-2-methoxy-phenyl]-5-methyl-nicotinamide; and
1-{3-[(5-Methyl-pyridine-3-carbonyl)-amino]-benzyl}-azepane-4-carboxylic acid tert-butylamide;
or a pharmaceutically acceptable salt thereof.

11. The compound according to claim 1 selected from the group consisting of:
5-Amino-pyridine-2-carboxylic acid [3-(4-tert-butylcarbamoyl-piperidin-1-ylmethyl)-phenyl]-amide;
5-Chloro-1-oxy-pyridine-2-carboxylic acid {3-[4-(1,1-dimethyl-propylcarbamoyl)-piperidin-1-ylmethyl]-phenyl}-amide;
5-Chloro-1-oxy-pyridine-2-carboxylic acid [3-(4-tert-butylcarbamoyl-piperidin-1-ylmethyl)-phenyl]-amide;
5-Fluoro-1-oxy-pyridine-2-carboxylic acid {3-[4-(1,1-dimethyl-propylcarbamoyl)-piperidin-1-ylmethyl]-phenyl}-amide;
5-Fluoro-pyridine-2-carboxylic acid [3-(4-tert-butylcarbamoyl-piperidin-1-ylmethyl)-phenyl]-amide;
6-Trifluoromethyl-pyridine-2-carboxylic acid [3-((2R,4R)-4-cyclohexylcarbamoyl-2-methyl-piperidin-1-yl-methyl)-phenyl]-amide;
6-Trifluoromethyl-pyridine-2-carboxylic acid [3-((2S,4S)-4-cyclohexylcarbamoyl-2-methyl-piperidin-1-yl-methyl)-phenyl]-amide;
N-[3-((2S*,4S*)-4-Cyclohexylcarbamoyl-2-methyl-piperidin-1-ylmethyl)-phenyl]-5-methyl-nicotinamide;
N-[3-((2S*,4S*)-4-tert-Butylcarbamoyl-2-methyl-piperidin-1-ylmethyl)-phenyl]-5-methyl-nicotinamide;
6-Trifluoromethyl-pyridine-2-carboxylic acid [3-((2S*,4S*)-4-tert-butylcarbamoyl-2-methyl-piperidin-1-ylmethyl)-phenyl]-amide;
6-Trifluoromethyl-pyridine-2-carboxylic acid [3-((2S*,4S*)-4-cyclohexylcarbamoyl-2-methyl-piperidin-1-yl-methyl)-phenyl]-amide;
1-{3-[2-(2-Chloro-4-fluoro-phenyl)-acetylamino]-benzyl}-pyrrolidine-3-carboxylic acid tert-butylamide;
N-[3-(3-tert-Butylcarbamoyl-pyrrolidin-1-ylmethyl)-phenyl]-5-methyl-nicotinamide;
Benzothiazole-6-carboxylic acid [3-(4-tert-butylcarbamoyl-piperidin-1-ylmethyl)-phenyl]-amide;

5-[3-(4-Cyclohexylcarbamoyl-piperidin-1-ylmethyl)-phenylcarbamoyl]-nicotinic acid methyl ester;

5-[3-(4-tert-Butylcarbamoyl-piperidin-1-ylmethyl)-phenylcarbamoyl]-nicotinic acid methyl ester;

1-Oxy-5-trifluoromethyl-pyridine-2-carboxylic acid [3-(4-tert-butylcarbamoyl-piperidin-1-ylmethyl)-phenyl]-amide;

1-Oxy-5-trifluoromethyl-pyridine-2-carboxylic acid {3-[4-(1,1-dimethyl-propylcarbamoyl)-piperidin-1-ylmethyl]-phenyl}-amide;

1-Oxy-6-trifluoromethyl-pyridine-2-carboxylic acid {3-[4-(1,1-dimethyl-propylcarbamoyl)-piperidin-1-ylmethyl]-phenyl}-amide;

1-Oxy-6-trifluoromethyl-pyridine-2-carboxylic acid [3-(4-tert-butylcarbamoyl-piperidin-1-ylmethyl)-phenyl]-amide;

6-Bromo-pyridine-2-carboxylic acid [3-(4-tert-butyl carbamoyl-piperidin-1-ylmethyl)-phenyl]-amide;

5-Chloro-3-fluoro-pyridine-2-carboxylic acid {3-[4-(1,1-dimethyl-propylcarbamoyl)-piperidin-1-ylmethyl]-phenyl}-amide;

5-Trifluoromethyl-pyridine-2-carboxylic acid {3-[4-(1,1-dimethyl-propylcarbamoyl)-piperidin-1-ylmethyl]-phenyl}-amide;

5-Chloro-3-fluoro-pyridine-2-carboxylic acid [3-(4-tert-butylcarbamoyl-piperidin-1-ylmethyl)-phenyl]-amide;

5-Chloro-pyridine-2-carboxylic acid [3-(4-tert-butyl carbamoyl-piperidin-1-ylmethyl)-phenyl]-amide;

5-Chloro-pyridine-2-carboxylic acid {3-[4-(1,1-dimethyl-propylcarbamoyl)-piperidin-1-ylmethyl]-phenyl}-amide;

1-{3-[(E)-(3-Phenyl-acryloyl)amino]-benzyl}-piperidine-4-carboxylic acid tert-butylamide;

Benzo[1,2,3]thiadiazole-5-carboxylic acid [3-(4-tert-butylcarbamoyl-piperidin-1-ylmethyl)-phenyl]-amide;

1-[3-((E)-But-2-enoylamino)-benzyl]-piperidine-4-carboxylic acid tert-butylamide;

1-[2-Ethyl-5-(4-fluoro-benzoylamino)-benzyl]-piperidine-4-carboxylic acid tert-butylamide;

6-Trifluoromethyl-pyridine-2-carboxylic acid [3-(4-tert-butylcarbamoyl-piperidin-1-ylmethyl)-4-ethyl-phenyl]-amide;

1-[4-Ethyl-3-(4-fluoro-benzoylamino)-benzyl]-piperidine-4-carboxylic acid tert-butylamide;

N-[5-(4-tert-Butylcarbamoyl-piperidin-1-ylmethyl)-2-ethyl-phenyl]-5-methyl-nicotinamide; and 6-Trifluoromethyl-pyridine-2-carboxylic acid [5-(4-tert-butylcarbamoyl-piperidin-1-ylmethyl)-2-ethyl-phenyl]-amide;

or a pharmaceutically acceptable salt thereof.

12. A pharmaceutical composition comprising, as active principle, one or more compounds according to claim 1, or a pharmaceutically acceptable salt thereof, and at least one therapeutically inert excipient.

13. A method of treating a disease or disorder comprising administering to a subject in need thereof an effective amount of a compound according to claim 1, or a pharmaceutically acceptable salt thereof, wherein the disease or disorder is a cancer, an autoimmune disorder, an inflammatory disease, transplant rejection, or fibrosis.

14. A method of treating a tumor comprising administering to a subject in need thereof an effective amount of the compound of formula (I) according to claim 1, or a pharmaceutically acceptable salt thereof, wherein said effective amount leads to a change of tumor properties, and wherein said change is achieved by modulating a CXCL12 receptor pathway.

15. A method of modulating an immune response comprising administering to a subject in need thereof an effective amount of the compound of formula (I) according to claim 1, or a pharmaceutically acceptable salt thereof, wherein said effective amount modulates an inflammatory disease and wherein said response is mediated by the CXCL12 receptor pathway.

16. The compound according to claim 2, wherein

X represents a direct bond; methylene; ethylene; ethane-1,1-diyl; propane-2,2-diyl; 2-methyl-propan-1,1-diyl; —CH(OH)—; cyclopropylene; or —CH$_2$—O—, wherein the oxygen is linked to the R$^3$ group; and R$^3$ represents aryl which is unsubstituted, mono-, di- or tri-substituted, wherein the substituents are independently selected from the group consisting of (C$_{1-4}$)alkyl; (C$_{1-4}$)alkoxy; (C$_{1-3}$)fluoroalkyl; (C$_{1-3}$)fluoroalkoxy; halogen; and cyano; or R$^3$ represents 5- to 10-membered heteroaryl; which is unsubstituted, mono-, di- or tri-substituted, wherein the substituents are independently selected from the group consisting of (C$_{1-4}$)alkyl; (C$_{1-4}$)alkoxy; (C$_{1-3}$)fluoroalkyl; halogen; (C$_{3-6}$)cycloalkyl; and —NR$^6$R$^7$, wherein R$^6$ and R$^7$ independently represent hydrogen or (C$_{1-3}$)alkyl, or R$^6$ and R$^7$ together with the nitrogen atom to which they are attached to form a 5- or 6-membered ring selected from pyrrolidinyl, morpholinyl, piperidinyl, and piperazinyl optionally substituted at the vacant nitrogen atom with methyl; wherein in case said 5- to 10-membered heteroaryl is pyridine, such pyridine may additionally be present in form of the respective N-oxide; or X represents a direct bond or methylene; and R$^3$ represents bicyclo[4.2.0]octa-1(6),2,4-triene-7-yl, indane-1-yl, 2,3-dihydro-1H-indole-3-yl, 2,3-dihydro-benzofuran-3-yl, or 7-chloro-2,3-dihydro-benzofuran-4-yl; or X represents a direct bond or methylene; and R$^3$ represents cyclopropyl, cyclobutyl, cyclopentyl, cyclohexyl, cycloheptanyl, bicyclo[2,2,1]heptan-2-yl 2,2-dimethylcyclopropyl, 2,2,3,3-tetramethylcyclopropyl, tetrahydrofuranyl or tetrahydropyranyl; or X represents a direct bond; and R$^3$ represents (C$_{2-6}$)alkyl; or a pharmaceutically acceptable salt thereof.

17. The compound according to claim 16, wherein R$^1$ represents (C$_{1-6}$)alkyl which is unsubstituted, or mono-substituted with (C$_{1-4}$)alkoxy or hydroxy;

(C$_{2-3}$)fluoroalkyl;

(C$_{3-8}$)cycloalkyl; wherein the (C$_{3-8}$)cycloalkyl group optionally contains a ring oxygen atom; wherein the (C$_{3-8}$)cycloalkyl is unsubstituted, or mono- or di-substituted wherein the substituents are independently selected from the group consisting of (C$_{1-4}$)alkyl, fluoro, hydroxy-methyl, and hydroxy;

a 1,2,3,4-tetrahydronaphthalenyl or an indanyl group, which groups are attached to the rest of the molecule through a carbon atom that is part of the non-aromatic ring;

and R$^2$ represents hydrogen, methyl, or ethyl; or

R$^1$ and R$^2$ together with the nitrogen atom to which they are attached to represent an azetidine, pyrrolidine, piperidine, morpholine, or azepane ring, wherein said ring is unsubstituted, or mono- or di-substituted, wherein the substituents are independently fluorine or methyl;

or a pharmaceutically acceptable salt thereof.

18. The compound according to claim 17, wherein $R^4$ represents hydrogen or methyl;
or a pharmaceutically acceptable salt thereof.

19. The compound according to claim 18, wherein $R^{5a}$ represents hydrogen, methyl, or fluorine; $R^{5b}$ represents hydrogen; and p represents the integer 1;
or a pharmaceutically acceptable salt thereof.

20. A pharmaceutical composition comprising, as an active principle, one or more compounds according to claim 10, or a pharmaceutically acceptable salt thereof, and at least one therapeutically inert excipient.

21. A pharmaceutical composition comprising, as an active principle, one or more compounds according to claim 11, or a pharmaceutically acceptable salt thereof, and at least one therapeutically inert excipient.

22. A method of treating a disease or disorder comprising administering to a subject in need thereof an effective amount of a compound according to claim 10, or a pharmaceutically acceptable salt thereof, wherein the disease or disorder is a cancer, an autoimmune disorder, an inflammatory disease, transplant rejection, or fibrosis.

23. A method of treating cancer comprising administering to a subject in need thereof an effective amount of a compound according to claim 10, or a pharmaceutically acceptable salt thereof.

* * * * *